United States Patent
Branon et al.

(10) Patent No.: US 12,110,522 B2
(45) Date of Patent: Oct. 8, 2024

(54) ENGINEERED PROMISCUOUS BIOTIN LIGASES FOR EFFICIENT PROXIMITY LABELING

(71) Applicant: The Board of Trustees of the Leland Stanford Junior University, Stanford, CA (US)

(72) Inventors: Tess Branon, Stanford, CA (US); Alice Y. Ting, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1118 days.

(21) Appl. No.: 16/962,792

(22) PCT Filed: Jan. 11, 2019

(86) PCT No.: PCT/US2019/013195
§ 371 (c)(1),
(2) Date: Jul. 16, 2020

(87) PCT Pub. No.: WO2019/143529
PCT Pub. Date: Jul. 25, 2019

(65) Prior Publication Data
US 2021/0214708 A1 Jul. 15, 2021

Related U.S. Application Data

(60) Provisional application No. 62/618,344, filed on Jan. 17, 2018.

(51) Int. Cl.
| | | |
|---|---|---|
| C12N 9/00 | (2006.01) | |
| G01N 33/58 | (2006.01) | |
| G01N 33/68 | (2006.01) | |

(52) U.S. Cl.
CPC ........ *C12N 9/93* (2013.01); *C12Y 603/04015* (2013.01); *G01N 33/58* (2013.01); *G01N 33/6842* (2013.01)

(58) Field of Classification Search
CPC .................................. C12N 9/00; C12N 9/93
See application file for complete search history.

(56) References Cited

U.S. PATENT DOCUMENTS 9,624,524 B2    4/2017  Ting et al.
2005/0233389 A1  10/2005  Ting et al.

FOREIGN PATENT DOCUMENTS

| KR | 1020170102116 A | 2/2019 |
| WO | 2009062241 A1 | 5/2009 |
| WO | 2012174479 A1 | 12/2012 |
| WO | 2014070227 A1 | 5/2014 |

OTHER PUBLICATIONS

Henke et al. (2014) Successful Conversion of the Bacillus subtilis BMA Group II Biotin Protein Ligase into a Group I Ligase. PLoS One 9(5):e96757.
Wilson et al. (1992) *Escherichia coli*-biotin holoenzyme synthetase/bio repressor crystal structure delineates the biotin- and DNA-binding domains. Proc Natl Acad Sci U.S.A. 89(19):9257-9261.
Kim et al. (2016) Filling the Void: Proximity-Based Labeling of Proteins in Living Cells. Trends in Cell Biology 26:804-817.
Choi-Rhee et al. (2004) Promiscuous protein biotinylation by *Escherichia coli* biotin protein ligase. Protein Sci. 13:3043-3050.
Roux et al. (2012) A promiscuous biotin ligase fusion protein identifies proximal and interacting proteins in mammalian cells. J. Cell Biol. 196:801-810.
Gupta et al. (2015) A Dynamic Protein Interaction Landscape of the Human Centrosome-Cilium Interface. Cell 163:1483-1499.
Kim et al. (2014) Probing nuclear pore complex architecture with proximity-dependent biotinylation. Proc. Natl. Acad. Sci. 111:E2453-E2461.
Lin et al. (2017) Screening of Proximal and Interacting Proteins in Rice Protoplasts by Proximity-Dependent Biotinylation Front. Plant Sci. 8:749.
Morriswood et al. (2013) Novel bilobe components in Trypanosoma brucei identified using proximity-dependent biotinylation. Eukaryot. Cell 12:356-367.
Chen et al. (2015) Novel components of the toxoplasma inner membrane complex revealed by BioID. MBio 6(1):e02357-14.
Uezu et al. (2016) Identification of an elaborate complex mediating postsynaptic inhibition. Science 353:1123-1129.
Nadipuram et al. (2016) In Vivo biotinylation of 5 the toxoplasma parasitophorous vacuole reveals novel dense granule proteins important for parasite growth and pathogenesis. MBio 7(4):e00808-16.
Chen et al. (2017) Novel insights into the composition and function of the Toxoplasma IMC sutures. Cell. Microbiol. 19(4):10.
Long et al. (2017) Calmodulin-like proteins localized to the conoid regulate motility and cell invasion by Toxoplasma gondii. PLoS Pathog. 13(5):e1006379.
Zhou et al. (2016) An EF-hand-containing protein in Trypanosoma brucei regulates cytokinesis initiation by maintaining the stability of the cytokinesis initiation factor CIF1. J. Biol. Chem. 291:14395-14409.
Dang et al. (2017) Proximity interactions among basal body components in trypanosoma brucei identify novel regulators of basal body biogenesis and inheritance. MBio 8(1):e02120-16.
Kehrer et al. (2016) Proteomic Analysis of the Plasmodium berghei Gametocyte Egressome and Vesicular bioID of Osmiophilic Body Proteins Identifies Merozoite TRAP-like Protein (MTRAP) as an Essential Factor for Parasite Transmission. Mol. Cell. Proteomics 15:2852-2862.

(Continued)

*Primary Examiner* — Tekchand Saidha
(74) *Attorney, Agent, or Firm* — Jenny L. Buchbinder; Bozicevic, Field & Francis LLP

(57) ABSTRACT

Engineered promiscuous biotin ligases and methods of using them in proximity labeling are described. In particular, the invention provides novel biotin ligase variants having increased promiscuous biotinylation activity capable of proximity labeling of proteins in live cells in as little as 10 minutes.

21 Claims, 84 Drawing Sheets
Specification includes a Sequence Listing.

(56) References Cited

OTHER PUBLICATIONS

Gaji et al. (2015) Phosphorylation of a Myosin Motor by TgCDPK3 Facilitates Rapid Initiation of Motility during Toxoplasma gondii egress. PLoS Pathog. 11(11):e1005268).
Batsios et al. (2016) Protein of the Inner Nuclear Membrane Interacting with the Dictyostelium Lamin NE81. Cells 5(1):13.
Kim et al. (2016) An improved smaller biotin ligase for BioID proximity labeling. Mol. Biol. Cell 27:1188-1196.
Han et al. (2017) Proximity Biotinylation as a Method for Mapping Proteins Associated with mtDNA in Living Cells. Cell Chem. Biol. 24:404-414.
Rhee et al. (2013) Proteomic Mapping of Mitochondria in Living Cells via Spatially Restricted Enzymatic Tagging. Science 339(6125):1328-1331.
Paek et al. (2017) Multidimensional Tracking of GPCR Signaling via Peroxidase-Catalyzed Proximity Labeling. Cell 169:338-349. e11.
Lobingier et al. (2017) An Approach to Spatiotemporally Resolve Protein Interaction Networks in Living Cells. Cell 169:350-360.e12.
International Search Report for PCT/US2019/013195.

| 1 | R118G | 5 | K2E, R118S, M157T, I279T, L298P, K307N |
| 2 | Q65P, R118S, L151P, I305V | 6 | Q65P, R118S, L151P, I305V, Y111H, R118S |
| 3 | K2E, R118S, M157T, L298P | 7 | Q65P, R118S, S150G, L151P, T192A, I305V |
| 4 | K2E, R33G, R118S, M157T, L298P | 8 | Q65P, R118S, L151P, I231V, I305V |

| 1 | Q65P, R118S, S150G, L151P, T192A, I305V |
| 2 | N37S, Q65P, R118S, S150G, L151P, T192V, E266L, I305V |
| 3 | Q65P, R118S, S150G, L151P, T192A, I280V, I305V, A318V |
| 4 | Q65P, R118S, Q142R, S150G, L151P, T192A, M209V, I305V |

| 1 | APEX2-NES |
| --- | --- |
| 2 | R118G |
| 3 | Q65P, R118S, S150G, L151P, T192A, I305V |
| 4 | Q65P, R118S, Q142R, S150G, L151P, T192A, M209V, I305V |

| 1 | Q65P, R118S, S150G, L151P, T192A, I305V | 5 | Q65P, I87V, R118S, E141K, S150G, L151P, V160A, T192A, M209V, I305V |
| 2 | Q65P, R118S, Q142R, S150G, L151P, T192A, M209V, I305V | 6 | Q65P, I87V, R118S, E141K, S150G, L151P, T192A, I305V |
| 3 | Q65P, R118S, Q142R, S150G, L151P, T192A, I305V | 7 | Q65P, R118S, S150G, L151P, V160A, T192A, M209V, I305V |
| 4 | Q65P, R118S, S150G, L151P, T192A, M209V, I305V | 8 | Q65P, R118S, Q142R, S150G, L151P, V160A, T192A, M209V, I305V |

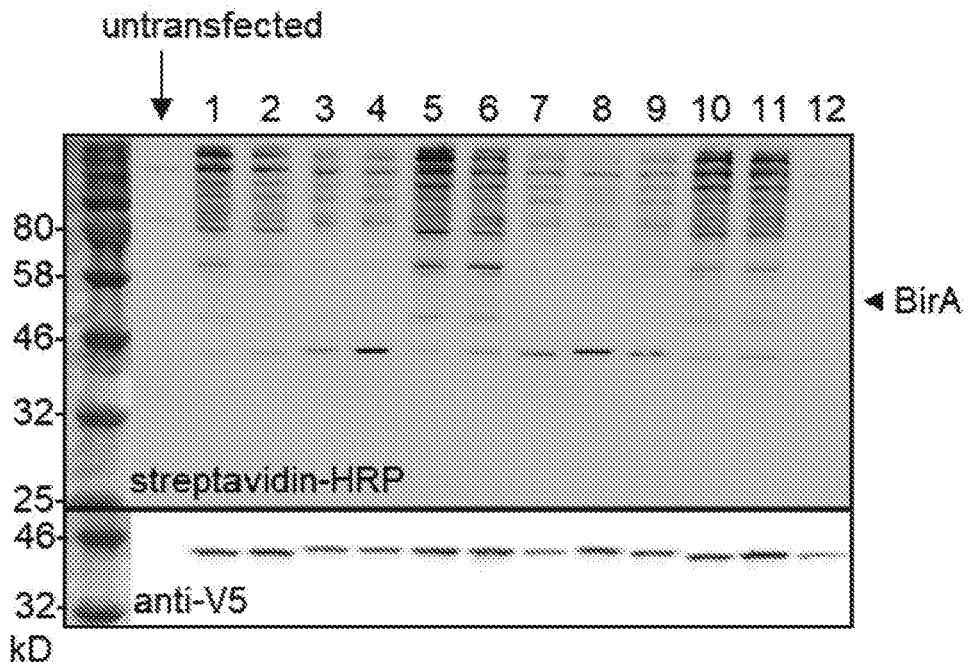

| | | | |
|---|---|---|---|
| 1 | Q65P, I87V, R118S, E141K, Q142R, S150G, L151P, V160A, T192A, M209V, I305V | 7 | Q65P, I87V, R118S, G120R, E141K, Q142R, S150G, L151P, V160A, T192A, D197G, M209V, M241V, I305V, E313K |
| 2 | Q65P, I87V, R118S, E141K, Q142R, S150G, L151P, V160A, T192A, I201V, M209V, I305V | 8 | Q65P, I87V, R118S, E141K, Q142R, S150G, L151P, V160A, V162A, A166V, T192A, M209V, I305V, E313K |
| 3 | Q65P, I87V, R118S, K140R, E141K, Q142R, S150G, L151P, V160A, T192A, M209V, K267R, I305V, E313K | 9 | Q65P, I87V, R118S, E141K, Q142R, S150G, L151P, V160A, T192A, M209V, I305V, E307R, E313K |
| 4 | Q65P, I87V, R118S, E141K, Q142R, S150G, L151P, V160A, T192A, M209V, I305V, I306V, E313K | 10 | E27D, Q65P, I87V, R118S, E141K, Q142R, S150G, L151P, V160A, T192A, M209V, E251K, I305V |
| 5 | Q65P, I87V, I98V, R118S, E141K, Q142R, S150G, L151P, V160A, T192A, M209V, I305V | 11 | Q65P, I87V, R118S, E141K, Q142R, S150G, L151P, V160A, T192A, M209V, M241T, I305V |
| 6 | Q65P, I87V, R118S, E141K, Q142R, S150G, L151P, V160A, T192A, A199T, M209V, D303G, I305V | 12 | Q65P, I87V, R118S, E141K, Q142R, S150G, L151P, V160A, T192A, M209V, N270D, I305V |

FIG. 11L

| 1 | Q65P, I87V, R118S, E141K, Q142R, S150G, L151P, V160A, T192A, M209V, I305V |
| 2 | Q65P, I87V, I98V, R118S, E141K, Q142R, S150G, L151P, V160A, T192A, M209V, I305V |
| 3 | E27D, Q65P, I87V, R118S, E141K, Q142R, S150G, L151P, V160A, T192A, M209V, E251K, I305V |
| 4 | Q65P, I87V, R118S, E141K, Q142R, S150G, L151P, V160A, T192A, M209V, M241T, I305V |

| 1 | Q65P, I87V, R118S, E141K, Q142R, S150G, L151P, V160A, T192A, M209V, I305V |
| 2 | Δ(1-63) Q65P, I87V, R118S, E141K, Q142R, S150G, L151P, V160A, T192A, M209V, I305V |
| 3 | Q65P, I87V, R118S, E141K, Q142R, S150G, L151P, V160A, T192A, M209V, M241T, I305V |
| 4 | Δ(1-63) Q65P, I87V, R118S, E141K, Q142R, S150G, L151P, V160A, T192A, M209V, M241T, I305V |

| | | | |
|---|---|---|---|
| 1 | R118G (18 hr) | 6 | Δ(1-63) Q65P, I87V, R118S, E141K, Q142R, S150G, L151P, V160A, T192A, K194I, M209V, I305V |
| 2 | Q65P, I87V, R118S, E141K, Q142R, S150G, L151P, V160A, T192A, M209V, I305V | 7 | Δ(1-63) Q65P, I87V, R118S, E141K, Q142R, S150G, L151P, V160A, T192A, M209V, M241T, S263P, I305V |
| 3 | Δ(1-63) Q65P, I87V, R118S, E141K, Q142R, S150G, L151P, V160A, T192A, M209V, I305V | 8 | Δ(1-63) Q65P, I87V, R118S, E141K, Q142R, S150G, L151P, V160A, T192A, K194I, M209V, M241T, I305V |
| 4 | Δ(1-63) Q65P, I87V, R118S, E141K, Q142R, S150G, L151P, V160A, T192A, M209V, M241T, I305V | 9 | Δ(1-63) Q65P, I87V, R118S, E141K, Q142R, S150G, L151P, V160A, T192A, K194I, M209V, S263P, I305V |
| 5 | Δ(1-63) Q65P, I87V, R118S, E141K, Q142R, S150G, L151P, V160A, T192A, M209V, S263P, I305V | | |

SEQUENCE LISTING

```
<160> NUMBER OF SEQ ID NOS: 38

<210> SEQ ID NO 1
<211> LENGTH: 56
<212> TYPE: DNA
<213> ORGANISM: Artificial Sequence
<220> FEATURE:
```

```
<223> OTHER INFORMATION: forward primer
<220> FEATURE:
<221> NAME/KEY: source
<222> LOCATION: (1)..(56)
<223> OTHER INFORMATION: sequence is synthesized

<400> SEQUENCE: 1
ctagtggtgg aggaggctct ggtggaggcg gtagcggagg cggagggtcg gctagc      56

<210> SEQ ID NO 2
<211> LENGTH: 56
<212> TYPE: DNA
<213> ORGANISM: Artificial Sequence
<220> FEATURE:
<223> OTHER INFORMATION: reverse primer
<220> FEATURE:
<221> NAME/KEY: source
<222> LOCATION: (1)..(56)
<223> OTHER INFORMATION: sequence is synthesized

<400> SEQUENCE: 2
tatcagatct cgagctatta caagtcctct tcagaaataa gcttttgttc ggatcc      56

<210> SEQ ID NO 3
<211> LENGTH: 37
<212> TYPE: DNA
<213> ORGANISM: Artificial Sequence
<220> FEATURE:
<223> OTHER INFORMATION: forward primer
<220> FEATURE:
<221> NAME/KEY: source
<222> LOCATION: (1)..(37)
<223> OTHER INFORMATION: sequence is synthesized

<400> SEQUENCE: 3
caaggtctgc aggctagtgg tggaggaggc tctggtg                           37

<210> SEQ ID NO 4
<211> LENGTH: 38
<212> TYPE: DNA
<213> ORGANISM: Artificial Sequence
<220> FEATURE:
<223> OTHER INFORMATION: reverse primer
<220> FEATURE:
<221> NAME/KEY: source
<222> LOCATION: (1)..(38)
<223> OTHER INFORMATION: sequence is synthesized

<400> SEQUENCE: 4
ctacactgtt gttatcagat ctcgagctat tacaagtc                          38

<210> SEQ ID NO 5
<211> LENGTH: 38
<212> TYPE: DNA
<213> ORGANISM: Artificial Sequence
<220> FEATURE:
<223> OTHER INFORMATION: V5-BirA-mut _F primer
<220> FEATURE:
<221> NAME/KEY: source
<222> LOCATION: (1)..(38)
<223> OTHER INFORMATION: sequence is synthesized

<400> SEQUENCE: 5
ccgcggccgc ccccttcacc atgggcaagc ccatcccc                          38

<210> SEQ ID NO 6
<211> LENGTH: 41
<212> TYPE: DNA
<213> ORGANISM: Artificial Sequence
```

```
<220> FEATURE:
<223> OTHER INFORMATION: V5-BirA-mut _R primer
<220> FEATURE:
<221> NAME/KEY: source
<222> LOCATION: (1)..(41)
<223> OTHER INFORMATION: sequence is synthesized

<400> SEQUENCE: 6
gggtcggcgc gcccacccTt ctattagtcc agggtcaggc g                              41

<210> SEQ ID NO 7
<211> LENGTH: 321
<212> TYPE: PRT
<213> ORGANISM: Escherichia coli
<300> PUBLICATION INFORMATION:
<308> DATABASE ACCESSION NUMBER: NCBI/WP_023308552
<309> DATABASE ENTRY DATE: 2015-05-29
<313> RELEVANT RESIDUES IN SEQ ID NO: (1)..(321)

<400> SEQUENCE: 7

Met Lys Asp Asn Thr Val Pro Leu Lys Leu Ile Ala Leu Leu Ala Asn
 1               5                  10                  15

Gly Glu Phe His Ser Gly Glu Gln Leu Gly Glu Thr Leu Gly Met Ser
             20                  25                  30

Arg Ala Ala Ile Asn Lys His Ile Gln Thr Leu Arg Asp Trp Gly Val
         35                  40                  45

Asp Val Phe Thr Val Pro Gly Lys Gly Tyr Ser Leu Pro Glu Pro Ile
     50                  55                  60

Gln Leu Leu Asn Ala Lys Gln Ile Leu Gly Gln Leu Asp Gly Gly Ser
 65                  70                  75                  80

Val Ala Val Leu Pro Val Ile Asp Ser Thr Asn Gln Tyr Leu Leu Asp
                 85                  90                  95

Arg Ile Gly Glu Leu Lys Ser Gly Asp Ala Cys Val Ala Glu Tyr Gln
            100                 105                 110

Gln Ala Gly Arg Gly Arg Arg Gly Arg Lys Trp Phe Ser Pro Phe Gly
        115                 120                 125

Ala Asn Leu Tyr Leu Ser Met Phe Trp Arg Leu Glu Gln Gly Pro Ala
    130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205

Met Ala Met Arg Arg Val Glu Glu Ser Val Val Asn Gln Gly Trp Ile
    210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
        275                 280                 285

Ser Arg Gly Ile Asp Lys Gln Gly Ala Leu Leu Leu Glu Gln Asp Gly
    290                 295                 300
```

Ile Ile Lys Pro Trp Met Gly Gly Glu Ile Ser Leu Arg Ser Ala Glu
305                 310                 315                 320

Lys

<210> SEQ ID NO 8
<211> LENGTH: 957
<212> TYPE: DNA
<213> ORGANISM: Artificial Sequence
<220> FEATURE:
<223> OTHER INFORMATION: BioID
<220> FEATURE:
<221> NAME/KEY: source
<222> LOCATION: (1)..(957)
<223> OTHER INFORMATION: sequence produced by mutagenesis of E. coli
      BirA

<400> SEQUENCE: 8
aaggataaca ccgtgcccct gaaactgatt gctctgctgg ctaatggcga gttccatagt      60
ggcgaacagc tgggagaaac cctgggcatg tccaggccg ctatcaacaa gcacattcag     120
actctgcgcg actggggcgt ggacgtgttc accgtgcccg aaagggcta ctctctgccc     180 gagcctatcc agctgctgaa cgctaaacag attctgggac agctggacgg cgggagcgtg     240
gcagtcctgc ctgtgatcga ctccaccaat cagtacctgc tggatcgaat cggcgagctg     300
aagagtgggg atgcttgcat tgcagaatat cagcaggcag gaagaggagg gagagggagg     360
aaatggttct ctccttttgg agctaacctg tacctgagta tgttttggcg cctggagcag     420
ggaccagcag caatcggcct gagcctggtc atcggaattg tcatggcaga agtgctgcga     480
aagctgggag cagacaaggt gcgagtcaaa tggcccaatg acctgtatct gcaggataga     540
aagctggcag catcctggt ggagctgacc ggaaaaacag gcgatgctgc acagatcgtc     600
attggcgccg ggattaacat ggctatgagg cgcgtggagg aaagcgtggt caatcagggc     660
tggatcacac tgcaggaagc agggattaac ctggacagga atactctggc cgctatgctg     720
atccgagagc tgcgggcagc cctggaactg ttcgagcagg aaggcctggc tccatatctg     780
tcacggtggg agaagctgga taacttcatc aatagacccg tgaagctgat cattggggac     840
aaagagattt tcgggattag ccgggaaatt gataaacagg gagccctgct gctgaacag     900 gacggaatta tcaaaccctg gatgggcgga gaaatcagtc tgcggtctgc cgaaaag      957

<210> SEQ ID NO 9
<211> LENGTH: 319
<212> TYPE: PRT
<213> ORGANISM: Artificial Sequence
<220> FEATURE:
<223> OTHER INFORMATION: BioID

<400> SEQUENCE: 9

Lys Asp Asn Thr Val Pro Leu Lys Leu Ile Ala Leu Leu Ala Asn Gly
1               5                   10                  15

Glu Phe His Ser Gly Glu Gln Leu Gly Glu Thr Leu Gly Met Ser Arg
            20                  25                  30

Ala Ala Ile Asn Lys His Ile Gln Thr Leu Arg Asp Trp Gly Val Asp
        35                  40                  45

Val Phe Thr Val Pro Gly Lys Gly Tyr Ser Leu Pro Glu Pro Ile Gln
    50                  55                  60

Leu Leu Asn Ala Lys Gln Ile Leu Gly Gln Leu Asp Gly Gly Ser Val
65                  70                  75                  80

Ala Val Leu Pro Val Ile Asp Ser Thr Asn Gln Tyr Leu Leu Asp Arg

```
                        85                  90                  95

Ile Gly Glu Leu Lys Ser Gly Asp Ala Cys Ile Ala Glu Tyr Gln Gln
                100                 105                 110

Ala Gly Arg Gly Gly Arg Gly Arg Lys Trp Phe Ser Pro Phe Gly Ala
            115                 120                 125

Asn Leu Tyr Leu Ser Met Phe Trp Arg Leu Glu Gln Gly Pro Ala Ala
        130                 135                 140

Ile Gly Leu Ser Leu Val Ile Gly Ile Val Met Ala Glu Val Leu Arg
145                 150                 155                 160

Lys Leu Gly Ala Asp Lys Val Arg Val Lys Trp Pro Asn Asp Leu Tyr
                165                 170                 175

Leu Gln Asp Arg Lys Leu Ala Gly Ile Leu Val Glu Leu Thr Gly Lys
            180                 185                 190

Thr Gly Asp Ala Ala Gln Ile Val Ile Gly Ala Gly Ile Asn Met Ala
        195                 200                 205

Met Arg Arg Val Glu Glu Ser Val Val Asn Gln Gly Trp Ile Thr Leu
    210                 215                 220

Gln Glu Ala Gly Ile Asn Leu Asp Arg Asn Thr Leu Ala Ala Met Leu
225                 230                 235                 240

Ile Arg Glu Leu Arg Ala Ala Leu Glu Leu Phe Glu Gln Glu Gly Leu
                245                 250                 255

Ala Pro Tyr Leu Ser Arg Trp Glu Lys Leu Asp Asn Phe Ile Asn Arg
            260                 265                 270

Pro Val Lys Leu Ile Ile Gly Asp Lys Glu Ile Phe Gly Ile Ser Arg
        275                 280                 285

Gly Ile Asp Lys Gln Gly Ala Leu Leu Leu Glu Gln Asp Gly Ile Ile
    290                 295                 300

Lys Pro Trp Met Gly Gly Glu Ile Ser Leu Arg Ser Ala Glu Lys
305                 310                 315

<210> SEQ ID NO 10
<211> LENGTH: 771
<212> TYPE: DNA
<213> ORGANISM: Artificial Sequence
<220> FEATURE:
<223> OTHER INFORMATION: MiniTurbo
<220> FEATURE:
<221> NAME/KEY: source
<222> LOCATION: (1)..(771)
<223> OTHER INFORMATION: sequence produced by mutagenesis of BioID

<400> SEQUENCE: 10
atcccgctgc tgaacgctaa acagattctg gacagctgg acggcgggag cgtggcagtc      60
ctgcctgtgg tcgactccac caatcagtac ctgctggatc gaatcggcga gctgaagagt    120
ggggatgctt gcattgcaga atatcagcag gcagggagag aagcagagg gaggaaatgg    180 ttctctcctt ttggagctaa cctgtacctg agtatgtttt ggcgcctgaa gcggggacca    240
gcagcaatcg gcctgggccc ggtcatcgga attgtcatgg cagaagcgct gcgaaagctg    300
ggagcagaca aggtgcgagt caaatggccc aatgacctgt atctgcagga tagaaagctg    360
gcaggcatcc tggtggagct ggccggaata acaggcgatg ctgcacagat cgtcattggc    420
gccgggatta acgtggctat gaggcgcgtg gaggaaagcg tggtcaatca gggctggatc    480
acactgcagg aagcagggat taacctggac aggaatactc tggccgctat gctgatccga    540
gagctgcggg cagccctgga actgttcgag caggaaggcc tggctccata tctgtcacgg    600
tgggagaagc tggataactt catcaataga cccgtgaagc tgatcattgg ggacaaagag    660
```

```
atttttcggga ttagccgggg gattgataaa cagggagccc tgctgctgga acaggacgga    720
gttatcaaac cctggatggg cggagaaatc agtctgcggt ctgccgaaaa g             771
```

<210> SEQ ID NO 11
<211> LENGTH: 257
<212> TYPE: PRT
<213> ORGANISM: Artificial Sequence
<220> FEATURE:
<223> OTHER INFORMATION: MiniTurbo

<400> SEQUENCE: 11

```
Ile Pro Leu Leu Asn Ala Lys Gln Ile Leu Gly Gln Leu Asp Gly Gly
1               5                   10                  15

Ser Val Ala Val Leu Pro Val Val Asp Ser Thr Asn Gln Tyr Leu Leu
            20                  25                  30

Asp Arg Ile Gly Glu Leu Lys Ser Gly Asp Ala Cys Ile Ala Glu Tyr
        35                  40                  45

Gln Gln Ala Gly Arg Gly Ser Arg Gly Arg Lys Trp Phe Ser Pro Phe
    50                  55                  60

Gly Ala Asn Leu Tyr Leu Ser Met Phe Trp Arg Leu Lys Arg Gly Pro
65                  70                  75                  80

Ala Ala Ile Gly Leu Gly Pro Val Ile Gly Ile Val Met Ala Glu Ala
                85                  90                  95

Leu Arg Lys Leu Gly Ala Asp Lys Val Arg Val Lys Trp Pro Asn Asp
            100                 105                 110

Leu Tyr Leu Gln Asp Arg Lys Leu Ala Gly Ile Leu Val Glu Leu Ala
        115                 120                 125

Gly Ile Thr Gly Asp Ala Ala Gln Ile Val Ile Gly Ala Gly Ile Asn
    130                 135                 140

Val Ala Met Arg Arg Val Glu Glu Ser Val Val Asn Gln Gly Trp Ile
145                 150                 155                 160

Thr Leu Gln Glu Ala Gly Ile Asn Leu Asp Arg Asn Thr Leu Ala Ala
                165                 170                 175

Met Leu Ile Arg Glu Leu Arg Ala Ala Leu Glu Leu Phe Glu Gln Glu
            180                 185                 190

Gly Leu Ala Pro Tyr Leu Ser Arg Trp Glu Lys Leu Asp Asn Phe Ile
        195                 200                 205

Asn Arg Pro Val Lys Leu Ile Ile Gly Asp Lys Glu Ile Phe Gly Ile
    210                 215                 220

Ser Arg Gly Ile Asp Lys Gln Gly Ala Leu Leu Leu Glu Gln Asp Gly
225                 230                 235                 240

Val Ile Lys Pro Trp Met Gly Gly Glu Ile Ser Leu Arg Ser Ala Glu
                245                 250                 255

Lys
```

<210> SEQ ID NO 12
<211> LENGTH: 957
<212> TYPE: DNA
<213> ORGANISM: Artificial Sequence
<220> FEATURE:
<223> OTHER INFORMATION: TurboID
<220> FEATURE:
<221> NAME/KEY: source
<222> LOCATION: (1)..(957)
<223> OTHER INFORMATION: sequence produced by mutagenesis of BioID

<400> SEQUENCE: 12

```
aaagacaata ctgtgcctct gaagctgatc gctctcctgg ctaatggcga gttccatagt    60
ggcgaacagc tgggagaaac cctgggcatg tccagggccg ctatcaacaa gcacattcag   120
actctgcgcg actggggcgt ggacgtgttc accgtgcccg gaaagggcta ctctctgccc   180
gagcctatcc cgctgctgaa cgctaaacag attctgggac agctggacgg cgggagcgtg   240
gcagtcctgc ctgtggtcga ctccaccaat cagtacctgc tggatcgaat cggcgagctg   300
aagagtgggg atgcttgcat tgcagaatat cagcaggcag ggagaggaag cagagggagg   360
aaatggttct ctccttttgg agctaacctg tacctgagta tgttttggcg cctgaagcgg   420
ggaccagcag caatcggcct gggcccggtc atcggaattg tcatggcaga agcgctgcga   480
aagctgggag cagacaaggt gcgagtcaaa tggcccaatg acctgtatct gcaggataga   540
aagctggcag catcctggt ggagctggcc ggaataacag gcgatgctgc acagatcgtc   600
attggcgccg ggattaacgt ggctatgagg cgcgtggagg aaagcgtggt caatcagggc   660
tggatcacac tgcaggaagc agggattaac ctggacagga atactctggc cgctacgctg   720
atccgagagc tgcgggcagc cctggaactg ttcgagcagg aaggcctggc tccatatctg   780
ccacggtggg agaagctgga taacttcatc aatagacccg tgaagctgat cattggggac   840
aaagagattt tcgggattag ccggggggatt gataaacagg gagccctgct gctggaacag   900
gacggagtta tcaaaccctg gatgggcgga gaaatcagtc tgcggtctgc cgaaaag     957
```

<210> SEQ ID NO 13
<211> LENGTH: 319
<212> TYPE: PRT
<213> ORGANISM: Artificial Sequence
<220> FEATURE:
<223> OTHER INFORMATION: TurboID

<400> SEQUENCE: 13

```
Lys Asp Asn Thr Val Pro Leu Lys Leu Ile Ala Leu Leu Ala Asn Gly
1               5                   10                  15

Glu Phe His Ser Gly Glu Gln Leu Gly Glu Thr Leu Gly Met Ser Arg
            20                  25                  30

Ala Ala Ile Asn Lys His Ile Gln Thr Leu Arg Asp Trp Gly Val Asp
        35                  40                  45

Val Phe Thr Val Pro Gly Lys Gly Tyr Ser Leu Pro Glu Pro Ile Pro
    50                  55                  60

Leu Leu Asn Ala Lys Gln Ile Leu Gly Gln Leu Asp Gly Gly Ser Val
65                  70                  75                  80

Ala Val Leu Pro Val Val Asp Ser Thr Asn Gln Tyr Leu Leu Asp Arg
                85                  90                  95

Ile Gly Glu Leu Lys Ser Gly Asp Ala Cys Ile Ala Glu Tyr Gln Gln
            100                 105                 110

Ala Gly Arg Gly Ser Arg Gly Arg Lys Trp Phe Ser Pro Phe Gly Ala
        115                 120                 125

Asn Leu Tyr Leu Ser Met Phe Trp Arg Leu Lys Arg Gly Pro Ala Ala
    130                 135                 140

Ile Gly Leu Gly Pro Val Ile Gly Ile Val Met Ala Glu Ala Leu Arg
145                 150                 155                 160

Lys Leu Gly Ala Asp Lys Val Arg Val Lys Trp Pro Asn Asp Leu Tyr
                165                 170                 175

Leu Gln Asp Arg Lys Leu Ala Gly Ile Leu Val Glu Leu Ala Gly Ile
            180                 185                 190

Thr Gly Asp Ala Ala Gln Ile Val Ile Gly Ala Gly Ile Asn Val Ala
```

```
            195                 200                 205
Met Arg Arg Val Glu Ser Val Val Asn Gln Gly Trp Ile Thr Leu
    210                 215                 220

Gln Glu Ala Gly Ile Asn Leu Asp Arg Asn Thr Leu Ala Ala Thr Leu
225                 230                 235                 240

Ile Arg Glu Leu Arg Ala Ala Leu Glu Leu Phe Glu Gln Glu Gly Leu
                245                 250                 255

Ala Pro Tyr Leu Pro Arg Trp Glu Lys Leu Asp Asn Phe Ile Asn Arg
            260                 265                 270

Pro Val Lys Leu Ile Ile Gly Asp Lys Glu Ile Phe Gly Ile Ser Arg
                275                 280                 285

Gly Ile Asp Lys Gln Gly Ala Leu Leu Leu Glu Gln Asp Gly Val Ile
            290                 295                 300

Lys Pro Trp Met Gly Gly Glu Ile Ser Leu Arg Ser Ala Glu Lys
305                 310                 315
```

<210> SEQ ID NO 14
<211> LENGTH: 10
<212> TYPE: PRT
<213> ORGANISM: Artificial Sequence
<220> FEATURE:
<223> OTHER INFORMATION: myc localization sequence for transient
      mammalian cytosol expression

<400> SEQUENCE: 14

```
Glu Gln Lys Leu Ile Ser Glu Glu Asp Leu
1               5                   10
```

<210> SEQ ID NO 15
<211> LENGTH: 12
<212> TYPE: PRT
<213> ORGANISM: Artificial Sequence
<220> FEATURE:
<223> OTHER INFORMATION: NES

<400> SEQUENCE: 15

```
Leu Gln Leu Pro Pro Leu Glu Arg Leu Thr Leu Asp
1               5                   10
```

<210> SEQ ID NO 16
<211> LENGTH: 7
<212> TYPE: PRT
<213> ORGANISM: Artificial Sequence
<220> FEATURE:
<223> OTHER INFORMATION: cleavage recognition site for TEV protease

<400> SEQUENCE: 16

```
Glu Asn Leu Tyr Phe Gln Gly
1               5
```

<210> SEQ ID NO 17
<211> LENGTH: 15
<212> TYPE: PRT
<213> ORGANISM: Artificial Sequence
<220> FEATURE:
<223> OTHER INFORMATION: linker

<400> SEQUENCE: 17

```
Gly Gly Gly Gly Ser Gly Gly Gly Ser Gly Gly Gly Gly Ser
1               5                   10                  15
```

<210> SEQ ID NO 18
<211> LENGTH: 10

```
<212> TYPE: PRT
<213> ORGANISM: Artificial Sequence
<220> FEATURE:
<223> OTHER INFORMATION: myc localization sequence for inducible yeast
      cell surface expression for yeast display

<400> SEQUENCE: 18

Glu Gln Lys Leu Ile Ser Glu Glu Asp Leu
1               5                   10

<210> SEQ ID NO 19
<211> LENGTH: 14
<212> TYPE: PRT
<213> ORGANISM: Artificial Sequence
<220> FEATURE:
<223> OTHER INFORMATION: V5l localization sequence for transient
      mammalian cytosol expression

<400> SEQUENCE: 19

Gly Lys Pro Ile Pro Asn Pro Leu Leu Gly Leu Asp Ser Thr
1               5                   10

<210> SEQ ID NO 20
<211> LENGTH: 12
<212> TYPE: PRT
<213> ORGANISM: Artificial Sequence
<220> FEATURE:
<223> OTHER INFORMATION: NES

<400> SEQUENCE: 20

Leu Gln Leu Pro Pro Leu Glu Arg Leu Thr Leu Asp
1               5                   10

<210> SEQ ID NO 21
<211> LENGTH: 14
<212> TYPE: PRT
<213> ORGANISM: Artificial Sequence
<220> FEATURE:
<223> OTHER INFORMATION: V5 localization sequence for transient
      mammalian nucleus expression

<400> SEQUENCE: 21

Gly Lys Pro Ile Pro Asn Pro Leu Leu Gly Leu Asp Ser Thr
1               5                   10

<210> SEQ ID NO 22
<211> LENGTH: 24
<212> TYPE: PRT
<213> ORGANISM: Artificial Sequence
<220> FEATURE:
<223> OTHER INFORMATION: NLS

<400> SEQUENCE: 22

Asp Pro Lys Lys Lys Arg Lys Val Asp Pro Lys Lys Lys Arg Lys Val
1               5                   10                  15

Asp Pro Lys Lys Lys Arg Lys Val
            20

<210> SEQ ID NO 23
<211> LENGTH: 24
<212> TYPE: PRT
<213> ORGANISM: Artificial Sequence
<220> FEATURE:
<223> OTHER INFORMATION: mitochondrial matrix targeting sequence from
      COX4

<400> SEQUENCE: 23
```

```
Met Leu Ala Thr Arg Val Phe Ser Leu Val Gly Lys Arg Ala Ile Ser
1               5                   10                  15

Thr Ser Val Cys Val Arg Ala His
            20
```

<210> SEQ ID NO 24
<211> LENGTH: 14
<212> TYPE: PRT
<213> ORGANISM: Artificial Sequence
<220> FEATURE:
<223> OTHER INFORMATION: mitochondrial matrix targeting sequence from V5

<400> SEQUENCE: 24

```
Gly Lys Pro Ile Pro Asn Pro Leu Leu Gly Leu Asp Ser Thr
1               5                   10
```

<210> SEQ ID NO 25
<211> LENGTH: 27
<212> TYPE: PRT
<213> ORGANISM: Artificial Sequence
<220> FEATURE:
<223> OTHER INFORMATION: endoplasmic reticulum membrane anchor derived
      from cytochrome P450

<400> SEQUENCE: 25

```
Met Asp Pro Val Val Val Leu Gly Leu Cys Leu Ser Cys Leu Leu Leu
1               5                   10                  15

Leu Ser Leu Trp Lys Gln Ser Tyr Gly Gly Gly
            20                  25
```

<210> SEQ ID NO 26
<211> LENGTH: 4
<212> TYPE: PRT
<213> ORGANISM: Artificial Sequence
<220> FEATURE:
<223> OTHER INFORMATION: linker

<400> SEQUENCE: 26

```
Gly Ser Gly Ser
1
```

<210> SEQ ID NO 27
<211> LENGTH: 19
<212> TYPE: PRT
<213> ORGANISM: Artificial Sequence
<220> FEATURE:
<223> OTHER INFORMATION: linker

<400> SEQUENCE: 27

```
Gly Ser Gly Ser Gly Ser Gly Ser Gly Ser Gly Ser Gly Ser Gly Ser
1               5                   10                  15

Gly Ser Gly
```

<210> SEQ ID NO 28
<211> LENGTH: 14
<212> TYPE: PRT
<213> ORGANISM: Artificial Sequence
<220> FEATURE:
<223> OTHER INFORMATION: V5 localization sequence for transient
      mammalian ER membrane expression

<400> SEQUENCE: 28

```
Gly Lys Pro Ile Pro Asn Pro Leu Leu Gly Leu Asp Ser Thr
1               5                   10
```

```
<210> SEQ ID NO 29
<211> LENGTH: 21
<212> TYPE: PRT
<213> ORGANISM: Artificial Sequence
<220> FEATURE:
<223> OTHER INFORMATION: Ig K-chain ss

<400> SEQUENCE: 29

Met Glu Thr Asp Thr Leu Leu Leu Trp Val Leu Leu Trp Val Pro
1               5                   10                  15

Gly Ser Thr Gly Asp
            20

<210> SEQ ID NO 30
<211> LENGTH: 9
<212> TYPE: PRT
<213> ORGANISM: Artificial Sequence
<220> FEATURE:
<223> OTHER INFORMATION: HA localization sequence for transient
      mammalian ER lumen expression

<400> SEQUENCE: 30

Tyr Pro Tyr Asp Val Pro Asp Tyr Ala
1               5

<210> SEQ ID NO 31
<211> LENGTH: 14
<212> TYPE: PRT
<213> ORGANISM: Artificial Sequence
<220> FEATURE:
<223> OTHER INFORMATION: V5 localization sequence for transient
      mammalian ER lumen expression

<400> SEQUENCE: 31

Gly Lys Pro Ile Pro Asn Pro Leu Leu Gly Leu Asp Ser Thr
1               5                   10

<210> SEQ ID NO 32
<211> LENGTH: 14
<212> TYPE: PRT
<213> ORGANISM: Artificial Sequence
<220> FEATURE:
<223> OTHER INFORMATION: V5 sequence for inducible yeast cytosol
      expression

<400> SEQUENCE: 32

Gly Lys Pro Ile Pro Asn Pro Leu Leu Gly Leu Asp Ser Thr
1               5                   10

<210> SEQ ID NO 33
<211> LENGTH: 6
<212> TYPE: PRT
<213> ORGANISM: Artificial Sequence
<220> FEATURE:
<223> OTHER INFORMATION: His 6

<400> SEQUENCE: 33

His His His His His His
1               5

<210> SEQ ID NO 34
<211> LENGTH: 4
<212> TYPE: PRT
<213> ORGANISM: Artificial Sequence
<220> FEATURE:
<223> OTHER INFORMATION: linker

<400> SEQUENCE: 34
```

```
<210> SEQ ID NO 35
<211> LENGTH: 5
<212> TYPE: PRT
<213> ORGANISM: Artificial Sequence
<220> FEATURE:
<223> OTHER INFORMATION: linker

<400> SEQUENCE: 35

Gly Gly Ser Ser Gly
1               5

<210> SEQ ID NO 36
<211> LENGTH: 14
<212> TYPE: PRT
<213> ORGANISM: Artificial Sequence
<220> FEATURE:
<223> OTHER INFORMATION: V5 sequence for Entry vector for Gateway LR
      recombination into destination vector

<400> SEQUENCE: 36

Gly Lys Pro Ile Pro Asn Pro Leu Leu Gly Leu Asp Ser Thr
1               5                   10

<210> SEQ ID NO 37
<211> LENGTH: 14
<212> TYPE: PRT
<213> ORGANISM: Artificial Sequence
<220> FEATURE:
<223> OTHER INFORMATION: V5 sequence for generating transgenic flies for
      Gal4-inducible expression

<400> SEQUENCE: 37

Gly Lys Pro Ile Pro Asn Pro Leu Leu Gly Leu Asp Ser Thr
1               5                   10

<210> SEQ ID NO 38
<211> LENGTH: 27
<212> TYPE: PRT
<213> ORGANISM: Artificial Sequence
<220> FEATURE:
<223> OTHER INFORMATION: 3xHA for intestinal expression

<400> SEQUENCE: 38

Tyr Pro Tyr Asp Val Pro Asp Tyr Ala Tyr Pro Tyr Asp Val Pro Asp
1               5                   10                  15

Tyr Ala Tyr Pro Tyr Asp Val Pro Asp Tyr Ala
            20                  25
```

```
Gly Gly Gly Ser
1
```

ENGINEERED PROMISCUOUS BIOTIN LIGASES FOR EFFICIENT PROXIMITY LABELING

CROSS-REFERENCE

This application claims the benefit of U.S. Provisional Patent Application No. 62/618,344 filed Jan. 17, 2018, which application is incorporated herein by reference in its entirety.

STATEMENT REGARDING FEDERALLY SPONSORED RESEARCH OR DEVELOPMENT

This invention was made with government support under contract CA186568 awarded by the National Institutes of Health. The government has certain rights in the invention.

TECHNICAL FIELD

The present invention pertains generally to proximity labeling with biotin ligases. In particular, the invention relates to engineered promiscuous biotin ligases designed to improve efficiency of proximity labeling and their use in proximity labeling.

BACKGROUND

Proximity labeling (PL) has emerged as an alternative to immunoprecipitation and biochemical fractionation for the proteomic analysis of macromolecular complexes, organelles, and protein interaction networks (Kim et al. (2016) Trends in Cell Biology 26, 804-817). In PL, a promiscuous labeling enzyme is targeted by genetic fusion to a specific protein or subcellular region. Addition of a small molecule substrate, such as biotin, initiates covalent tagging of endogenous proteins within a few nanometers of the promiscuous enzyme. Subsequently, the biotinylated proteins are harvested using streptavidin-coated beads and identified by mass spectrometry (MS).

Two enzymes are commonly used for PL: APEX2, an engineered variant of soybean ascorbate peroxidase (Rhee et al. (2013) Science 339, 1328-1331; Lam et al. (2014) Nat. Methods 12, 51-54), and BirA-R118G (here, referred to as "BioID"), a point mutant of E. coli biotin ligase (Choi-Rhee et al. (2004) Protein Sci. 13, 3043-3050; Roux et al. (2012) J. Cell Biol. 196, 801-810). The main advantage of APEX2 is its speed: proximal proteins can be tagged in 1 minute or less, enabling dynamic analysis of protein interaction networks (Paek et al. (2017) Cell 169, 338-349.e11; Lobingier et al. (2017) Cell 169, 350-360.e12). However, APEX labeling requires the use of $H_2O_2$, which is toxic to cells and difficult to deliver into live organisms without causing severe tissue damage. By contrast, BioID is attractive because of the simplicity of its labeling protocol and non-toxic labeling conditions—only biotin needs to be added to initiate tagging. These attributes have resulted in over 100 applications of BioID over the past 5 years, in cultured mammalian cells (Roux et al. (2012) J. Cell Biol. 196, 801-810; Gupta et al. (2015) Cell 163, 1483-1499; Kim et al. (2014) Proc. Natl. Acad. Sci. 111, E2453-E2461), plant protoplasts (Lin et al. (2017) Front. Plant Sci. 8:749), parasites (Morriswood et al. (2013) Eukaryot. Cell 12, 356-367; Chen et al. (2015) MBio 6(1), e02357-14; Nadipuram et al. (2016) MBio 7(4), pii: e00808-16; Chen et al. (2017) Cell. Microbiol. 19; Long et al. (2017) PLoS Pathog. 13(5):e1006379; Zhou et al. (2016) J. Biol. Chem. 291, 14395-14409; Dang et al. (2017) MBio 8(1) pii, e02120-16; Kehrer et al. (2016) Mol. Cell. Proteomics 15, 2852-2862; Gaji et al. (2015) PLoS Pathog. 11(11), e1005268), slime mold (Batsios et al. (2016) Cells 5(1) pii, E13; Meyer et al. (2017) Eur. J. Cell Biol. 96, 119-130), and mouse (Uezu et al. (2016) Science 353, 1123-1129). BioID has been used, for example, to map the protein composition of the centrosome-cilium interface (Gupta et al. (2015) Cell 163, 1483-1499) and the inhibitory post-synaptic region (Uezu et al. (2016) Science 353, 1123-1129), each with nanometer spatial specificity.

The major disadvantage of BioID, however, is its slow kinetics, which necessitates labeling with biotin for 18-24 hours, and sometimes much longer (Uezu et al., supra), to accumulate sufficient quantities of biotinylated material for proteomic analysis. This precludes the use of BioID for studying dynamic processes that occur on the timescale of minutes or even a few hours. Furthermore, low catalytic activity makes BioID difficult or impossible to apply in certain contexts—for example, in the ER lumen of mammalian cells, and in organisms such as yeast, worms, and flies.

A more efficient variant of BioID would greatly expand its utility, enabling the study of dynamic processes with minimal toxicity, and the extension of PL to new settings and organisms.

SUMMARY

The present invention relates to engineered promiscuous biotin ligases and their use in proximity-labeling of proteins.

In one aspect, the invention includes a modified biotin ligase comprising at least one mutation comprising an amino acid substitution selected from the group consisting of Q65P, M209V, V160A, S150G, L151P, I305V, I87V, R118S, T192A, K194I, E140K, Q141R, M241T, and S263P, wherein positions of the amino acids are numbered relative to the reference wild-type biotin ligase sequence of SEQ ID NO:7.

In certain embodiments, the biotin ligase further comprises an N-terminal deletion of at least the first amino acid up to the first 63 amino acids as numbered relative to the reference wild-type biotin ligase sequence of SEQ ID NO:7, including any number of amino acids in between, such as an N-terminal deletion of 1, 2, 3, 4, 5, 6, 7, 8, 9, 10, 12, 14, 16, 18, 20, 22, 24, 26, 28, 30, 32, 34, 36, 38, 40, 42, 44, 46, 48, 50, 51, 52, 53, 54, 55, 56, 57, 58, 59, 60, 61, 62, or 63 amino acids. In one embodiment, the biotin ligase comprises an N-terminal deletion of the first 63 amino acids (Δ(1-63)), as numbered relative to the reference wild-type biotin ligase sequence of SEQ ID NO:7.

In certain embodiments, the modified biotin ligase comprises:
 a) Q65P, R118S, L151P, I305V, and E313K amino acid substitutions,
 b) R118S and E313K amino acid substitutions,
 c) Q65P, R118S, L151P, I305V, and E313R amino acid substitutions,
 d) R118S and E313R amino acid substitutions,
 e) R118S, L151P, and I305V amino acid substitutions,
 f) K2E, R118S, M157T, and L298P amino acid substitutions,
 g) R118S and L297P amino acid substitutions,
 h) R118S, I313N amino acid substitutions,
 i) R118S, L151P, and I305V amino acid substitutions,
 j) Q65P, R118S, and I305V amino acid substitutions,
 k) Q65P, R118S, and L151P amino acid substitutions, l) R118S, L151P, I305V, and K313R amino acid substitutions,
m) Q65P, R118S, I305V, and K313R amino acid substitutions,
n) Q65P, R118S, and K313R amino acid substitutions,
o) R118S, L151P, and K313R amino acid substitutions,
p) R118S, I305V, and K313R amino acid substitutions,
q) Q65P and R118S amino acid substitutions,
r) R118S and L151P amino acid substitutions,
s) R118S and I305V amino acid substitutions,
t) R118S and M157T amino acid substitutions,
u) R118S and L298P amino acid substitutions,
v) K2E, R33G, R118S, M157T, and L298P amino acid substitutions,
w) K2E, R118S, M157T, I279T, L298P, and K307N amino acid substitutions,
x) Q65P, R118S, L151P, I305V, Y111H, and R118S amino acid substitutions,
y) Q65P, R118S, S150G, L151P, T192A, I305V amino acid substitutions,
z) Q65P, R118S, L151P, I23IV, and I305V amino acid substitutions,
aa) Q65P, R118S, L151P, T192A, and I305V amino acid substitutions,
bb) Q65P, R118S, S150G, L151P, and I305V amino acid substitutions,
cc) R33G, Q65P, R118S, S150G, L151P, T192A, and I305V amino acid substitutions,
dd) N37S, Q65P, R118S, S150G, L151P, T192V, E266L, and I305V amino acid substitutions,
ee) Q65P, R118S, S150G, L151P, T192A, I280V, I305V, and A318V amino acid substitutions,
ff) Q65P, R118S, Q142R, S150G, L151P, T192A, M209V, and I305V amino acid substitutions,
gg) Q65P, R118S, S150G, L151P, T192A, and I305V amino acid substitutions,
hh) Q65P, R118S, Q142R, S150G, L151P, T192A, and I305V amino acid substitutions,
ii) Q65P, R118S, S150G, L151P, T192A, M209V, and I305V amino acid substitutions,
jj) Q65P, I87V, R118S, E141K, S150G, L151P, V160A, T192A, M209V, and I305V amino acid substitutions,
kk) Q65P, I87V, R118S, E141K, S150G, L151P, T192A, and I305V amino acid substitutions,
ll) Q65P, R118S, S150G, L151P, V160A, T192A, M209V, and I305V amino acid substitutions,
mm) Q65P, R118S, Q142R, S150G, L151P, V160A, T192A, M209V, and I305V amino acid substitutions,
nn) Q65P, I87V, R118S, E141K, S150G, L151P, V160A, T192A, M209V, and I305V amino acid substitutions,
oo) Q65P, I87V, R118S, Q142R, S150G, L151P, T192A, M209V, and I305V amino acid substitutions,
pp) Q65P, R118S, E141K, Q142R, S150G, L151P, T192A, M209V, and I305V amino acid substitutions,
qq) Q65P, R118S, E141K, Q142R, S150G, L151P, V160A, T192A, M209V, and I305V amino acid substitutions,
rr) Q65P, I87V, R118S, E141K, Q142R, S150G, L151P, T192A, and I305V amino acid substitutions,
ss) Q65P, I87V, R118S, E141K, S150G, L151P, T192A, M209V, and I305V amino acid substitutions,
tt) Q65P, R118S, S150G, Q142R, L151P, T192A, M209V, and I305V amino acid substitutions,
uu) Q65P, I87V, R118S, E141K, S150G, L151P, V160A, T192A, M209V, and I305V amino acid substitutions,
vv) Q65P, I87V, R118S, E141K, Q142R, S150G, L151P, V160A, T192A, I201V, M209V, and I305V amino acid substitutions,
ww) Q65P, I87V, R118S, K140R, E141K, Q142R, S150G, L151P, V160A, T192A, M209V, K267R, I305V, and E313K amino acid substitutions,
xx) Q65P, I87V, R118S, E141K, Q142R, S150G, L151P, V160A, T192A, M209V, I305V, I306V, and E313K amino acid substitutions,
yy) Q65P, I87V, I98V, R118S, E141K, Q142R, S150G, L151P, V160A, T192A, M209V, and I305V amino acid substitutions,
zz) Q65P, I87V, R118S, E141K, Q142R, S150G, L151P, V160A, T192A, A199T, M209V, D303G, and I305V amino acid substitutions,
aaa) Q65P, I87V, R118S, G120R, E141K, Q142R, S150G, L151P, V160A, T192A, D197G, M209V, M241V, I305V, and E313K amino acid substitutions,
bbb) Q65P, I87V, R118S, E141K, Q142R, S150G, L151P, V160A, V162A, A166V, T192A, M209V, I305V, and E313K amino acid substitutions,
ccc) Q65P, I87V, R118S, E141K, Q142R, S150G, L151P, V160A, T192A, M209V, I305V, E307R, and E313K amino acid substitutions,
ddd) E27D, Q65P, I87V, R118S, E141K, Q142R, S150G, L151P, V160A, T192A, M209V, E251K, and I305V amino acid substitutions,
eee) Q65P, I87V, R118S, E141K, Q142R, S150G, L151P, V160A, T192A, M209V, M241T, and I305V amino acid substitutions,
fff) Q65P, I87V, R118S, E141K, Q142R, S150G, L151P, V160A, T192A, M209V, N270D, and I305V amino acid substitutions,
ggg) K2R, F51L, Q65P, K70T, I87V, R118S, E141K, Q142R, S150G, L151P, V160A, T192A, M209V, I305V, I306V, and E313K amino acid substitutions,
hhh) Δ(1-63), Q65P, K70T, I87V, R118S, E141K, Q142R, S150G, L151P, V160A, T192A, M209V, I305V, I306V, and E313K amino acid substitutions,
iii) Δ(1-63), Q65P, I87V, R118S, E141K, Q142R, S150G, L151P, V160A, T192A, M209V, and I305V amino acid substitutions,
jjj) Q65P, I87V, R118S, E141K, Q142R, S150G, L151P, V160A, T192A, M209V, L252R, I305V, K307R, and G311D amino acid substitutions,
kkk) Q65P, I87V, R118S, E141K, Q142R, S150G, L151P, V160A, K168E, T192A, M209V, K267E, and I305V amino acid substitutions,
lll) Q65P, I87V, R118S, E141K, Q142R, S150G, L151P, V160A, T192A, M209V, E251K, and I305V amino acid substitutions,
mmm) Δ(1-63), Q65P, I87V, R118S, E141K, Q142R, S150G, L151P, V160A, T192A, M209V, E251K, and I305V amino acid substitutions,
nnn) Q65P, I87V, R118S, E141K, Q142R, S150G, L151P, V160A, T192A, M209V, M241T, and I305V amino acid substitutions,
ooo) Δ(1-63), Q65P, I87V, R118S, E141K, Q142R, S150G, L151P, V160A, T192A, M209V, M241T, and I305V amino acid substitutions,
ppp) Δ(1-63) Q65P, I87V, R118S, E141K, Q142R, S150G, L151P, V160A, T192A, M209V, M241T, I305V amino acid substitutions,
qqq) Δ(1-63), Q65P, I87V, R118S, E141K, Q142R, S150G, L151P, V160A, T192A, M209V, and I305V amino acid substitutions, rrr) Δ(1-63), Q65P, I87V, R118S, E141K, Q142R, S150G, L151P, V160A, L179M, T192A, M209V, N232S, I305V, and I306T amino acid substitutions, sss) Δ(1-63), Q65P, I87V, R118S, E141K, Q142R, S150G, L151P, V160A, T192A, M209V, I285V, and I305V amino acid substitutions, ttt) Δ(1-63), Q65P, I87V, R118S, E141K, Q142R, S150G, L151P, V160A, T192A, M209V, S289G, I305V, and M310V amino acid substitutions, uuu) Δ(1-63), Q65P, I87V, R118S, E141K, Q142R, S150G, L151P, V160A, D167G, T192A, M209V, N232S, and I305V amino acid substitutions, vvv) Δ(1-63), Q65P, I87V, I99V, R118S, E141K, Q142R, S150G, L151P, V160A, T192A, M209V, I305V, K307Q, and M310T amino acid substitutions, www) Q65P, I87V, R118S, E141K, Q142R, S150G, L151P, V160A, T192A, M209V, and I305V amino acid substitutions, xxx) Q65P, I87V, S89N, R118S, E141K, Q142R, S150G, L151P, V160A, T192A, M209V, and I305V amino acid substitutions, yyy) Δ(1-63) Q65P, I87V, R118S, E141K, Q142R, S150G, L151P, V160A, D167G, T192A, M209V, M241T, N232S, and I305V amino acid substitutions, zzz) Q65P, I87V, S89N, R118S, E141K, Q142R, S150G, L151P, V160A, T192A, M209V, M241T, and I305V amino acid substitutions, aaaa) Δ(1-63), Q65P, I87V, D88G, R118S, E141K, Q142R, S150G, L151P, V160A, T192A, M209V, K283E, and I305V amino acid substitutions, bbbb) Δ(1-63), Q65P, I87V, Y111H, R118S, E141K, Q142R, S150G, L151P, V160A, T192A, M209V, and I305V amino acid substitutions, cccc) Δ(1-63), Q65P, I87V, R118S, E141K, Q142R, S150G, L151P, V160A, T192A, M209V, S263P, and I305V amino acid substitutions, dddd) Δ(1-63), Q65P, I87V, R118S, E141K, Q142R, S150G, L151P, V160A, T192A, K194I, M209V, and I305V amino acid substitutions, eeee) Δ(1-63), Q65P, I87V, R118S, E141K, Q142R, S150G, L151P, V160A, T192A, M209V, and I305V amino acid substitutions, ffff) Δ(1-63), Q65P, I87V, R118S, E141K, Q142R, S150G, L151P, V160A, T192A, M241T, and I305V amino acid substitutions, gggg) Δ(1-63), Q65P, I87V, R118S, E141K, Q142R, S150G, L151P, V160A, T192A, K194I, M209V, and I305V amino acid substitutions, hhhh) Δ(1-63), Q65P, I87V, R118S, E141K, Q142R, S150G, L151P, V160A, T192A, M209V, M241T, S263P, and I305V amino acid substitutions, iiii) Δ(1-63), Q65P, I87V, R118S, E141K, Q142R, S150G, L151P, V160A, T192A, K194I, M241T, and I305V amino acid substitutions, jjjj) Δ(1-63), Q65P, I87V, R118S, E141K, Q142R, S150G, L151P, V160A, T192A, K194I, M209V, S263P, and I305V amino acid substitutions, kkkk) Δ(1-63), Q65P, I87V, R118S, E141K, Q142R, S150G, L151 P, V160A, T192A, M209V, and I305V amino acid substitutions, llll) Δ(1-63), Q65P, I87V, R118S, E141K, Q142R, S150G, L151 P, V160A, T192A, K194I, M209V, M241T, and I305V amino acid substitutions, mmmm) Δ(1-63), Q65P, I87V, R118S, E141K, Q142R, S150G, L151 P, V160A, T192A, K194I, M209V, M241T, S263P, and I305V amino acid substitutions, nnnn) Δ(1-63), Q65P, I87V, R118S, E141K, Q142R, S150G, L151P, V160A, T192A, K194I, M209V, S263P, and I305V amino acid substitutions, oooo) Q65P, I87V, R118S, E141K, Q142R, S150G, L151P, V160A, T192A, M209V, S263P, and I305V amino acid substitutions, pppp) Q65P, I87V, R118S, E141K, Q142R, S150G, L151P, V160A, T192A, K194I, M209V, and I305V amino acid substitutions, qqqq) Q65P, I87V, R118S, E141K, Q142R, S150G, L151P, V160A, T192A, M209V, M241T, S263P, and I305V amino acid substitutions, rrrr) Q65P, I87V, R118S, E141K, Q142R, S150G, L151P, V160A, T192A, K194I, M209V, M241T, and I305V amino acid substitutions, and ssss) Q65P, I87V, R118S, E141K, Q142R, S150G, L151P, V160A, T192A, K194I, M209V, M241T, S263P, and I305V amino acid substitutions.

In certain embodiments, the modified biotin ligase comprises an amino acid sequence having at least about 80-99% identity to the amino acid sequence of SEQ ID NO:7, including any percent identity within this range, such as at least about 80, 81, 82, 83, 84, 85, 86, 87, 88, 89, 90, 91, 92, 93, 94, 95, 96, 97, 98, or 99% sequence identity, and at least one mutation comprising an amino acid substitution selected from the group consisting of Q65P, M209V, V160A, S150G, L151P, I305V, I87V, R118S, T192A, K194I, E140K, Q141R, M241T, and S263P, wherein the biotin ligase is capable of proximity-dependent biotinylation of proteins.

In another embodiment, the biotin ligase comprises the Q65P, M209V, V160A, S150G, L151P, I305V, I87V, R118S, T192A, K194I, E140K, and Q141R amino acid substitutions.

In another embodiment, the biotin ligase comprises the Q65P, M209V, V160A, S150G, L151P, I305V, I87V, R118S, T192A, K194I, E140K, Q141R, M241T, and S263P amino acid substitutions.

In certain embodiments, the modified biotin ligase is substantially purified. For example, a composition comprising the modified biotin ligase may comprise at least 50%, preferably at least 80%-85%, more preferably at least 90-99% of the composition, including any percentage within these ranges such as at least about 80%, 81%, 82%, 83%, 84%, 85%, 86%, 87%, 88%, 89%, 90%, 91%, 92%, 93%, 94%, 95%, 96%, 97%, 98%, or 99% of the composition.

In certain embodiments, the modified biotin ligase further comprises a targeting sequence that directs the biotin ligase to a subcellular region of interest. Exemplary targeting sequences include a secretory protein signal sequence, a membrane protein signal sequence, a nuclear localization sequence, a mitochondrial localization sequence, an outer mitochondrial membrane sequence, an endoplasmic reticulum localization sequence, an endoplasmic reticulum membrane targeting sequence, a nucleolar localization signal sequence, a nuclear export signal sequence, a peroxisome localization sequence, and a protein binding motif sequence.

In other embodiments, the modified biotin ligase is covalently linked to a peptide or protein that directs the biotin ligase to the subcellular region of interest, such as a cytosolic protein, a nuclear protein, a membrane protein, a mitochondrial protein, a P-body protein, or a secretory pathway protein.

In another embodiment, the modified biotin ligase is covalently linked to an antibody specific for an epitope in the subcellular region of interest.

In another aspect, the invention includes a method of using a modified biotin ligase described herein for biotinylating a protein in a sample, the method comprising: a) contacting the sample with a modified biotin ligase described herein; and b) adding biotin (or a biotin derivative such as desthiobiotin) and ATP to the sample, wherein the modified biotin ligase biotinylates the protein.

In another aspect, the invention includes a method of using a modified biotin ligase described herein for proximity labeling of proteins in a cell, the method comprising: a) introducing the biotin ligase into a cell, wherein the modified biotin ligase is targeted to a subcellular region of interest; and b) contacting the cell with biotin (or a biotin derivative such as desthiobiotin) and ATP, wherein proteins in proximity to the biotin ligase are biotinylated. In some embodiments, step (b) is performed in 10 minutes or less.

The cell can be any type of cell, including any eukaryotic cell, prokaryotic cell, or archaeon cell. For example, the cell may be an animal cell, plant cell, fungal cell, or protist cell. Alternatively, the cell can be an artificial cell, such as a nanoparticle, liposome, polymersome, or microcapsule encapsulating proteins. The cell may be a live cell or a fixed cell. In certain embodiments, the cell is a mammalian cell such as, but not limited to, a primate (e.g., human or non-human), rodent, or carnivoran cell. In another embodiment, the method further comprises lysing the cell.

In another embodiment, the method further comprises isolating the biotinylated proteins using a biotin-binding protein that binds to the biotinylated proteins such as streptavidin or avidin. The biotin-binding protein may be immobilized on a solid support such as, but not limited to, a magnetic bead, non-magnetic bead, microtiter plate well, glass plate, nylon, agarose, or acrylamide.

In another embodiment, the method further comprises calculating the frequencies of one or more proteins that are present within the subcellular region of interest.

In certain embodiments, the method further comprises labeling the biotinylated proteins with a biotin-binding protein conjugated to a detectable label such as, but not limited to, a fluorescent, bioluminescent, or chemiluminescent label. In another embodiment, the method further comprises imaging luminescence (e.g., fluorescence, bioluminescence, or chemiluminescence) emitted from the detectable label.

In another embodiment, the method further comprises identifying at least one biotinylated protein. Exemplary methods that can be used in identifying biotinylated proteins include mass spectrometry, liquid chromatography-mass spectrometry (LC/MS), an enzyme-linked immunosorbent assay (ELISA), a Western blot, immunostaining, high-performance liquid chromatography (HPLC), protein sequencing, or peptide mass fingerprinting.

In certain embodiments, the modified biotin ligase comprises a targeting sequence that directs the biotin ligase to the subcellular region of interest. Exemplary targeting sequences include a secretory protein signal sequence, a membrane protein signal sequence, a nuclear localization sequence, a mitochondrial localization sequence, an outer mitochondrial membrane sequence, an endoplasmic reticulum localization sequence, an endoplasmic reticulum membrane targeting sequence, a nucleolar localization signal sequence, a nuclear export signal sequence, a peroxisome localization sequence, and a protein binding motif sequence.

In other embodiments, the modified biotin ligase is covalently linked to a peptide or protein that directs the biotin ligase to the subcellular region of interest, such as a cytosolic protein, a nuclear protein, a membrane protein, a mitochondrial protein, a P-body protein, or a secretory pathway protein, In another embodiment, the modified biotin ligase is covalently linked to an antibody specific for an epitope in the subcellular region of interest.

In another embodiment, introducing the modified biotin ligase into the cell comprises transfecting the cell with a recombinant polynucleotide encoding the modified biotin ligase. The recombinant polynucleotide may comprise an expression vector, for example, a bacterial plasmid vector or a viral expression vector, such as, but not limited to, an adenovirus, retrovirus (e.g., α-retrovirus and lentivirus), poxvirus, adeno-associated virus, baculovirus, or herpes simplex virus vector. In another embodiment, the recombinant polynucleotide encoding the modified biotin ligase is integrated into the genome of a cell at a target locus.

Expression of a modified biotin ligase will generally depend on the presence of a promoter, which may be included in a vector or at a chromosomal locus in which the recombinant polynucleotide is integrated. The promoter may be a constitutive or an inducible promoter. In some embodiments, the promoter is a cell-type-specific or tissue-specific promoter. In certain embodiments, the recombinant polynucleotide comprises a promoter operably linked to a nucleotide sequence encoding the modified biotin ligase.

In another embodiment, the invention includes a method of proximity labeling proteins in a host subject, the method comprising: a) introducing a recombinant polynucleotide comprising a nucleotide sequence encoding a modified biotin ligase described herein into the host subject, wherein the modified biotin ligase is expressed in the subject; and b) administering an effective amount of biotin or a derivative thereof to the subject, wherein proteins in proximity to the biotin ligase are biotinylated in the subject.

In certain embodiments, the host subject is a bacterium, an archaeon, a fungus, a protist, a plant, or an animal. In another embodiment, the host subject is a model organism.

In another aspect, the invention includes a transgenic animal whose genome comprises a nucleotide sequence encoding a modified biotin ligase described herein operably linked to a promoter, wherein the modified biotin ligase is expressed in the transgenic animal, and proteins in proximity to the expressed biotin ligase are biotinylated in the transgenic animal. In certain embodiments, the transgenic animal is a model organism (e.g., *Drosophila melanogaster* or *Caenorhabditis elegans*).

In certain embodiments, the cell or whole live organism is exposed to a test condition prior to contacting the cell with the biotin ligase. For example, a test condition may comprise exposing a cell or live organism to a drug, a ligand for a receptor, a hormone, a second messenger, a pathogen, or a genetic modification. For example, the cell or organism can be genetically modified by introducing a vector, short hairpin RNA (shRNA), small interfering RNA (siRNA), microRNA (miRNA), or CRISPR-associated system into the cell or organism. Alternatively, a test condition may comprise exposing a cell to a change in temperature, growth media, membrane potential, or osmotic pressure.

In another aspect, the invention includes a method of mapping subcellular localization of nucleic acids in a cell, the method comprising: a) introducing a modified biotin ligase described herein into the cell, wherein the modified biotin ligase is targeted to a subcellular region of interest; b) contacting the cell with biotin and ATP, wherein proteins in proximity to the biotin ligase are biotinylated; and c) contacting the cell with a crosslinking agent before or after step (b), wherein the crosslinking agent covalently couples the biotinylated proteins to nearby nucleic acids to produce biotinylated protein-nucleic acid fusions; d) isolating the biotinylated protein-nucleic acid fusions using a biotin-binding protein that binds to the biotinylated protein-nucleic acid fusions; and e) analyzing the biotinylated protein-nucleic acid fusions to produce a map of the subcellular localization of the nucleic acids.

Crosslinking of proteins and nucleic acids can be performed with any suitable crosslinking agent or technique known in the art. Exemplary crosslinking agents include formaldehyde, glutaraldehyde, dimethyl suberimidate, N-hydroxysuccinimide, and compounds comprising reactive groups, such as adiazomethane, diazoacetyl, or carbodiimide functional groups. Crosslinking can also be performed using click chemistry with suitable compounds comprising reactive azide or alkyne functional groups. Alternatively, crosslinking can be performed using ultraviolet light.

RNA isolated and mapped by the methods described herein can be animal RNA, bacterial RNA, fungal RNA, protist RNA, or plant RNA. In one embodiment, the RNA is human RNA.

In another embodiment, the method further comprises amplifying at least one RNA or DNA molecule. RNA molecules may be amplified, for example, by performing reverse transcription polymerase chain reaction (RT-PCR).

In another embodiment, the method further comprises sequencing at least one RNA from the isolated biotinylated protein-RNA fusions.

In another embodiment, the method further comprises multiplex sequencing of the biotinylated protein-nucleic acid fusions. For example, sequencing may comprise performing deep sequencing or next-generation sequencing.

In another embodiment, the method further comprises identifying at least one RNA or DNA molecule in the biotinylated protein-nucleic acid fusions (e.g., of a messenger RNA, a ribosomal RNA, a transfer RNA, a non-coding RNA, and a regulatory RNA).

In another embodiment, the method further comprises identifying at least one ribonucleoprotein (RNP) interaction.

In another embodiment, the method further comprises calculating the frequencies of one or more RNA molecules that are present within the intracellular spatial location.

In another embodiment, the method further comprises quantitating one or more RNA molecules that are present within the intracellular spatial location.

In certain embodiments, a map of the subcellular localization of protein or RNA molecules, produced by the methods described herein, is compared to a reference map. For example, a map of the subcellular localization of the protein or RNA molecules from a cell that is exposed to the test condition can be compared to a reference map of a cell that is not exposed to the test condition. In another embodiment, the method further comprises comparing a map of the subcellular localization of the protein or RNA molecules within the intracellular spatial location to a reference map for a cell at the same or a different developmental stage.

In another aspect, the invention includes a polynucleotide selected from the group consisting of: a) a polynucleotide encoding a polypeptide comprising an amino acid sequence selected from the group consisting of SEQ ID NO:11 and SEQ ID NO:13; b) a polynucleotide encoding a polypeptide comprising an amino acid sequence having at least about 80-99% identity to a sequence selected from the group consisting of SEQ ID NO:11 and SEQ ID NO:13, including any percent identity within this range, such as at least about 80, 81, 82, 83, 84, 85, 86, 87, 88, 89, 90, 91, 92, 93, 94, 95, 96, 97, 98, or 99% sequence identity, wherein the encoded biotin ligase comprises at least the Q65P, M209V, V160A, S150G, L151P, I305V, I87V, R118S, T192A, K194I, E140K, and Q141R amino acid substitutions and is capable of proximity-dependent biotinylation of proteins; c) a polynucleotide comprising a nucleotide sequence selected from the group consisting of SEQ ID NO:10 and SEQ ID NO:12; and d) a polynucleotide comprising a sequence having at least about 80-99% identity to the nucleotide sequence selected from the group consisting of SEQ ID NO:10 and SEQ ID NO:12, including any percent identity within this range, such as at least about 80, 81, 82, 83, 84, 85, 86, 87, 88, 89, 90, 91, 92, 93, 94, 95, 96, 97, 98, or 99% sequence identity, wherein the encoded biotin ligase comprises at least the Q65P, M209V, V160A, S150G, L151P, I305V, I87V, R118S, T192A, K194I, E140K, and Q141R amino acid substitutions and is capable of proximity-dependent biotinylation of proteins.

In another embodiment, the invention includes a recombinant polynucleotide comprising a promoter operably linked to a polynucleotide encoding a modified biotin ligase described herein. In another embodiment, the recombinant polynucleotide is provided by a vector. In another embodiment, the invention includes a host cell or host subject comprising the recombinant polynucleotide.

In another embodiment, the invention includes a method for producing a modified biotin ligase, the method comprising: a) transforming a host cell with a recombinant polynucleotide comprising a promoter operably linked to a polynucleotide encoding a modified biotin ligase described herein; b) culturing the transformed host cell under conditions whereby the modified biotin ligase is expressed; and c) isolating the modified biotin ligase from the host cell.

In another embodiment, the invention includes a method for producing a modified biotin ligase in a host subject, the method comprising introducing into the host subject a recombinant polynucleotide comprising a promoter operably linked to a nucleotide sequence encoding the modified biotin ligase, wherein the modified biotin ligase is expressed in the host subject in an amount sufficient to biotinylate proteins in the subject.

In another aspect, the invention includes a kit comprising a modified biotin ligase described herein. Such kits may further include instructions (e.g., in written or electronic form) for using the modified biotin ligase in proximity labeling of proteins.

In certain embodiments, the kit comprises a modified biotin ligase comprising an amino acid sequence selected from the group consisting of SEQ ID NO:11 and SEQ ID NO:13, or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the biotin ligase comprises at least the Q65P, M209V, V160A, S150G, L151P, I305V, I87V, R118S, T192A, K194I, E140K, and Q141R amino acid substitutions and is capable of proximity-dependent biotinylation of proteins.

These and other embodiments of the subject invention will readily occur to those of skill in the art in view of the disclosure herein.

BRIEF DESCRIPTION OF THE FIGURES

FIG. 1A shows proximity-dependent biotinylation by promiscuous biotin ligases. Ligases catalyze the formation of biotin-5'-AMP anhydride, which diffuses out of the active site to biotinylate proximal endogenous proteins on nucleophilic residues such as lysine. FIG. 1B shows yeast display-based selection scheme. A >10^7 library of ligase variants is displayed on the yeast surface as a fusion to mating protein Aga2p. All mutants have a C-terminal myc epitope tag. Biotin and ATP are added to the yeast library for between 10 minutes and 24 hours. Ligase-catalyzed promiscuous biotinylation is detected by staining with streptavidin-phycoetythrin and ligase expression is detected by staining with anti-myc antibody. Two-dimensional FACS sorting enables enrichment of cells displaying a high ratio of streptavidin to myc staining. FIG. 1C shows tyramide signal amplification (TSA) protocol improves biotin detection sensitivity on yeast. In the top row, the three indicated yeast samples were labeled with exogenous biotin for 18 hours then stained for FACS as in (FIG. 1B). The y-axis shows biotinylation extent, as measured by streptavidin-phycoerythrin staining intensity, and the x-axis quantifies ligase expression level, BirA-R118S is the template for the original ligase mutant library. G1 is the winning clone from the first generation of evolution. In the second row, after 18 hours of biotin treatment, the three yeast samples were stained with streptavidin-HRP, reacted with biotin-phenol[2] to create additional biotinylation sites, then stained with streptavidin-phycoerythrin and anti-myc antibody before FACS. The third row is the same as the second row, but with the 18 hour biotin treatment omitted. Percentage of cells in upper right quadrant (Q2/(Q2+Q4)) indicated in top right of each graph. All plots display 10,000 cells. This experiment was performed once, but similar results under the same conditions have been repeated at least twice for each individual mutant in separate experiments. FIG. 1D shows the biotin ligase structure (PDB: 2EWN[26]) in gray with sites mutated in TurboID (left) and miniTurbo (right) colored red. The N-terminal domain (aa1-63) is also removed in the miniTurbo diagram. A non-hydrolyzable analog of biotin-5'-AMP, biotinol-5'-AMP, is shown in yellow stick. FIG. 1E shows FACS plots summarizing progress of directed evolution. Same presentation as in (c). G1-G3 are the winning clones after generations 1-3 of directed evolution. G3Δ is G3 with the N-terminal domain deleted. miniTurbo (mTb) and TurboID (TbID) are our final promiscuous biotin ligases. All ligases were compared in parallel, with either 6 hours of 50 μM biotin+ATP incubation (top row), or growth in biotin-deficient media (bottom row). All plots display 10,000 cells. This experiment was repeated one time (except for G3Δ and the "biotin omitted" conditions in "biotin depleted media' which were performed only once under these conditions). FIG. 1F shows a comparison of ligase variants in HEK cytosol. The indicated ligases were expressed as NES (nuclear export signal) fusions in the HEK cytosol. 50 μM exogenous biotin was added for 3 hours, then whole cell lysates were analyzed by streptavidin blotting. Ligase expression detected by anti-V5 blotting. U, untransfected. Asterisks indicate ligase self-biotinylation. BioID labeling for 18 hours (50 μM biotin) shown for comparison (last lane). This experiment was performed once. FIG. 1G shows quantitation of streptavidin blot data in (FIG. 1F) and from a 30 minute labeling experiment (blot shown in FIG. 8A). Quantitation is of promiscuous labeling bands and excludes self-biotinylation band. Sum intensity of each lane is normalized to that of BioID, 18 hours, which is set to 1.0.

FIG. 2A shows characterization of promiscuous biotinylation activity in HEK cells. Ligases were transiently expressed in the cytosol and 50 μM (+biotin) or 500 μM (++biotin) exogenous biotin was added for 1 hour. Whole cell lysates were analyzed by streptavidin blotting and ligase expression was detected by anti-V5 staining. U, untransfected. Asterisks indicate ligase self-biotinylation. BioID 18 hour labeling is shown in right-most lane for comparison. This experiment was performed once, but results under these conditions have been replicated for BioID three times. FIG. 2B shows quantitation of streptavidin blot data in (FIG. 2A) in addition to multiple other experiments using 18 hours, 6 hours, and 10 minutes labeling times (blots shown in FIGS. 8B-8D). Intensities are normalized to that of BioID, 18 hours, as in FIG. 1G. FIG. 2C shows a comparison of promiscuous ligases in multiple HEK organelles. Each ligase was fused to a peptide targeting sequence (see Methods) directing them to the organelles indicated in the scheme at right. BioID samples were treated with 50 UM biotin for 18 hours. TurboID and miniTurbo samples were labeled for 10 minutes. Whole cell lysates were analyzed by streptavidin blotting. Ligase expression detected by anti-V5 blotting. ±indicates treatment with 50 μM biotin; ++ indicates treatment with 500 μM biotin. U, untransfected. Asterisks indicate ligase self-biotinylation. This experiment was repeated >3 times for nuclear constructs, twice for mitochondrial constructs, three times for ER membrane constructs, and once for ER lumen constructs. FIG. 2D shows mass spectrometry-based proteomic experiment using TurboID, miniTurbo, and BioID. Experimental design and labeling conditions. HEK stably expressing TurboID or miniTurbo in the mitochondrial matrix ("mito") or transiently in the nucleus (NLS) were treated with 500 μM exogenous biotin for 10 minutes. BioID samples expressed in the same manner were treated with 50 μM biotin for 18 hours. After lysis, biotinylated proteins were enriched with streptavidin beads, digested to peptides, and conjugated to TMT labels. All six samples from each experiment were combined and analyzed by LC-MS/MS. This experiment was performed once with two replicates for each construct. FIG. 2E shows a specificity analysis for each proteomic dataset. Graph indicates the fraction of each proteome with prior mitochondrial or nuclear annotation (according to GOCC[41,42], MitoCarta[43], or literature). Entire human proteome (according to GOCC[41,42]) shown for comparison. Number of proteins in each proteomic dataset shown across top.

FIG. 3A shows yeast ligases, which were expressed in the cytosol of EBY100 *S. cerevisiae*. 50 μM exogenous biotin was added for 18 hours. Whole cell lysates were analyzed by streptavidin blotting. Ligase expression detected by anti-V5 blotting. U, untransfected. Asterisks indicate ligase self-biotinylation. This experiment was repeated once. (FIG. 3B) E coil. Ligases fused at their N-terminal ends to maltose binding protein were expressed in the cytosol of BL21 *E coli* and 50 μM exogenous biotin was added for 18 hours. Whole cell lysates were analyzed by streptavidin blotting. Ligase expression detected by anti-His6 blotting. U, untransfected. Asterisks indicate ligase self-biotinylation. This experiment was repeated once. FIG. 3C shows *D. melanogaster*. Schematic of tissue-specific labeling of endogenous proteins in fly wing disc. ptc-Gal4 induces expression of the indicated UAS-BirA enzyme in a strip of cells within the wing imaginal disc that borders the anterior/posterior compartments. Flies were fed with biotin-supplemented food for 5 days before dissecting and imaging. FIG. 3D shows imaging of larval wing discs prepared as described in (FIG. 3C). Biotinylated proteins are detected by staining with streptavidin-AlexaFluor555, and ligase expression is detected by anti-V5 staining. Panels show the pouch region of the wing disc, indicated by the dashed line in (FIG. 3C). Scale bar, 40 μm. Each experimental condition has at least three technical replicates, one representative image is shown. This experiment was performed once. Similar experiments using temporally controlledptc-Gal4 expression, or an earlier version of TurboID (G3), showed similar results (not shown). FIG. 3E shows quantitation of signal intensity of streptavidin-AlexaFluor555 in (FIG. 3D). Error bars in s.e.m. Average fold-change shown as text above plot lane. Sample size values (n) from left column to right: 5, 6, 3. FIG. 3F shows *D. melanogaster*. Scheme of ubiquitous labeling of endogenous proteins in flies. Act-Gal4 drives expression of the indicated U44S-BirA enzyme in all cells at all developmental time points. Flies were provided food supplemented with 100 μM biotin for 13 days after egg deposition, then the whole body of adult flies were lysed. FIG. 3G shows Western blotting of fly lysates prepared as described in (e). Biotinylated proteins detected by blotting with streptavidin-FHP, ligase expression detected by anti-V5 blotting. In control sample, Act-Gal4 drives expression of USA-luciferase in all cells at all developmental time points. This experiment was repeated once. FIG. 3H shows *C. elegans*. Scheme of tissue-specific labeling of endogenous proteins in the *C. elegans* embryonic intestine. ges-lp promoter drives expression of BirA mutant G3 (see Table 1) in the intestine beginning approximately 150 minutes after the first cell cleavage. Transgenic strains are fed OP50 bacteria (biotin-+), or biotin-auxotrophic bacteria (MGI655bioB:kan; biotin-) for two generations to deplete excess biotin. Embryos are then assayed 6-7 hours into development, making the biotin labeling window approximately 4 hours. FIG. 3I shows imaging of *C. elegans* embryos prepared as described in (FIG. 3H). Biotinylated proteins are detected by staining with streptavidin-AF488, and BirA-G3 expression is detected by anti-HA staining. Intestine is outlined by a white dotted line. Scale bars, 5 μm. This experiment was performed once with at least 5 biological replicates. FIG. 3J shows quantitation of mean ratios of streptavidin pixel intensity to anti-HA intensity for biotin+(n=8, mean=1.3939±0.5236), or biotin-(n=5, mean=0.2469±0.0726) embryos. Wilcoxon rank sum test was used to determine the difference between the two populations, p=0.007937. Mean is shown as a large blue dot for each condition.

FIG. 5A shows employing TSA to amplify biotinylation signal on the yeast surface. Yeast are labeled with 50 μM biotin and 1 mM ATP for 10-24 hours. Prior to staining with fluorophores, yeast are stained with streptavidin-HRP. HRP labeling is then carried out on the yeast surface by addition of biotin phenol and hydrogen peroxide to biotinylate many more sites on the yeast surface[2]. Yeast are then stained with streptavidin-phycoerythrin to visualize biotinylation and anti-myc to quantify ligase expression. Yeast are then sorted using FACS sorting to enrich cells displaying a high ratio of streptavidin to myc staining. FIG. 5B shows evolution of G1 clone from starting template, BirA-R118S. Selection conditions used in rounds 1-6 are shown. All clones and pools were analyzed here in parallel, under three different conditions: 18 hours of treatment with 50 μM biotin and 1 mM ATP, followed by TSA signal amplification as in (FIG. 5A) (top row): same but without TSA signal amplification (middle row); or no treatment and no amplification (bottom row). Cells were stained with streptavidin-phycoerythrin to detect biotinylation sites (y axis) and anti-myc antibody to quantify ligase expression level (x axis). On the top right of each FACS plot is the percentage of cells in quadrant Q2 divided by the sum of cells in Q2+Q4; where absent, this value is <0.5%. After round 6, two clones were selected, R6-1 and R6-2 (sequences shown in Table 1). An E313K mutation was removed from R6-2 to give clone G1 (sequence in Table 1). All plots display 10,000 cells. This experiment was performed once, but similar results under the same conditions have been replicated at least once for each individual sample in separate experiments. FIG. 5C shows employing TCEP treatment to de-enrich self-labeling mutants. Yeast are labeled with 50 μM biotin and 1 mM ATP for 10-24 hours. Prior to staining with fluorophores, yeast are treated with TCEP to reduce the disulfide bonds through which the Aga2p-ligase fusion is attached to the yeast surface, allowing the ligase to be removed from yeast and washed away. TSA as in (FIG. 5A) can be employed after TCEP treatment to amplify remaining biotinylation signal on yeast surface. Yeast are then stained with streptavidin-phycoerythrin to visualize biotinylation and anti-my to quantify ligase expression. Yeast are then sorted using FACS sorting to enrich cells with streptavidin signal, which represent mutants with promiscuous labeling capabilities. FIG. 5D shows evolution of clone G2 from clone G1. Presentation is the same as in panel (FIG. 5B). Selection conditions used in rounds 1-6 shown, with rounds 2 and 6 employing TCEP to de-enrich self-labeling mutants as in (FIG. 5C). The three analysis conditions used here are 6 hours, 3 hours, or 0 hours of 50 μM biotin and 1 mM ATP. All plots display 10,000 cells. This experiment was performed once, but similar results under the same conditions have been replicated at least once for each individual sample in separate experiments. FIG. 5E shows evolution of G3 from G2. Same presentation as in (FIG. 5B). Selection conditions used in rounds 1-4 shown. The three analysis conditions used here are 3 hours, 30 minutes, or 0 minutes of 50 μM biotin and 1 mM ATP. This experiment was performed once, but similar results under the same conditions have been replicated at least once for each individual sample in separate experiments. FIG. 5F shows FACS plots showing that G3 gives biotinylation in the absence of exogenous biotin. When G3 yeast are cultured in biotin-depleted media, this signal is no longer detected (second column). Deletion of the N-terminal domain to give G3Δ reduces biotin affinity and consequently biotinylation activity prior to exogenous biotin addition (third and fourth columns). All plots display 10,000 cells. This experiment was performed once, but similar results under the same conditions have been replicated at least once for each individual sample in separate experiments. FIG. 5G shows employment of negative selections to de-enrich mutants that carry out biotinylation in the absence of exogenous biotin. After ligase expression is induced, labeling with exogenous biotin and ATP is omitted. Yeast are then stained with streptavidin-phycoerythrin to visualize biotinylation and anti-myc to quantify ligase expression. Yeast are then sorted using FACS sorting to enrich cells with high anti-myc signal but without streptavidin signal. FIG. 5H shows evolution of miniTurbo from G3Δ. Same presentation as in (FIG. 5B).

Seven rounds of selection were performed, with rounds 5 and 6 being negative selections to remove clones able to carry about biotinylation in the absence of exogenous biotin addition as in (FIG. 5G) Asterisks denote selections performed in biotin-depleted media. The three analysis conditions used here are 3 hours, 30 minutes, or 0 hours of 50 μM biotin and 1 mM ATP, all in biotin-depleted media. All plots display 10,000 cells. This experiment was performed once, but similar results under the same conditions have been replicated at least once for each individual sample in separate experiments. FIG. 5I shows evolution using (3 as starting template. Same presentation as in (FIG. 5B). Six rounds of selection were performed, with rounds 4 and 6 being negative selections as in (FIG. 5G) to remove clones that are able to carry out biotinylation in the absence of exogenous biotin addition. Asterisks denote selections performed in biotin-depleted media. The three analysis conditions used here are 3 hours, 30 minutes, or 0 hours of 50 μM biotin and 1 mM ATP, all in biotin-depleted media. All plots display 10,000 cells. This experiment was performed once, but similar results under the same conditions have been replicated at least once for each individual sample in separate experiments (except G3+M241T which was only performed once). FIG. 5J shows examples of various gates drawn for FACS sorting. Top 3 plots indicate gates used to analyze single-cell yeast populations, bottom 3 plots indicate gates used to retain yeast for positive selections (left), positive selections using TCEP (middle), and negative selections (right). X and y-axes indicated for each plot. Gates are drawn in red with the relevant resulting population written next to it. SSC-A is side-scatter area, FSC-A is forward-scatter area, SSC-H is side-scatter height, SSC-W is side-scatter width, FSC-H is forward-scatter height, FSC-W is forward-scatter width.

(FIG. 8a) The indicated ligases were transiently expressed in the cytosol of HEK 239T cells. 50 LIM exogenous biotin was added for 30 minutes, then whole cell lysates were analyzed by streptavidin blotting. Ligase expression detected by anti-V; blotting. U, untransfected. S. BirA-R118S. Asterisks indicate ligase self-biotinylation. BioID labeling for 18 hours shown in the last lane for comparison. This experiment was performed once. (FIGS. 8B-8D show the same as (FIG. 8A) but with different labeling times, as indicated. In the "++" lanes, 500 μM exogenous biotin was added to cells. These experiments were performed once, but has been repeated for BioID under 6 hours labeling conditions twice; and BioID tinder 18 hours labeling conditions (FIG. 5B) and TurboID and miniTurbo under 10 minutes labeling conditions (FIG. 8D) have been repeated more than three times.

FIGS. 9A and 9B show quality control gel analysis of (FIG. 9A) nuclear and (FIG. 9B) mitochondrial matrix proteomic samples. 2.5% of whole cell lysate was used for analysis by streptavidin blotting and ligase expression detection by anti-V5 staining (left). Ponceau staining (middle) shows equal loading of samples. Right: 5% of streptavidin beads were boiled in SDS buffer to elute biotinylated proteins. Eluted proteins were separated on SDS-PAGE and detected by silver stain (right). The proteomics experiment was performed once with two replicates for each construct, but small scale pulldown experiments were repeated once for both nuclear and mitochondrial matrix samples. FIGS. 9C and 9D show characterization of biotin-labeled cells by fluorescence microscopy. HEK prepared and labeled as in FIG. 2D were fixed and stained with neutravidin-AlexFluor647 to visualize biotinylated proteins. DAPI was also used to stain nuclei in (c), and anti-Tom20 antibody to stain mitochondria in (FIG. 9D). Scale bars, 20 μm. In the BioID and TurboID mitochondrial samples, we also observe some neutravidin staining in the cytosol and nucleus, which we believe results from (1) some mis-targeting of subpopulations of each ligase, perhaps due to promiscuous biotinylation of N-terminal mitochondrial targeting sequences (Table 2), which may impair mitochondrial import, and (2) ligases being more active in the cytosol and nucleus than in the mitochondrial matrix. (FIG. 9E) Determination of optimal TMT ratio cutoffs for both replicates of nuclear proteomes. For every possible TMT ratio cutoff, the true positive rate (TPR) was plotted against the false positive rate (FPR) in a receiver operating characteristic (ROC) curve (top). TPR is defined as the fraction of detected true positive proteins above the cutoff FPR is defined as the fraction of detected false positive proteins above the cutoff. The bottom graph plots the difference between the TPR and FPR at every TMT ratio cutoff. Cutoff is made at the TMT ratio at which TPR-FPR is maximal, and it is depicted in the histogram in (FIG. 9G) as a dashed line. FIG. 9F show same as (FIG. 9E), but for mitochondrial proteomes. FIG. 9G shows histograms that illustrate how cutoffs were determined to identify proteins biotinylated by the indicated ligase. True positives (i.e., nuclear annotated proteins) are plotted in the green histogram, and potential false positives are plotted in red histograms. Receiver-operating characteristic analysis from (e) was applied to determine the TMT ratio cutoff value that maximized true positives while minimizing false positives. FIG. 9H shows same as (FIG. 9G), but for mitochondrial proteomes. FIG. 9I shows coverage analysis for each proteomic dataset. Graph indicates the fraction of true positive proteins recalled in each proteome. True positive proteins used for this analysis were curated from literature and FIG. 9J shows overlap of BioID (blue), TurboID (orange) and miniTurbo (green) derived proteomes for the nucleus (left) and mitochondrial matrix (right). Proteins that were only labeled by BioID or proteins that were only labeled by TurboID or miniTurbo were less specific for the compartment being mapped. For example, for the mitochondrial matrix proteomes, only 33% of BioID-only detected proteins and 35% of TurboID/miniTurbo-only detected proteins had previous mitochondrial annotation, whereas 93% of proteins detected by all three ligases had previous mitochondrial annotation; and for the nucleus, 71% of BioID-only detected proteins and 62% of TurboID/miniTurbo-only detected proteins had previous nuclear annotation, whereas 84% of proteins detected by all three ligases had previous nuclear annotation.

FIG. 10A shows a viability assay. Act-Gal4 drives expression of the indicated UAS-BirA enzyme in all cells at all developmental time points. In control flies, Act-Gal4 drives expression of UAS-luciferase in all cells at all developmental time points. Graph indicates the percentage of surviving flies that are ubiquitously expressing the indicated BirA enzyme. Dashed line indicates expected frequency of flies expressing BirA (50%). Flies were either raised on control food or biotin food. Biotin food is control food supplemented with 100 µM biotin. Sample size values (n) from left column to right: 512, 286, 586, 524, 466, 513, 563, 459. This experiment was performed twice with similar results, and the counts combined. FIG. 10B shows an image of two adult Act-Gal4, UAS-luciferase flies and two adult Act-Gal4, UAS-TurboID flies from (a) that are grown on control food and control food supplemented with 100 µM biotin (+Bio). Vertical black lines illustrate size difference between flies expressing TurboID that are raised on normal food versus biotin food. Adult flies shown are all female. FIG. 10C shows a schematic of tissue specific expression of BirA enzymes in wing imaginal disc. nub-Gall drives expression of the indicated UAS-BirA in the wing disc pouch, which gives rise to the adult wing blade. Flies were provided food supplemented with 100 µM biotin for 13 days after egg deposition, then the wings were dissected from adult flies. FIG. 10D shows images of adult wings as prepared in (FIG. 10C). Control flies are untransfected (w1118). Flies were raised on control food, or control food supplemented with 100 µM biotin. Scale bar is 0.5 mm. Adult wings shown are all from females. FIG. 10E shows quantitation of wing area of specimens prepared as described in (FIG. 10C). Control flies are non-transgenic (w1118). Biotin food is control food supplemented with 100 µM biotin. Sample size values (n) from left column to right: 17, 14, 17, 15, 19, 18, 19, 18. Error bars in s.e.m. This experiment repeated twice.

FIG. 11A shows results with 50 WM exogenous biotin added to the cells for 12 or 24 hours. ((FIGS. 11E-10G show results with 50 µM exogenous biotin added to the cells for 1 hour. In FIG. 11F, sample 1 also shows APEX2-NES for comparison, labeled for 1 minute with 500 µM biotin phenol and 1 mM hydrogen peroxide at room temperature. FIG. 11L shows results with 50 µM exogenous biotin added to the cells for 10 minutes. FIG. 11Y shows results with 500 µM exogenous biotin added to the cells for 10 minutes. For comparison, sample 1 shows BirA (R118G) labeling for 18 hours with 50 µM exogenous biotin.

FIG. 12A shows constructs targeting the ligases to the ER membrane (ERM), facing cytosol, and to the outer mitochondrial membrane (OMM), facing cytosol. ERM constructs were targeted using an endoplasmic reticulum membrane anchor derived from cytochrome P450 (C1 (1-29)); OMM constructs targeted using an outer mitochondrial membrane anchor derived from mitochondrial antiviral signaling protein (MAVS). FIG. 12B shows streptavidin blots showing promiscuous biotinylation by the indicated enzymes, in live HEK 293T cells. Constructs were stably expressed and biotinylation was performed for 18 hours for BioID, and for 10 minutes with TurboID and miniTurbo. Anti-V5 blot shows ligase expression levels. FIG. 12C is the same as FIG. 12B but with longer exposure. FIG. 12E shows blotting of streptavidin-enriched lysates from FIG. 12B with antibodies against the six endogenous marker proteins shown in FIG. 12D schematic (calreticulin in the ER lumen, NDUFS6 in the mitochondrial matrix, BCAP31 on the ERM facing cytosol, and Tom70, Tom20, and hexokinase I (HXK 1) on the OMM facing cytosol). "Pre" indicates whole cell lysate. "Post" indicates lysate after streptavidin bead enrichment and elution. Absence of signal in a "post" lane (such as for calreticulin and NDUFS6) indicates that that marker was not biotinylated by ERM1-ligase or OMM-ligase. The blots show that endogenous ERM protein BCAP31 is enriched by ERM-ligases but not by OMM-ligases. Endogenous OMM proteins Tom70, Tom20, and HXK I are preferentially enriched by OMM-ligases over ERM-ligases.

Figure 1A:
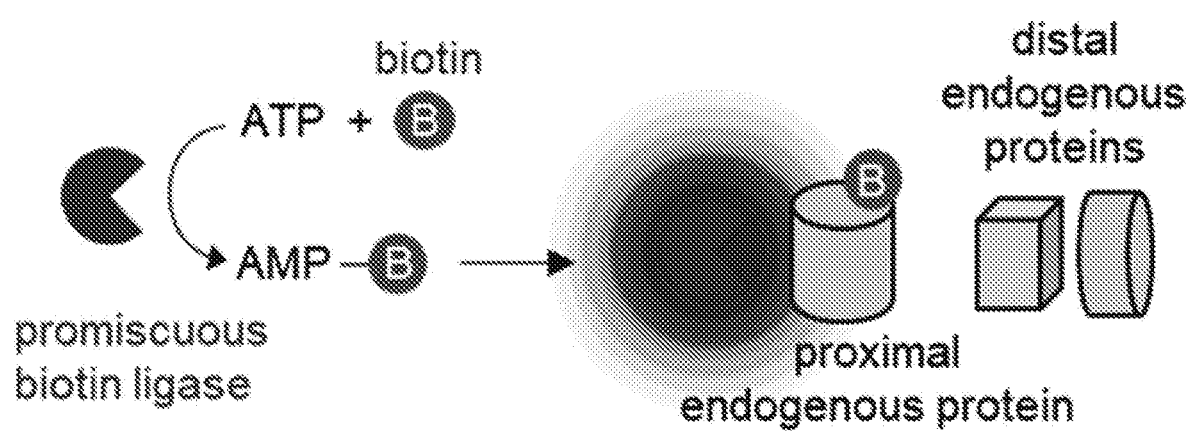
FIGS. 1A-1G show directed evolution of TurboID.

Note that in these experiments, OMM-miniTurbo expression level is very low, explaining the absence of enrichment.

DETAILED DESCRIPTION

The practice of the present invention will employ, unless otherwise indicated, conventional methods of pharmacology, chemistry, biochemistry, recombinant DNA techniques and immunology, within the skill of the art. Such techniques are explained fully in the literature. See, e.g., A. L. Lehninger, *Biochemistry* (Worth Publishers, Inc., current addition); Sambrook, et al., *Molecular Cloning: A Laboratory Manual* (3$^{rd}$ Edition, 2001); *RNA: Methods and Protocols* (Methods in Molecular Biology, edited by H. Nielsen, Humana Press, 1st edition, 2010); Rio et al. *RNA: A Laboratory Manual* (Cold Spring Harbor Laboratory Press; 1st edition, 2010); Farrell *RNA Methodologies: Laboratory Guide for Isolation and Characterization* (Academic Press, 4$^{th}$ edition, 2009); *Methods In Enzymology* (S. Colowick and N. Kaplan eds., Academic Press, Inc.).

All publications, patents and patent applications cited herein, whether supra or infra, are hereby incorporated by reference in their entireties.

I. Definitions

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a protein" includes a mixture of two or more proteins, and the like.

The term "about," particularly in reference to a given quantity, is meant to encompass deviations of plus or minus five percent.

As used herein, a "cell" refers to any type of cell from a prokaryotic, eukaryotic, or archaeon organism, including bacteria, archaea, fungi, protists, plants, and animals, including cells from tissues, organs, and biopsies, as well as recombinant cells, cells from cell lines cultured in vitro, and cellular fragments, cell components, or organelles comprising nucleic acids. The term also encompasses artificial cells, such as nanoparticles, liposomes, polymersomes, or microcapsules encapsulating nucleic acids. A cell may include a fixed cell or a live cell. The methods described herein can be performed, for example, on a sample comprising a single cell or a population of cells.

A "live cell," as used herein, refers to an intact cell, naturally occurring or modified. The live cell may be isolated from other cells, mixed with other cells in a culture, or within a tissue (partial or intact) or an organism. In some embodiments, the live cell is a cell engineered to express a modified biotin ligase described herein. In some embodiments, the live cell expresses a biotin ligase that is targeted to a subcellular compartment or structure, for example, via a localization signal within or fused to the enzyme.

The terms "nucleic acid," "nucleic acid molecule," "polynucleotide," and "oligonucleotide" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. There is no intended distinction in length between the terms "nucleic acid," "nucleic acid molecule," "polynucleotide," and "oligonucleotide" and these terms will be used interchangeably.

The terms "protein," "polypeptide," and "peptide" refer to any compound comprising naturally or synthetic amino acid polymers or amino acid-like molecules including but not limited to compounds comprising amino and/or imino molecules. No particular size is implied by use of the terms "protein," "polypeptide," and "peptide," and these terms are used interchangeably.

As used herein, the term "binding pair" refers to first and second molecules that specifically bind to each other, such as a ligand and a receptor, an antigen and an antibody, or biotin and streptavidin. "Specific binding" of the first member of the binding pair to the second member of the binding pair in a sample is evidenced by the binding of the first member to the second member, or vice versa, with greater affinity and specificity than to other components in the sample. The binding between the members of the binding pair is typically noncovalent.

As used herein, a "solid support" refers to a solid surface such as a magnetic bead, non-magnetic bead, microtiter plate well, glass plate, nylon, agarose, acrylamide, and the like.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The terms "fusion protein," "fusion polypeptide," or "fusion peptide" as used herein refer to a fusion comprising a biotin ligase in combination with a protein of interest as part of a single continuous chain of amino acids, which chain does not occur in nature. The biotin ligase and the protein of interest may be connected directly to each other by peptide bonds or may be separated by intervening amino acid sequences. The protein of interest may be, for example, a cytosolic protein, a nuclear protein, a membrane protein, a mitochondrial protein, a P-body protein, a secretory pathway protein, an antibody specific for an epitope of interest, or any other protein, wherein mapping its location and/or identifying it binding partners and/or nearby nucleic acids in a cell is of interest. The fusion protein may also contain other sequences such as targeting or localization sequences and/or tag sequences.

By "fragment" is intended a molecule consisting of only a part of the intact full-length sequence and structure. The fragment can include a C-terminal deletion an N-terminal deletion, and/or an internal deletion of the polypeptide. Active fragments of a particular protein or polypeptide will generally include at least about 5-14 contiguous amino acid residues of the full length molecule, but may include at least about 15-25 contiguous amino acid residues of the full-length molecule, and can include at least about 20-50 or more contiguous amino acid residues of the full-length molecule, or any integer between 5 amino acids and the full-length sequence, provided that the fragment in question retains biological activity.

"Substantially purified" generally refers to isolation of a substance (compound, polynucleotide, protein, polypeptide, peptide composition) such that the substance comprises the majority percent of the sample in which it resides. Typically, in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a protein, polypeptide or peptide, that the indicated molecule is separate and discrete from the whole organism with which the molecule is found in nature or is present in the substantial absence of other biological macro molecules of the same type. The term "isolated" with respect to a nucleic acid is a nucleic acid molecule devoid, in whole or part, of sequences normally associated with it in nature; or a sequence, as it exists in nature, but having heterologous sequences in association therewith; or a molecule disassociated from the chromosome.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells," "host cells," "cells", "cell lines," "cell cultures," and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single stranded DNA (e.g., a M13 origin of replication), at least one multiple cloning site, and a "mammalian" origin of replication (e.g., a SV40 or adenovirus origin of replication).

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (2001) Molecular Cloning, a laboratory manual, 3rd edition, Cold Spring Harbor Laboratories, New York, Davis et al. (1995) Basic Methods in Molecular Biology, 2nd edition, McGraw-Hill, and Chu et al. (1981) Gene 13:197. Such techniques can be used to introduce one or more exogenous DNA moieties into suitable host cells. The term refers to both stable and transient uptake of the genetic material, and includes uptake of peptide- or antibody-linked DNAs.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, alphaviruses, pox viruses and vaccinia viruses.

The term "subject" or "host subject" includes bacteria, archaea, fungi, protists, plants, and animals (both vertebrates and invertebrates), including, without limitation, plants such as flowering plants (e.g., *Arabidopsis thaliana*), conifers and other gymnosperms, ferns, clubmosses, hornworts, liverworts, mosses (e.g., *Physcomitrella patens*), and green algae (e.g., *Chlamydomonas reinhardtii*); fungi such as molds and yeasts (e.g., *Saccharomyces cerevisiae, Schizosaccharomyces pombe*), protists such as amoebae, *flagellates*, and ciliates (e.g., *Tetrahymena thermophila*); worms (e.g., *Caenorhabditis elegans*), insects such as beetles, ants, bees, moths, butterflies, and flies (e.g., *Drosophila melanogaster*), amphibians such as frogs (e.g., *Xenopus tropicalis, Xenopus laevis*) and salamanders (e.g., axolotls); fish (e.g., *Danio*

*rerio, Fundulus heteroclitus, Nothobranchius furzeri*); reptiles; mammals, including human and non-human mammals such as non-human primates, including chimpanzees and other apes and monkey species; laboratory animals such as mice, rats, rabbits, hamsters, guinea pigs, and chinchillas; domestic animals such as dogs and cats; farm animals such as sheep, goats, pigs, horses and cows; and birds such as domestic, wild and game birds, including chickens, turkeys and other gallinaceous birds, ducks, and geese. In some cases, the methods of the invention find use in experimental animals, in veterinary application, and in the development of animal models for disease, including, but not limited to, rodents including mice, rats, and hamsters; primates, and transgenic animals.

The term "animal" is used herein to include all vertebrate and invertebrate animals, except humans. The term also includes animals at all stages of development, including embryonic and fetal stages.

A "transgenic organism" is an organism containing one or more cells bearing genetic material received, directly or indirectly, by deliberate genetic manipulation at a subcellular level, such as by microinjection or infection with recombinant virus. An introduced DNA molecule may be integrated within a chromosome, or it may be extrachromosomally replicating DNA. If a DNA molecule is introduced into a germ line cell, the genetic material containing the DNA molecule may be transferred to offspring. An offspring possessing some or all of that genetic material is also considered to be a transgenic organism.

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of mutations that improve the efficiency of proximity labeling by biotin ligase. The inventors used yeast display-based directed evolution to engineer two mutants of biotin ligase, referred to as TurboID and miniTurbo, which have much greater catalytic efficiency than BioID. The inventors have shown that TurboID and miniTurbo have the ability to carry out proximity labeling in live cells in much shorter periods of time (e.g., as little as 10 minutes) that BioID with a non-toxic and easily deliverable biotin substrate. The inventors have further demonstrated the effectiveness of their engineered biotin ligases in proximity labeling of proteins in yeast, *Drosophila*, and *C. elegans* (see Example 1).

In order to further an understanding of the invention, a more detailed discussion is provided below regarding the engineered biotin ligases and their use in proximity labeling of cellular proteins.

A. Engineered Biotin Ligases

More efficient proximity labeling of proteins can be achieved with biotin ligase variants engineered to provide faster vicinal labeling of proteins. Native biotin ligases catalyze the reaction of biotin with ATP to produce biotinoyl-5'-AMP as a reaction intermediate. Normally, this reaction intermediate is retained in the active site of the enzyme until the biotin group is transferred to a specific target protein. However, variant forms of biotin ligase such as BirA release this reaction intermediate from the active site such that it nonspecifically biotinylates any nearby protein with exposed lysine residues (i.e., proximity labeling). BirA biotin ligase can be further modified to enhance promiscuous biotinylation activity.

In particular, a biotin ligase may be modified to increase promiscuous biotinylation activity by introducing at least one amino acid substitution selected from the group consisting of Q65P, M209V, V160A, S150G, L151P, I305V, I87V, R118S, T192A, K194I, E140K, Q141R, M241T, and S263P into the enzyme. The foregoing numbering is relative to the reference sequence of the BirA biotin ligase from *Escherichia coli* (SEQ ID NO:7), but it is to be understood that the corresponding positions in other biotin ligases obtained from other species are also intended to be encompassed by the present invention. In one embodiment, a modified biotin ligase comprises Q65P, M209V, V160A, S150G, L151P, I305V, I87V, R118S, T192A, K194I, E140K, and Q141R amino acid substitutions. In another embodiment, a modified biotin ligase comprises Q65P, M209V, V160A, S150G, L151P, I305V, I87V, R118S, T192A, K194I, E140K, Q141R, M241T, and S263P amino acid substitutions.

In some embodiments, the modified biotin ligase further comprises an N-terminal deletion of at least the first amino acid up to the first 63 amino acids (as numbered relative to the reference BirA biotin ligase sequence of SEQ ID NO:7), including any number of amino acids in between, such as an N-terminal deletion of 1, 2, 3, 4, 5, 6, 7, 8, 9, 10, 12, 14, 16, 18, 20, 22, 24, 26, 28, 30, 32, 34, 36, 38, 40, 42, 44, 46, 48, 50, 51, 52, 53, 54, 55, 56, 57, 58, 59, 60, 61, 62, or 63 amino acids, wherein the biotin ligase retains promiscuous biotinylation activity. In one embodiment, the modified biotin ligase comprises an N-terminal deletion of the first 63 amino acids (Δ(1-63)). In particular, truncated smaller biotin ligase variants may be useful in protein fusions to minimize interference with biological function and/or protein trafficking of proteins to which the biotin ligase is fused.

In certain embodiments, the modified biotin ligase comprises:
a) Q65P, R118S, L151P, I305V, and E313K amino acid substitutions,
b) R118S and E313K amino acid substitutions,
c) Q65P, R118S, L151P, I305V, and E313R amino acid substitutions,
d) R118S and E313R amino acid substitutions,
e) R118S, L151P, and I305V amino acid substitutions,
f) K2E, R118S, M157T, and L298P amino acid substitutions,
g) R118S and L297P amino acid substitutions,
h) R118S, I313N amino acid substitutions,
i) R118S, L151P, and I305V amino acid substitutions,
j) Q65P, R118S, and I305V amino acid substitutions,
k) Q65P, R118S, and L151P amino acid substitutions,
l) R118S, L151P, I305V, and K313R amino acid substitutions,
m) Q65P, R118S, I305V, and K313R amino acid substitutions,
n) Q65P, R118S, and K313R amino acid substitutions,
o) R118S, L151P, and K313R amino acid substitutions,
p) R118S, I305V, and K313R amino acid substitutions,
q) Q65P and R118S amino acid substitutions,
r) R118S and L151P amino acid substitutions,
s) R118S and I305V amino acid substitutions,
t) R118S and M157T amino acid substitutions, u) R118S and L298P amino acid substitutions,
v) K2E, R33G, R118S, M157T, and L298P amino acid substitutions,
w) K2E, R118S, M157T, I279T, L298P, and K307N amino acid substitutions,
x) Q65P, R118S, L151P, I305V, Y111H, and R118S amino acid substitutions,
y) Q65P, R118S, S150G, L151P, T192A, I305V amino acid substitutions,
z) Q65P, R118S, L151P, 123IV, and I305V amino acid substitutions,
aa) Q65P, R118S, L151P, T192A, and I305V amino acid substitutions,
bb) Q65P, R118S, S150G, L151P, and I305V amino acid substitutions,
cc) R33G, Q65P, R118S, S150G, L151P, T192A, and I305V amino acid substitutions,
dd) N37S, Q65P, R118S, S150G, L151P, T192V, E266L, and I305V amino acid substitutions,
ee) Q65P, R118S, S150G, L151P, T192A, 1280V, I305V, and A318V amino acid substitutions,
ff) Q65P, R118S, Q142R, S150G, L151P, T192A, M209V, and I305V amino acid substitutions,
gg) Q65P, R118S, S150G, L151P, T192A, and I305V amino acid substitutions,
hh) Q65P, R118S, Q142R, S150G, L151P, T192A, and I305V amino acid substitutions,
ii) Q65P, R118S, S150G, L151P, T192A, M209V, and I305V amino acid substitutions,
jj) Q65P, I87V, R118S, E141K, S150G, L151P, V160A, T192A, M209V, and I305V amino acid substitutions,
kk) Q65P, I87V, R118S, E141K, S150G, L151P, T192A, and I305V amino acid substitutions, 11) Q65P, R118S, S150G, L151P, V160A, T192A, M209V, and I305V amino acid substitutions,
mm) Q65P, R118S, Q142R, S150G, L151P, V160A, T192A, M209V, and I305V amino acid substitutions,
nn) Q65P, I87V, R118S, E141K, S150G, L151P, V160A, T192A, M209V, and I305V amino acid substitutions,
oo) Q65P, 187V, R118S, Q142R, S150G, L151P, T192A, M209V, and 1305V amino acid substitutions,
pp) Q65P, R118S, E141K, Q142R, S150G, L151P, T192A, M209V, and I305V amino acid substitutions,
qq) Q65P, I87V, R118S, E141K, Q142R, S150G, L151P, V160A, T192A, M209V, and I305V amino acid substitutions,
rr) Q65P, I87V, R118S, E141K, Q142R, S150G, L151P, T192A, and I305V amino acid substitutions,
ss) Q65P, I87V, R118S, E141K, S150G, L151P, T192A, M209V, and I305V amino acid substitutions,
tt) Q65P, R118S, S150G, Q142R, L151P, T192A, M209V, and I305V amino acid substitutions,
uu) Q65P, I87V, R118S, E141K, S150G, L151P, V160A, T192A, M209V, and I305V amino acid substitutions,
vv) Q65P, I87V, R118S, E141K, Q142R, S150G, L151P, V160A, T192A, I201V, M209V, and I305V amino acid substitutions,
ww) Q65P, I87V, R118S, K140R, E141K, Q142R, S150G, L151P, V160A, T192A, M209V, K267R, I305V, and E313K amino acid substitutions,
xx) Q65P, I87V, R118S, E141K, Q142R, S150G, L151P, V160A, T192A, M209V, I305V, I306V, and E313K amino acid substitutions,
yy) Q65P, I87V, I98V, R118S, E141K, Q142R, S150G, L151P, V160A, T192A, M209V, and I305V amino acid substitutions,
zz) Q65P, I87V, R118S, E141K, Q142R, S150G, L151P, V160A, T192A, A199T, M209V, D303G, and I305V amino acid substitutions,
aaa) Q65P, I87V, R118S, G120R, E141K, Q142R, S150G, L151P, V160A, T192A, D197G, M209V, M241V, I305V, and E313K amino acid substitutions,
bbb) Q65P, I87V, R118S, E141K, Q142R, S150G, L151P, V160A, V162A, A166V, T192A, M209V, I305V, and E313K amino acid substitutions,
ccc) Q65P, I87V, R118S, E141K, Q142R, S150G, L151P, V160A, T192A, M209V, I305V, E307R, and E313K amino acid substitutions,
ddd) E27D, Q65P, I87V, R118S, E141K, Q142R, S150G, L151P, V160A, T192A, M209V, E251K, and I305V amino acid substitutions,
eee) Q65P, I87V, R118S, E141K, Q142R, S150G, L151P, V160A, T192A, M209V, M241T, and I305V amino acid substitutions,
fff) Q65P, I87V, R118S, E141K, Q142R, S150G, L151P, V160A, T192A, M209V, N270D, and I305V amino acid substitutions,
ggg) K2R, F51L, Q65P, K70T, I87V, R118S, E141K, Q142R, S150G, L151P, V160A, T192A, M209V, I305V, I306V, and E313K amino acid substitutions,
hhh) Δ(1-63), Q65P, K70T, I87V, R118S, E141K, Q142R, S150G, L151P, V160A, T192A, M209V, I305V, I306V, and E313K amino acid substitutions,
iii) Δ(1-63), Q65P, I87V, R118S, E141K, Q142R, S150G, L151P, V160A, T192A, M209V, and I305V amino acid substitutions,
jjj) Q65P, I87V, R118S, E141K, Q142R, S150G, L151P, V160A, T192A, M209V, L252R, I305V, K307R, and G311 D amino acid substitutions,
kkk) Q65P, I87V, R118S, E141K, Q142R, S150G, L151P, V160A, K168E, T192A, M209V, K267E, and I305V amino acid substitutions,
lll) Q65P, 187V, R118S, E141K, Q142R, S150G, L151P, V160A, T192A, M209V, E251K, and I305V amino acid substitutions,
mmm) Δ(1-63), Q65P, I87V, R118S, E141K, Q142R, S150G, L151P, V160A, T192A, M209V, E251K, and I305V amino acid substitutions,
nnn) Q65P, I87V, R118S, E141K, Q142R, S150G, L151P, V160A, T192A, M209V, M241T, and I305V amino acid substitutions,
ooo) Δ(1-63), Q65P, I87V, R118S, E141K, Q142R, S150G, L151P, V160A, T192A, M209V, M241T, and I305V amino acid substitutions,
ppp) Δ(1-63) Q65P, I87V, R118S, E141K, Q142R, S150G, L151P, V160A, T192A, M209V, M241T, I305V amino acid substitutions,
qqq) Δ(1-63), Q65P, I87V, R118S, E141K, Q142R, S150G, L151P, V160A, T192A, M209V, and I305V amino acid substitutions,
rrr) Δ(1-63), Q65P, I87V, R118S, E141K, Q142R, S150G, L151P, V160A, L179M, T192A, M209V, N232S, I305V, and I306T amino acid substitutions,
sss) Δ(1-63), Q65P, I87V, R118S, E141K, Q142R, S150G, L151P, V160A, T192A, M209V, I285V, and I305V amino acid substitutions,
ttt) Δ(1-63), Q65P, I87V, R118S, E141K, Q142R, S150G, L151P, V160A, T192A, M209V, S289G, I305V, and M310V amino acid substitutions,
uuu) Δ(1-63), Q65P, I87V, R118S, E141K, Q142R, S150G, L151P, V160A, D167G, T192A, M209V, N232S, and I305V amino acid substitutions, vvv) Δ(1-63), Q65P, I87V, I99V, R118S, E141K, Q142R, S150G, L151P, V160A, T192A, M209V, I305V, K307Q, and M310T amino acid substitutions, www) Q65P, I87V, R118S, E141K, Q142R, S150G, L151P, V160A, T192A, M209V, and I305V amino acid substitutions, xxx) Q65P, I87V, S89N, R118S, E141K, Q142R, S150G, L151P, V160A, T192A, M209V, and I305V amino acid substitutions, yyy) Δ(1-63) Q65P, I87V, R118S, E141K, Q142R, S150G, L151P, V160A, D167G, T192A, M209V, M241T, N232S, and I305V amino acid substitutions, zzz) Q65P, I87V, S89N, R118S, E141K, Q142R, S150G, L151P, V160A, T192A, M209V, M241T, and I305V amino acid substitutions, aaaa) Δ(1-63), Q65P, I87V, D88G, R118S, E141K, Q142R, S150G, L151P, V160A, T192A, M209V, K283E, and I305V amino acid substitutions, bbbb) Δ(1-63), Q65P, I87V, Y111H, R118S, E141K, Q142R, S150G, L151P, V160A, T192A, M209V, and I305V amino acid substitutions, cccc) Δ(1-63), Q65P, I87V, R118S, E141K, Q142R, S150G, L151P, V160A, T192A, M209V, S263P, and I305V amino acid substitutions, dddd) Δ(1-63), Q65P, I87V, R118S, E141K, Q142R, S150G, L151P, V160A, T192A, K194I, M209V, and I305V amino acid substitutions, eeee) Δ(1-63), Q65P, I87V, R118S, E141K, Q142R, S150G, L151P, V160A, T192A, M209V, and I305V amino acid substitutions, ffff) Δ(1-63), Q65P, I87V, R118S, E141K, Q142R, S150G, L151P, V160A, T192A, M209V, M241T, and I305V amino acid substitutions, gggg) Δ(1-63), Q65P, I87V, R118S, E141K, Q142R, S150G, L151P, V160A, T192A, K194I, M209V, and I305V amino acid substitutions, hhhh) Δ(1-63), Q65P, I87V, R118S, E141K, Q142R, S150G, L151P, V160A, T192A, M209V, M241T, S263P, and I305V amino acid substitutions, iiii) Δ(1-63), Q65P, I87V, R118S, E141K, Q142R, S150G, L151P, V160A, T192A, K194I, M209V, M241T, and I305V amino acid substitutions, jjjj) Δ(1-63), Q65P, I87V, R118S, E141K, Q142R, S150G, L151P, V160A, T192A, K194I, M209V, S263P, and I305V amino acid substitutions, kkkk) Δ(1-63), Q65P, I87V, R118S, E141K, Q142R, S150G, L151 P, V160A, T192A, M209V, and I305V amino acid substitutions, llll) Δ(1-63), Q65P, I87V, R118S, E141K, Q142R, S150G, L151 P, V160A, T192A, K194I, M209V, M241T, and I305V amino acid substitutions, mmmm) Δ(1-63), Q65P, I87V, R118S, E141K, Q142R, S150G, L151 P, V160A, T192A, K194I, M209V, M241T, S263P, and I305V amino acid substitutions, nnnn) Δ(1-63), Q65P, I87V, R118S, E141K, Q142R, S150G, L151P, V160A, T192A, K194I, M209V, S263P, and I305V amino acid substitutions, oooo) Q65P, I87V, R118S, E141K, Q142R, S150G, L151P, V160A, T192A, M209V, S263P, and I305V amino acid substitutions, pppp) Q65P, I87V, R118S, E141K, Q142R, S150G, L151P, V160A, T192A, K194I, M209V, and I305V amino acid substitutions, qqqq) Q65P, I87V, R118S, E141K, Q142R, S150G, L151P, V160A, T192A, M209V, S263P, and I305V amino acid substitutions, rrrr) Q65P, I87V, R118S, E141K, Q142R, S150G, L151P, V160A, T192A, K194I, M209V, M241T, and I305V amino acid substitutions, and ssss) Q65P, I87V, R118S, E141K, Q142R, S150G, L151P, V160A, T192A, K194I, M209V, M241T, S263P, and I305V amino acid substitutions.

In certain embodiments, a modified biotin ligase comprises a polypeptide comprising an amino acid sequence selected from the group consisting of SEQ ID NO:11 and SEQ ID NO:13, or a sequence displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the biotin ligase is capable of proximity-dependent biotinylation of proteins.

Modified biotin ligases may be obtained by recombinant techniques or produced synthetically. The biotin ligase to be modified may be derived from any source. Representative biotin ligase sequences are presented in SEQ ID NOS:7-13 for the BirA biotin ligase from *E. coli*, the BioID biotin ligase, and the engineered MiniTurbo and TurboID biotin ligases described in Example 1. In addition, BirA biotin ligase sequences from a number of bacterial species are listed in the National Center for Biotechnology Information (NCBI) database. See, for example, NCBI entries: Accession Nos. YP_002410237, NP 312927, WP_063115295, WP 063082625, WP_060615925, NP 844010, NP 844010, NP_390125, WP_044306464, WP 011109968, NP_390125, WP_060398894, WP 041117801, WP 041109603, YP 499991, WP_042909036, WP_031903905, NP 359307, WP_061816626, WP 061767634, NP_252970, NP 790457, YP_237632, WP 057960767, WP_057400631, WP_061193045, YP 237632, WP_058975108, WP_052967038, WP 054095365, WP_003292971, WP_046622626, WP 025240331, NP_764699, NP 715854, YP 352592, NP_952984, YP 205808, NP 639277, YP 001034965, YP_003029217, NP 771543, NP_301572, YP_006969295, NP 213397, NP 225061, NP_220244, and YP_001004658; all of which sequences (as entered by the date of filing of this application) are herein incorporated by reference. Any of these sequences, or a biologically active fragment thereof, or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to produce a modified biotin ligase as described herein.

Polynucleotides encoding biotin ligases can be produced in any number of ways, all of which are well known in the art. For example, polynucleotides can be generated using recombinant techniques, well known in the art. One of skill in the art can readily determining nucleotide sequences that encode the desired proteins using standard methodology and the teachings herein.

Oligonucleotide probes can be devised based on known gene sequences and used to probe genomic or cDNA libraries. The polynucleotides with desired sequences can then be further isolated using standard techniques and, e.g., restriction enzymes employed to truncate a gene at desired portions of the full-length sequence. Similarly, polynucleotides with sequences of interest can be isolated directly from cells and tissues containing the same, using known techniques, such as phenol extraction and the sequence further manipulated to produce desired biotin ligase variants. See, e.g., Sambrook et al., supra, for a description of techniques used to obtain and isolate DNA.

The sequences encoding biotin ligase variants can also be produced synthetically, for example, based on known sequences. The nucleotide sequence can be designed with the appropriate codons for the particular amino acid sequence desired. The complete sequence is generally assembled from overlapping oligonucleotides prepared by standard methods and assembled into a complete coding sequence. See, e.g., Edge (1981) Nature 292:756; Nambair et al. (1984) Science 223:1299; Jay et al. (1984) J. Biol. Chem. 259:6311; Stemmer et al. (1995) Gene 164:49-53.

Recombinant techniques are readily used to clone sequences encoding biotin ligases that can then be mutagenized in vitro by the replacement of the appropriate base pair(s) to result in the codon for the desired amino acid. Such a change can include as little as one base pair, effecting a change in a single amino acid, or can encompass several base pair changes. Alternatively, the mutations can be effected using a mismatched primer that hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al, (1990) PCR Applications: Protocols for Functional Genomics; Zoller and Smith, Methods Enzymol. (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. Proc. Natl. Acad. Sci. USA (1982) 79:6409.

Such modified biotin ligases can be used generally for biotinylation of proteins. Contacting the modified biotin ligase with its substrates, biotin (or a biotin derivative such as desthiobiotin) and ATP, results in biotinylation of proteins in proximity to the biotin ligase. For example, a modified biotin ligase can be used for in vitro biotinylation of proteins (e.g., individual purified proteins in a test tube or unpurified proteins such as in a cell lysate). In addition, modified biotin ligases can be used for proximity labeling of proteins in a cell or live organism. For example, a modified biotin ligase can be introduced into a cell or live organism, and contacted with biotin (or a biotin derivative such as desthiobiotin) and ATP, wherein proteins in proximity to the biotin ligase are biotinylated.

Biotinylated proteins can be isolated with a biotin-binding protein, such as streptavidin or avidin. The biotin-binding protein may be immobilized on a solid support, such as, but not limited to, a magnetic bead, non-magnetic bead, microtiter plate well, glass plate, nylon, agarose, or acrylamide to facilitate removal of biotinylated proteins from a liquid. The isolated biotinylated proteins can then be analyzed by any appropriate method for protein identification such as, but not limited to, mass spectrometry, liquid chromatography-mass spectrometry (LC/MS), immunoassay (e.g., enzyme-linked immunosorbent assay (ELISA), immunoprecipitation), Western blot, immunoelectrophoresis, immunostaining, high-performance liquid chromatography (HPLC), protein sequencing, and peptide mass fingerprinting.

The methods of the invention may be applied to cell samples comprising a single cell or a population of cells of interest and can be performed on any type of cell, including any cell from a prokaryotic, eukaryotic, or archaeon organism, including bacteria, archaea, fungi, protists, plants, and animals. Cells from tissues, organs, and biopsies, as well as recombinant cells, cells from cell lines cultured in vitro, and artificial cells (e.g., nanoparticles, liposomes, polymersomes, or microcapsules encapsulating nucleic acids) may all be used in the practice of the invention. The methods of the invention are also applicable for investigating protein and/or nucleic acid localization in cellular fragments, cell components, or organelles comprising nucleic acids.

In some embodiments, proximity-dependent biotinylation is performed on an intact cell, naturally occurring or modified. The cell may be isolated from other cells, mixed with other cells in a culture, or within a tissue (partial or intact), or a whole live organism. Although the methods for proximity labeling and the related reagents, materials and compositions described herein are well suited for use in live cells or whole live organisms, it should be appreciated that their use is not so limited, but that they can also be applied to fixed cells and tissues, for example, fixed cells and tissues obtained from a subject, e.g., in a clinical setting as well as lysed cells.

In general, the methods and strategies for proximity-dependent biotinylation of cellular proteins employ a modified biotin ligase engineered for improved efficiency. The biotin ligase catalyzes a reaction with biotin and ATP that generates a reactive unstable biotinoyl-5'-AMP reaction intermediate that is capable of covalently labeling nearby proteins. The half-life of the reaction intermediate generated by the biotin ligase determines how far the reagent can travel from its point of generation before reacting with a molecule. Accordingly, the half-life of biotinoyl-5'-AMP determines its labeling radius. Because the enzyme generated reaction intermediate has a short half-life in cells, only proteins in proximity to the biotin ligase and the reaction intermediate generated by the biotin ligase (typically a few tens to hundreds of nanometers) are sufficiently close to be covalently modified (i.e., biotinylated).

The biotin ligase can be introduced into a cell and contacted with the biotin and ATP substrates under conditions suitable for the biotin ligase to produce the reactive biotinoyl-5'-AMP intermediate, which biotinylates proteins in the vicinity of the enzyme. The biotin ligase may be delivered to the cell interior or exterior, depending on which region of the cell is being analyzed. In some embodiments, the biotin ligase is delivered to the interior of the cell, and in some instances, to specific subcellular compartments. In some embodiments, the biotin ligase is delivered to a tissue. The biotin ligase may also be introduced into a cell by transfecting the cell with a recombinant polynucleotide comprising a promoter operably linked to a polynucleotide encoding the biotin ligase. The recombinant polynucleotide may comprise an expression vector, for example, a bacterial plasmid vector or a viral expression vector, such as, but not limited to, an adenovirus, retrovirus (e.g., γ-retrovirus and lentivirus), poxvirus, adeno-associated virus, baculovirus, or herpes simplex virus vector.

In some embodiments, the modified biotin ligase is introduced into a whole live organism. For example, the modified biotin ligase can be introduced into bacteria, archaea, fungi, protists, plants, and animals (both vertebrates and invertebrates), including, without limitation, plants such as flowering plants, conifers and other gymnosperms, ferns, clubmosses, hornworts, liverworts, mosses, and green algae; fungi such as molds and yeasts; protists such as amoebae, flagellates, and ciliates; worms; insects such as beetles, ants, bees, moths, butterflies, and flies; amphibians such as frogs and salamanders (e.g., axolotls); fish; reptiles; mammals, including human and non-human mammals such as non-human primates, including chimpanzees and other apes and monkey species; laboratory animals such as mice, rats, rabbits, hamsters, guinea pigs, and chinchillas; domestic animals such as dogs and cats; farm animals such as sheep, goats, pigs, horses and cows; and birds such as domestic, wild and game birds, including chickens, turkeys and other gallinaceous birds, ducks, geese; and transgenic animals.

In some embodiments, the modified biotin ligase is introduced into a model organism, such as an animal model or test subject for use in scientific or biomedical research or drug screening. Model organisms include, but are not limited to, prokaryotic model organisms such as bacteria (e.g., *Escherichia coli*) and eukaryotic model organisms such as yeasts (e.g., *Saccharomyces cerevisiae* and *Schizosaccharomyces pombe*), plants, including flowering plants (e.g., *Arabidopsis thaliana*), mosses (e.g., *Physcomitrella patens*), and unicellular green alga (e.g., *Chlamydomonas reinhardtii*); protists (e.g., *Tetrahymena thermophila*); invertebrates such as worms (e.g., *Caenorhabditis elegans*) and flies (e.g., *Drosophila melanogaster*); amphibians such as frogs (e.g., *Xenopus tropicalis, Xenopus laevis*) and salamanders (e.g., axolotls); fish (e.g., *Danio rerio, Fundulus heteroclitus, Nothobranchius furzeri*), mammals such as rodents, including guinea pigs (e.g., *Cavia porcellus*), mice (e.g., *Mus musculus*), and rats (e.g., *Rattus norvegicus*), and non-human primates such as the rhesus macaque and chimpanzee. Model organisms can be used, for example, to study disease pathology, development, toxicology, aging, gene function, signaling pathways, intracellular processes, and physiological systems, and in production and screening of therapeutics and vaccines.

In some embodiments, the biotin ligase is engineered to improve its capability in proximity labeling at a particular subcellular location. For example, the biotin ligase can be engineered to be expressed and/or active only within a subcellular compartment or structure of interest. The biotin ligase may also be engineered to comprise one or more mutations that enhance its catalytic activity in a subcellular compartment or structure of interest.

The biotin ligase can be directed to a specific protein or cellular compartment of interest in a number of ways. For example, the biotin ligase may be modified to include a targeting sequence that directs the biotin ligase to the subcellular region of interest. Targeting sequences that can be used include, but are not limited to, a secretory protein signal sequence, a membrane protein signal sequence, a nuclear localization sequence, a mitochondrial localization sequence, an outer mitochondrial membrane sequence, an endoplasmic reticulum localization sequence, an endoplasmic reticulum membrane targeting sequence, a nucleolar localization signal sequence, a nuclear export signal sequence, a peroxisome localization sequence, and a protein binding motif sequence.

In other embodiments, the biotin ligase is covalently linked to a peptide or protein that directs the biotin ligase to a subcellular region of interest, such as a cytosolic protein, a nuclear protein, a membrane protein, a mitochondrial protein, a P-body protein, or a secretory pathway protein. Attachment to the protein of interest results in proximity labeling of proteins surrounding the protein of interest in the locations where it resides in the cell. Alternatively, the biotin ligase can be covalently linked to an antibody that specifically binds a particular epitope found on certain proteins in a subcellular region of interest, which similarly allows proximity labeling of surrounding nearby proteins.

In addition, proximity-dependent biotinylation of proteins can be combined with crosslinking of nucleic acids to the labeled proteins to identify nucleic acids within or near a particular subcellular compartment in vivo and for mapping protein-nucleic acid interactions within a cell. Crosslinking of nucleic acids to the biotinylated cellular proteins allows identification of nucleic acids (e.g., RNA or DNA) in the vicinity of the biotinylated proteins. Furthermore, such crosslinking allows nucleic acids to be mapped to particular organelles, including subcompartments of organelles without subcellular fractionation.

Crosslinking agents that can be used for crosslinking proteins and nucleic acids include, but are not limited to, dimethyl suberimidate, N-hydroxysuccinimide, formaldehyde, and glutaraldehyde. In addition, carboxyl-reactive chemical groups such as diazomethane, diazoacetyl, and carbodiimide can be included for crosslinking carboxylic acids to primary amines. In particular, the carbodiimide compounds, 1-ethyl-3-(-3-dimethylaminopropyl) carbodiimide hydrochloride (EDC) and N',N'-dicyclohexyl carbodiimide (DCC) can be used for conjugation with carboxylic acids. In order to improve the efficiency of crosslinking reactions, N-hydroxysuccinimide (NHS) or a water-soluble analog (e.g., Sulfo-NHS) may be used in combination with a carbodiimide compound. The carbodiimide compound (e.g., EDC or DCC) couples NHS to carboxyl groups to form an NHS ester intermediate, which readily reacts with primary amines at physiological pH. In addition, ultraviolet light can be used for crosslinking proteins to nucleic acids. For a description of various crosslinking agents and techniques, see, e.g., Wong and Jameson *Chemistry of Protein and Nucleic Acid Cross-Linking and Conjugation* (CRC Press, $2^{nd}$ edition, 2011), Hermanson *Bioconjugate Techniques* (Academic Press, $3^{rd}$ edition, 2013), herein incorporated by reference in their entireties.

In certain embodiments, crosslinking of proteins and nucleic acids is performed using click chemistry. Crosslinking of proteins and nucleic acids using click chemistry can be performed with suitable crosslinking agents comprising reactive azide or alkyne functional groups. See, e.g., Kolb et al., 2004, Angew Chem Int Ed 40:3004-31; Evans, 2007, Aust J Chem 60:384-95; Millward et al. (2013) Integr Biol (Camb) 5(1):87-95), Lallana et al. (2012) Pharm Res 29(1): 1-34, Gregoritza et al. (2015) Eur J Pharm Biopharm. 97(Pt B):438-453, Musumeci et al. (2015) Curr Med Chem. 22(17):2022-2050, McKay et al. (2014) Chem Biol21(9): 1075-1101, Ulrich et al. (2014) Chemistry 20(1):34-41, Pasini (2013) Molecules 18(8):9512-9530, and Wangler et al. (2010) Curr Med Chem. 17(11):1092-1116; herein incorporated by reference in their entireties.

In particular, crosslinking can be performed using strain-promoted azide-alkyne cycloaddition (SPAAC) click chemistry, a Cu-free variation of click chemistry that is generally biocompatible with cells. SPAAC utilizes a substituted cyclooctyne having an internal alkyne in a strained ring system. Ring strain together with electron-withdrawing substituents in the cyclooctyne promote a [3+2] dipolar cycloaddition with an azide functional group. SPAAC can be used for bioconjugation and crosslinking by attaching azide and cyclooctyne moieties to molecules. For a description of SPAAC, see, e.g., Baskin et al. (2007) Proc Natl Acad Sci USA 104(43):16793-16797, Agard et al. (2006) ACS Chem. Biol. 1: 644-648, Codelli et al. (2008) J. Am. Chem. Soc. 130:11486-11493, Gordon et al. (2012) J. Am. Chem. Soc. 134:9199-9208, Jiang et al. (2015) Soft Matter 11(30):6029-6036, Jang et al. (2012) Bioconjug Chem. 23(11):2256-2261, Ornelas et al. (2010) J Am Chem Soc. 132(11):3923-3931; herein incorporated by reference in their entireties.

Crosslinked biotinylated protein-nucleic acid fusions, produced as described herein, can be isolated with a biotin-binding protein, such as streptavidin or avidin. The biotin-binding protein may be immobilized on a solid support (e.g., streptavidin beads or magnetic beads as described above to facilitate removal from a liquid. The isolated protein-nucleic acid fusions can then be analyzed to identify nucleic acids and/or proteins by any appropriate method (e.g., mass spectrometry or immunoassays for identification of proteins and sequencing or polymerase chain reaction (PCR) with suitable primers for identification of nucleic acids). RNA may be reverse transcribed into cDNA with a reverse transcriptase prior to performing PCR (i.e., RT-PCR) and/or sequencing.

Any high-throughput technique for sequencing the nucleic acids can be used in the practice of the invention. Deep sequencing of nucleic acids can be used, for example, to improve sequence accuracy and for determining the frequency of RNA molecules in particular subcellular compartments or regions. DNA sequencing techniques include dideoxy sequencing reactions (Sanger method) using labeled terminators or primers and gel separation in slab or capillary, sequencing by synthesis using reversibly terminated labeled nucleotides, pyrosequencing, 454 sequencing, sequencing by synthesis using allele specific hybridization to a library of labeled clones followed by ligation, real time monitoring of the incorporation of labeled nucleotides during a polymerization step, polony sequencing, SOLID sequencing, and the like.

Certain high-throughput methods of sequencing comprise a step in which individual molecules are spatially isolated on a solid surface where they are sequenced in parallel. Such solid surfaces may include nonporous surfaces (such as in Solexa sequencing, e.g. Bentley et al, Nature, 456: 53-59 (2008) or Complete Genomics sequencing, e.g. Drmanac et al, Science, 327: 78-81 (2010)), arrays of wells, which may include bead- or particle-bound templates (such as with 454, e.g. Margulies et al, Nature, 437: 376-380 (2005) or Ion Torrent sequencing, U.S. patent publication 2010/0137143 or 2010/0304982), micromachined membranes (such as with SMRT sequencing, e.g. Eid et al, Science, 323: 133-138 (2009)), or bead arrays (as with SOLiD sequencing or polony sequencing, e.g. Kim et al, Science, 316: 1481-1414 (2007)). Such methods may comprise amplifying the isolated molecules either before or after they are spatially isolated on a solid surface. Prior amplification may comprise emulsion-based amplification, such as emulsion PCR, or rolling circle amplification.

Of particular interest is sequencing on the Illumina MiSeq, NextSeq, and HiSeq platforms, which use reversible-terminator sequencing by synthesis technology (see, e.g., Shen et al. (2012) BMC Bioinformatics 13:160; Junemann et al. (2013) Nat. Biotechnol. 31(4):294-296; Glenn (2011) Mol. Ecol. Resour. 11(5):759-769; Thudi et al. (2012) Brief Funct. Genomics 11(1):3-11; herein incorporated by reference).

As discussed above, biotin ligases can be genetically targeted to a cellular region of interest to identify proteins and/or nucleic acids in the vicinity of tagged proteins within a specific subcellular compartment or region (e.g., the nucleus, endoplasmic reticulum, Golgi, mitochondria, mitochondria outer membrane, mitochondria inner membrane, mitochondria matrix space, chloroplasts, synaptic cleft, presynaptic membrane, postsynaptic membrane, dendritic spines, transport vesicles, regions of contact between mitochondria and endoplasmic reticulum, nuclear membrane, etc.) can be specifically tagged. In some embodiments, proteins within particular cell types (e.g., astrocytes, dendrocytes, stem cells, etc.) can be specifically tagged, for example, proteins within a specific cell type within a complex tissue, animal, or cell population. In some embodiments, proteins within particular macromolecular complexes (e.g., protein complexes such as ribosomes, replisome, transcription complex, spliceosome, DNA repair complex, fatty acid synthase, polyketide synthase, non-ribosomal peptide synthase, glutamate receptor signaling complex, neurexin-neuroligin signaling complex, etc.) can be tagged. In each context, the tagged proteins or protein-nucleic acid fusions can be analyzed (e.g., isolated and identified) to map protein and/or nucleic acid localization in specific cells, cellular compartments or regions, or macromolecular complexes of interest. This information can be used for research, diagnostic, therapeutic, and other applications.

For example, cells may be isolated from a patient, amplified or differentiated using IPS cell technology (induced pluripotent stem cell), contacted with a vector (e.g., a viral vector) that expresses a biotin ligase, for example, a biotin ligase fused to a localization signal effecting localization of the biotin ligase in a specific subcellular compartment. Labeling and/or crosslinking can be performed in the living cells, as described herein, and the resulting tagged proteins or protein-nucleic acid fusions can be analyzed, for example, to identify patient specific information that can be useful to assist in diagnostic, prognostic, and/or therapeutic decisions, and in drug screening assays.

In some embodiments, the reactive intermediate, once created, biotinylates (i.e., labels) proteins that are within the vicinity of the biotin ligase. The term "within the vicinity" refers to the spatial location around the enzyme and/or substrate that is labeled. Proteins that are further from the biotin ligase are generally labeled to a lesser extent than proteins that are closer to the biotin ligase. Proteins that are not within the vicinity of the biotin ligase are not exposed to the reactive intermediate and hence not labeled. Some proteins in the vicinity of the modified biotin ligase may fail to get labeled, e.g. if they are sterically buried or do not have any exposed residues capable of being biotinylated.

In some embodiments, in vivo protein tagging is performed with a biotin ligase that can be genetically targeted to any part of a live cell. In some embodiments, the biotin ligase is present and/or active in all regions of the cell. In some embodiments, the biotin ligase is present and/or active only in a subcellular compartment of the cell. In some embodiments, biotin substrate can be added or uncaged for the desired window of time, to permit precise temporal control of labeling. In some embodiments, it is preferable for the reactive species not to cross cell membranes, to allow mapping of membrane-bounded structures.

In some embodiments, a biotin ligase is engineered to be expressed and/or targeted in vivo or in situ to specific cells, cellular compartments (e.g., endoplasmic reticulum, Golgi apparatus, mitochondria, nucleus, the synaptic cleft, transport vesicles, etc.), and/or macromolecular complexes (e.g., protein complexes such as ribosomes, nuclear pore complex, fatty acid synthases) of interest. In some embodiments, a biotin ligase is engineered to tag proteins that are located within a limited distance of the biotin ligase. As a result, in some embodiments, proteins that are located within the targeted cell, cellular compartment, and/or macromolecular complex (e.g., protein complex) are specifically tagged relative to other proteins that are not located near the biotin ligase. It should be appreciated that the tagging process itself does not need to be protein specific. For example, in some embodiments, it is the specific localization of the biotin ligase that results in the specific tagging of a subset of proteins of interest. In some embodiments, proteins that are present within the vicinity of the biotin ligase may be tagged for further analysis. In some embodiments, all proteins present within the vicinity of the biotin ligase may be tagged. Various versions of the methodology offer a range of labeling radii, from about 500 nm to less than 10 nm, e.g., tagging radii of about 500 nm, about 400 nm, about 300 nm, about 250 nm, about 200 nm, about 100 nm, about 90 nm, about 80 nm, about 70 nm, about 60 nm, about 50 nm, about 40 nm, about 30 nm, about 20 nm, about 10 nm, about 5 nm, about 2.5 nm, or about 1 nm.

In some embodiments, the reactive intermediate produced by the biotin ligase is inactivated by contacting it with a quenching agent (e.g., water for an unstable reaction intermediate such as produced by biotin ligase). As a result, the reactive moiety can have a short half-life and only modify proteins that are located within a short distance of the site of production (the biotin ligase) before being inactivated. Accordingly, the zone of tagging can be limited by the diffusion rate and half-life of the reactive reaction intermediate.

The methods provided herein can also be used to map protein and/or nucleic acid localization in specific cell types within complex tissues or heterogeneous cell populations, or of specific subcellular structures or organelles within specific cells in complex tissues or populations. The methods are particularly useful for mapping subcellular localization of proteins and/or nucleic acids in rare cells within complex cell populations.

Maps of subcellular localization of proteins and/or nucleic acids can be developed not only for different cells, subcellular compartments, tissues, or organisms but also for cells, tissues, or organisms exposed to different conditions or environments. For example, cells or organisms exposed to different therapeutic agents, different concentrations of therapeutic agents, and/or combinations of therapeutic agents may be mapped and analyzed independently or compared against one another to examine changes occurring within a cell, tissue, or organism. Additionally, changes in protein and/or nucleic acid localization in cells, tissues, or organisms over time associated with diseased states can be monitored by comparison of mapped nucleic acid localization in cells, tissues, or organisms in diseased and normal (i.e. healthy control, not having the disease) states.

In certain embodiments, a map of the subcellular localization of proteins and/or nucleic acids molecules, produced by the methods described herein, is compared to a reference map. For example, a map of the subcellular localization of the protein and/or RNA molecules from a cell that is exposed to a test condition can be compared to a reference map of a cell that is not exposed to the test condition. A test condition may comprise, for example, exposing the cell to a drug, a ligand for a receptor, a hormone, a second messenger, a pathogen, or a genetic modification. For example, the cell can be genetically modified by introducing a vector, short hairpin RNA (shRNA), small interfering RNA (siRNA), microRNA (miRNA), or CRISPR-associated system into the cell. Alternatively, a test condition may comprise exposing the cell to a change in temperature, growth media, membrane potential, or osmotic pressure. In certain embodiments, the cell is exposed to a test condition prior to said contacting the cell with the tagging substrate or the cross-linking agent.

Maps of subcellular localization of proteins and/or nucleic acids can also be developed for cells, subcellular compartments, tissues, or organisms at different developmental stages. For example, a map of the subcellular localization of proteins and/or nucleic acids can be compared to reference maps for cells, subcellular compartments, tissues, or organisms at the same or different developmental stages.

B. Nucleic Acids Encoding Modified Biotin Ligases

Nucleic acids encoding modified biotin ligases or biologically active fragments thereof can be used for production of biotin ligases and proximity-dependent biotinylation of proteins inside cells and whole live organisms. Coding sequences for the modified biotin ligases can be isolated and/or synthesized and cloned into any suitable vector or replicon for expression in a suitable host cell or host subject. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention. The ability of constructs to produce modified biotin ligases inside host cells or organisms can be empirically determined (e.g., see Examples for a description of methods of detecting biotinylated proteins with streptavidin-phycoerythrin).

Expression cassettes typically include control elements operably linked to the coding sequence, which allow for the expression of the gene in vivo in the subject species. In certain embodiments, the nucleic acid encoding the biotin ligase is under transcriptional control of a promoter. A "promoter" refers to a DNA sequence recognized by the synthetic machinery of the cell, or introduced synthetic machinery, required to initiate the specific transcription of a gene. The term promoter will be used here to refer to a group of transcriptional control modules that are clustered around the initiation site for a bacterial RNA polymerase or eukaryotic RNA polymerase (e.g., RNA polymerase I, II, or III). For example, typical promoters for mammalian cell expression include the SV40 early promoter, a CMV promoter such as the CMV immediate early promoter, the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. Typical promoters for bacterial expression include the Tac, RecA, LacZ, pBAD, OXB1-20, OXB1, ctc, gsiB, Pspv, and T7 promoters (see, e.g., Goldstein et al. (1995) Biotechnol. Annu. Rev. 1:105-128). Examples of promoters for expression in *Drosophila* include COPIA, ACT5C, and the heat shock protein 70 (HSP70) promoter. Examples of promoters for expression in plants include the CaMV 35S, Xa27, FMV, opine promoters, plant ubiquitin promoter (Ubi), rice actin 1 promoter (Act-1), maize alcohol dehydrogenase 1 promoter (Adh-1), and various other plant pathogen, synthetic, and native promoters (see, e.g., Liu et al. (2016) Curr. Opin. Biotechnol. 37:36-44, Dey et al. (2015) Planta 242(5):1077-1094, Jeong et al. (2015) J. Integr. Plant Biol. 57(11):913-924, Hernandez-Garcia et al. (2014) Plant Sci. 217-218:109-119). These and other promoters can be obtained from commercially available vectors, using techniques well known in the art.

See, e.g., Sambrook et al., supra. Enhancer elements may be used in association with a promoter to increase expression levels of the constructs.

An expression vector for expressing a biotin ligase comprises a promoter "operably linked" to a polynucleotide encoding the biotin ligase. The phrase "operably linked" or "under transcriptional control" as used herein means that the promoter is in the correct location and orientation in relation to a polynucleotide to control the initiation of transcription by RNA polymerase and expression of the polynucleotide. In some embodiments, the expression of the modified biotin ligase is under the control of a cell type or tissue-specific promoter which drives the expression of the biotin ligase in a specific type of cell or tissue. Tissue-specific and/or cell type-specific promoters include, but are not limited to, the albumin promoter (e.g., liver-specific albumin promoter; see Pinkert et al. (1987) Genes Dev 1:268-277); lymphoid-specific promoters (Calame and Eaton (1988) Adv Immunol 43:235-275), such as promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748); neuron-specific promoters (e.g., the neurofilament promoter; see Byrne and Ruddle (1989) PNAS 86:5473-5477); pancreas-specific promoters (Edlund et al. (1985) Science 230:912-916); mammary gland-specific promoters (e.g., milk whey promoter; see U.S. Pat. No. 4,873,316 and European Application Publication No. 264,166); and developmentally regulated promoters, e.g., the murine hox promoters (Kessel and Gruss (1990) Science 249:374-379) and the alpha-fetoprotein promoter (Campes and Tilghman (1989) Genes Dev 3:537-546).

Typically, transcription terminator/polyadenylation signals may also be present in the expression construct. Bacterial terminator sequences may include Rho-independent or Rho-dependent transcription terminator sequences. Examples of eukaryotic terminator sequences include, but are not limited to, those derived from SV40, as described in Sambrook et al., supra, bovine growth hormone terminator sequence (see, e.g., U.S. Pat. No. 5,122,458), and plant terminator sequences such as the *Agrobacterium* nopaline synthase (NOS) terminator (see, e.g., International Patent Application Publication No. WO 2013/012729, Chung et al. (2005) Trends Plant Sci. 10(8):357-361). Additionally, 5'-UTR sequences can be placed adjacent to the coding sequence in order to enhance expression of the same. Such sequences may include UTRs comprising an internal ribosome entry site (IRES). Inclusion of an IRES permits the translation of one or more open reading frames from a vector. The IRES element attracts a eukaryotic ribosomal translation initiation complex and promotes translation initiation. See, e.g., Kaufman et al., *Nuc. Acids Res.* (1991) 19:4485-4490; Gurtu et al., *Biochem. Biophys. Res. Comm.* (1996) 229:295-298; Rees et al., *BioTechniques* (1996) 20:102-110; Kobayashi et al., *BioTechniques* (1996) 21:399-402; and Mosser et al., *BioTechniques* (1997 22 150-161.

Enhancer elements may also be used herein to increase expression levels of the constructs. Examples include the SV40 early gene enhancer, as described in Dijkema et al., EMPO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777 and elements derived from human CMV, as described in Boshart et al., Cell (1985) 41:521, such as elements included in the CMV intron A sequence.

Once complete, the constructs encoding modified biotin ligases can be administered to a subject (i.e., host organism) using standard gene delivery protocols. Methods for gene delivery are known in the art. See, e.g., U.S. Pat. Nos. 5,399,346, 5,580,859, 5,589,466. Genes can be delivered either directly to a host subject or, alternatively, delivered ex vivo, to cells derived from the subject and the cells reimplanted in the subject.

A number of viral based systems have been developed for gene transfer into cells. These include adenoviruses, retroviruses (γ-retroviruses and lentiviruses), poxviruses, adeno-associated viruses, baculoviruses, and herpes simplex viruses (see e.g., Warnock et al. (2011) Methods Mol. Biol. 737:1-25; Walther et al. (2000) Drugs 60(2):249-271; and Lundstrom (2003) Trends Biotechnol. 21(3):117-122; herein incorporated by reference).

For example, retroviruses provide a convenient platform for gene delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; Boris-Lawrie and Temin (1993) Cur. Opin. Genet. Develop. 3:102-109; and Ferry et al. (2011) Curr Pharm Des. 17(24):2516-2527). Lentiviruses are a class of retroviruses that are particularly useful for delivering polynucleotides to cells because they are able to infect both dividing and nondividing cells (see e.g., Lois et al (2002) Science 295:868-872; Durand et al. (2011) Viruses 3(2):132-159; herein incorporated by reference).

A number of adenovirus vectors have also been described. Unlike retroviruses which integrate into the host genome, adenoviruses persist extrachromosomally thus minimizing the risks associated with insertional mutagenesis (Haj-Ahmad and Graham, J. Virol. (1986) 57:267-274; Bett et al., J. Virol. (1993) 67:5911-5921; Mittereder et al., Human Gene Therapy (1994) 5:717-729; Seth et al., J. Virol. (1994) 68:933-940; Barr et al., Gene Therapy (1994) 1:51-58; Berkner, K. L. BioTechniques (1988) 6:616-629; and Rich et al., Human Gene Therapy (1993) 4:461-476). Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., Molec. Cell. Biol. (1988) 8:3988-3996; Vincent et al., Vaccines 90 (1990) (Cold Spring Harbor Laboratory Press); Carter, B. J. Current Opinion in Biotechnology (1992) 3:533-539; Muzyczka, N. Current Topics in Microbiol. and Immunol. (1992) 158:97-129; Kotin, R. M. Human Gene Therapy (1994) 5:793-801; Shelling and Smith, Gene Therapy (1994) 1:165-169; and Zhou et al., J. Exp. Med. (1994) 179:1867-1875.

Another vector system useful for delivering the polynucleotides of the present invention is the enterically administered recombinant poxvirus vaccines described by Small, Jr., P. A., et al. (U.S. Pat. No. 5,676,950, issued Oct. 14, 1997, herein incorporated by reference).

Additional viral vectors which will find use for delivering the nucleic acid molecules encoding modified biotin ligases of interest include those derived from the pox family of viruses, including vaccinia virus and avian poxvirus. By way of example, vaccinia virus recombinants expressing modified biotin ligases can be constructed as follows. The DNA encoding the particular modified biotin ligase protein coding sequence is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the coding sequences of interest into the viral genome. The resulting TK-recombinant can be selected by culturing the cells in the presence of 5-bromodeoxyuridine and picking viral plaques resistant thereto.

Alternatively, avipoxviruses, such as the fowlpox and canarypox viruses, can also be used to deliver the genes. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with. respect to the production of vaccinia viruses. See, e.g., WO 91/12882; WO 89/03429; and WO 92/03545.

Molecular conjugate vectors, such as the adenovirus chimeric vectors described in Michael et al., J. Biol. Chem. (1993) 268:6866-6869 and Wagner et al., Proc. Natl. Acad. Sci. USA (1992) 89:6099-6103, can also be used for gene delivery.

Members of the Alphavirus genus, such as, but not limited to, vectors derived from the Sindbis virus (SIN), Semliki Forest virus (SFV), and Venezuelan Equine Encephalitis virus (VEE), will also find use as viral vectors for delivering the polynucleotides of the present invention. For a description of Sindbis-virus derived vectors useful for the practice of the instant methods, see, Dubensky et al. (1996) J. Virol. 70:508-519; and International Publication Nos. WO 95/07995, WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998, both herein incorporated by reference. Particularly preferred are chimeric alphavirus vectors comprised of sequences derived from Sindbis virus and Venezuelan equine encephalitis virus. See, e.g., Perri et al. (2003) J. Virol. 77: 10394-10403 and International Publication Nos. WO 02/099035, WO 02/080982, WO 01/81609, and WO 00/61772; herein incorporated by reference in their entireties.

A vaccinia based infection/transfection system can be conveniently used to provide for inducible, transient expression of the coding sequences of interest (for example, a modified biotin ligase expression cassette) in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation products. See, e.g., Elroy-Stein and Moss, Proc. Natl. Acad. Sci. USA (1990) 87:6743-6747; Fuerst et al., Proc. Natl. Acad. Sci. USA (1986) 83:8122-8126.

As an alternative approach to infection with vaccinia or avipox virus recombinants, or to the delivery of genes using other viral vectors, an amplification system can be used that will lead to high level expression following introduction into host cells. Specifically, a T7 RNA polymerase promoter preceding the coding region for T7 RNA polymerase can be engineered. Translation of RNA derived from this template will generate T7 RNA polymerase which in turn will transcribe more template. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, J. Mol. Biol. (1986) 189:113-130; Deng and Wolff, Gene (1994) 143:245-249; Gao et al., Biochem. Biophys. Res. Commun. (1994) 200:1201-1206; Gao and Huang, Nuc. Acids Res. (1993) 21:2867-2872; Chen et al., Nuc. Acids Res. (1994) 22:2114-2120; and U.S. Pat. No. 5,135, 855.

The synthetic expression cassette of interest can also be delivered without a viral vector. For example, the synthetic expression cassette can be packaged as DNA or RNA in liposomes prior to delivery to the subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, Biochim. Biophys. Acta. (1991.) 1097:1-17; Straubinger et al., in Methods of Enzymology (1983), Vol. 101, pp. 512-527.

Liposomal preparations for use in the present invention include cationic (positively charged), anionic (negatively charged) and neutral preparations, with cationic liposomes particularly preferred. Cationic liposomes have been shown to mediate intracellular delivery of plasmid DNA (Felgner et al., Proc. Natl. Acad. Sci. USA (1987) 84:7413-7416); mRNA (Malone et al., Proc. Natl. Acad. Sci. USA (1989) 86:6077-6081); and purified transcription factors (Debs et al., J. Biol. Chem. (1990) 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner et al., Proc. Natl. Acad. Sci. USA (1987) 84:7413-7416). Other commercially available lipids include (DDAB/DOPE) and DOTAP/DOPE (Boerhinger). Other cationic liposomes can be prepared from readily available materials using techniques well known in the art. See, e.g., Szoka et al., Proc. Natl. Acad. Sci. USA (1978) 75:4194-4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as, from Avanti Polar Lipids (Birmingham, AL), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., in METHODS OF IMMUNOLOGY (1983), Vol. 101, pp. 512-527; Szoka et al., Proc. Natl. Acad. Sci. USA (1978) 75:4194-4198; Papahadjopoulos et al., Biochim. Biophys. Acta (1975) 394:483; Wilson et al., Cell (1979) 17:77); Deamer and Bangham, Biochim. Biophys. Acta (1976) 443:629; Ostro et al., Biochem. Biophys. Res. Commun. (1977) 76:836; Fraley et al., Proc. Natl. Acad. Sci. USA (1979) 76:3348); Enoch and Strittmatter, Proc. Natl. Acad. Sci. USA (1979) 76:145); Fraley et al., J. Biol. Chem. (1980) 255:10431; Szoka and Papahadjopoulos, Proc. Natl. Acad. Sci. USA (1978) 75:145; and Schaefer-Ridder et al., Science (1982) 215:166.

The DNA and/or polypeptide(s) can also be delivered in cochleate lipid compositions similar to those described by Papahadjopoulos et al., Biochim. Biophys. Acta. (1975) 394:483-491. See, also, U.S. Pat. Nos. 4,663,161 and 4,871,488.

The expression cassette of interest may also be encapsulated, adsorbed to, or associated with, particulate carriers. Examples of particulate carriers include those derived from a polymethyl methacrylate polymers, as well as microparticles derived from poly(lactides) and poly(lactide-co-glycolides), known as PLG. See, e.g., Jeffery et al., Pharm. Res. (1993) 10:362-368; McGee J. P., et al., J Microencapsul. 14(2):197-210, 1997; O'Hagan D. T., et al., Vaccine 11(2):149-54, 1993.

Furthermore, other particulate systems and polymers can be used for the in vivo or ex vivo delivery of the nucleic acid of interest. For example, polymers such as polylysine, polyarginine, polyornithine, spermine, spermidine, as well as conjugates of these molecules, are useful for transferring a nucleic acid of interest. Similarly, DEAE dextran-mediated transfection, calcium phosphate precipitation or precipitation using other insoluble inorganic salts, such as strontium phosphate, aluminum silicates including bentonite and kaolin, chromic oxide, magnesium silicate, talc, and the like, will find use with the present methods. See, e.g., Felgner, P. L., Advanced Drug Delivery Reviews (1990) 5:163-187, for a review of delivery systems useful for gene transfer. Peptoids (Zuckerman, R. N., et al., U.S. Pat. No. 5,831,005, issued Nov. 3, 1998, herein incorporated by reference) may also be used for delivery of a construct of the present invention.

Additionally, biolistic delivery systems employing particulate carriers such as gold and tungsten, are especially useful for delivering synthetic expression cassettes of the present invention. The particles are coated with the synthetic expression cassette(s) to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744. Also, needle-less injection systems can be used (Davis, H. L., et al, Vaccine 12:1503-1509, 1994; Bioject, Inc., Portland, Oreg.).

Recombinant vectors carrying a synthetic expression cassette of the present invention are formulated into compositions for delivery to a host subject. The compositions will comprise an "effective amount" of the nucleic acid of interest such that a sufficient amount of the modified biotin ligase can be produced in vivo for detectable proximity-dependent biotinylation of proteins in the host subject to which it is administered. An appropriate effective amount can be readily determined by one of skill in the art.

The compositions will generally include one or more "pharmaceutically acceptable excipients or vehicles" such as water, saline, glycerol, polyethyleneglycol, hyaluronic acid, ethanol, etc. Additionally, auxiliary substances, such as wetting or emulsifying agents, pH buffering substances, surfactants and the like, may be present in such vehicles. Certain facilitators of nucleic acid uptake and/or expression can also be included in the compositions or coadministered.

Once formulated, the compositions of the invention can be administered directly to the subject (e.g., as described above) or, alternatively, delivered ex vivo, to cells derived from the subject, using methods such as those described above. For example, methods for the ex vivo delivery and reimplantation of transformed cells into a subject are known in the art and can include, e.g., dextran-mediated transfection, calcium phosphate precipitation, polybrene mediated transfection, lipofectamine and LT-1 mediated transfection, protoplast fusion, electroporation, encapsulation of the polynucleotide(s) in liposomes, and direct microinjection of the DNA into nuclei.

Direct delivery of synthetic expression cassette compositions in vivo will generally be accomplished with or without viral vectors, as described above, by injection using either a conventional syringe, needless devices such as Bioject or a gene gun, such as the Accell gene delivery system (PowderMed Ltd, Oxford, England).

In some embodiments, a linear DNA molecule encoding the biotin ligase is used for gene delivery. Rather than cloning the linear DNA molecule into a vector prior to transformation, cells can be transformed with an empty vector together with the linear DNA molecule encoding the biotin ligase, which subsequently integrates into the vector in vivo, e.g., by homologous recombination.

Once an expression construct has been delivered into a cell, the nucleic acid encoding the biotin ligase may be positioned and expressed at different sites. In certain embodiments, the nucleic acid encoding the gene is stably integrated into the genome of the cell via homologous recombination. This integration may be in the cognate location and orientation (gene replacement), within a gene (gene disruption), or in a random, non-specific location (gene augmentation). Integration of a construct at a target locus that disrupts a gene may be acceptable as long as the gene disruption does not interfere with cell growth or survival of a host organism. In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In another embodiment, the expression construct is used to produce a transgenic non-human animal comprising cells that express a modified biotin ligase. This may be accomplished by methods known in the art, such as by introduction of a nucleic acid encoding the modified biotin ligase into a fertilized egg, an embryo, or a blastocyst and subsequent implantation in an animal for gestation followed by birth.

Transgenic animals may be confirmed as containing a nucleic acid construct encoding a modified biotin ligase by a variety of methods, including immunostaining the biotin ligase or sampling of cells for the presence of biotinylated proteins in the animal. The progeny of such transgenic animals may also be transgenic and capable of producing the modified biotin ligase as long as the progeny retain an expression construct encoding the modified biotin ligase. Alternatively, nucleic acid constructs encoding modified biotin ligases described herein may be introduced into cells of an animal while in utero.

C. Kits

The modified biotin ligases described herein or nucleic acids encoding them may be included in kits with suitable instructions and other necessary reagents for proximity labeling of proteins. Kits may also include the substrates, ATP and biotin (or a derivative thereof such as desthiobiotin), and other reagents that are required for proximity labeling. The kit may further include a biotin-binding protein such as avidin or streptavidin, which may be immobilized on a solid support (e.g., magnetic beads, latex beads) for isolation of biotinylated proteins. Alternatively or additionally, the kit may contain a biotin-binding protein conjugated to a detectable label (e.g., streptavidin-fluorophore conjugate) for imaging biotinylated proteins in a cell. The kit will normally contain in separate containers the different agents, including modified biotin ligases, substrates (e.g., ATP and biotin), biotin-binding proteins, and other reagents that are required for proximity labeling. Instructions (e.g., written, CD-ROM, DVD, Blu-ray, flash drive, digital download, etc.) for proximity labeling of protein usually will be included in the kit. The kit can also contain, depending on the particular assay used, other packaged reagents and materials (e.g., crosslinking agents, wash buffers, and the like). Proximity labeling of proteins, as described herein, can be conducted using these kits.

In certain embodiments, the kit comprises a modified biotin ligase comprising an amino acid sequence selected from the group consisting of SEQ ID NO:11 and SEQ ID NO:13, or a sequence displaying at least about 80-100% sequence identity thereto, including any percent identity within this range, such as 80, 81, 82, 83, 84, 85, 86, 87, 88, 89, 90, 91, 92, 93, 94, 95, 96, 97, 98, 99% sequence identity thereto, wherein the biotin ligase comprises at least the Q65P, M209V, V160A, S150G, L151P, I305V, I87V, R118S, T192A, K194I, E140K, and Q141R amino acid substitutions and is capable of proximity-dependent biotinylation of proteins. In another embodiment, the kit further comprises biotin and ATP. In another embodiment, the kit further comprises a biotin-binding protein, such as streptavidin or avidin, which may be immobilized on a solid support (e.g., magnetic or latex beads) or conjugated to a detectable label.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Directed Evolution of TurboID for Efficient Proximity Labeling in Living Cells and Organisms Here, we report the directed evolution of E. coli biotin ligase to give two promiscuous variants, TurboID (35 kD) and miniTurbo (28 kD). Both are 7-26-fold more active than BioID, enabling proteomic labeling in just 10 minutes instead of the 18 hours commonly used for BioID. Furthermore, in 1 hour, TurboID can produce more biotinylated material than BioID produces in 18 hours. This enhanced activity also enabled us to perform biotin-based PL in new settings, including yeast, worm, and flies. Hence TurboID and miniTurbo broaden the scope of PL and should enable new discoveries related to spatial proteomes in living cells and organisms.

Results

Figure 4:
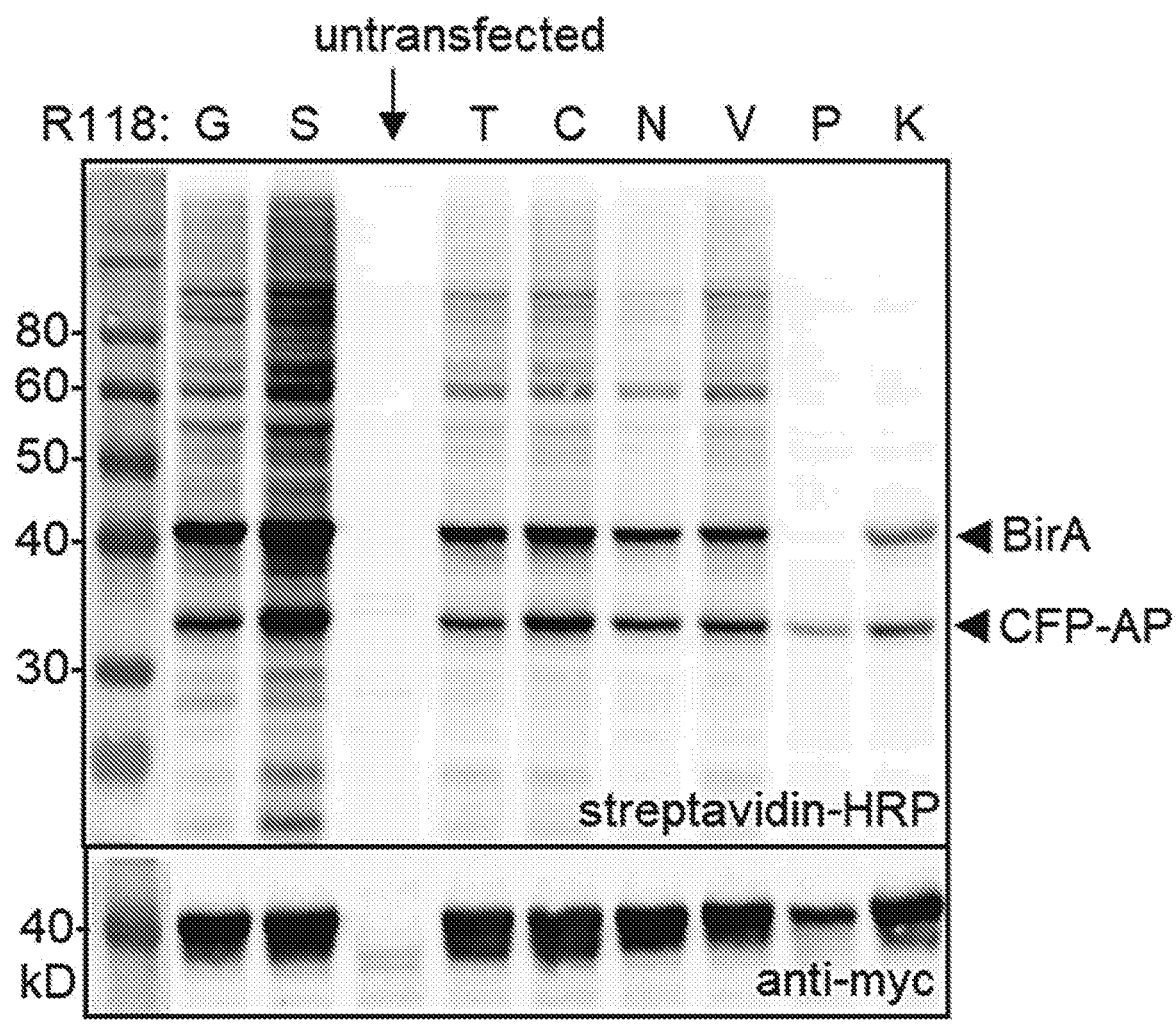
FIG. 4 shows testing mutations at R118 of BirA. BirA ligases with the indicated mutations were transiently expressed as NES (nuclear export signal) fusions in the HEK cytosol. All samples were co-transfected with AP-CFP (acceptor peptide fused to cyan fluorescent protein), which is site-specifically biotinylated by BirA[1]. 50 μM exogenous biotin was added to the cells for 18 hours, then whole cell lysates were analyzed by streptavidin-IRP blotting. Ligase expression was detected by anti-myc blotting. Self-biotinylation bands are indicated ("BirA"). This experiment was performed once, but comparison of BirA-R118G to BirA-R118S under these conditions was repeated once.

In an initial 2004 report, Cronan et al. tested three variants of E. coli biotin ligase and found that BirA-R118G (BioID) was the most promiscuous[4]. We started our engineering efforts by examining 7 other mutations at the R118 position, and found that R118S is ~2-fold more active than BioID (FIG. 4). Hence, we selected BirA-R118S as our template for directed evolution.

Figure 1B:
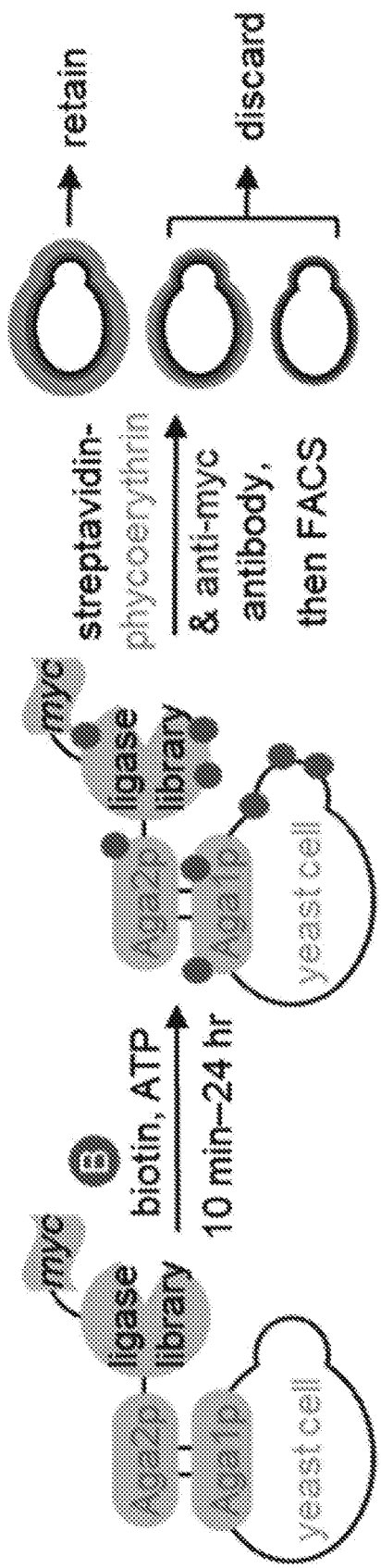

In previous work, we used yeast display as our platform for directed evolution of APEX2[3] and split-HRP[23] enzymes. When coupled to fluorescence activated cell sorting (FACS), yeast display provides outstanding dynamic range, enabling separation of highly active enzyme mutants from moderately active ones. To employ this platform for directed evolution of promiscuous biotin ligase, we fused BirA-R118S or a library of R118S-derived mutants (generated by error prone PCR) to the yeast cell surface mating protein Aga2p. We incubated the yeast cells with biotin and ATP for 18 hours to enable ligase-catalyzed PL to occur on the surface of each cell. We then stained the cells with streptavidin-phycoerythrin to visualize biotinylation sites, and anti-myc antibody to quantify ligase expression level, before two dimensional FACS sorting as shown in FIG. 1B.

Figure 1C:
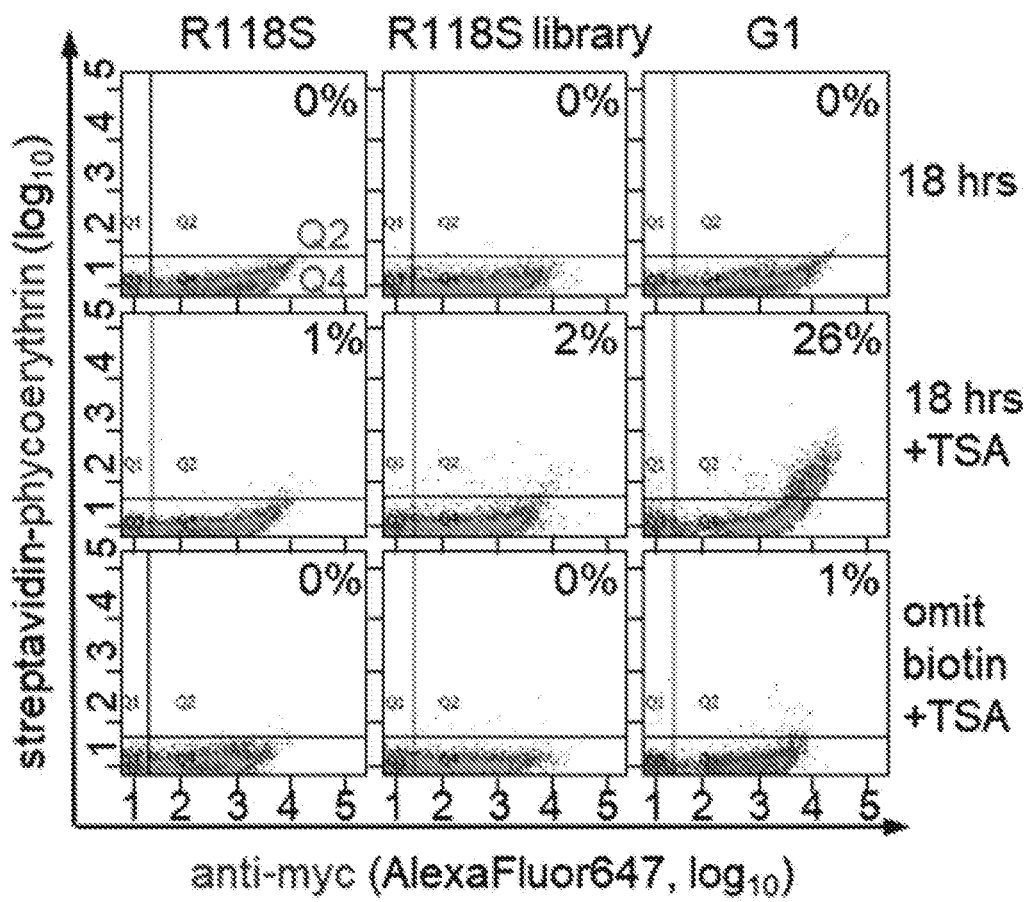
Figure 5A:
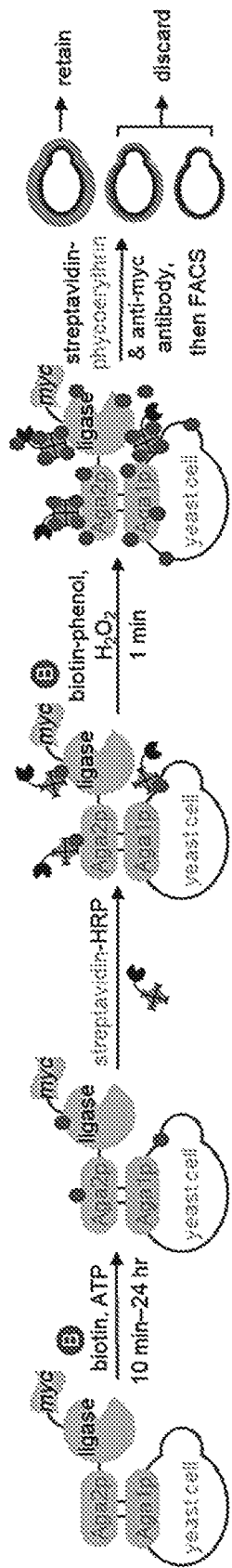
FIGS. 5A-5J show evolution of TurboID and miniTurbo on yeast.
Figure 5B:
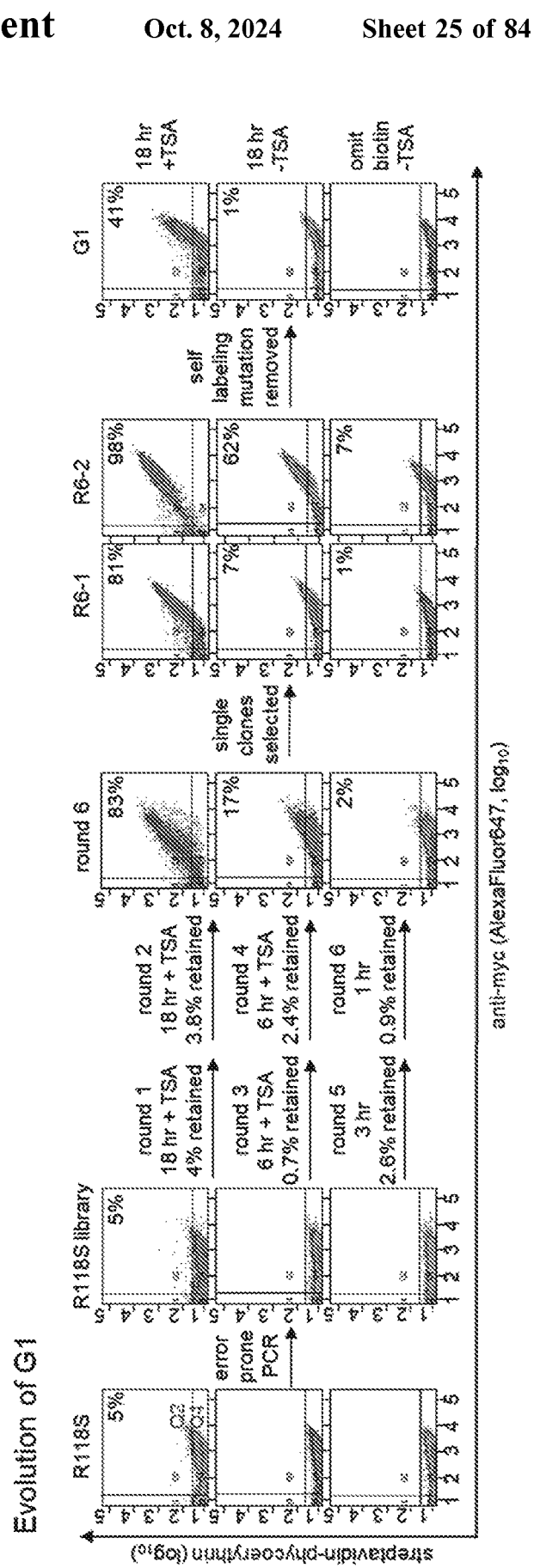

FIG. 1C shows that biotinylation activity was undetectable by FACS for both BirA-R118S and our mutant library on the yeast surface, even with a labeling time of 18 hours. We could not proceed with a selection if none of the clones in our library showed activity above background. To increase the sensitivity of our assay, we explored amplification of biotin signal using the "tyramide signal amplification (TSA)" approach[24]. Instead of directly staining for biotinylation sites on the yeast surface with streptavidin-phycoerythrin, we first stained with streptavidin-horseradish peroxidase conjugate, then reacted with biotin-phenol to create more biotinylation sites[2], and finally stained with streptavidin-phycoerythrin (FIG. 5A). This approach made it possible to detect a small amount of signal over background (FIG. 1C), and allowed us to begin directed evolution. We performed our first four rounds of selection using this amplification procedure, and reduced the labeling time gradually from 18 hours to 6 hours. After round four, activity of the pool was sufficient to omit the amplification step, and we again decreased our biotin labeling time from 3 hours to 1 hour (FIG. 5B).

Figure 5C:
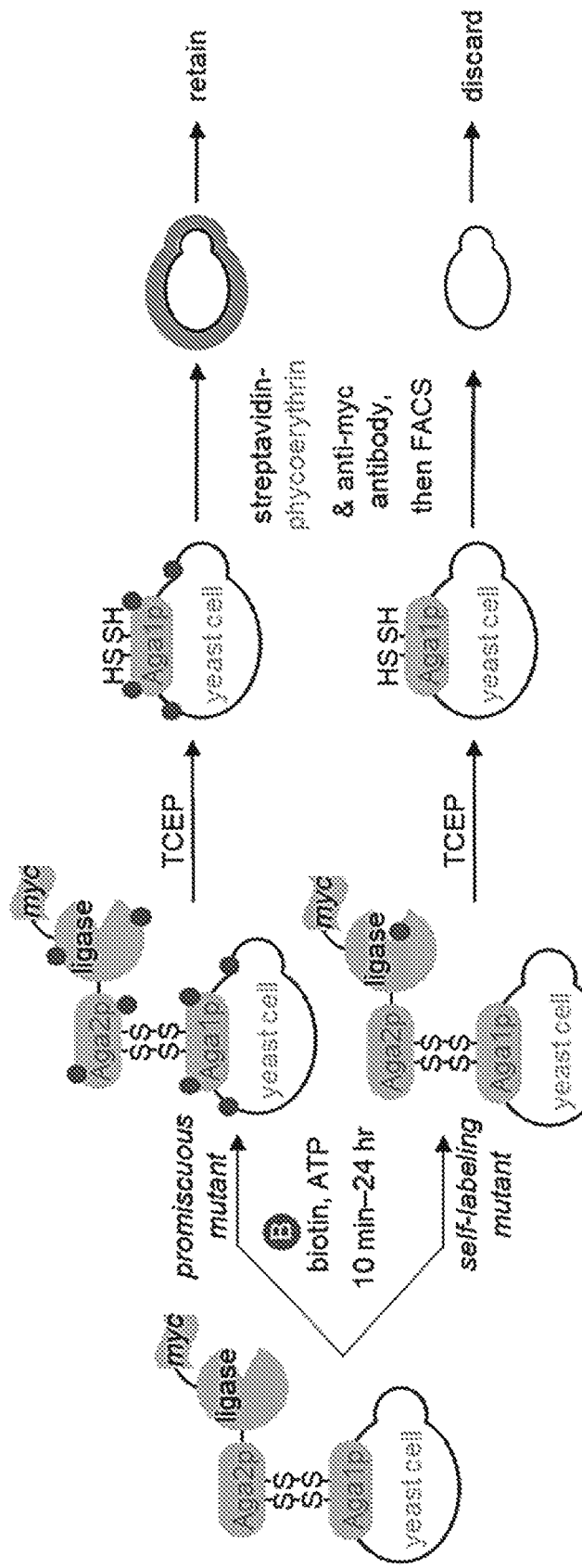
Figure 5D:
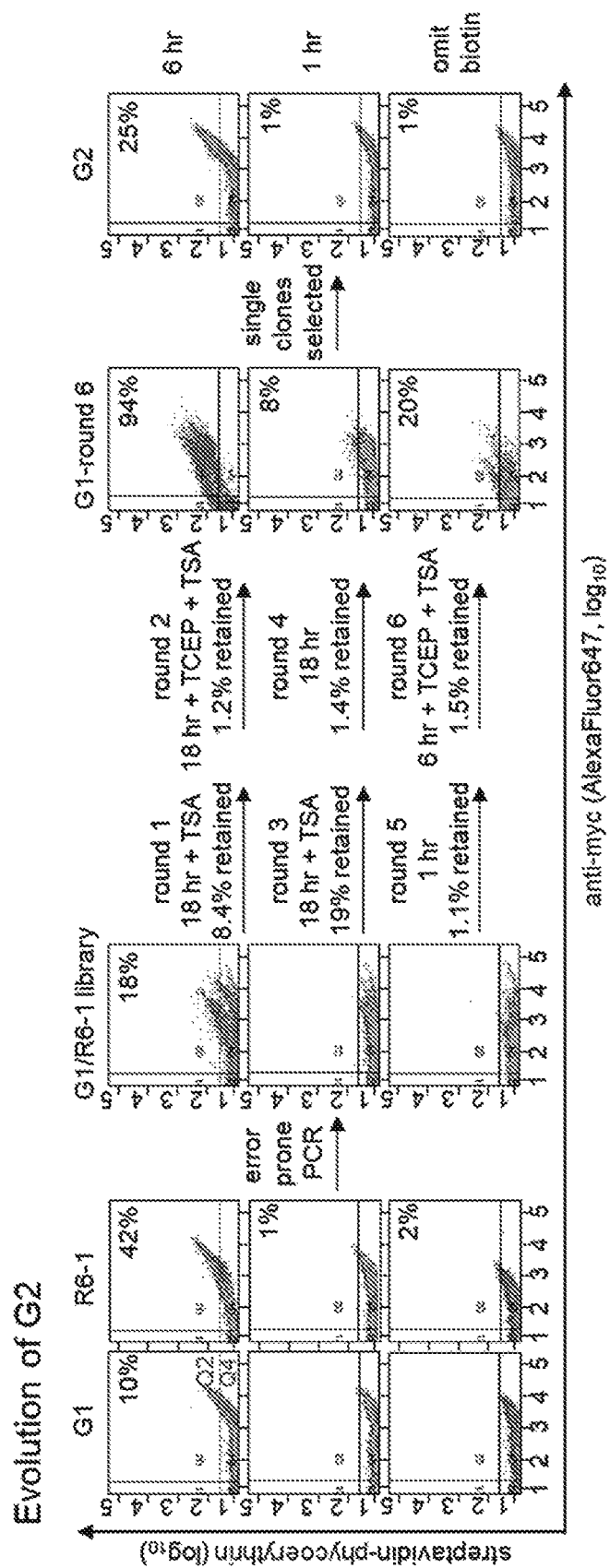

Characterization of BirA mutant clones after six rounds of selection revealed that we had enriched some with high self-biotinylation activity. For example, clone R6-2 contains an E313K mutation that points directly into the BirA active site. We used mutagenesis to remove this lysine, and found that the resulting mutant, now called "G1", still had ~8-fold greater promiscuous biotinylation activity than our starting template, BirA-R118S (FIG. 5B). Hence, we used G1 together with another clone, R6-1, as starting templates for a second library and a second generation of directed evolution. This time, to avoid enriching mutants with strong self-biotinylation, we treated the yeast, in some rounds of selection, with the reducing agent TCEP prior to streptavidin and myc staining, in order to cleave the Agalp-Aga2p disulfide bonds that retain clones on the yeast surface (FIG. 5C). Six rounds of selection produced clone G2, with six mutations, as our best ligase mutant (FIG. 5D; see Methods for additional details on selection conditions, and Table 1 for sequences G1, G2, and other key clones).

Figure 5E:
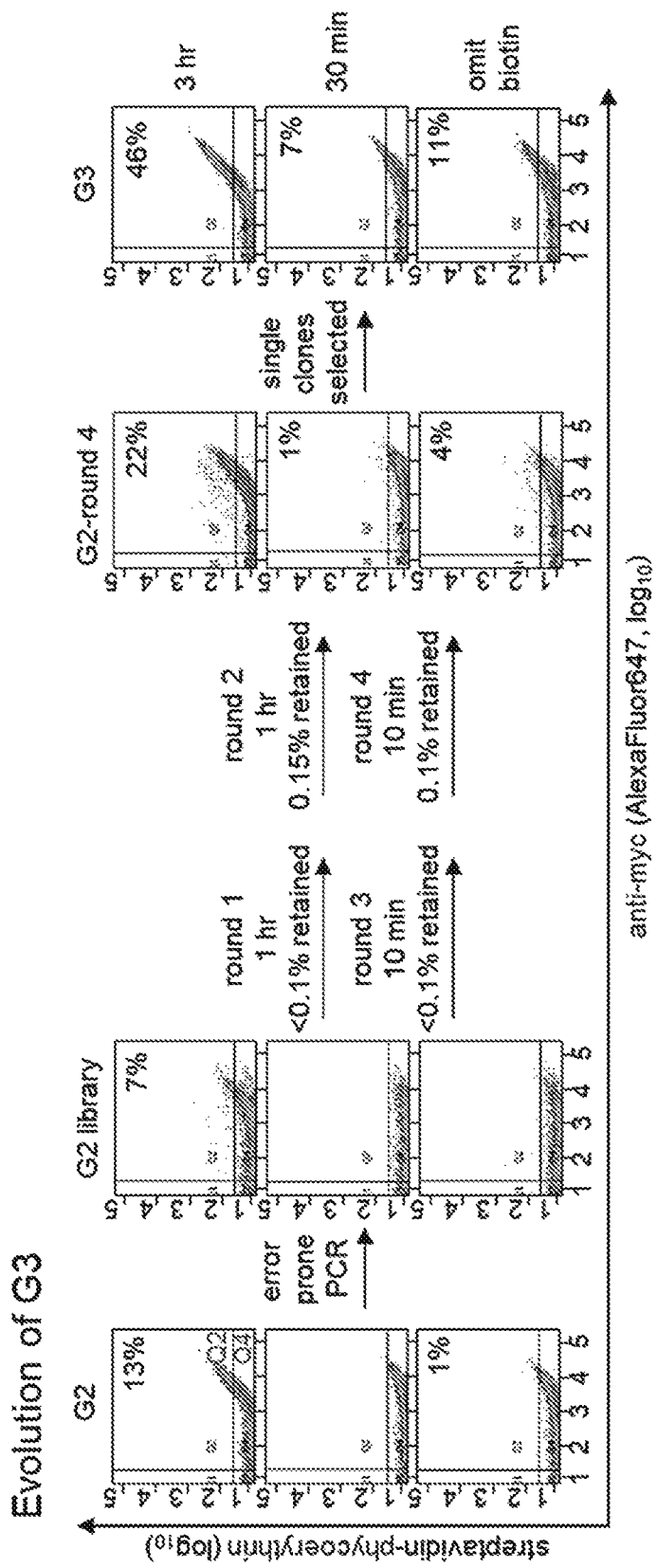
Figure 5F:
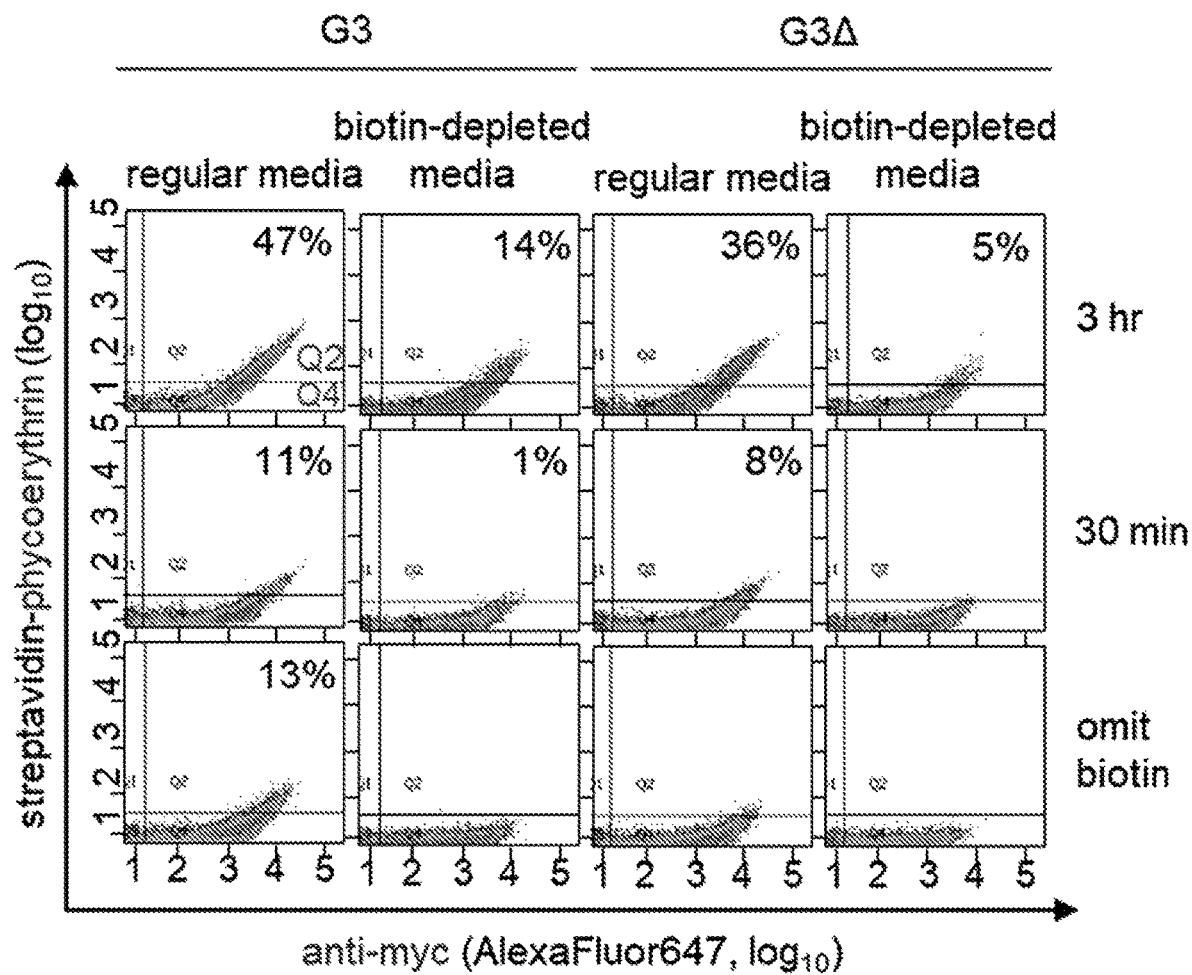

We continued with a third generation of directed evolution. Over four rounds, biotin labeling time was reduced to 10 minutes. The resulting winner, G3, was ~17-fold more active than our starting template, BirA-R118S, but we noticed considerable activity on the yeast surface even without exogenous biotin addition (FIG. 5E). This suggests that G3 had evolved higher affinity for biotin and was able to utilize the low levels of biotin present in yeast culture media. An experiment in biotin-depleted media confirmed this hypothesis (FIG. 5F). We recognized the importance of remedying this problem because a BirA mutant that is capable of biotinylating prior to exogenous biotin addition prevents precise temporal control over the PL reaction. Starting from G3, we took two divergent paths.

Figure 1D:
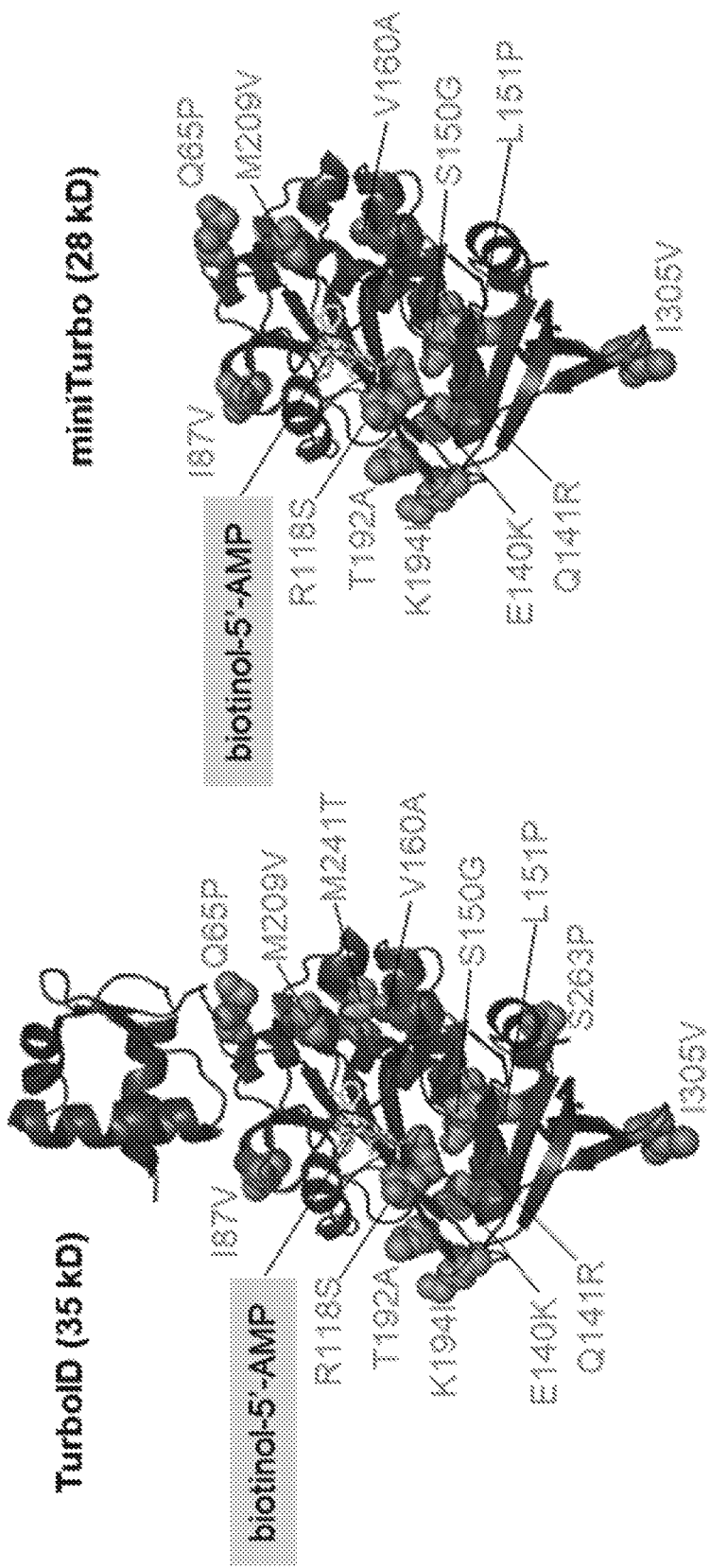
Figure 5G:
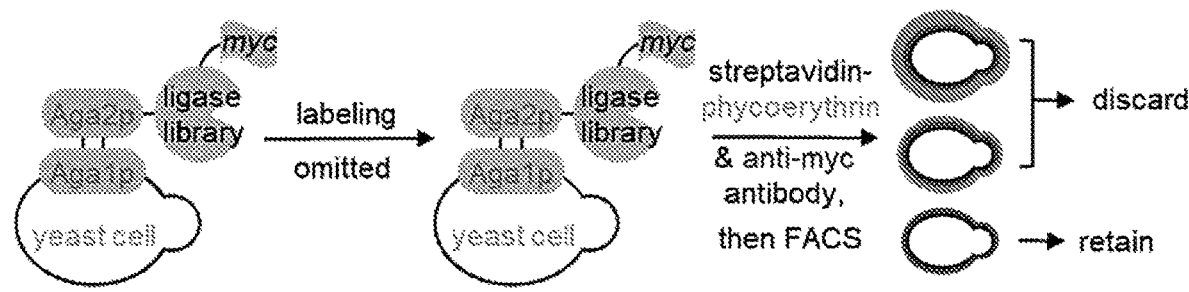
Figure 5H:
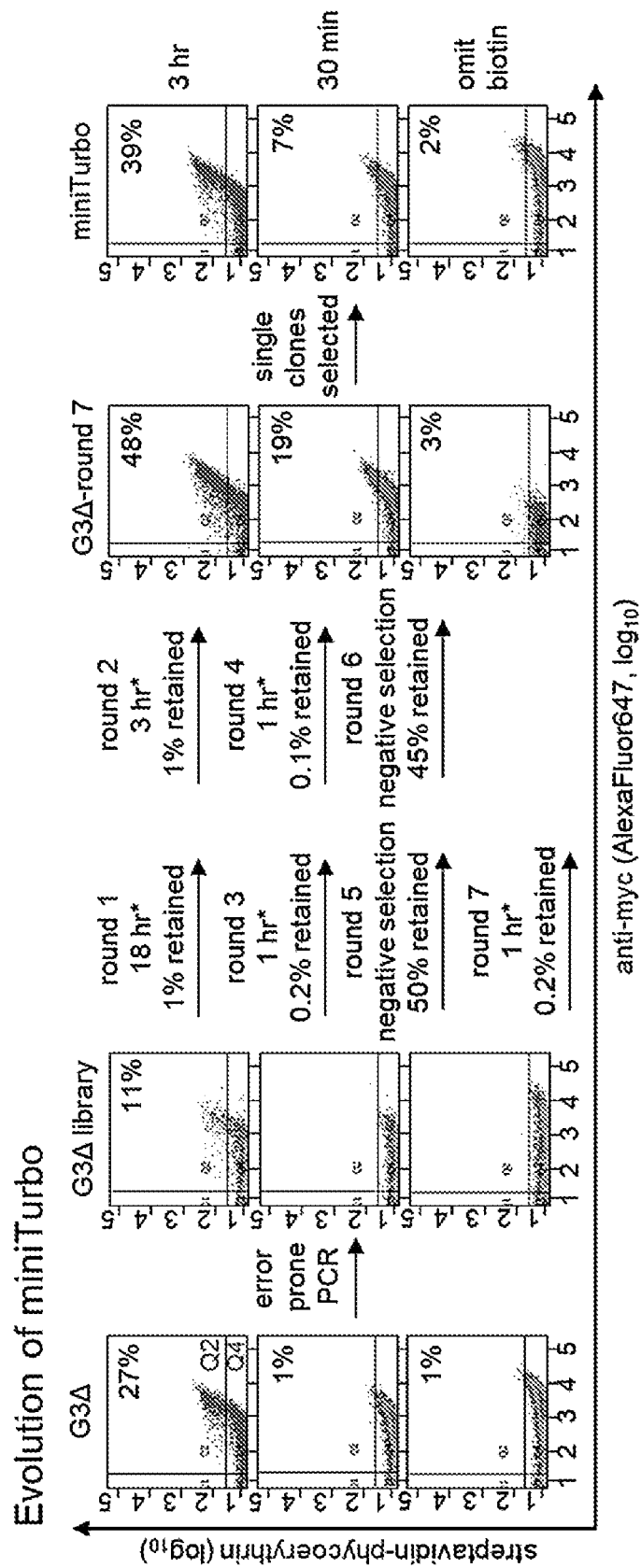

For one path, we conducted a fourth generation of directed evolution, starting from a G3 mutant with its N-terminal domain (residues 1-63) deleted ("G3Δ"). FIG. 5F shows that this deletion alone reduces G3's affinity for biotin, consistent with previous studies[15]. We conducted seven rounds of selection, including negative selections in which exogenous biotin was withheld (FIG. 5G). The result was miniTurbo, with 12 mutations relative to wild-type BirA (FIG. 5H and FIG. 1D).

Figure 5I:
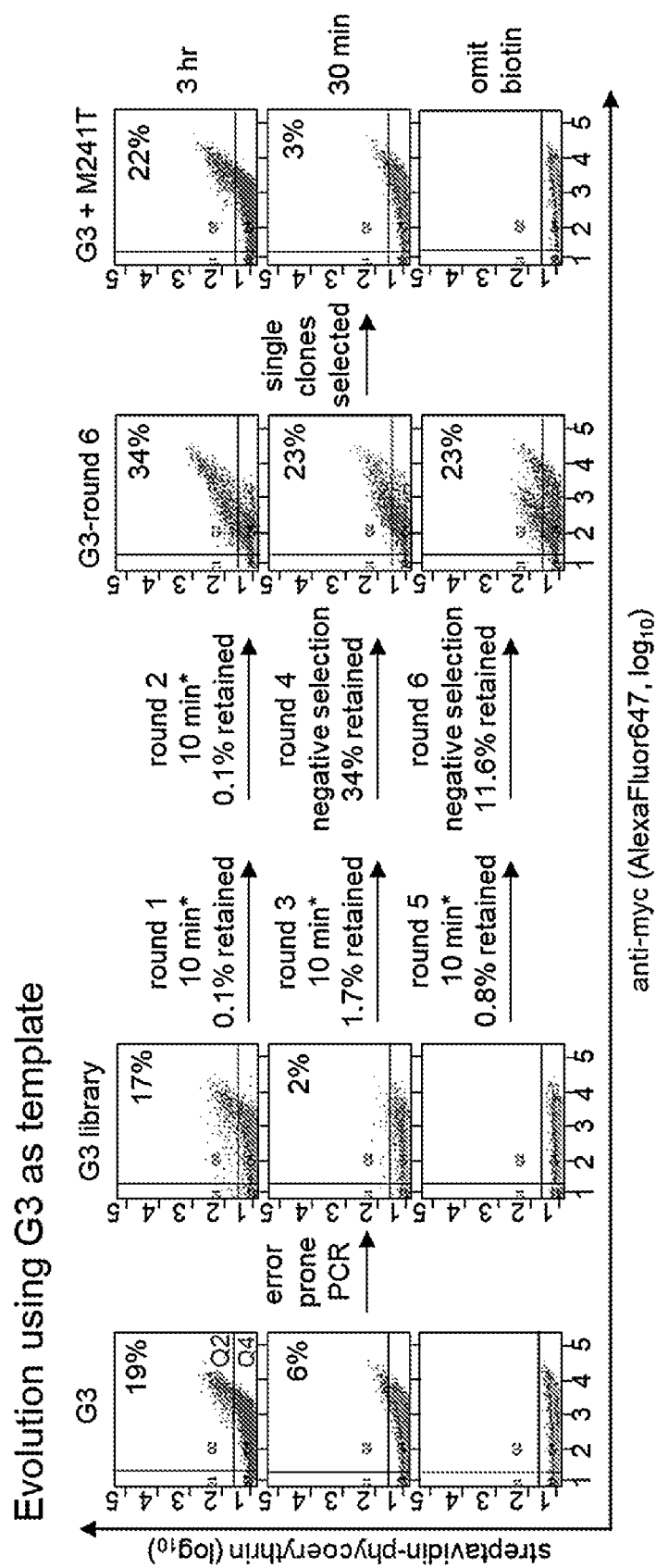

In a second path, we performed a series of positive and negative selections on a library derived from full-length G3 (FIG. 5I). One evolved mutation was retained, and we also carried over two mutations discovered in the evolution of miniTurbo. The result was TurboID, with 14 total mutations relative to wild-type BirA (FIG. 1D).

Figure 1E:
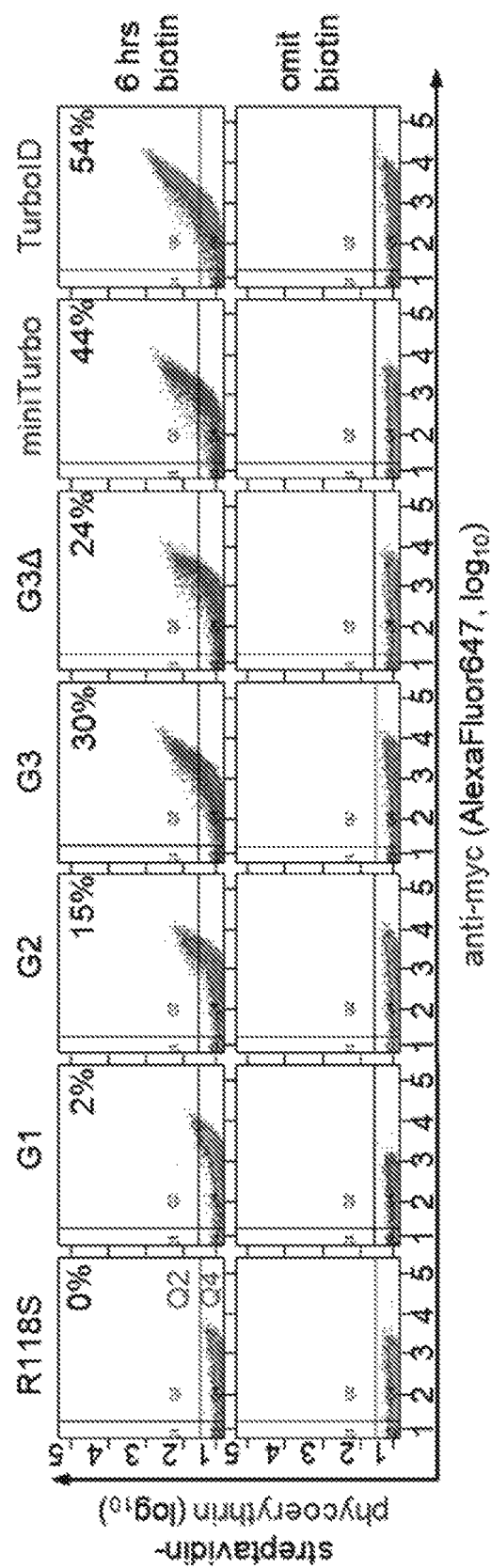
Figure 6:
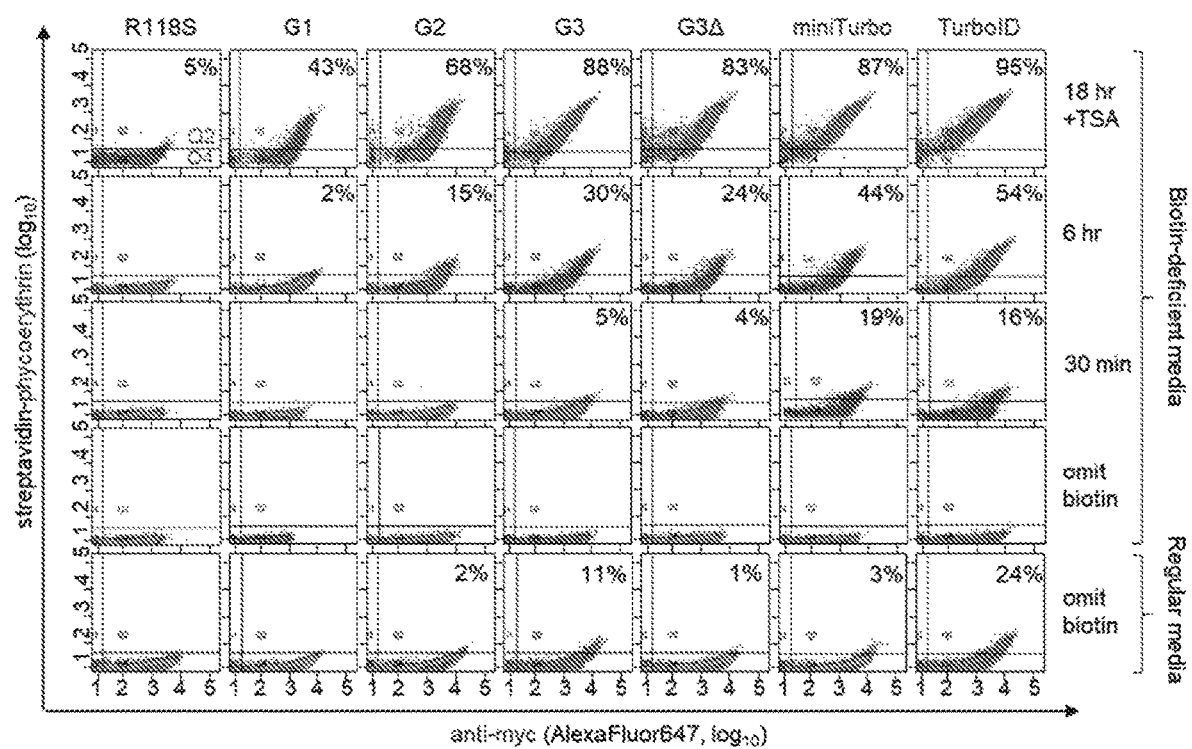
FIG. 6 shows FACS plots summarizing progress of evolution (same as FIG. 1E, but with more time points). In addition to 6 hours of labeling with 50 μM biotin, the results of 18 hours and 30 minutes labeling are shown. The first four rows were carried out in biotin-depleted media, while the last row was in regular yeast media. All plots display 10,000 cells. This experiment was repeated one time (except for G3Δ and the "biotin omitted" conditions in "biotin depleted media" which were performed only once under these conditions).

On the yeast surface, we compared the activities of TurboID and miniTurbo to that of our starting template, BirA-R118S, and to various intermediate clones from our evolution (FIG. 1E and FIG. 6). Each generation of evolution produced an increase in activity, while truncation of G3 to G3Δ decreased activity slightly. The most active mutants are miniTurbo and TurboID, with ~17-fold and ~19-fold higher activities than BirA-R118S on the yeast surface, respectively. Although TurboID has higher activity than miniTurbo, it also gives higher signal when exogenous biotin is omitted. Like G3, TurboID is able to utilize low levels of biotin present in regular yeast culture media.

Figure 1F:
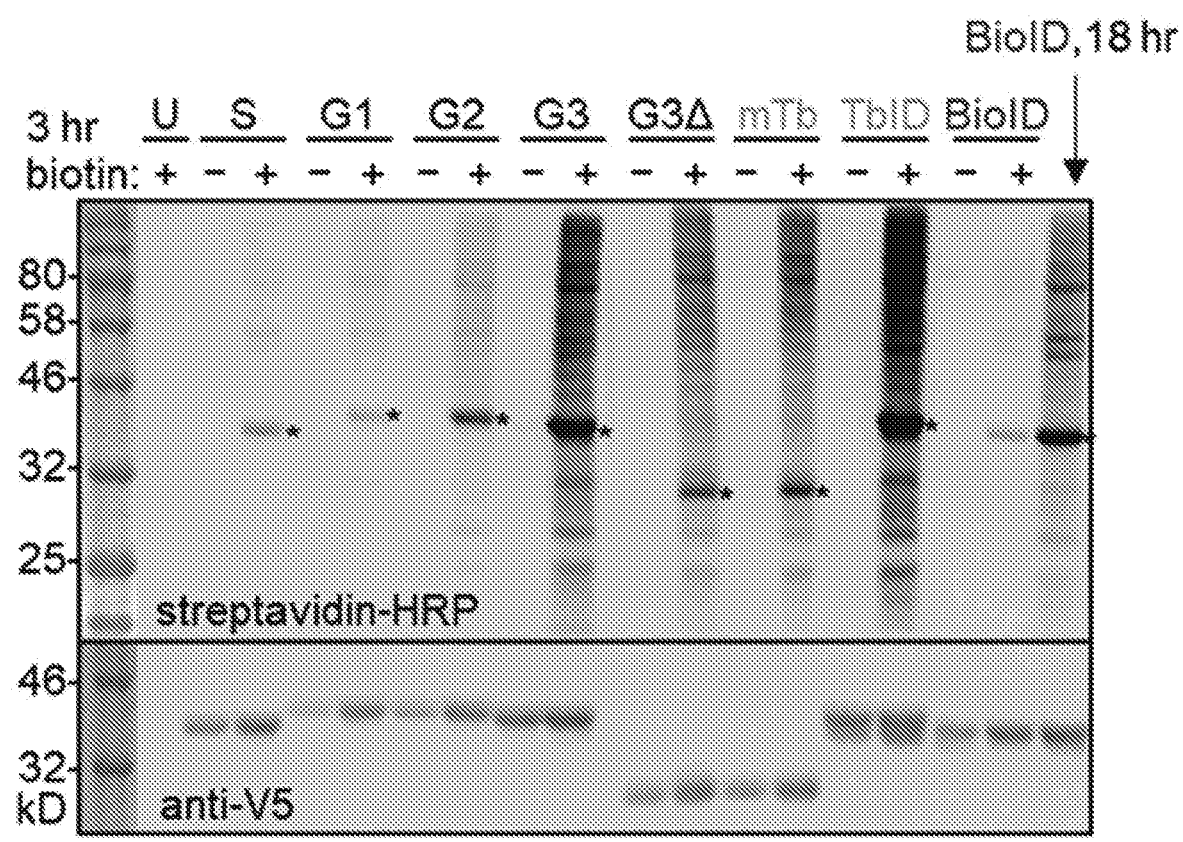
Figure 1G:
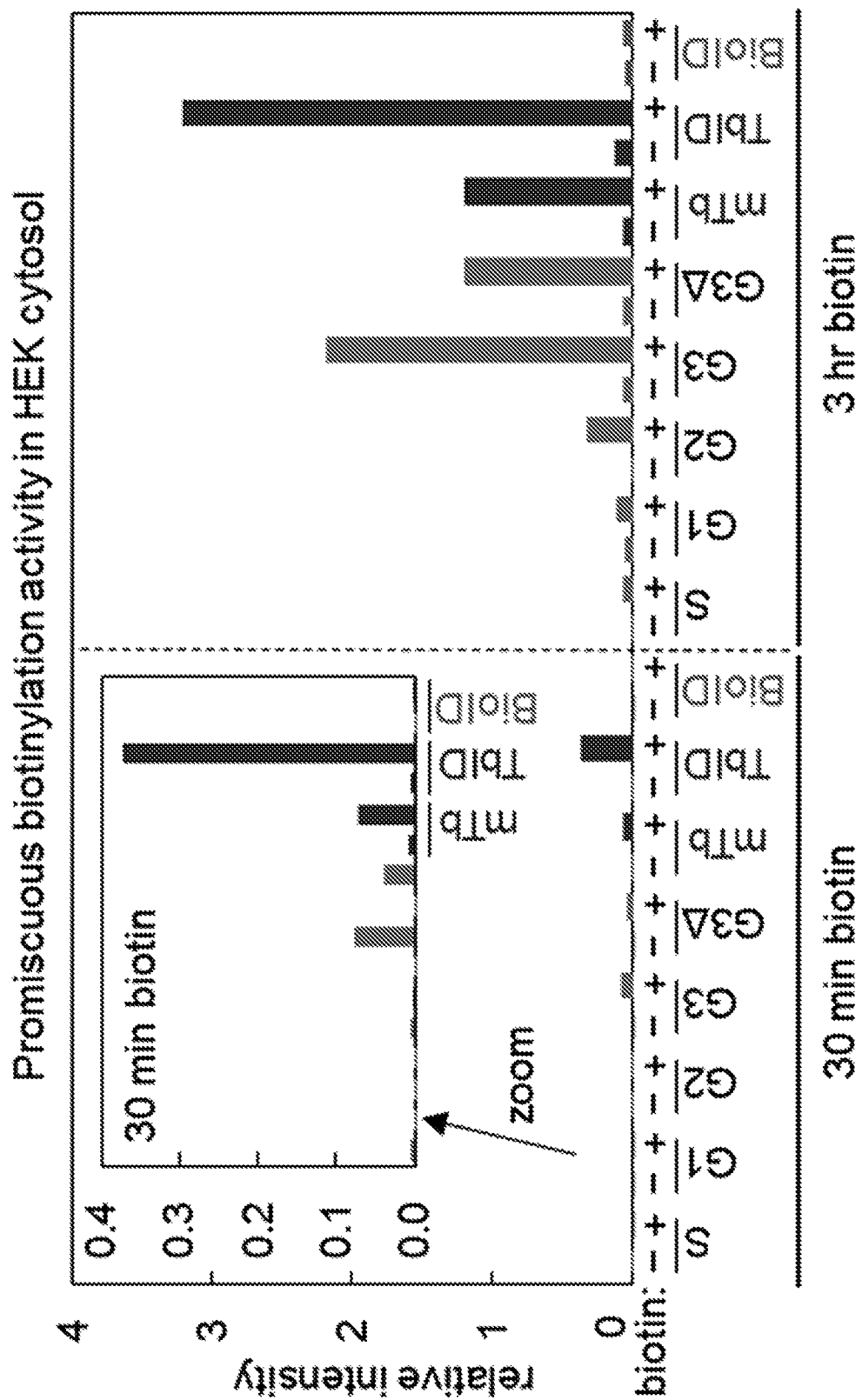
Figure 2A:
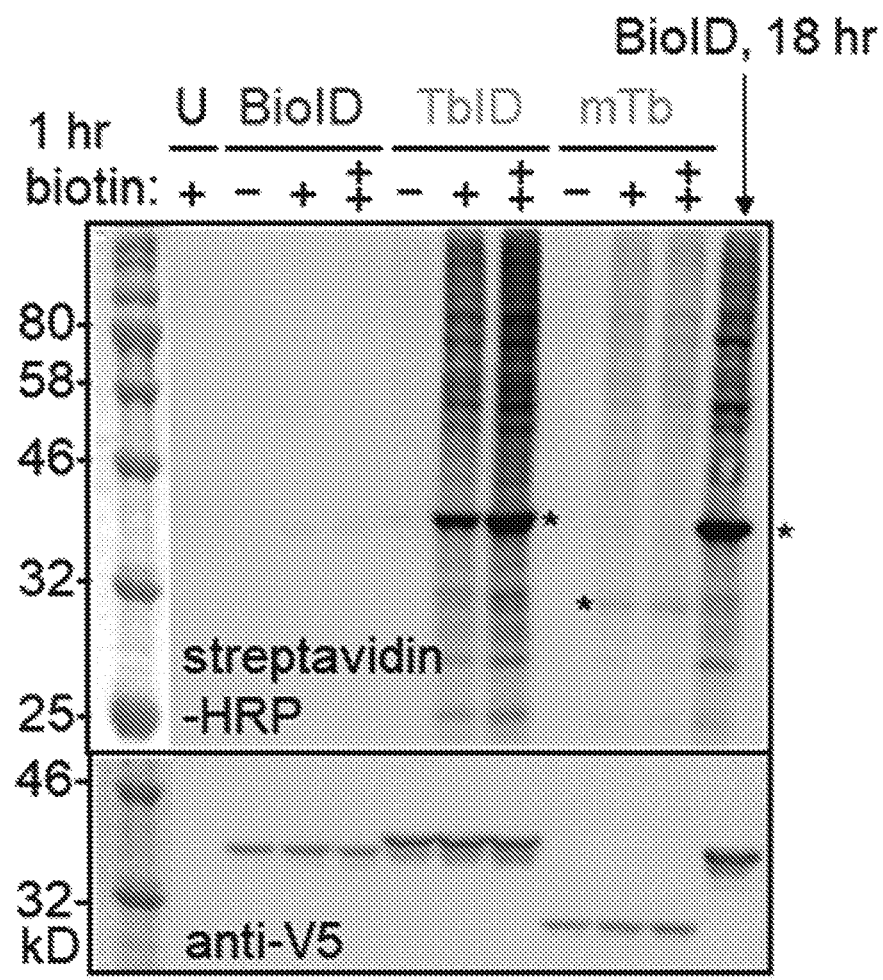
FIGS. 2A-2E show characterization of TurboID and miniTurbo in mammalian cells.
Figure 2B:
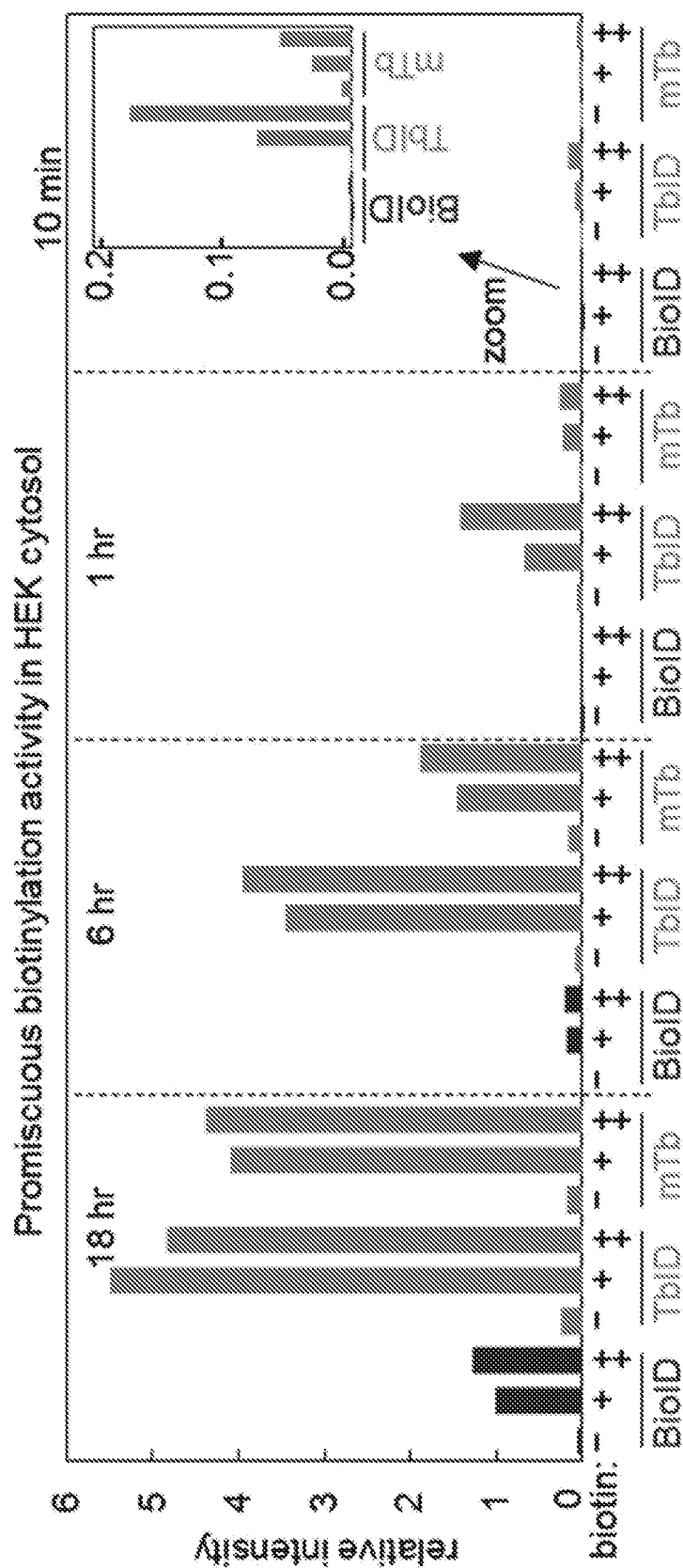
Figure 7A:
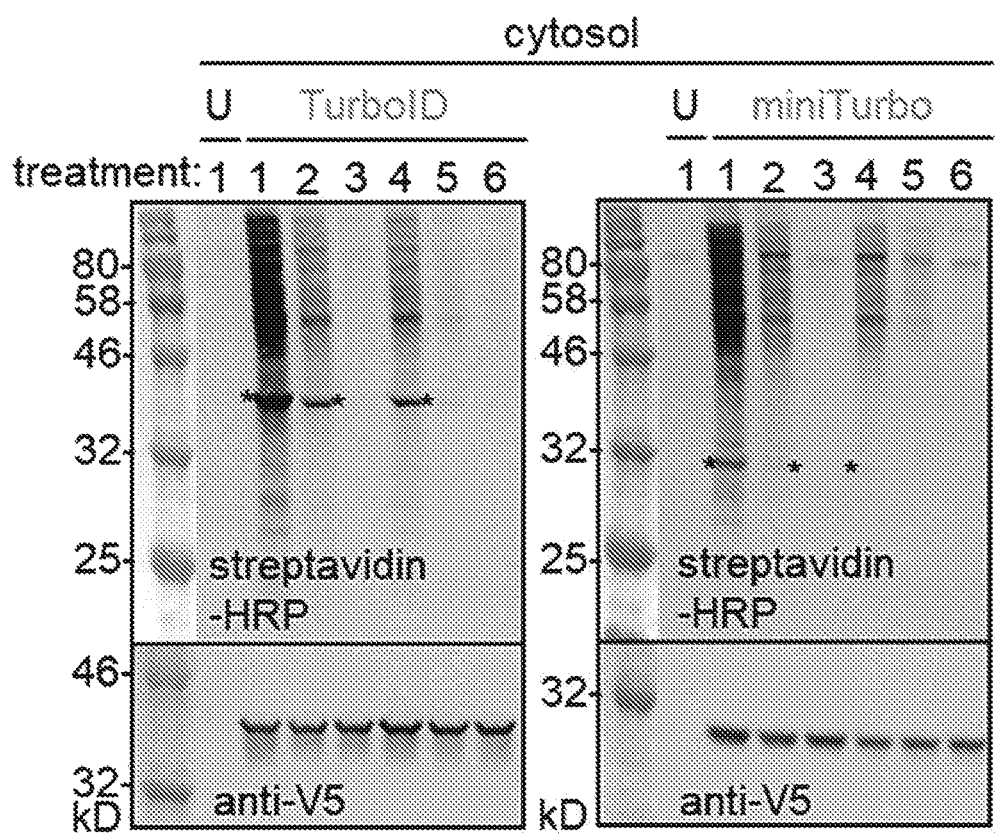
FIGS. 7A and 7B show halting of promiscuous labeling by TurboID and miniTurbo by lowering temperature to 4° C. The indicated ligases were transiently expressed in HEK 293T cells targeted to (FIG. 7A) the cytosol or (FIG. 7B) the cell surface. Labeling was carried out under the following conditions as indicated: 1 Incubation with 500 μM biotin for 70 min at 37° C. 2. Incubation with 500 μM biotin for 10 minutes at 37° C. 3. No biotin incubation. 4. Incubation with 500 μM biotin for 10 min at 37° C., then moved to 4° C. for 60 more minutes 5. Incubation with 500 μM biotin for 60 min at 4° C. 6. Incubation with 500 μM biotin for 10 min at 4° C. For (FIG. 7B), samples were also incubated with 0.5 mM ATP) and 1.25 mM magnesium acetate. After labeling, whole cell lysates were analyzed by streptavidin blotting. Ligase expression detected by anti-V5 blotting. U, untransfected. Asterisks indicate ligase self-biotinylation. This experiment was performed once, but similar results were replicated for BirA-G3.
Figure 7B:
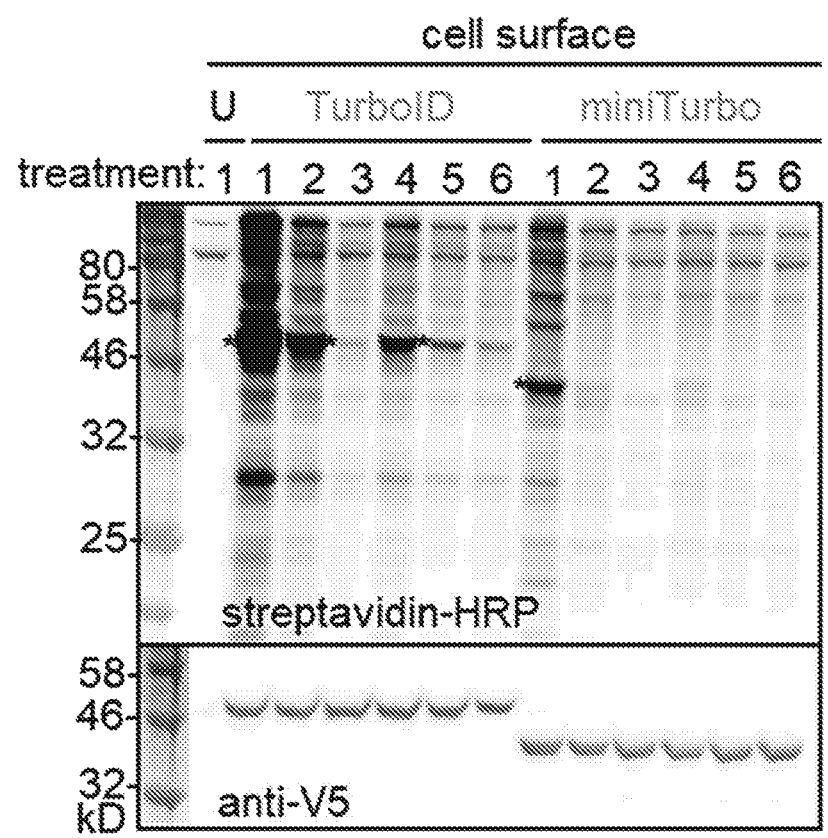
Figure 8A:
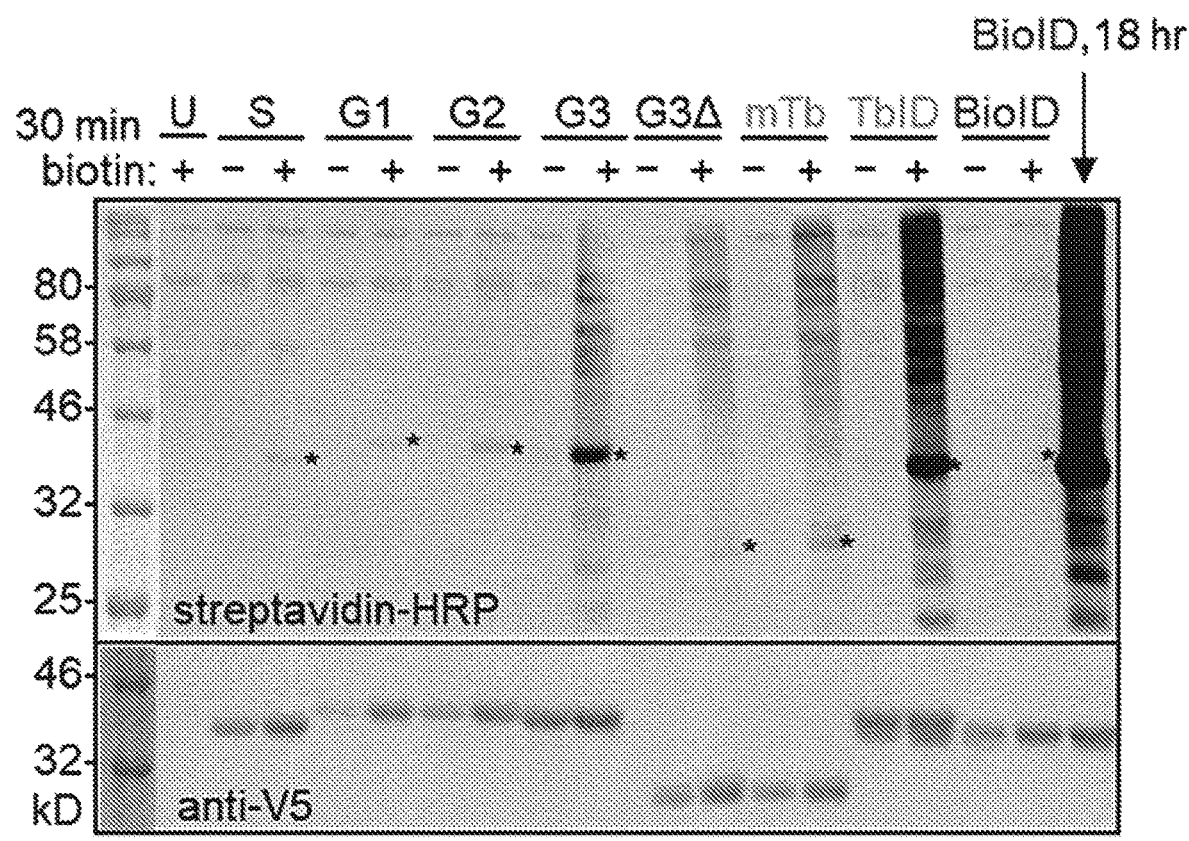
FIGS. 8A-8D show comparison of ligase activities in HEK cytosol.
Figure 8B:
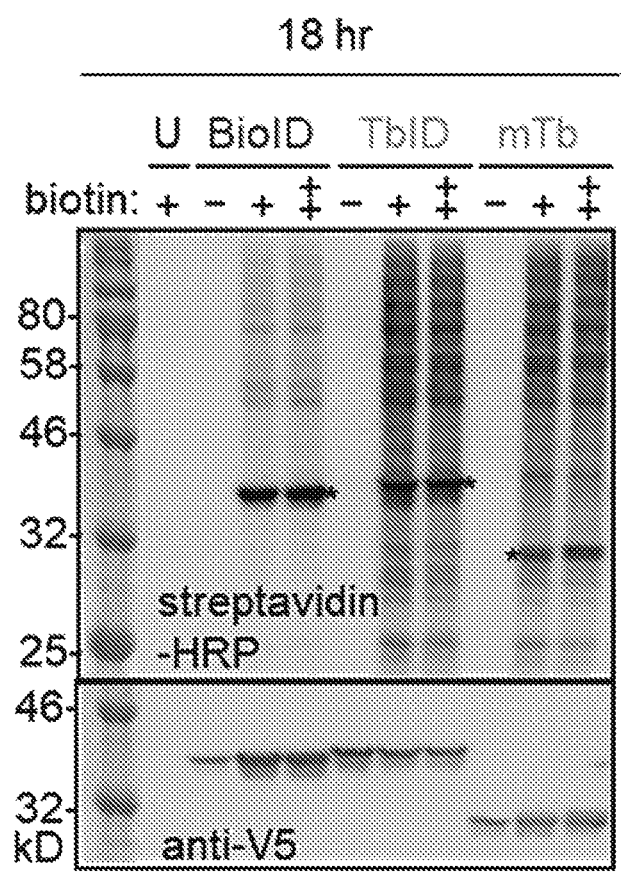
Figure 8C:
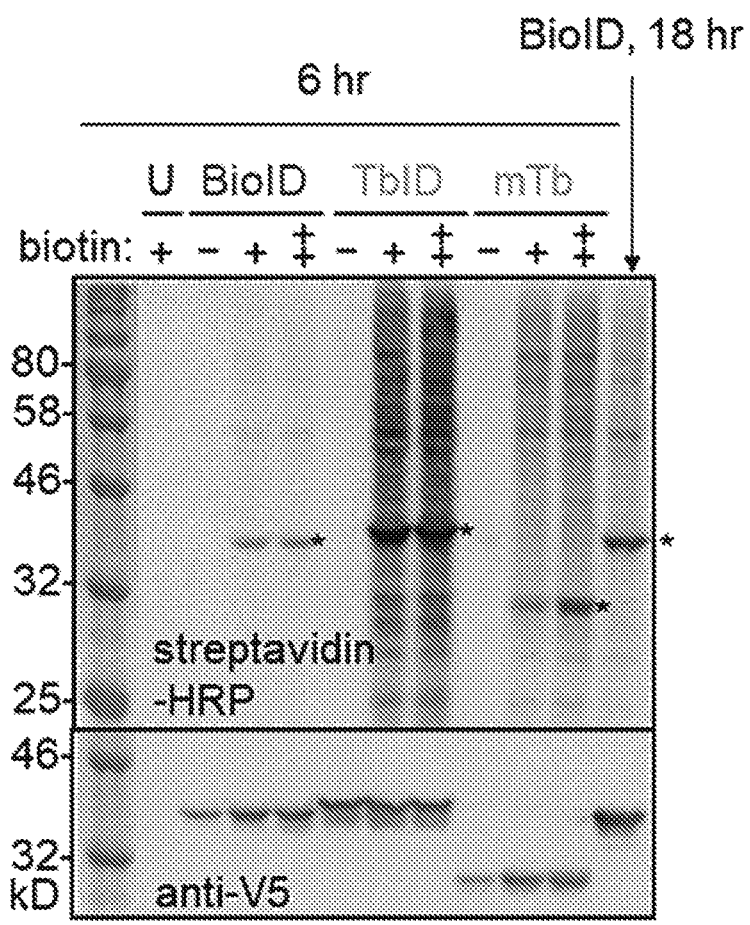
Figure 8D:
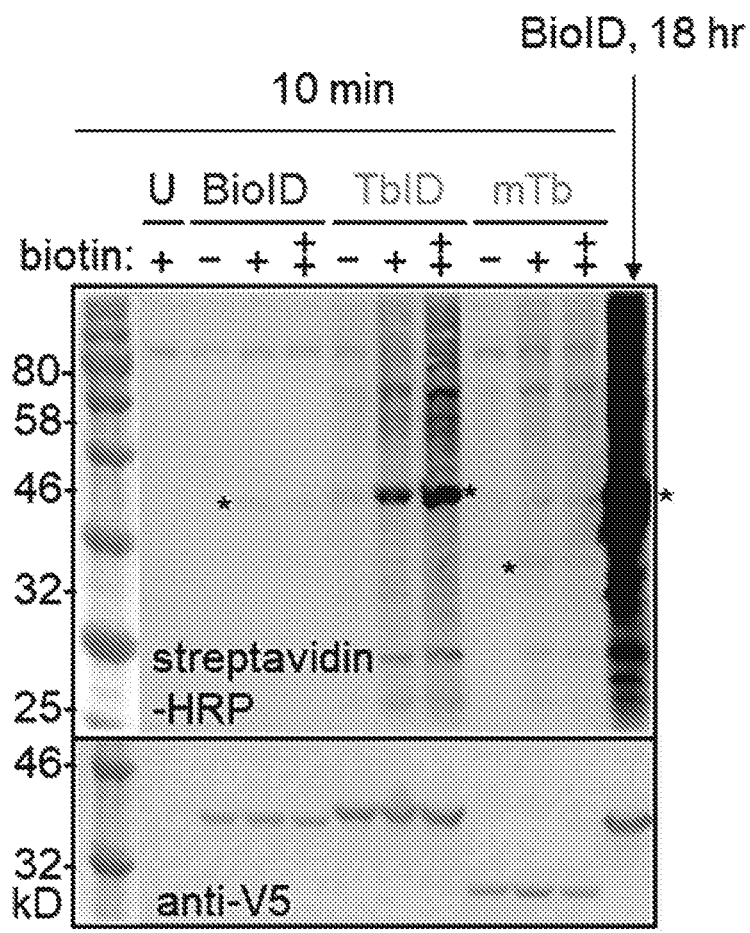

We next tested whether these activity differences would replicate in a different context, the cytosol of cultured mammalian cells. We transfected NES (nuclear export signal)-tagged constructs into HEK293T cells, incubated with exogenous biotin for various lengths of time, terminated labeling by transferring cells to 4° C. and washing away excess biotin (FIG. 7), and then lysed the cells and blotted the lysates with streptavidin-HRP. FIGS. 1F, 1G, 8A show that TurboID and miniTurbo are again the most active clones. For instance, TurboID gives more signal in 1 hour than the original BioID enzyme gives in 18 hours (FIG. 2A). Both TurboID and miniTurbo produced easily detectable signal after just 10 minutes of incubation with exogenous biotin, while BioID signal was barely visible after 3 hours of biotin incubation (FIG. 1F, 8B-8D). Quantitation of Western blots, accounting for differences in ligase expression levels, showed that TurboID is 9-31-fold more active than BioID, while miniTurbo is 7-26-fold more active than BioID (FIG. 2B). The decreased differences in activity between TurboID/miniTurbo and BioID at longer labeling times may result from saturation of available labeling sites.

Why do TurboID and miniTurbo have greater catalytic activity than BioID? Site-specific biotinylation catalyzed by wild-type BirA occurs via two half reactions: generation of the biotin-5'-AMP anhydride from biotin and ATP, followed by transfer onto a specific lysine of an acceptor peptide or protein[4]. It has been proposed that BirA-R118G (BioID) catalyzes promiscuous biotinylation by prematurely releasing biotin-5'-AMP into solution, for covalent tagging of nearby nucleophiles. FIG. 1D shows that the 14 mutations in TurboID and miniTurbo are distributed throughout the ligase structure[26, 27], with the majority far away (>10 Å) from the bound biotin-5'-AMP. Hence, if these mutations affect biotin-5'-AMP formation rate and/or affinity, it is likely via long-range and indirect mechanisms. Previous studies have shown that wild-type BirA dimerizes upon biotin-5'-AMP formation, and disruption of this dimer decreases affinity for biotin-5'-AMP[27]. Although every mutant in our study contains an A146 deletion that decreases dimerization[28], it is possible that some of our evolved mutations further reduce dimerization; E140K, Q141R, T192A, and K194I mutations in TurboID map to the dimer interface[26,27]. In addition, removal of the N-terminal domain is known to decrease biotin-5'-AMP affinity[25]. TurboID has two mutations, Q65P and I87V, at the junction between the N-terminal domain and the catalytic core, which may alter their structural relationship, leading to reduced biotin-5'-AMP affinity.

Figure 2C:
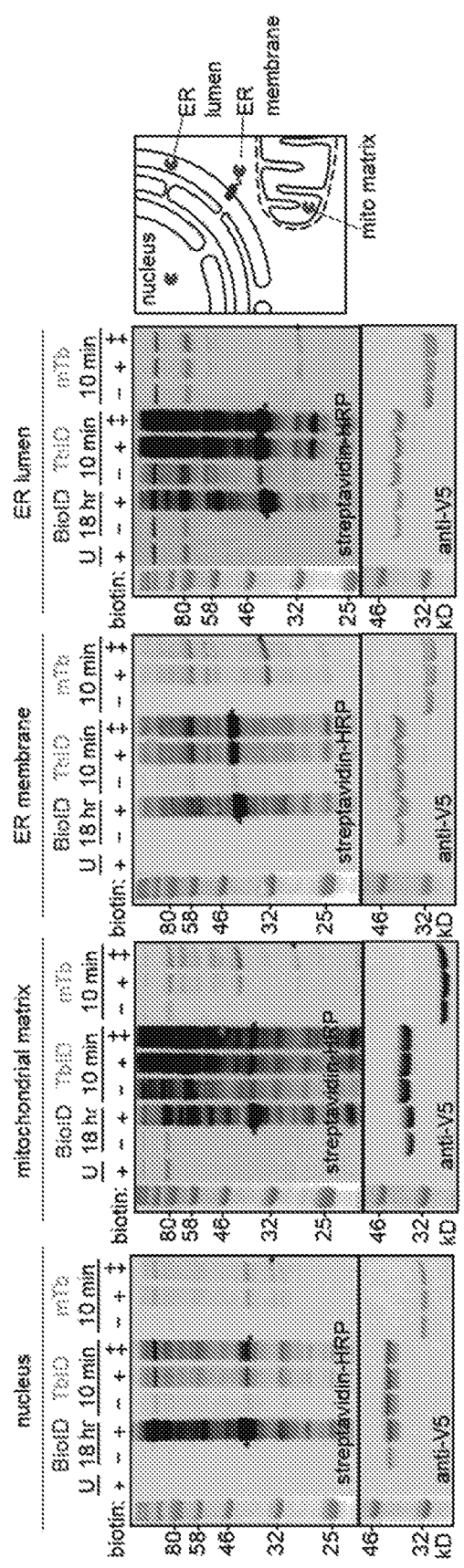

Different organelles have different pH, redox environments, and endogenous nucleophile concentrations, which may influence PL activity. We therefore compared TurboID, miniTurbo, and BioID in the nucleus, mitochondrial matrix, ER lumen, and ER membrane of HEK 293T cells (FIG. 2C). While ligase activities varied by compartment, we were able to detect biotinylation by TurboID in 10 minutes, that was in some cases stronger than biotinylation by BioID in 18 hours. This was particularly striking in the ER lumen, where BioID activity was quite low, even after 18 hours, while TurboID gave robust labeling in 10 minutes. This activity difference is likely to be a consequence of our performing TurboID evolution in the oxidizing environment of the yeast secretory pathway.

Figure 2D:
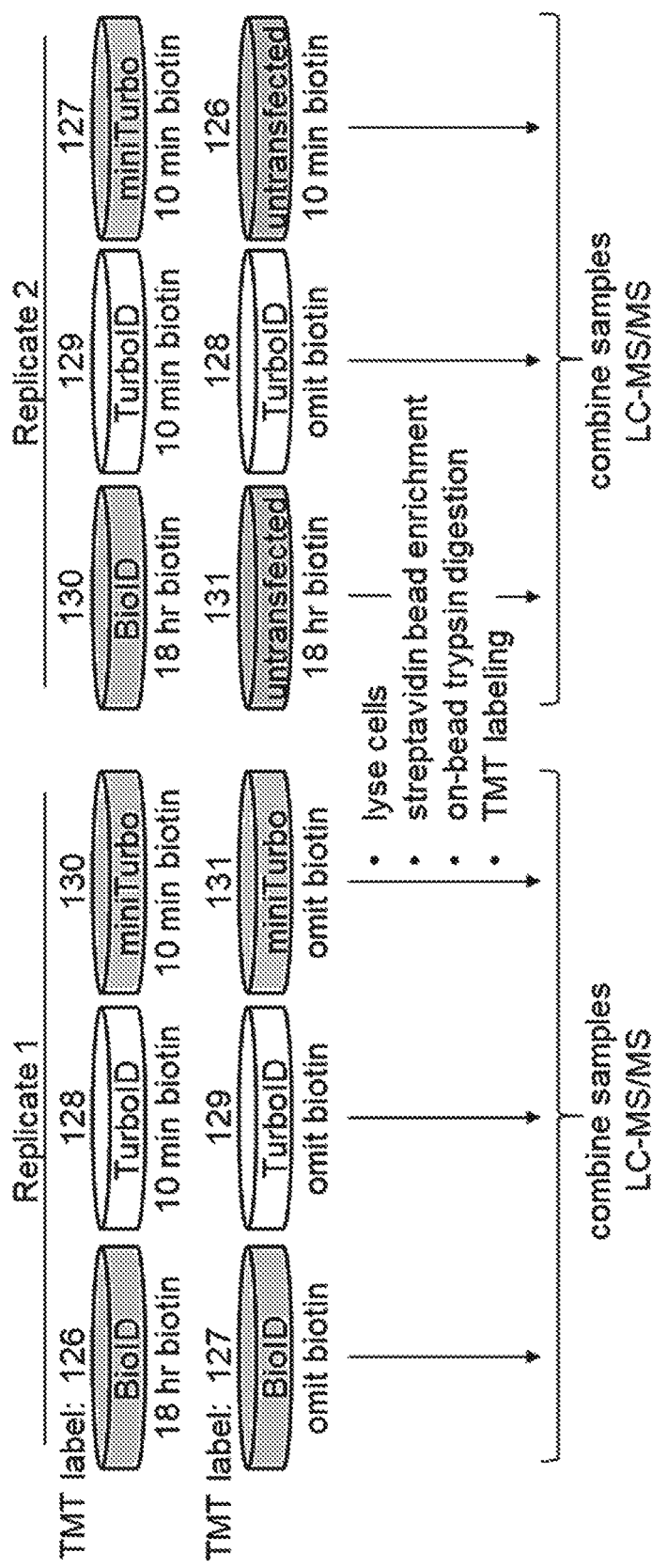
Figure 2E:
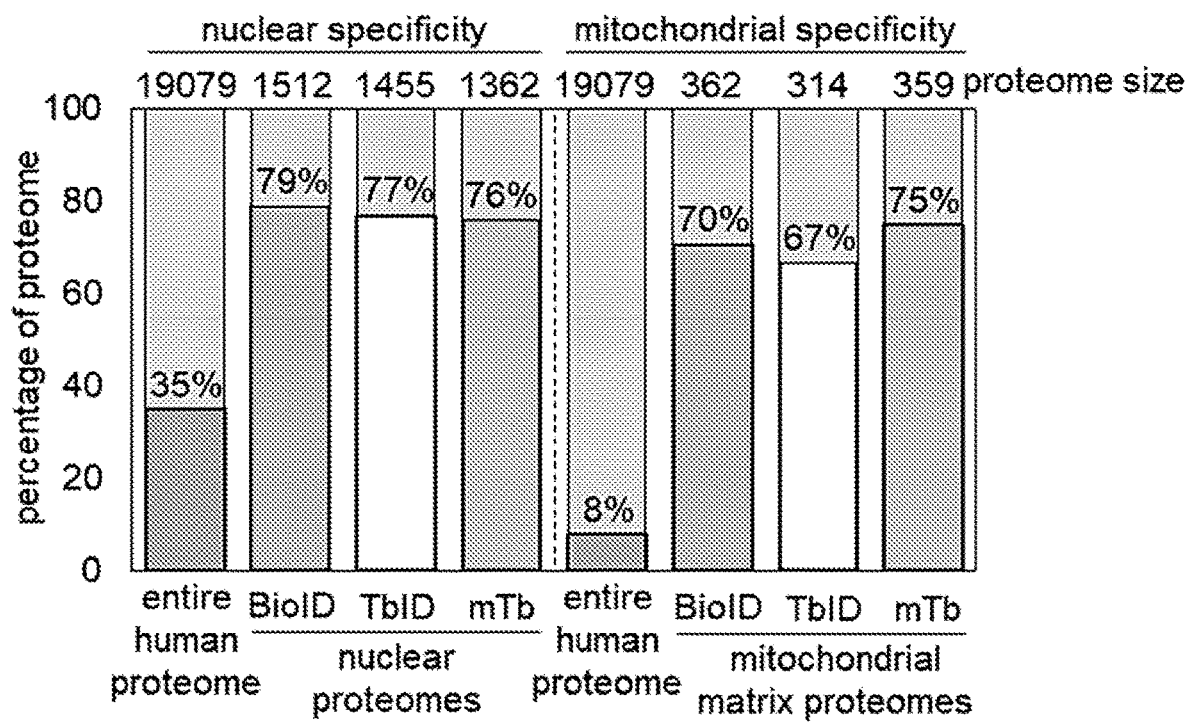

Next, we tested TurboID and miniTurbo side-by-side with BioID in two quantitative proteomic experiments in the mammalian nucleus and mitochondrial matrix. For TurboID and miniTurbo, we supplied exogenous biotin for only 10 minutes; for BioID, we used 18 hours. Experiments were performed in replicate, alongside negative controls with ligases omitted or biotin omitted (FIGS. 2D, 9). After work up of the MS data as previously described[29], we found that all three ligases gave proteomes of similar size and specificity (FIG. 2E). The depth-of-coverage was somewhat smaller for TurboID and miniTurbo compared to BioID (FIG. 9I), but this could be a consequence of labeling for a 100-fold shorter time period.

Figure 3A:
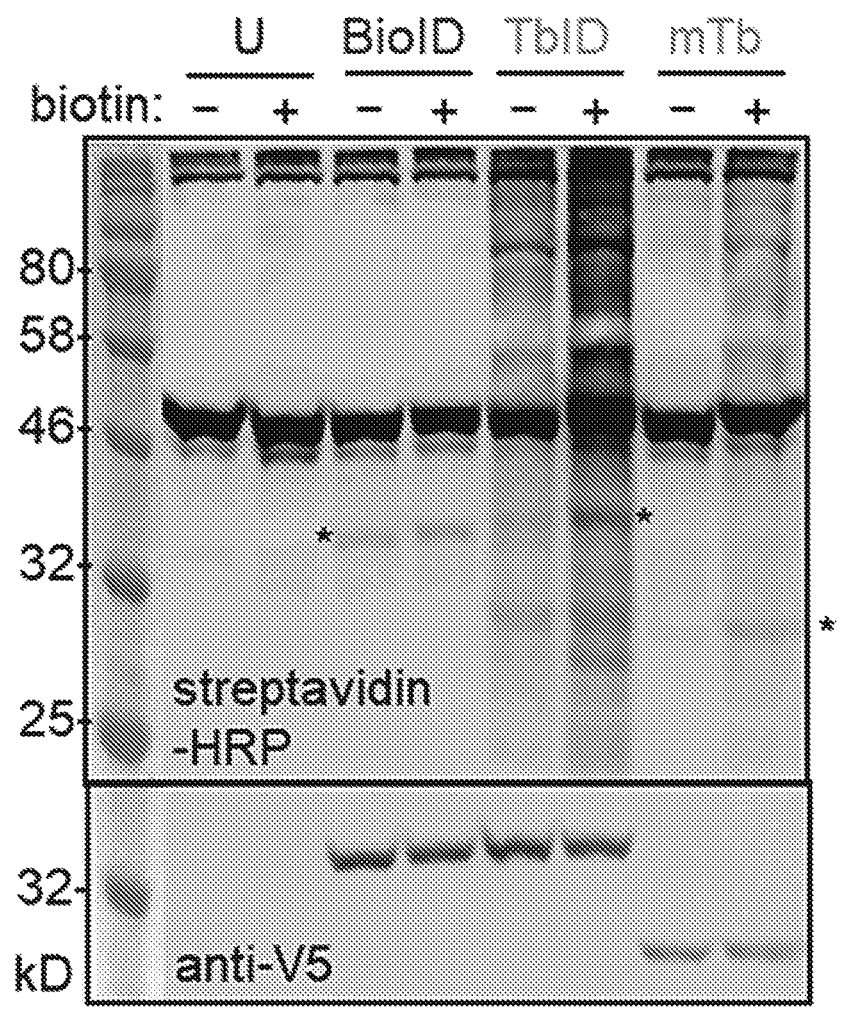
FIGS. 3A-3J show TurboID and miniTurbo in other species.
Figure 3B:
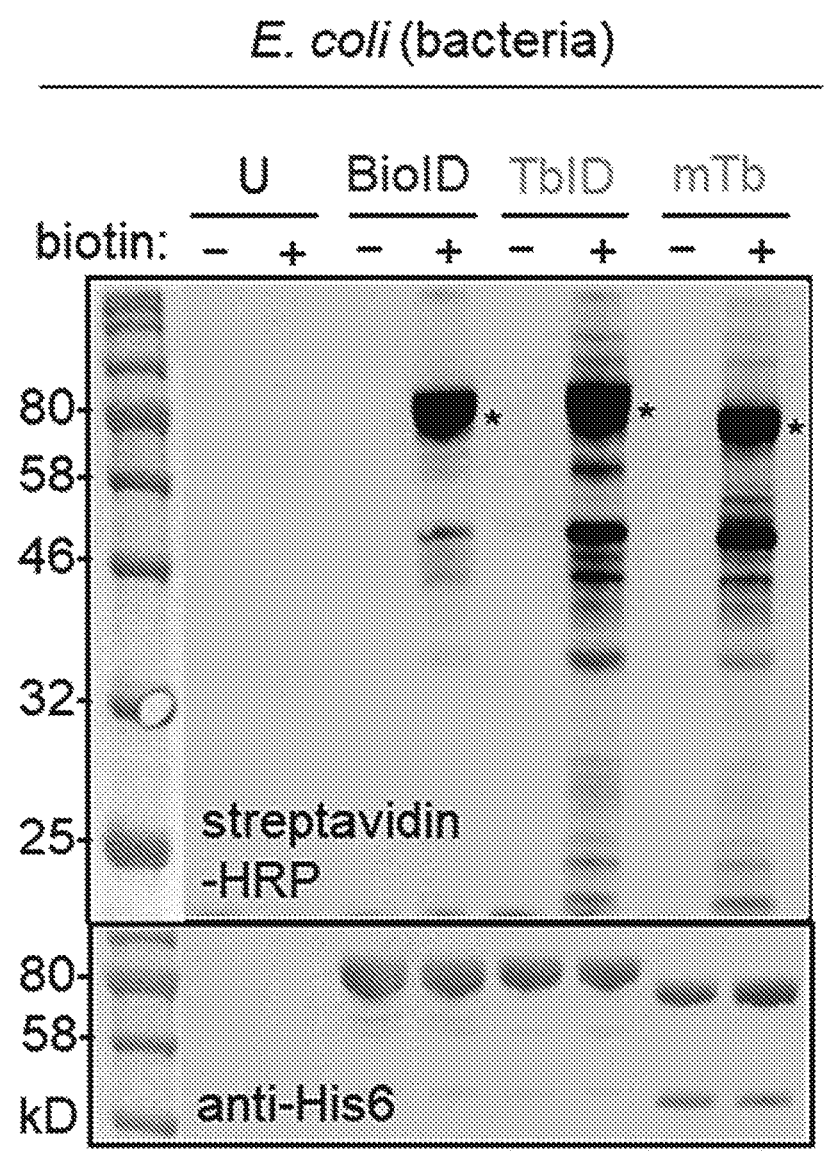

Despite the widespread application of BioID, there has only been a single in vivo demonstration to date, in mice[22], and certain cell types, such as yeast, are noticeably absent from published studies. We suspect that this is a consequence of BioID's low catalytic activity, which makes it difficult or impossible to perform PL in certain cell types and organisms (for example, the mouse study required biotin addition for 7 days[22]). Though we carried out our directed evolution in the yeast secretory pathway, our starting template, BirA-R118S, gave almost undetectable signal in this context (FIG. 1C). Consistent with this, we observed no promiscuous BioID activity at all in the yeast cytoplasm (FIG. 3A). In contrast, TurboID and miniTurbo both gave robust labeling in this context. We also compared the three ligases in the bacterial cytosol. Here, TurboID and miniTurbo were also more active than BioID (FIG. 3B).

Figure 3C:
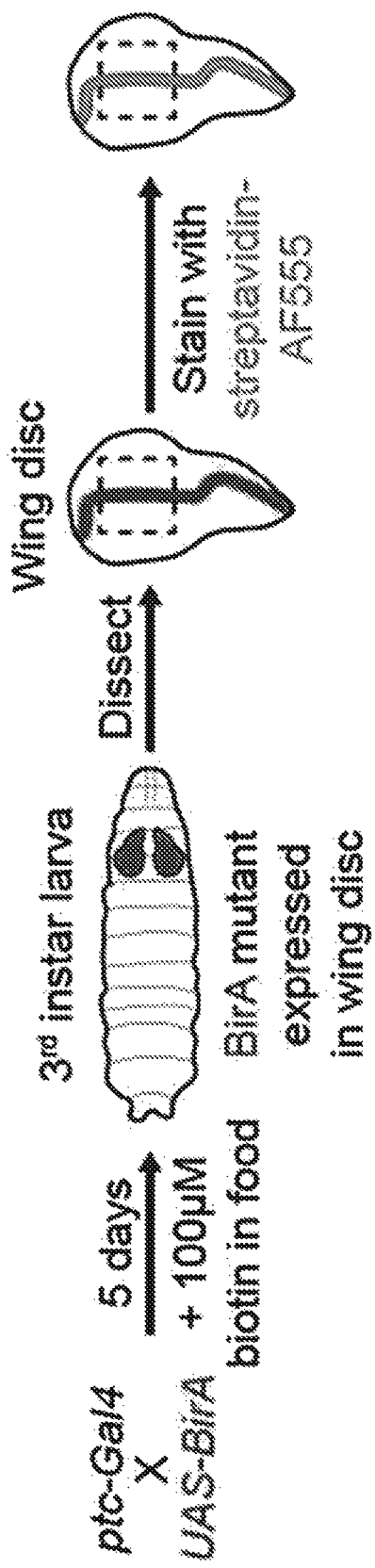
Figure 3D:
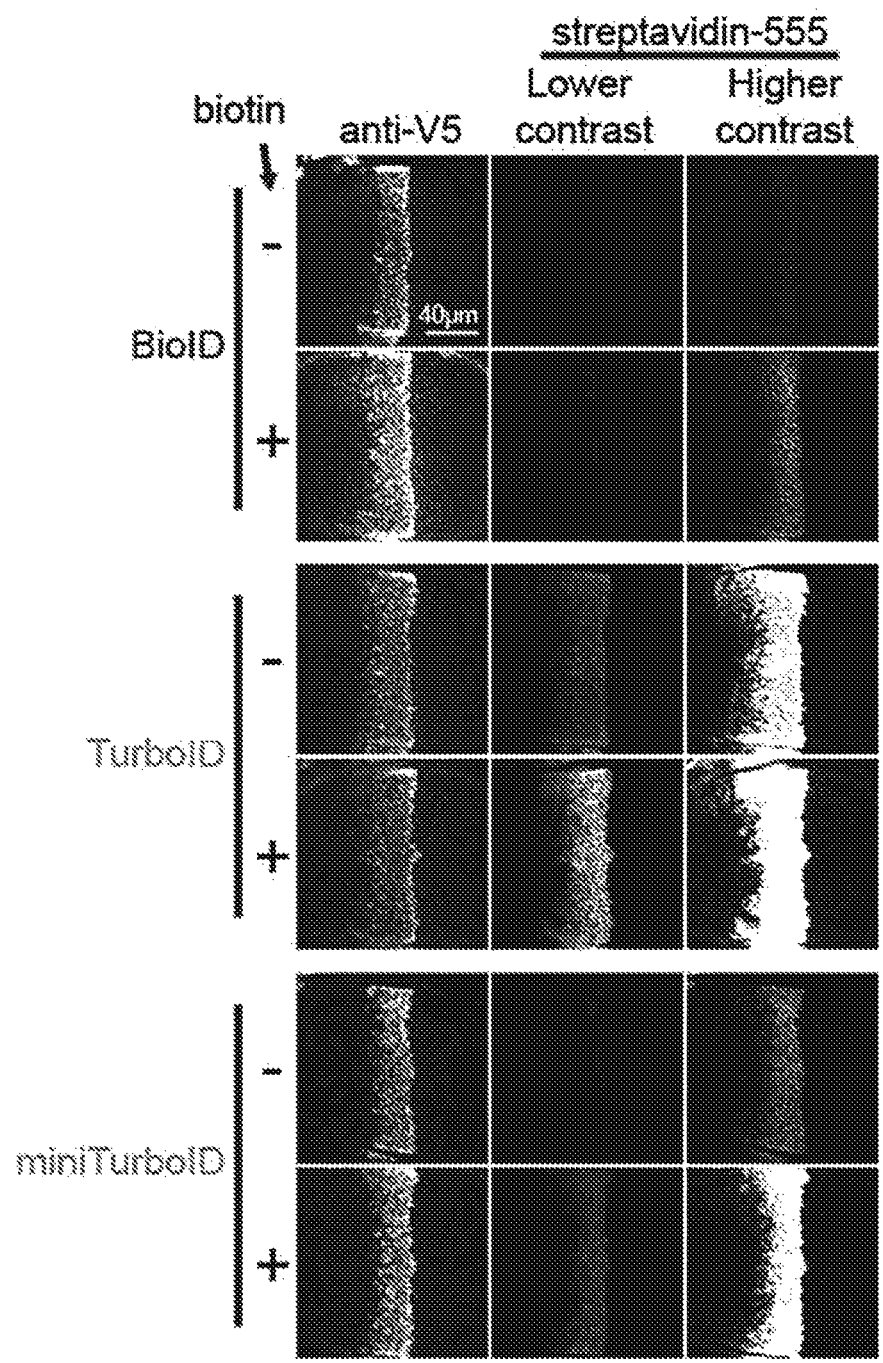
Figure 3E:
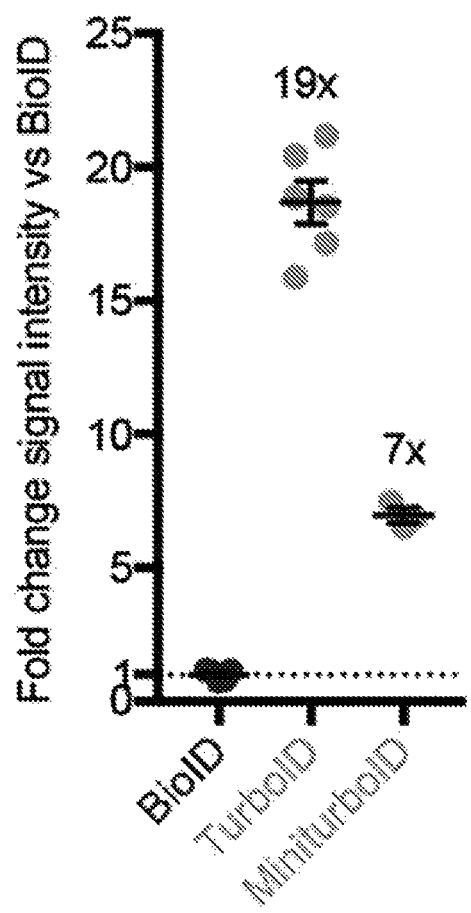
Figure 3F:
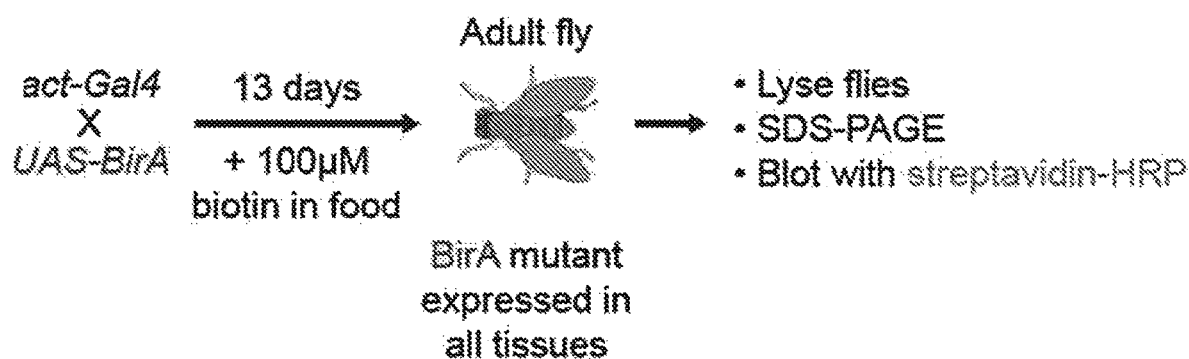
Figure 3G:
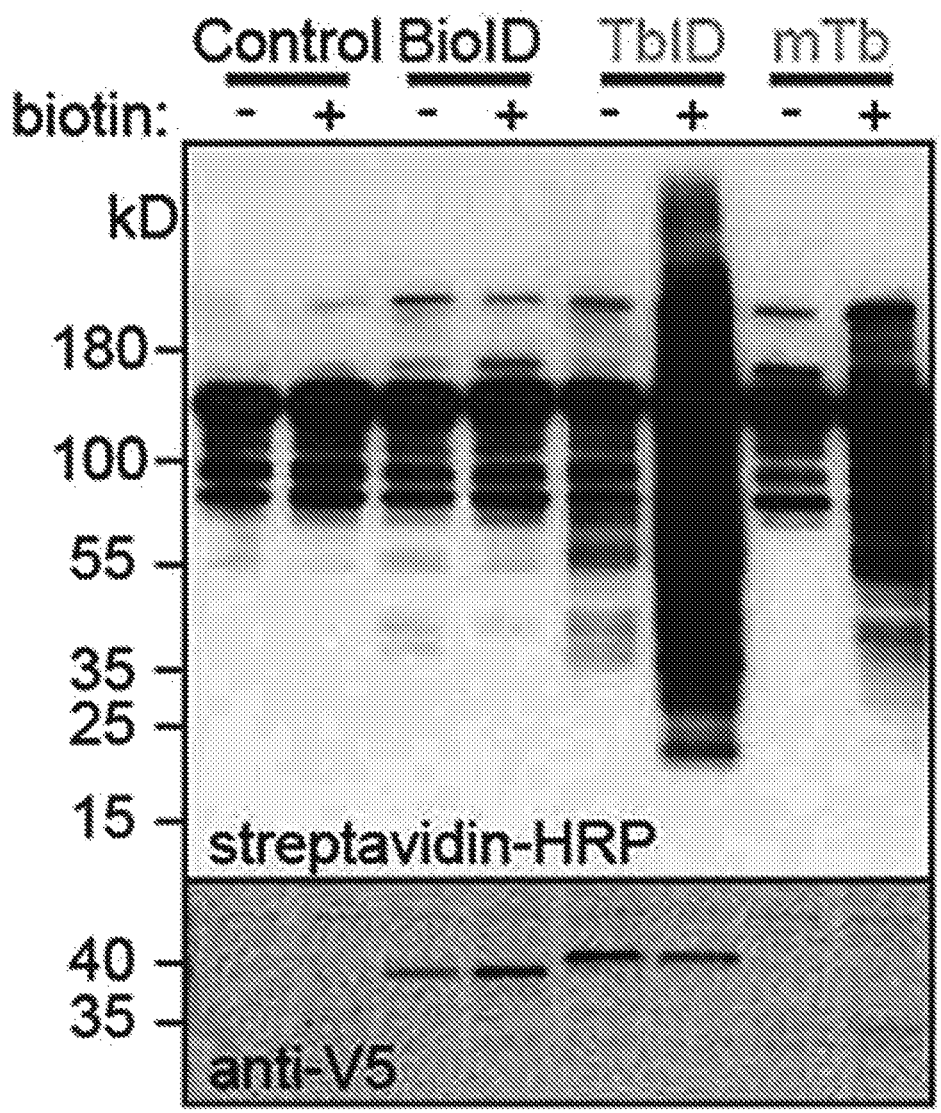

Two model organisms, Drosophila and C. elegans, are frequently used for biological studies due to their genetic tractability. In principle, they are also well-suited for BioID because biotin can be easily delivered to various organ systems through food[30]. Yet no published studies document the use of BioID in either organism. Here, we sought to test the applicability of biotin-based PL to these animals. In Drosophila, we expressed BioID, TurboID, or miniTurbo either ubiquitously, or selectively in the larval wing disc, which gives rise to the adult wing. After 5-13 days of feeding on biotin-containing food, we stained dissected wing discs with streptavidin-fluorophore (FIG. 3C-3E), or lysed the adult flies and ran a streptavidin blot (FIGS. 3F, 3G). In FIGS. 3C-3E, TurboID and miniTurbo signals are 19-fold and 7-fold higher, respectively, than BioID signal in the wing disc. Consistent with our observations in HEK 293T cells, TurboID also gives some low signal in flies fed regular food (without biotin supplementation).

In the fly streptavidin blots, BioID activity is undetectable, whereas TurboID and miniTurbo both give robust biotinylation signal (FIGS. 3F, 3G). The absence of detectable BioID signal here versus when the ligase is expressed in a specific tissue may be due to endogenous biotinylated proteins drowning out specific signal in the streptavidin blot.

Separately, we performed adult survival and wing morphology assays to check for possible toxic effects of BioID, TurboID, or miniTurbo expression in flies (FIG. 10).

When expressed ubiquitously, BioID and miniTurbo were non-toxic, but TurboID flies showed decreased survival and were smaller in size when grown without biotin supplementation. We hypothesize that TurboID consumes all the biotin, effectively biotin-starving cells, when expressed ubiquitously. In support of this, toxicity can be rescued by supplementing the fly's food with exogenous biotin. Furthermore, none of the ligases were toxic when expressed in the wing disc, since adult wings were observed to be normal in morphology and size.

Figure 3H:
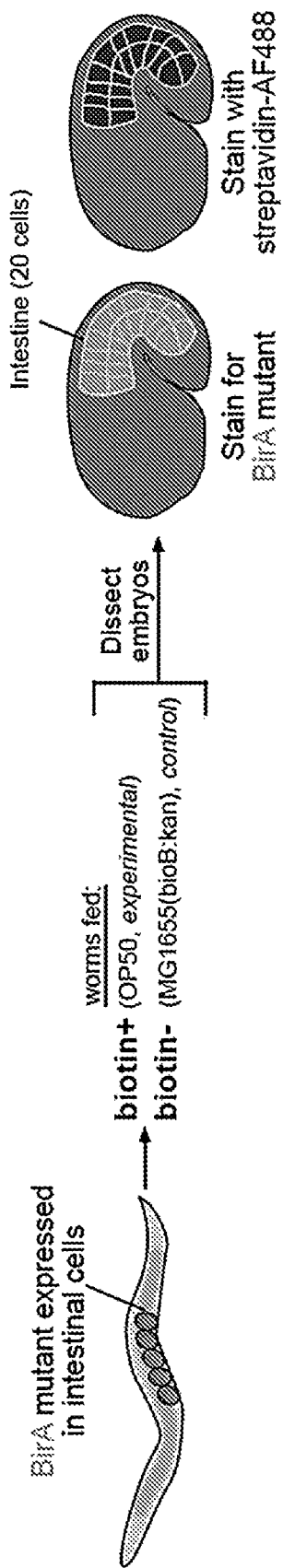
Figure 3I:
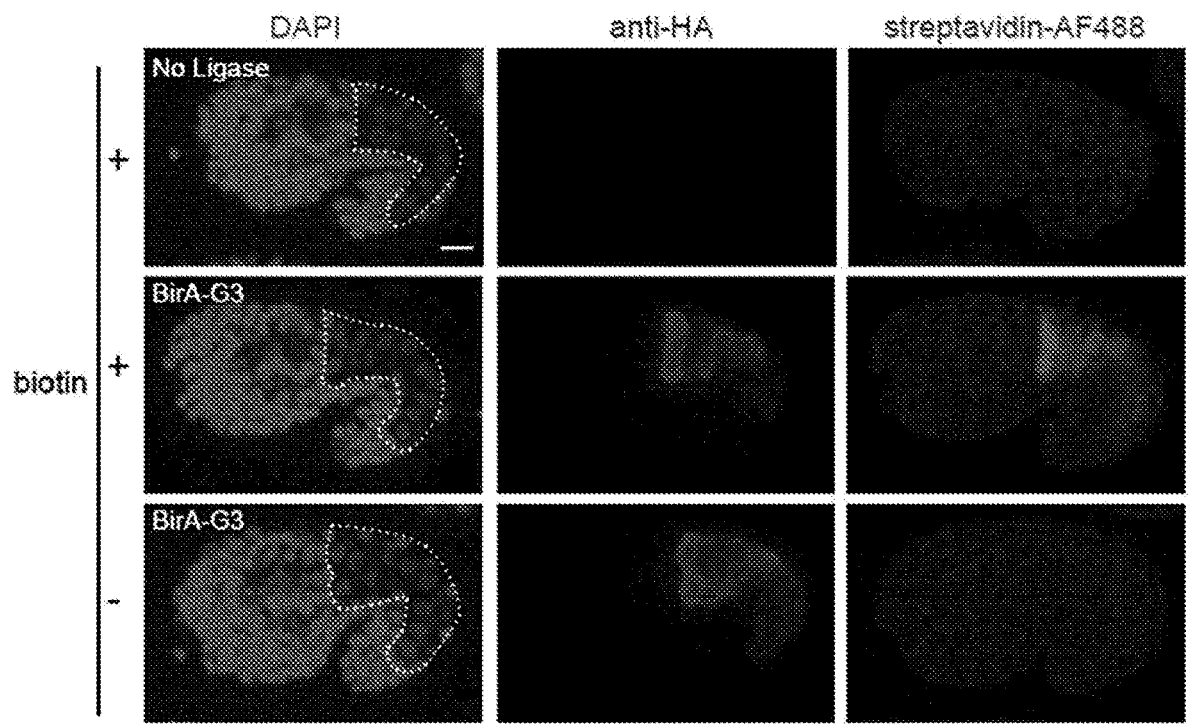
Figure 3J:
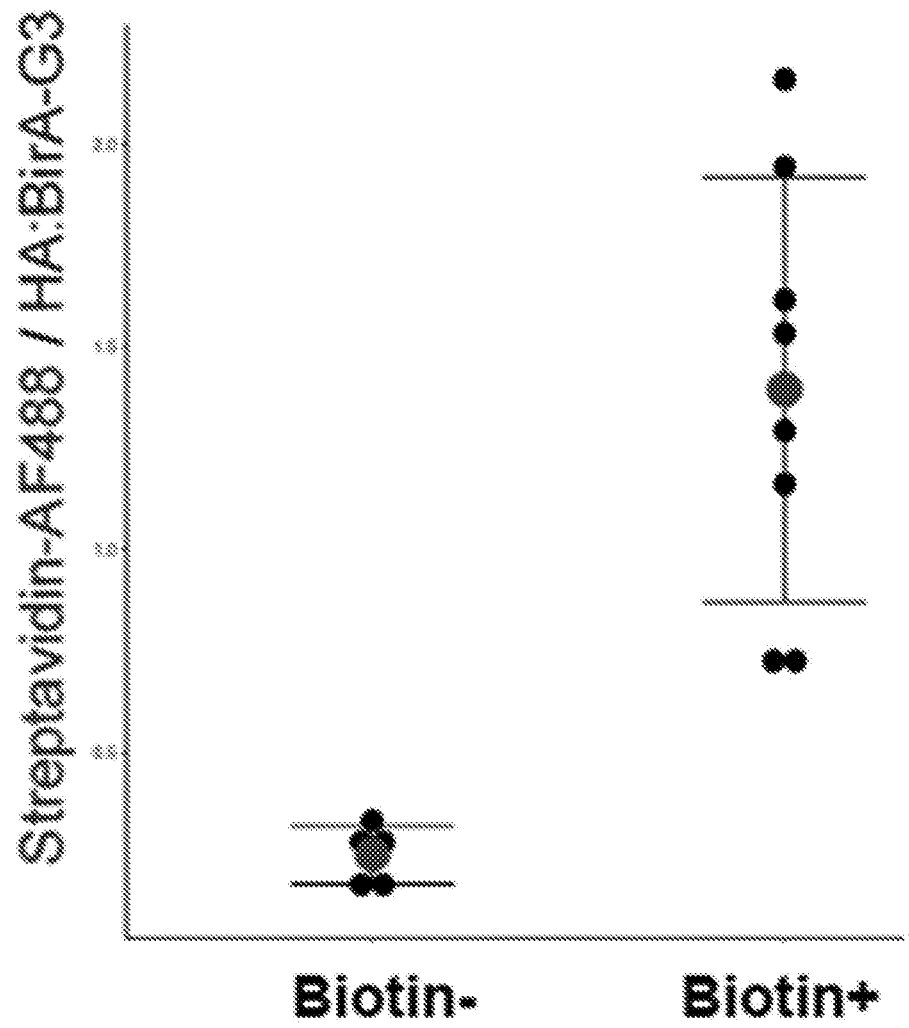

In C. elegans, we tested our TurboID precursor, BirA-G3, in the embryonic intestine, a simple epithelial tube composed of 20 cells. The intestinal lineage is specified 35 minutes after the 2-cell stage of the embryo and intestinal cells begin to differentiate about 4 hours later[31,32]. Thus, performing PL during the early stages of intestinal development requires a ligase with sufficient activity to label within a window of only a few hours. We expressed BirA-G3 early in the intestinal lineage (approximately 150 min after the first cleavage) and assayed biotinylation activity approximately 4 hours later. BirA-G3 showed robust biotinylation activity in embryos from worms fed biotin-producing bacteria (FIGS. 3H-3J). In contrast, embryos from worms fed bacteria unable to biosynthesize biotin showed the same low level of biotinylation in the intestinal cells as embryos that lacked the G3 ligase (FIGS. 3H-3J).

Discussion

In summary, we have used yeast display-based directed evolution to engineer two BirA variants, TurboID and miniTurbo, with much greater promiscuous biotinylation activity than the original BioID enzyme, BirA-R118G. BioID has already had tremendous impact in the proteomics field, enabling sub-compartment mappings[8,22] and protein-protein interaction[19,33] discovery with greater specificity and sensitivity than traditional approaches, such as biochemical fractionation and immunoprecipitation, allow. The introduction of these two new enzymes, which enable live cell proximity biotinylation with greater signal in shorter time windows—as little as 10 minutes instead of the 18-24 hours typically used for BioID—should further expand the scope of this important methodology.

We engineered two enzymes in this study instead of one, because they each have unique properties and tradeoffs. TurboID is the most active, and should be used when the priority is to maximize biotinylation yield and sensitivity/recovery. However, in many contexts, we observe a small amount of promiscuous biotinylation before exogenous biotin is supplied, indicating that TurboID can utilize the low levels of biotin present in cells and organisms grown in typical biotin-containing media/food. Nearly all eukaryotes import biotin, as they cannot biosynthesize their own[34]. Interestingly, bacteria, which can make their own biotin, did not give TurboID background before exogenous biotin addition (FIG. 3B). Perhaps bacteria have lower levels of free biotin due to feedback regulation of its synthesis.

If, on the other hand, the priority is to precisely restrict promiscuous biotinylation to a specific window of time, then miniTurbo is recommended over TurboID. miniTurbo is not as active as TurboID, but it gives much less background than TurboID in the absence of exogenous biotin addition. Another benefit of miniTurbo is that it is 20% smaller than TurboID (28 versus 35 kD), which may decrease the probability of negative impact on the trafficking and/or function of the proteins to which it is fused.

In addition to decreasing the time window of labeling and increasing signal, TurboID and miniTurbo enable BirA-based proximity labeling in new contexts that we showed are problematic for the original BioID enzyme. We believe that the beneficial properties of TurboID and miniTurbo arise from the fact that they were evolved in the yeast secretory pathway at 30° C. (the normal culturing temperature for yeast), while wild-type BirA normally functions in the cytosol of E. coli at 37° C.[4]. Hence, TurboID was much more active than BioID in the mammalian ER lumen, and TurboID gave robust biotinylation in the yeast cytosol (at 30° C.), where BioID activity was undetectable. Our BirA variants were also efficacious in flies which grow at 25° C. and in worms which grow at 20° C.

Despite the popularity of enzyme-catalyzed proximity labeling, there have been very few in vivo applications to date. BioID has only been used in the mouse brain for mapping of the inhibitory post-synapse, where biotin was supplied by IP injection for 7 days[22], and in a xenograft model, where biotin was supplied by IP injection for 2 days[33]. APEX peroxidase has been used in three in vivo studies, but in each case, genetic modification to compromise cuticle integrity[35,36] or manual dissection of tissue had to be performed[37] to deliver APEX chemical substrates to the relevant cells. APEX also relies on $H_2O_2$ which is toxic. Hence TurboID and miniTurbo expand the possibilities for non-toxic but rapid proximity biotinylation, with facile substrate delivery, in in vivo systems.

Our lab has previously used yeast display-based directed evolution to improve the catalytic efficiency of APEX2 and split HRP enzymes. However, here we faced new challenges that required a number of innovations. First, starting signal was far too low, and required the development of a signal amplification procedure. TSA has been used on fixed mammalian cells for fluorescence microscopy applications[38], but not, as far as we are aware, on live yeast cells, or for FACS. Second, to distinguish promiscuous biotinylation activity from self-biotinylation activity, we developed a strategy to remove ligases from the yeast surface prior to staining and FACS. Third, we found it essential to implement negative selections to eliminate ligases with increased biotin affinity that would enable them to use the low levels of biotin present in normal media. These strategies may be beneficial to others seeking to use the yeast display platform to evolve new enzymatic activities.

Recently, a BioID variant from *Aquifex* aeolicus was reported, called BioID2[39]. BioID2 is 25% smaller than BioID, and more active at higher temperatures, but not claimed (or shown) to be faster or more catalytically efficient than BioID. One follow-up study used BioID2 for proteomic mapping of the inner nuclear membrane and employed a biotin tagging time of 16 hours[40]. BioID2 also has higher biotin affinity than BioID, described by the authors as an advantage, but this results in biotinylation activity in the absence of exogenous biotin addition, which prevents precise temporal control over labeling.

Methods

Cloning

See Table 2 for a list of genetic constructs used in this study, with detailed description of construct designs, linker orientations, epitope tags, and signal sequence identities. All BirA variants were derived from *E. coli* biotin protein ligase, and are codon optimized for expression in mammalian cells. For cloning, PCR fragments were amplified using Q5 polymerase (New England BioLabs (NEB)). The vectors were double-digested using standard enzymatic restriction digest and ligated to gel purified PCR products by T4 DNA ligation or Gibson assembly. Ligated plasmid products were introduced by heat shock transformation into competent XL1-Blue bacteria. Mutants of BirA were either generated using QuikChange mutagenesis (Stratagene) or isolated from individual yeast clones and transferred to mammalian expression vectors using standard cloning techniques.

Yeast Cell Culture

For yeast-display (FIGS. 1C, 1E, 5, and 6), *S. cerevisiae* strain EBY100 was cultured according to previously published protocols[44]. Cells were propagated at 30° C. in synthetic dextrose plus casein amino acid (SDCAA, "regular") medium supplemented with tryptophan (20 mg/L). Transformed cells containing the TRP1 gene were selected on SDCAA plates and propagated in SDCAA medium at 30° C. Protein expression was induced by inoculating saturated yeast culture into 10% SD/GCAA (SDCAA medium with 90% of dextrose replaced with galactose), or into "biotin-depleted" medium[45] (1.7 g/L YNB-Biotin (Sunrise Science Products), 5 g/L ammonium sulfate, 2 g/L dextrose, 18 g/L galactose, complete amino acids, 0.125 ng/mL d-biotin), at a 1:1000 dilution and incubating at 30° C. for 18-24 hours. Yeast cells were transformed with the yeast-display plasmid pCTCON2[44] using the Frozen E-Z Yeast Transformation II kit (Zymoprep) according to manufacturer protocols.

For comparison of BirA variants in the yeast cytosol (FIG. 3A), *S. cerevisiae* strain BY4741 cells were propagated at 30° C. in supplemented minimal medium (SMM; 6.7 g/L Difco nitrogen base without amino acids, 20 g/L dextrose, 0.54 g/L CSM-Ade-His -Leu-Lys-Trp-Ura (Sunrise Science Products), 20 mg/L adenine, 20 mg/L uracil, 20 mg/L histidine, 30 mg/L lysine) supplemented with leucine (20 mg/L). Transformed cells containing the LEU2 gene were selected on SMM plates (SMM with 20 g/L agar) and propagated in SMM at 30° C. Protein expression was induced by inoculating saturated yeast culture into 10% D/G SMM (SMM medium with 90% of dextrose replaced with galactose) at a 1:100 dilution and incubating at 30° C. for 18 hours. Yeast cells were transformed with pRS415 plasmids using the Frozen E-Z Yeast Transformation II kit (Zymoprep) according to manufacturer protocols.

Generation of BirA Libraries for Yeast Display

Libraries of BirA mutants were generated by error-prone PCR according to published protocols[46]. In brief, 150 ng of the template BirA in vector pCTCON2[44] were amplified for 10-20 rounds with 0.4 µM forward and reverse primers:

F:
(SEQ ID NO: 1)
5'-CTAGTGGTGGAGGAGGCTCTGGTGGAGGCGGTAGCGGAGGCGGAGGG

TCGGCTAGC-3',
and

R:
(SEQ ID NO: 2)
5'-TATCAGATCTCGAGCTATTACAAGTCCTCTTCAGAAATAAGCTTTTG

TTCGGATCC-3', 2 mM MgCl$_2$, 5 units of Taq polymerase (NEB), and 2-20 µM each of the mutagenic nucleotide analogs 8-oxo-2'-deoxyguanosine-5'-triphosphate (8-oxo-dGTP) and 2'-deoxy-P-nucleoside-5'-triphosphate (dPTP). The PCR products were then gel purified and reamplified for another 30 cycles under normal PCR conditions with the following primers:

F:
(SEQ ID NO: 3)
5'-CAAGGTCTGCAGGCTAGTGGTGGAGGAGGCTCTGGTG-3',

R:
(SEQ ID NO: 4)
5'-CTACACTGTTGTTATCAGATCTCGAGCTATTACAAGTC-3'.

The inserts were then electroporated into electrocompetent *S. cerevisiae* EBY100[44] with the BamHI-NheI linearized pCTCON2 vector (10 µg insert/1 µg vector) backbone. The electroporated cultures were rescued in 100 mL of SDCAA medium supplemented with 50 units/mL penicillin and 50 µg/mL streptomycin for 2 days at 30° C. Refer to "Directed evolution of TurboID and miniTurbo" section below for further details on library generation for each generation of evolution.

Yeast Display Selections

For each round of evolution (FIGS. 5B, 5D, 5E, 5H, 5I) At least a ten-fold excess of yeast cells relative to the original library size (approximated via transformation efficiency) was propagated and labeled each round to ensure oversampling. Library protein expression was induced by inoculating saturated yeast culture into 10% SD/GCAA or biotin-depleted medium at a minimum of 1:100 dilution and incubating at 30° C. for 18-24 hours. For samples biotin labeled for "18 hours," yeast were induced in 10% SD/GCAA or biotin-depleted medium supplemented with 50 µM biotin, 1 mM ATP, and 5 mM MgCl2 at 30° C. for 24 hours. For samples labeled for shorter time points, yeast were induced in 10% SD/GCAA or biotin-depleted medium for 18 hours at 30° C. prior to supplementation with 50 µM biotin, 1 mM ATP, and 5 mM MgCl2 for the remaining labeling time indicated. After labeling, approximately 5 million cells were pelleted at 5000 g for 30 s at 4° C. and washed five times with 1 mL PBS (phosphate buffered saline)+0.5% bovine serum albumin (BSA; 1 mg/mL) (PBS-B).

For removal of ligase proteins via TCEP reduction ((FIG. 5C), yeast were incubated in 500 µL PBS-B+2 mM TCEP at 30° C. for 90 minutes, then washed four times with 1 mL PBS-B. For tyramide signal amplification (TSA, FIG. 5A), yeast cells were incubated in 50 µL PBS-B+1:100 streptavidin-horseradish peroxidase (HRP) for 1 hour at 4° C., then washed three times with 1 mL PBS-B. HRP labeling was performed by incubating yeast in 750 µL PBS-B with 50 µM biotin-phenol and 1 mM $H_2O$ for 1 min at room temperature. The reaction was quenched by adding 750 µL PBS-B+20 mM sodium ascorbate and 10 mM Trolox followed by rapid mixing via inversion. Cells were then washed two times with 1 mL PBS-B+10 mM sodium ascorbate and 5 mM Trolox, and once with 1 mL PBS-B.

Yeast cells were then incubated in 50 µL PBS-B+1:400 chicken anti-myc, and 1:50 rabbit anti-biotin when detecting biotinylated proteins with anti-biotin antibody, for 1 hour at 4° C., then washed three times with 1 mL PBS-B. Yeast cells were then incubated in 50 µL PBS-B+1:200 Alexa Fluor 647 goat anti-chicken IgG, and 1:50 phycoerythrin (PE) goat anti-rabbit IgG when detecting biotinylated proteins with anti-biotin antibody, or streptavidin-PE when detecting biotinylated proteins with streptavidin, for 1 hour at 4° C., then washed three times with 1 mL PBS-B for FACS analysis.

Figure 5J:
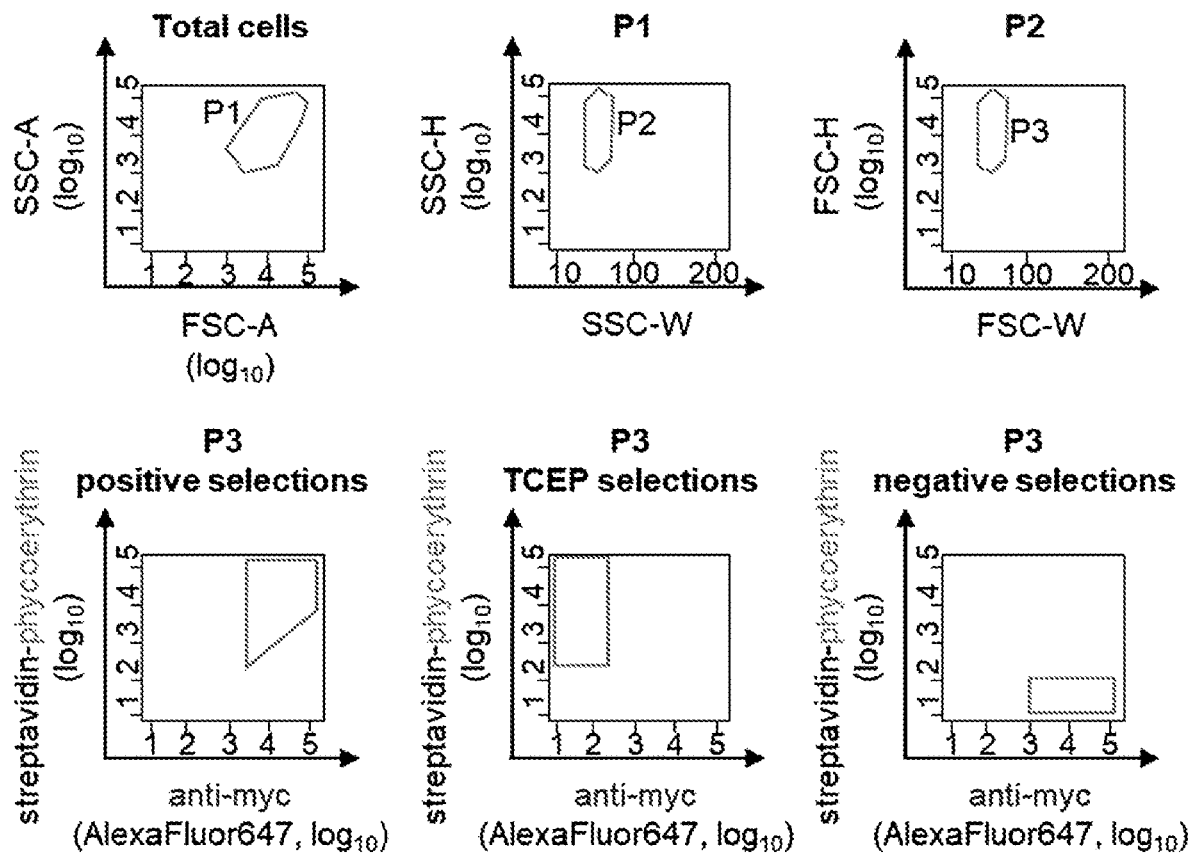

For two-dimensional FACS sorting, samples were resuspended in PBS-B at a maximal concentration of 100 million cells/mL and sorted on a BD FACS Aria II cell sorter (BD Biosciences) with the appropriate lasers and emission filters (561 nm and 530/30 for AF488, 640 nm and 575/26 for PE). To analyze and sort single yeast cells, cells were plotted by a forward-scatter area (FSC-A) and side-scatter area (SSC-A) and a gate was drawn around cells clustered between $10^4$-$10^5$ FSC-A, $10^3$-$10^5$ SSC-A to give population P1 (FIG. 5J). Cells from population P1 were then plotted by side-scatter width (SSC-W) and side-scatter height (SSC-h) and a gate was drawn around cells clustered between 10-100 SSC-W and $10^3$-$10^5$ SSC-H to give population P2 (FIG. 5J). Cells from population P2 were then plotted by forward-scatter width (FSC-W) and forward-scatter height (FSC-H) and a gate was drawn around cells clustered between 10-100 FSC-W and $10^3$-$10^5$ FSC-H to give population P3 (FIG. 5J). Population P3 often represented >90% of the total population analyzed.

From population P3, gates were drawn to collect yeast with the highest activity/expression ratio, i.e., positive for AF647 signal that also had high PE signal (FIG. 5J). For TCEP treated samples, gates were drawn to collect yeast with high PE signal and no AF647 signal above background (FIG. 5J). For negative selections (FIG. 5G), gates were drawn to collect yeast with AF647 signal and no PE signal above background (FIG. 5J). After sorting, yeast were collected in SDCAA medium containing 1% penicillin-streptomycin and incubated at 30° C. for 24 h. 1 mL of the growing culture was removed for DNA extraction using the Zymoprep yeast Plasmid Miniprep II (Zymo Research) kit according to manufacturer protocols (using 6 µL zymolyase, vigorously vortex after lysis), and at least ten-fold excess of the number of cells retained during sorting were propagated in SDCAA+1% pen-strep to ensure oversampling (yeast cells were passaged in this manner at least two times prior to the next round of selection). To analyze yeast populations and clones by FACS (FIGS. 1C, 1E, 5B, 5D, 5E, 5F, 5I1, 5J; and FIG. 6), yeast samples were prepared on a small scale (1 mL cultures) as described above, and analyzed on a BD Accuri flow cytometer (BD Biosciences). BD FACSDIVA software was used to analyze all data from FACS sorting and analysis. Refer to "Directed evolution of TurboID and miniTurbo" section below for further details on selections for each round of each generation of evolution. Refer to Table 3 for a list of antibodies used in this study.

Directed Evolution of TurboID and miniTurbo

Summaries of all yeast display directed evolution and resulting mutants are shown in FIGS. 1E, 5, 6, and Table 1.

For the first round of evolution (FIG. 5B), three libraries were generated using BirA-R118S (Table 2) as the starting template. The three libraries were generated using error prone PCR as described above, using the following conditions to result in varying levels of mutagenesis:
  Library 1: 2 µM 8-oxo-dGTP, 2 µM dPTP, 10 PCR cycles
  Library 2: 2 µM 8-oxo-dGTP, 2 µM dPTP, 20 PCR cycles
  Library 3: 20 µM 8-oxo-dGTP, 20 µM dPTP, 10 PCR cycles The library sizes, as calculated by transformation efficiency, were $1.4 \times 10^7$ for Library 1, $1.7 \times 10^7$ for Library 2, and $8 \times 10^6$ for Library 3. FACS analysis of the three libraries showed robust expression and wide range of activities for Library 1 and Library 2, however Library 3 showed poor expression and no activity. Sequencing of 24 clones in Library 1 revealed an average of 1.5 amino acid changes per BirA gene. Sequencing of 24 clones in Library 2 revealed an average of 2.4 amino acid changes per BirA gene.

Library 1 and Library 2 were combined and used as the initial population for the first round of selections. This combined library was induced as described above, supplemented with 50 µM biotin, 1 mM ATP, and 5 mM MgCl2, for 24 hours. From this culture, approximately $5 \times 10^8$ cells were prepared for sorting (assuming 1 $OD_{600} \approx 3 \times 10^7$ cells[47]) as described above with TSA treatment (FIG. 5A). $6.24 \times 10^7$ cells were sorted by FACS. A square gate that collected cells positive for both anti-myc and streptavidin (conjugated to fluorophores, see Table 3) was drawn, and approximately $2.5 \times 10^6$ cells were collected (4%) to give population E1-R1.

Population E1-R1 was passaged twice, and analyzed by FACS side-by-side with the original combined library and BirA-R118S to ensure the sort was successful (resulting population still had expression and had higher or equivalent activity). Sequencing of 24 clones from E1-R1 revealed an average of 1.5 mutations per BirA gene. Population E1-R1 was induced, supplemented with 50 µM biotin, 1 mM ATP, and 5 mM MgCl2, for 24 hours. From this culture, approximately 10-fold excess (i.e. >$2.5 \times 10^7$) cells were prepared for sorting with TSA treatment. A square gate that collected cells positive for both anti-myc and streptavidin was drawn, and approximately 3.8% of cells were collected to give population E1-R2.

Population E1-R2 was passaged twice, and analyzed by FACS side-by-side with previous rounds and BirA-R118S. Sequencing of 24 clones from E1-E1-R2 revealed an average of 1.5 mutations per BirA gene. Population E1-R2 was induced for ~18 hours then supplemented with 50 µM biotin, 1 mM ATP, and 5 mM $MgCl_2$ for 6 hours. From this culture, approximately 10-fold excess cells were prepared for sorting with TSA treatment. A square gate that collected cells positive for both anti-myc and streptavidin was drawn, and approximately 0.7% of cells were collected to give population E1-R3.

Population E1-R3 was passaged twice, and analyzed by FACS side-by-side with previous rounds and BirA-R118S. Population E1-R3 was induced for ~18 hours then supplemented with 50 µM biotin, 1 mM ATP, and 5 mM $MgCl_2$ for 6 hours. From this culture, approximately 10-fold excess cells were prepared for sorting with TSA treatment. A square gate that collected cells positive for both anti-myc and streptavidin was drawn, and approximately 2.4% of cells were collected to give population E1-R4.

Population E1-R4 was passaged twice, and analyzed by FACS side-by-side with previous rounds and BirA-R118S. Population E1-R4 was induced for ~18 hours then supplemented with 50 µM biotin, 1 mM ATP, and 5 mM $MgCl_2$ for 3 hours. From this culture, approximately 10-fold excess cells were prepared for sorting. A square gate that collected cells positive for both anti-myc and streptavidin was drawn, and approximately 2.6% of cells were collected to give population E1-R5.

Population E1-R5 was passaged twice, and analyzed by FACS side-by-side with previous rounds and BirA-R118S. Population E1-R5 was induced for ~18 hours then supplemented with 50 µM biotin, 1 mM ATP, and 5 mM $MgCl_2$ for 1 hour. From this culture, approximately 10-fold excess cells were prepared for sorting. A square gate that collected cells positive for both anti-myc and streptavidin was drawn, and approximately 0.9% of cells were collected to give population E1-R6.

Population E1-R6 was passaged twice, and analyzed by FACS side-by-side with previous rounds and BirA-R118S. Sequencing of E1-R6 revealed several mutants with the mutation E313K. Several mutants with and without this mutation were assayed as single clones on the yeast surface, and the most promising mutants, including two with the E313K mutation, were assayed in the mammalian cell cytosol. While neither of the E313K mutants showed significant difference in activity to R118S over 24 hours, they both showed very strong self-labeling at shorter time points, e.g. 1 hour. The crystal structure of BirA[26] shows that this residue points directly into the active site, where a lysine mutation could easily react with the phosphate group of biotin-5'-AMP. We removed this mutation from the two promising clones bearing it and assayed again in the mammalian cell cytosol. One of the mutants, denoted in this study as G1 (Table 1), displayed significantly higher promiscuous activity than R118S after 24 hours of labeling. Another mutant from the mammalian cell screen, denoted in this study as R6-1 (Table 1), also displayed significantly higher promiscuous activity than R118S after 24 hours of labeling. Both of these mutants, with 4 mutations each, had each of their mutations removed individually and in different combinations. Analysis of the resulting mutants in mammalian cells showed that each mutation was contributing to increased activity relative to R118S observed for R6-1 and G1.

For the second round of evolution (FIG. 5D), six libraries were generated. Three libraries were made using R6-1 (Table 2 P10) as the starting template, and the three libraries were made using G1 (Table 2 P12) as the starting template, both using error prone PCR with the following conditions:
 Library 1: R6-1, 2 µM 8-oxo-dGTP, 2 µM dPTP, 10 PCR cycles
 Library 2: R6-1, 2 µM 8-oxo-dGTP, 2 µM dPTP, 20 PCR cycles
 Library 3: R6-1, 20 µM 8-oxo-dGTP, 20 µM dPTP, 10 PCR cycles
 Library 4: G1, 2 µM 8-oxo-dGTP, 2 µM dPTP, 10 PCR cycles
 Library 5: G1, 2 µM 8-oxo-dGTP, 2 µM dPTP, 20 PCR cycles
 Library 6: G1, 20 µM 8-oxo-dGTP, 20 µM dPTP, 10 PCR cycles The library sizes, as calculated by transformation efficiency, were $3.8 \times 10^7$ for Library 1, $1.9 \times 10^7$ for Library 2, $1.6 \times 10^7$ for Library 3, $8 \times 10^7$ for Library 4, $3.9 \times 10^7$ for Library 5, and $3.9 \times 10^7$ for Library 6. FACS analysis of the three libraries showed robust expression and wide range of activities for Libraries 1, 2, 4, and 5, however Libraries 3 and 6 showed poor expression and no activity.

Libraries 1, 2, 4, and 5 were combined and used as the initial population for the first round of selections. This combined library was induced, supplemented with 50 µM biotin, 1 mM ATP, and 5 mM $MgCl_2$, for 24 hours. From this culture, approximately 10-fold excess cells were prepared for sorting with TSA treatment. A square gate that collected cells positive for both anti-myc and streptavidin was drawn, and approximately 8.4% of cells were collected to give population E2-R1.

Population E2-R1 was passaged twice, and analyzed by FACS side-by-side with the combined library template. Population E1-R5 was induced, supplemented with 50 µM biotin, 1 mM ATP, and 5 mM $MgCl_2$, for 24 hours. From this culture, approximately 10-fold excess cells were prepared for sorting with TCEP treatment (FIG. 5C) followed by TSA treatment. A square gate that collected cells positive for streptavidin but negative for anti-myc was drawn, and approximately 1.2% of cells were collected to give population E1-R2.

Population E2-R2 was passaged twice, and analyzed by FACS side-by-side with the combined library template and previous rounds. Population E2-R2 induced, supplemented with 50 µM biotin, 1 mM ATP, and 5 mM $MgCl_2$, for 24 hours. From this culture, approximately 10-fold excess cells were prepared for sorting with TSA treatment. A square gate that collected cells positive for both anti-myc and streptavidin was drawn, and approximately 19% of cells were collected to give population E1-R3.

Population E2-R3 was passaged twice, and analyzed by FACS side-by-side with previous rounds. Population E2-R3 was induced, supplemented with 50 µM biotin, 1 mM ATP, and 5 mM $MgCl_2$, for 24 hours. From this culture, approximately 10-fold excess cells were prepared for sorting. A trapezoidal gate that collected cells positive for both anti-myc and streptavidin, but with high streptavidin/anti-myc ratios, was drawn, and approximately 1.4% of cells were collected to give population E1-R4. From here on, only trapezoidal gates as described here were used for double-positive selections.

Population E2-R4 was passaged twice, and analyzed by FACS side-by-side with previous rounds. Population E2-R4 was induced for ~18 hours, then supplemented with 50 µM biotin, 1 mM ATP, and 5 mM $MgCl_2$ for 1 hour. From this culture, approximately 10-fold excess cells were prepared for sorting. A trapezoidal gate that collected cells positive for both anti-myc and streptavidin was drawn, and approximately 1.1% of cells were collected to give population E1-R5.

Population E2-R5 was passaged twice, and analyzed by FACS side-by-side with the combined library template and previous rounds. Population E2-R5 was induced for ~18 hours, then supplemented with 50 µM biotin, 1 mM ATP, and 5 mM $MgCl_2$ for 6 hours. From this culture, approximately 10-fold excess cells were prepared for sorting with TCEP treatment followed by TSA. A square gate that collected cells positive for streptavidin and negative for anti-myc was drawn, and approximately 1.5% of cells were collected to give population E1-R6.

Population E2-R6 was passaged twice, and analyzed by FACS side-by-side with previous rounds and the combined library template. Sequencing of E2-R6 revealed several mutations that appeared in multiple clones. Several of these mutants were assayed as single clones on the yeast surface, however it was found after re-sequencing that man of the most promising mutants had mutated stop codons. After mutating back the stop codons, the mutants were re-assayed on the yeast surface, and the mutants that remained promising were assayed in the mammalian cell cytosol. One of the mutants, denoted in this study as G2 (Table 1), displayed significantly higher promiscuous activity than R118S, G1 (its template), or any other mutant tested after 1 hour of labeling. G1, with 2 additional mutations relative to G1, had each or both of its mutations removed. Analysis of the resulting mutants in mammalian cells showed that each mutation was contributing to activity boost observed for G2.

For the third round of evolution (FIG. 5E), three libraries were made using G2 as the starting template (Table 2 P13) using error prone PCR with the following conditions:
Library 1: 2 µM 8-oxo-dGTP, 2 µM dPTP, 10 PCR cycles
Library 2: 2 µM 8-oxo-dGTP, 2 µM dPTP, 20 PCR cycles
Library 3: 10 µM 8-oxo-dGTP, 20 µM dPTP, 10 PCR cycles The library sizes, as calculated by transformation efficiency, were $3.5 \times 10^8$ for Library 1, $3.6 \times 10^7$ for Library 2, and $6.8 \times 10^6$ for Library 3. FACS analysis of the three libraries showed robust expression and wide range of activities for Library 1 and Library 2, however Library 3 showed weak expression and no activity.

Libraries 1 and 2 were combined and used as the initial population for the first round of selections. This combined library was induced for ~18 hours, then supplemented with 50 µM biotin, 1 mM ATP, and 5 mM $MgCl_2$ for 1 hour. From this culture, approximately 10-fold excess cells were prepared for sorting. A trapezoidal gate that collected cells positive for both anti-myc and streptavidin was drawn, and less than 0.1% of cells were collected to give population E3-R1.

Population E3-R1 was passaged twice, and analyzed by FACS side-by-side with G2 and the combined library template. Population E3-R1 was induced for ~18 hours, then supplemented with 50 µM biotin, 1 mM ATP, and 5 mM $MgCl_2$ for 1 hour. From this culture, approximately 10-fold excess cells were prepared for sorting. A trapezoidal gate that collected cells positive for both anti-myc and streptavidin was drawn, and 0.15% of cells were collected to give population E3-R2.

Population E3-R2 was passaged twice, and analyzed by FACS side-by-side with G2, the combined library template, and previous rounds. Population E3-R2 was induced for ~18 hours, then supplemented with 50 µM biotin, 1 mM ATP, and 5 mM $MgCl_2$ for 10 minutes. From this culture, approximately 10-fold excess cells were prepared for sorting. A trapezoidal gate that collected cells positive for both anti-myc and streptavidin was drawn, and less than 0.1% of cells were collected to give population E3-R3.

At E3-R3, it was noted that the population had strong streptavidin signal in the absence of exogenous biotin addition. Sequencing of population E3-R3 revealed that the majority of clones had a large insertion at the 5' of the BirA gene. Removal of this insertion restored biotin dependence, but also resulted in decreased activity (5-fold less than E3-R3). The library was "cleaned" by removing this insertion via PCR with primers that restored the wild-type N-terminal sequence, and subjected to one additional round of double-positive selection with 10 minute labeling and 0.1% cells collected. The resulting population was E3-R4.

Population E3-R4 was passaged twice, and analyzed by FACS side-by-side with previous rounds. Sequencing of E1-R6 revealed several mutations that appeared in multiple clones. Several of these mutants were assayed as single clones on the yeast surface, the most promising mutants were assayed in the mammalian cell cytosol. Two mutants had significantly higher activity than the template G2 or any other mutants. The mutations from these mutants were combined in various combinations, resulting in the highest activity mutant, denoted in this study as G3 (Table 1).

G3 was the highest activity mutant found to date, but it also appeared to have streptavidin signal without the addition of exogenous biotin. This was observed in yeast, where this signal proved to be biotin-dependent (FIG. 5F), and also in the mammalian cytosol (FIG. 8). From this point, we continued with two evolutions as follows:

In one path, we truncated the N-terminal domain (aa 1-63) of G3 to give G3Δ(Table 1). Consistent with literature[25,27], this truncation resulted in reduced streptavidin signal when exogenous biotin was omitted (FIG. 5F). Using G3Δ as the starting template (Table 2 P15) for another round of evolution (FIG. 5H), we generated three libraries using error prone PCR with the following conditions:
Library 1: 2 µM 8-oxo-dGTP, 2 µM dPTP, 10 PCR cycles
Library 2: 2 µM 8-oxo-dGTP, 2 µM dPTP, 20 PCR cycles
Library 3: 4 µM 8-oxo-dGTP, 2 µM dPTP, 20 PCR cycles The library sizes, as calculated by transformation efficiency, were $4.9 \times 10^8$ for Library 1, $4.6 \times 10^8$ for Library 2, and $3.7 \times 10^8$ for Library 3. FACS analysis of the three libraries showed robust expression and wide range of activities for all libraries, therefore all were combined and used for the first round of selections.

This combined library was induced in biotin-depleted media, supplemented with 50 µM biotin, 1 mM ATP, and 5 mM $MgCl_2$, for 18 hours. From this culture, approximately 10-fold excess cells were prepared for sorting with streptavidin. A trapezoidal gate that collected cells positive for both anti-myc and streptavidin was drawn, and 0.1% of cells were collected to give population E4-R1.

Population E4-R1 was passaged twice, and analyzed by FACS side-by-side with G3Δ and the combined library template. Population E4-R1 was induced for ~18 hours in biotin-depleted media, then supplemented with 50 µM biotin, 1 mM ATP, and 5 mM $MgCl_2$ for 3.5 hours. From this culture, approximately 10-fold excess cells were prepared for sorting with anti-biotin antibody. A trapezoidal gate that collected cells positive for both anti-myc and anti-biotin was drawn, and 1% of cells were collected to give population E5-R2.

Population E4-R2 was passaged twice, and analyzed by FACS side-by-side with G3Δ, the combined library template, and previous rounds. Population E4-R2 was induced for ~18 hours in biotin-depleted media, then supplemented with 50 µM biotin, 1 mM ATP, and 5 mM $MgCl_2$ for 1 hour. From this culture, approximately 10-fold excess cells were prepared for sorting with streptavidin. A trapezoidal gate that collected cells positive for both anti-myc and streptavidin was drawn, and 0.2% of cells were collected to give population E5-R3.

Population E4-R3 was passaged twice, and analyzed by FACS side-by-side with G3Δ, the combined library template, and previous rounds. Population E4-R3 was induced for ~18 hours in biotin-depleted media, then supplemented with 50 µM biotin, 1 mM ATP, and 5 mM $MgCl_2$ for 1 hour. From this culture, approximately 10-fold excess cells were prepared for sorting with anti-biotin antibody. A trapezoidal gate that collected cells positive for both anti-myc and anti-biotin was drawn, and 0.1% of cells were collected to give population E5-R4.

Population E4-R4 was passaged twice, and analyzed by FACS side-by-side with G3Δ, the combined library template, and previous rounds. Population E4-R4 was induced for ~18 hours in biotin-depleted media, labeling was omitted for negative selection (FIG. 5G). From this culture, approximately 10-fold excess cells were prepared for sorting with streptavidin. A square gate that collected cells positive for anti-myc and negative for streptavidin was drawn, and 50% of cells were collected to give population E5-R5.

Population E4-R5 was passaged twice, and analyzed by FACS side-by-side with G3Δ, the combined library template, and previous rounds. Two selections were performed on E4-R5. In the first selection, population E4-R5 was induced for ~18 hours in biotin-depleted media, labeling was omitted for negative selection. From this culture, approximately 10-fold excess cells were prepared for sorting with anti-biotin antibody. A square gate that collected cells positive for both anti-myc and anti-biotin was drawn, and 45% of cells were collected to give population E4-R6.1.

In the second selection, population E4-R5 was induced for ~18 hours in biotin-depleted media, then supplemented with 50 μM biotin, 1 mM ATP, and 5 mM MgCl$_2$ for 20 minutes. From this culture, approximately 10-fold excess cells were prepared for sorting with streptavidin. A trapezoidal gate that collected cells positive for both anti-myc and streptavidin was drawn, and 0.1% of cells were collected to give population E4-R5.2.

One more round of selections was performed on E4-R6.1, which was induced for ~18 hours in biotin-depleted media, then supplemented with 50 μM biotin, 1 mM ATP, and 5 mM MgCl$_2$ for 1 hour. From this culture, approximately 10-fold excess cells were prepared for sorting with streptavidin. A trapezoidal gate that collected cells positive for both anti-myc and streptavidin was drawn, and 0.2% of cells were collected to give population E4-R7.

Population E4-R7 was passaged twice, and analyzed by FACS side-by-side with previous rounds. Sequencing of E4-R7 revealed several mutations that appeared in multiple clones. Several of these mutations were assayed as single mutations and in various combinations in the mammalian cytosol. One mutation, K194I, was found to significantly increase activity while not increasing signal exogenous when biotin is omitted. Introducing K194I into G3Δ resulted in miniTurbo (Table 1).

In a second path, we continued with evolving G3 (FIG. 5I). Two libraries were made using G3 as the starting template (Table 2 P14) using error prone PCR with the following conditions:
Library 1: 2 μM 8-oxo-dGTP, 2 μM dPTP, 10 PCR cycles
Library 2: 2 μM 8-oxo-dGTP, 2 μM dPTP, 20 PCR cycles
The library sizes, as calculated by transformation efficiency, were 2×10$^7$ for Library 1 and 1.1×10$^7$ for Library 2. FACS analysis of the libraries showed robust expression and wide range of activities for Library 1 and Library 2.

Libraries 1 and 2 were combined and used as the initial population for the first round of selections. This combined library was induced for ~18 hours in biotin-depleted media, then supplemented with 50 μM biotin, 1 mM ATP, and 5 mM MgCl$_2$ for 10 minutes. From this culture, approximately 10-fold excess cells were prepared for sorting with anti-biotin antibody (Table 3) in place of streptavidin. A trapezoidal gate that collected cells positive for both anti-myc and anti-biotin was drawn, and 0.1% of cells were collected to give population E5-R1.

Population E5-R1 was passaged twice, and analyzed by FACS side-by-side with G3 and the combined library template. Population E5-R1 was induced for ~18 hours in biotin-depleted media, then supplemented with 50 μM biotin, 1 mM ATP, and 5 mM MgCl$_2$ for 10 minutes. From this culture, approximately 10-fold excess cells were prepared for sorting with anti-biotin antibody. A trapezoidal gate that collected cells positive for both anti-myc and anti-biotin was drawn, and 0.1% of cells were collected to give population E5-R2.

Population E5-R2 was passaged twice, and analyzed by FACS side-by-side with G3, the combined library template, and previous rounds. Population E5-R2 was induced for ~18 hours in biotin-depleted media, then supplemented with 50 μM biotin, 1 mM ATP, and 5 mM MgCl$_2$ for 10 minutes. From this culture, approximately 10-fold excess cells were prepared for sorting with anti-biotin antibody. A trapezoidal gate that collected cells positive for both anti-myc and anti-biotin was drawn, and 1.7% of cells were collected to give population E5-R3.

Population E5-R3 was passaged twice, and analyzed by FACS side-by-side with G3, the combined library template, and previous rounds. Population E5-R3 was induced for ~18 hours in regular media, labeling was omitted for negative selection. From this culture, approximately 10-fold excess cells were prepared for sorting with anti-biotin antibody. A square gate that collected cells positive for anti-myc and negative for anti-biotin was drawn, and 34% of cells were collected to give population E5-R4.

Population E5-R4 was passaged twice. FACS analysis side-by-side with G3, the combined library template, and previous rounds showed that the negative selection that resulted E5-R4 reduced overall activity of the population. Population E5-R2 was induced for ~18 hours in biotin depleted media, then supplemented with 50 μM biotin, 1 mM ATP, and 5 mM MgCl$_2$ for 10 minutes. From this culture, approximately 10-fold excess cells were prepared for sorting with streptavidin. A trapezoidal gate that collected cells positive for both anti-myc and streptavidin was drawn, and 0.8% of cells were collected to give population E5-R5.

Population E5-R5 was passaged twice, and analyzed by FACS side-by-side with G3, the combined library template, and previous rounds. Population E5-R5 was induced for ~18 hours in regular media, labeling was omitted for negative selection. From this culture, approximately 10-fold excess cells were prepared for sorting with anti-biotin antibody. A square gate that collected cells positive for anti-myc and negative for anti-biotin was drawn, and 11.6% of cells were collected to give population E5-R6.

Population E5-R6 was passaged twice, and analyzed by FACS side-by-side with previous rounds. Sequencing of E5-R6 revealed several mutations that appeared in multiple clones. Several of these mutations were assayed as single mutations and in various combinations in the mammalian cytosol. None of the mutations gave dramatic increases in activity, but one mutation M241T, appeared to impart benefits to activity.

Screening of mutations present in E4-R6.2 in the mammalian cell cytosol revealed one mutation, S263P, which boosted activity, but also increased signal when biotin was omitted. This mutation, along with K194I from E4-R7 and M241T from E5-R6, were introduced into G3 to give TurboID (Table 1). We also tested M241T in miniTurbo, however it was not added because it increased background signal when biotin was omitted.

Mammalian Cell Culture, Transfection, and Stable Cell Line Generation

HEK 293T cells from ATCC (passage number<25) were cultured as a monolayer in growth media (either MEM (Cellgro) or a 1:1 DMEM:MEM mixture (Cellgro) supplemented with 10% (w/v) fetal bovine serum (VWR), 50 units/mL penicillin, and 50 g/mL streptomycin at 37° C. under 5% $CO_2$. Mycoplasma testing was not performed before experiments. For confocal imaging experiments, cells were grown on 7×7 mm glass coverslips in 48-well plates. To improve adherence of HEK 293T cells, glass coverslips were pretreated with 50 µg/mL fibronectin (Millipore) in MEM for at least 20 min at 37° C. before cell plating. For Western blotting, cells were grown on polystyrene 6-well plates (Greiner).

For transient expression (FIGS. 1F, 2A, 2C, 2D, 7, 8, 9A, and 9C), cells were typically transfected at approximately 60% confluency using 0.8 µL Lipofectamine2000 (Life Technologies) and 200 ng plasmid per 300,000 cells in serum-free media for 3-4 hours, after which time Lipofectamine-containing media was replaced with fresh serum-containing media. BioID expressing-cells were typically labeled by supplementing media with 50 µM biotin for 18 hours, approximately 18 hours after transfection; for shorter time-points, labeling was initiated approximately 30-36 hours after transfection. TurboID and miniTurbo expressing-cells were typically labeled by supplementing 50 or 500 µM biotin for 10 min, approximately 36 hours after transfection; for longer time-points, labeling was initiated between 18-35 hours after transfection. Labeling was stopped by placing cells on ice and washing five times with PBS (FIG. 7).

For preparation of lentiviruses, HEK 293T cells in T25 flasks (BioBasic) were transfected at ~60-70% confluency with the lentiviral vector pLX304 containing the gene of interest (2500 ng; Table 2 P33-P35), and the lentiviral packaging plasmids pVSVG (250 ng; Table 2 P36) and A8.9 (2250 ng; Table 2 P36) with 30 µL Lipofectamine2000 for 3 hours. Approximately 60 hours after transfection, the cell medium containing the lentivirus was harvested and filtered through a 0.45-µm filter. HEK cells were then infected at ~50% confluency, followed by selection with 8 µg/mL blasticidin in growth medium for at least 7 days before further analysis (FIGS. 2C, 2D, 9B, 9D). Cells stably expressing BioID were labeled by supplementing media with 50 µM biotin for 18 hours. Cells stably expressing BioID were typically by supplementing media with 50 or 500 µM biotin for 10 minutes Labeling was stopped by placing cells on ice and washing five times with PBS (FIG. 7).

Synthesis of Homemade Neutravidin-AlexaFluor647 Conjugate.

A reaction mixture was assembled in a 1.5 mL Eppendorf tube with the following components (added in this order): 200 µL of 5 mg/mL Neutravidin (Life Technologies) in PBS, 20 µL of 1 M sodium bicarbonate in water, and 10 µL of 10 mg/mL AlexaFluor647-NHS Ester (Life Technologies) in anhydrous DMSO. The tube was incubated at room temperature with rotation in the dark for 3 h. The neutravidin-AlexaFluor647 conjugate was purified from unreacted dye using a NAP-5 size-exclusion column (GE Healthcare Life Sciences) according to the manufacturer's instructions. The conjugate was typically eluted from the column in 500 µL cold PBS. Absorbance values, determined using a Nanodrop 2000c UV-vis spectrophotometer (Thermo Scientific), were typically as follows: A280=~0.284 and A647=~1.625. The conjugate was stable at 4° C. in the dark for at least 4 months and was flash frozen and stored at −80° C. for longer term storage. For mammalian cell labeling experiments, the conjugate was diluted 1,000-fold in PBS containing 1% BSA.

Gels and Western Blots

For gels and Western blots experiments in FIGS. 1F, 2A, 2C, 4, 7, 8, 9A, 9B, HEK 293T cells expressing the indicated constructs were plated, transfected, and labeled with biotin as described above, and subsequently scraped and pelleted by centrifugation at 1500 rpm for 3 minutes The pellet was lysed by resuspending in RIPA lysis buffer (50 mM Tris, 150 mM NaCl, 0.1% SDS, 0.5% sodium deoxycholate, 1% Triton X-100, 1× protease inhibitor cocktail (Sigma-Aldrich), and 1 mM PMSF) by gentle pipetting and incubating for 5 min at 4° C. Lysates were clarified by centrifugation at 10000 rpm for 10 min at 4° C. Protein concentration in clarified lysate was estimated with Pierce BCA Protein Assay Kit (ThermoFisher) prior to separation on an SDS-PAGE gel. Silver-stained gels (FIGS. 9A, 9B) were generated using Pierce Silver Stain Kit (ThermoFisher).

For the Western blot experiment in FIG. 3A, BY4741 yeast expressing the indicated constructs (Table 2 P44-P46) were induced as described above and supplemented with 50 µM biotin for the duration of induction. After approximately 12 hours, the saturated induced culture was diluted 1:30 in fresh induction media supplemented with 50 µM biotin and allowed to grow for approximately 6 hours more until reaching $OD_{600}$ ~1. Three milliliters of this culture was pelleted (normalized across samples so that the same approximate amount of cells are collected for each sample), and lysed on ice in 50 µL 1.85 M NaOH+300 mM β-mercaptoethanol for 10 minutes on ice. The protein in the lysate was then precipitated by adding 50 µL 50% (w/v) TCA and incubating on ice for 15 minutes The protein was pelleted at 12000 g for 5 minutes, then dissolved in 120 µL urea/SDS buffer (0.48 g/mL urea, 50 mg/mL SDS, 29.2 mg/mL EDTA, 15.4 mg/mL DTT, 1 mg/mL bromophenol blue, 12 mg/mL Tris base, 0.2 mL/mL 1M Tris pH6.8). Proteins were boiled for 10 minutes prior to separation on an SDS-PAGE gel.

For the Western blot experiment in FIG. 3B, BL21 bacteria expressing the indicated constructs (Table 2 P47-49) were induced as described above, but overnight (18 hours) at 37° C. with 50 µM biotin supplemented for the duration of induction. Grown to approximately $OD_{600}$=0.6, 100 µL of each culture was pelleted (normalized across samples so that the same approximate amount of cells are collected for each sample) and resuspended in 15 µL 6× protein loading buffer (0.33 M Tris-HCl pH 0.8, 34% glycerol, 94 mg/mL SDS, 88 mg/mL DTT, 113 µg/mL bromophenol blue). The protein was boiled for 5 min, diluted to 1X, and then separated on an SDS-PAGE gel.

For all Western blots in FIGS. 1F, 2A, 2C, 3A, 3B, 4, 7, 8, 9A, and 9B gels were transferred to nitrocellulose membrane, stained by Ponceau S (5 min in 0.1% (w/v) Ponceau S in 5% acetic acid/water). The blots were then blocked in 5% (w/v) milk (LabScientific) in TBS-T (Tris-buffered saline, 0.1% Tween 20) for at least 30 min at room temperature, or as long as overnight at 4° C. Blots were then stained with primary antibodies (Table 3) in 3% BSA (w/v) in TBS-T for 1-16 hours at 4° C., washed four times with TBS-T for 5 min each, then stained with secondary antibodies or streptavidin-HRP (Table 3) in 3% BSA (w/v) in TBS-T for 1 at 4° C. The blots were washed four times with TBS-T for 5 min each prior to developing with Clarity Western ECL Blotting Substrates (BioRad) and imaging on a UVP BioSpectrum Imaging System. Quantitation of Western blots was performed using ImageJ.

Confocal Fluorescence Imaging of Cultured Cells

Figure 9A:
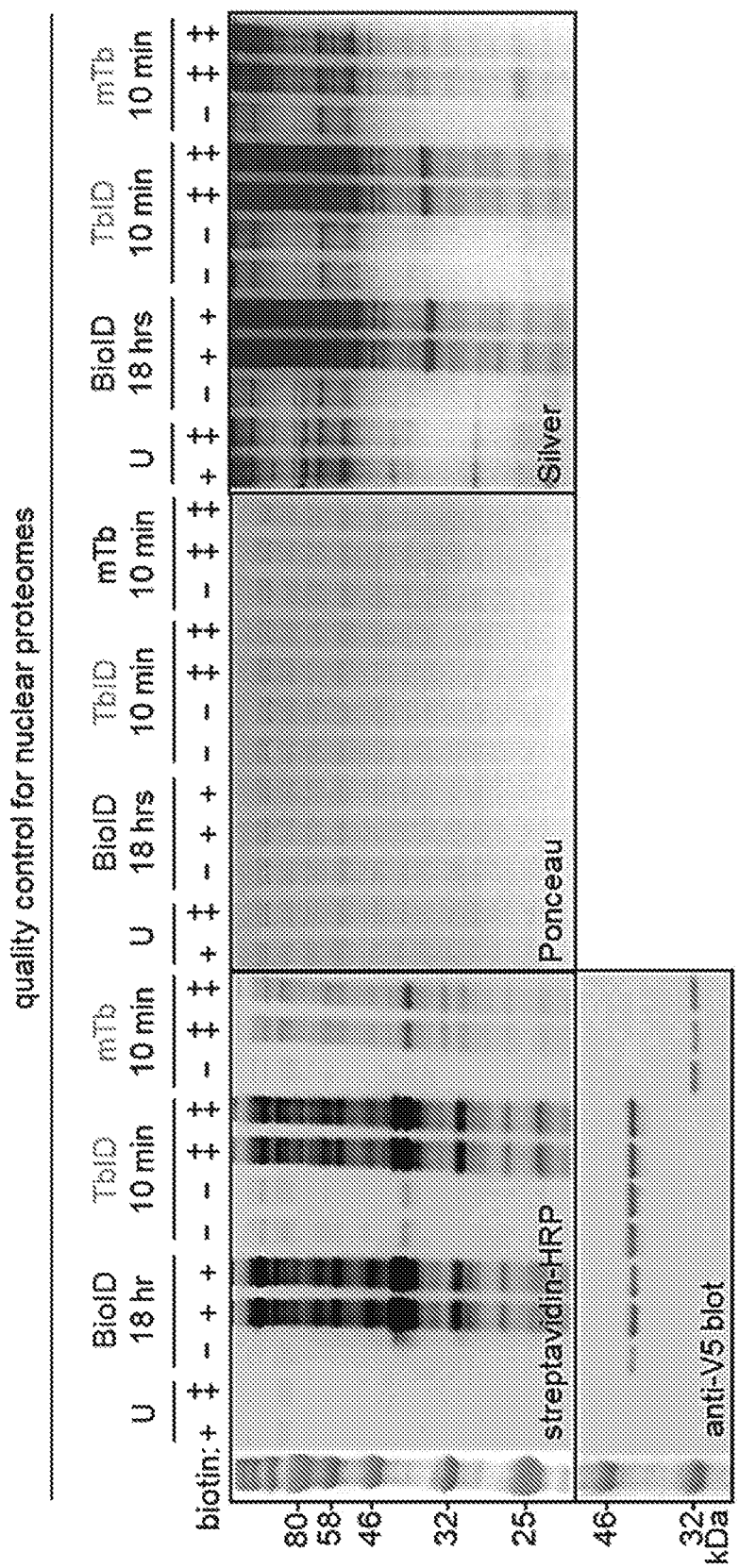
FIGS. 9A-9J show mass spectrometry-based proteomic experiment using TurboID, miniTurbo, and BioID.
Figure 9B:
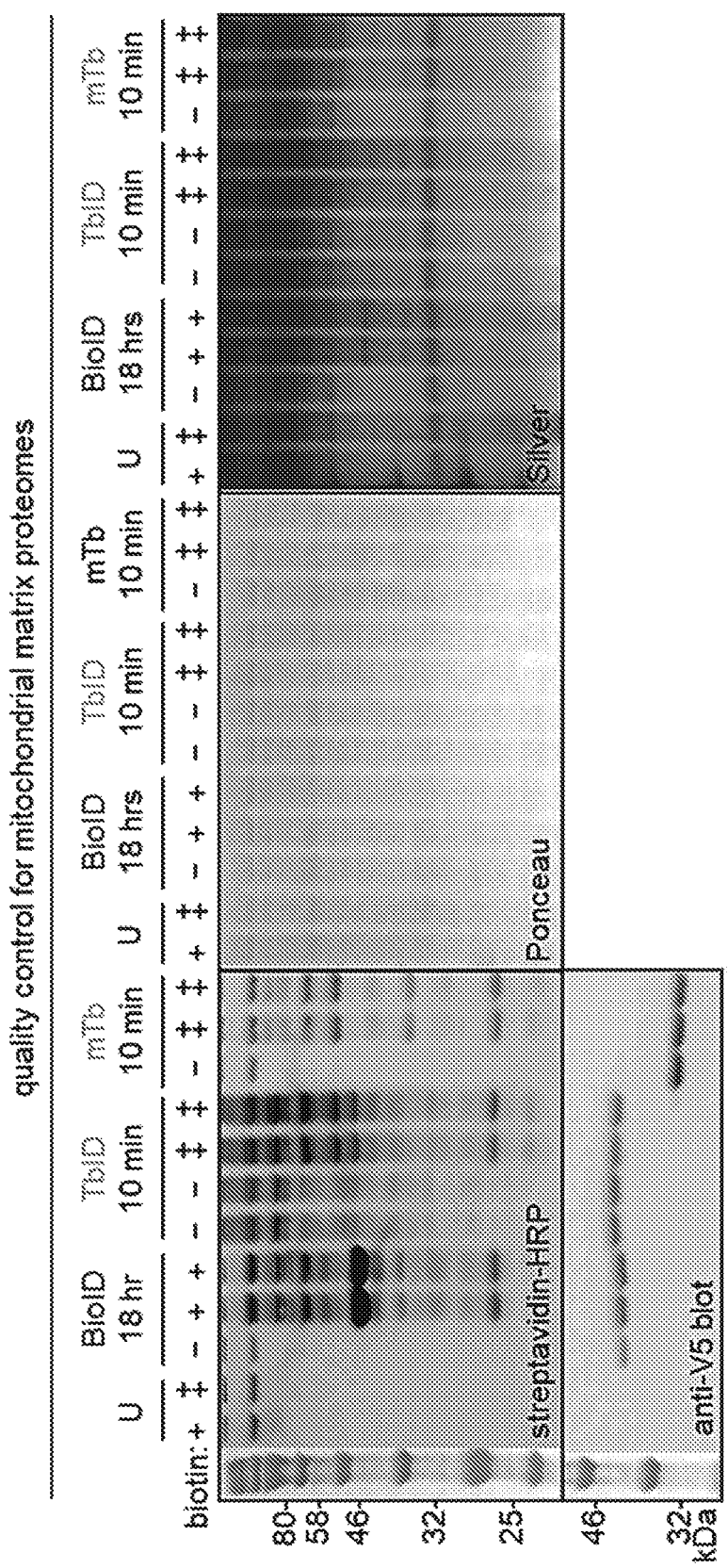
Figure 9C:
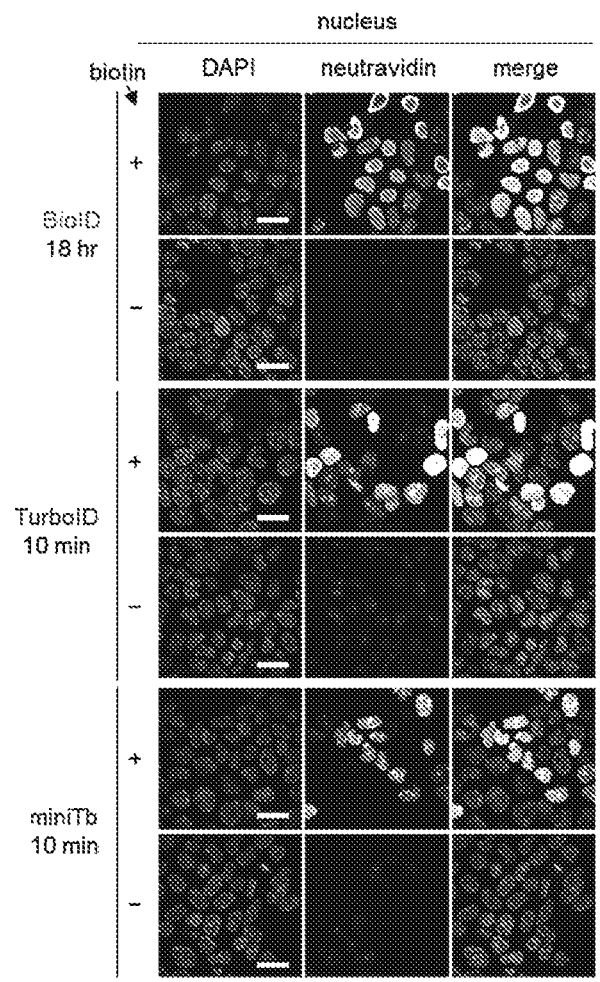
Figure 9D:
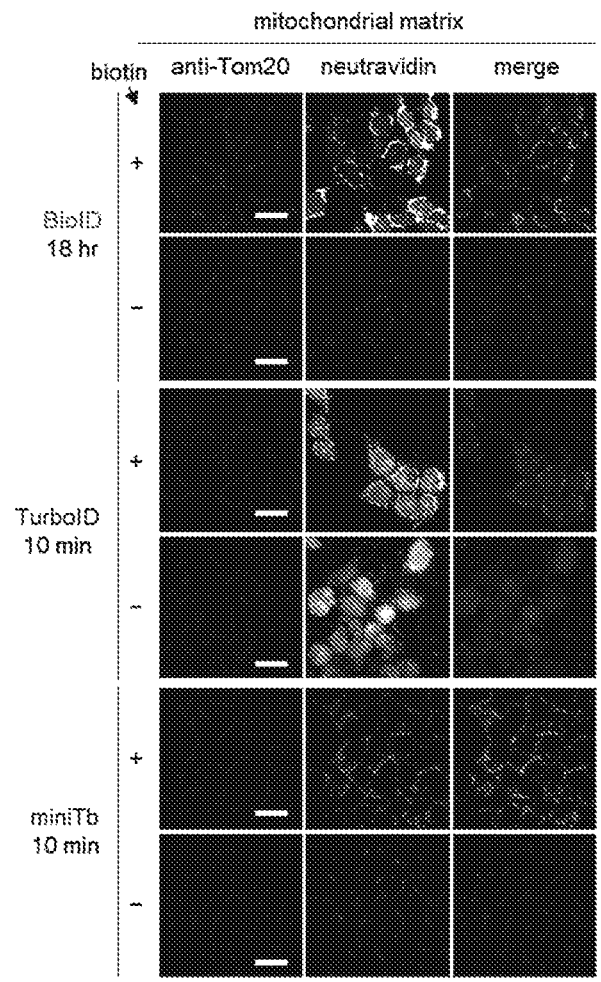
Figure 9E:
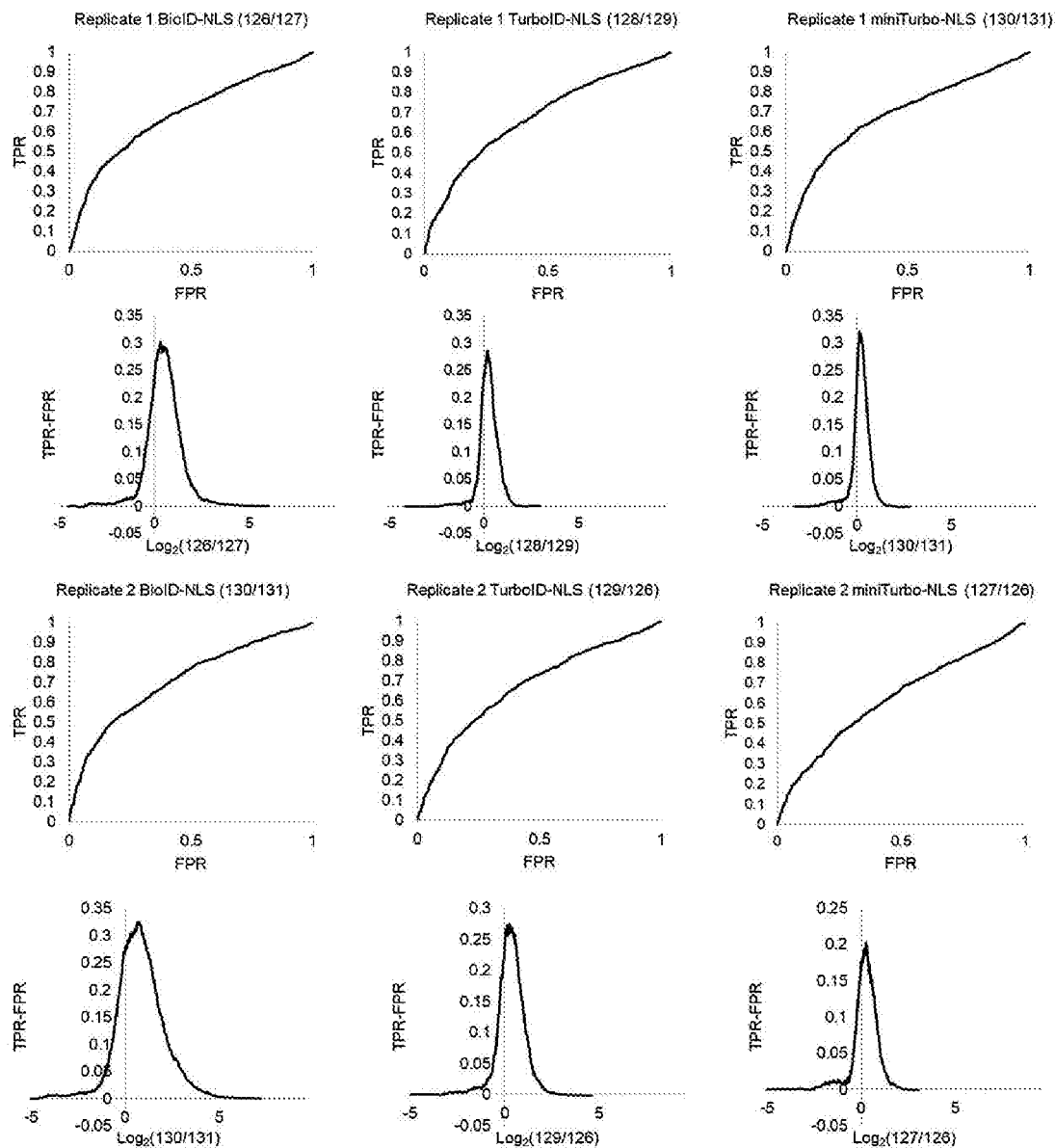
Figure 9F:
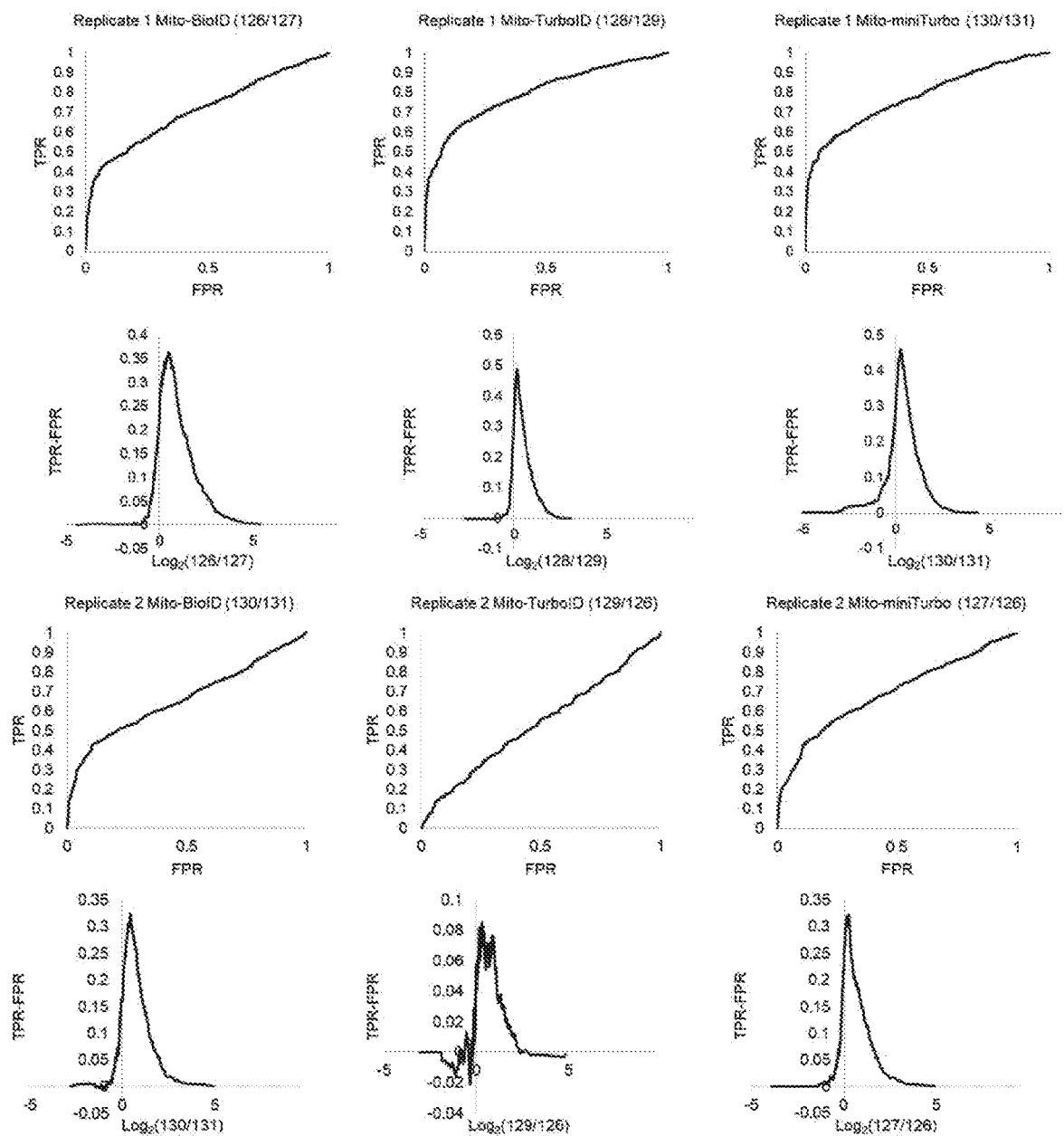
Figure 9G:
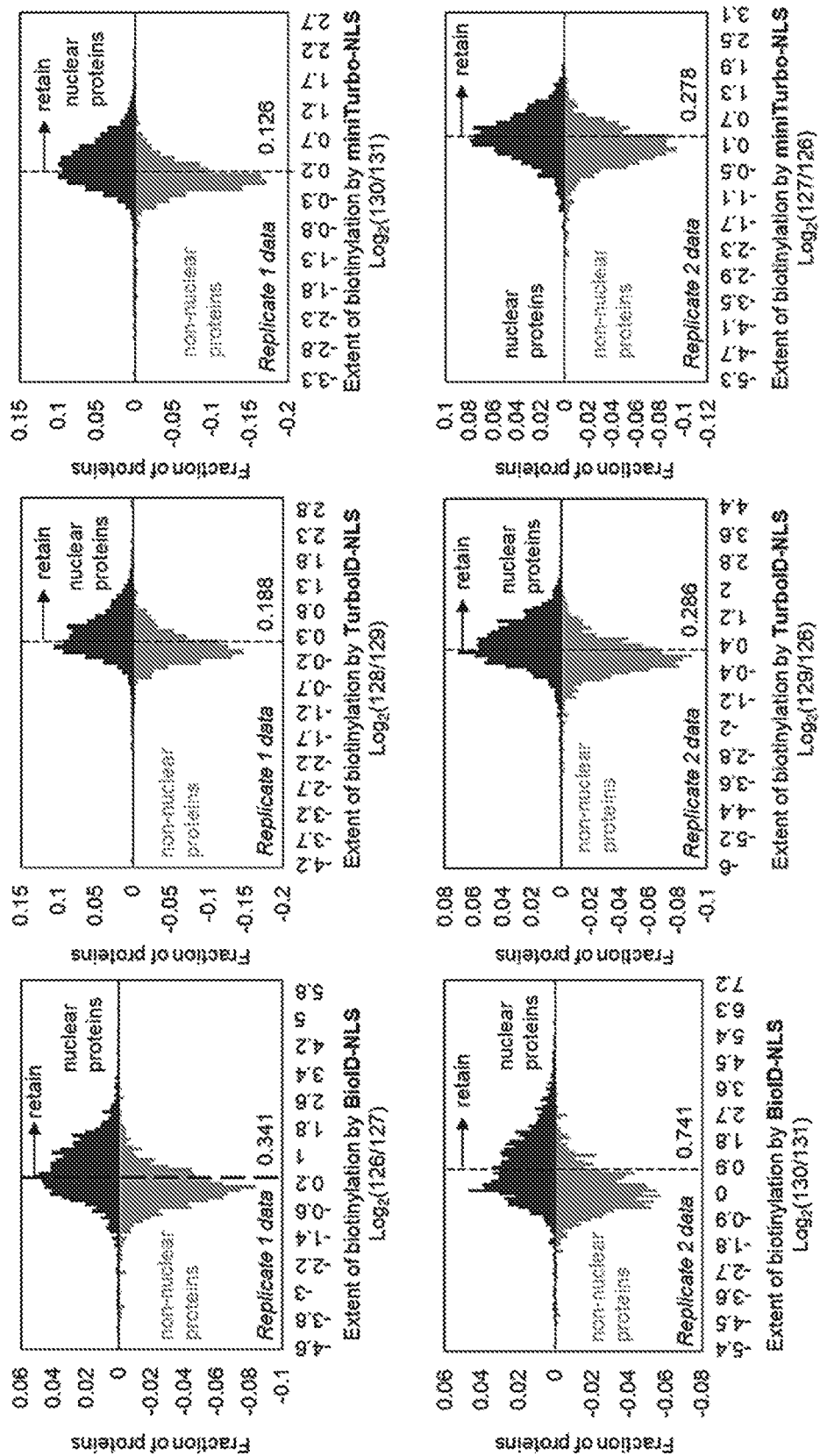
Figure 9H:
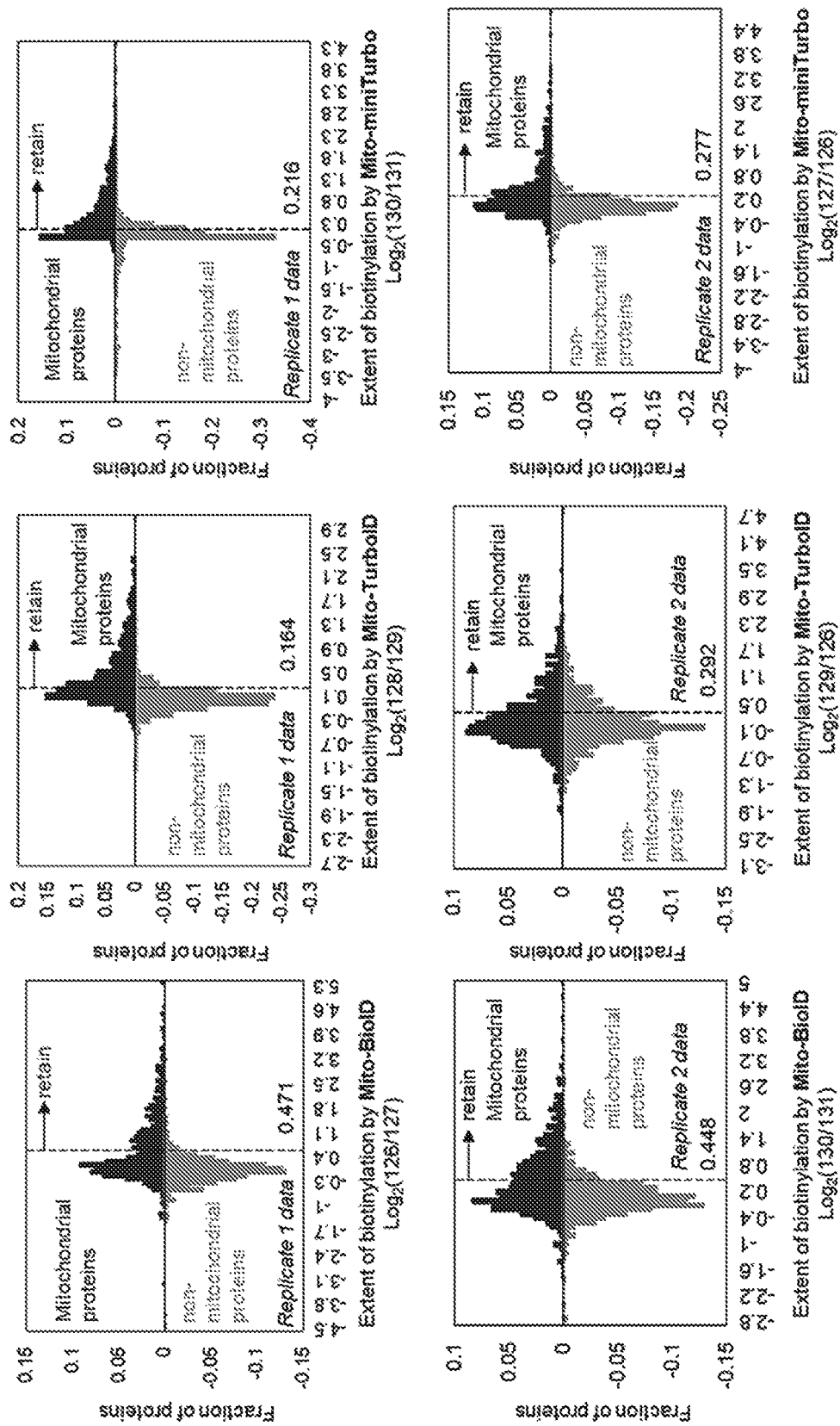

For fluorescence imaging experiments in FIGS. 9C, 9D, HEK 293T cells expressing the indicated constructs were plated, transfected, and labeled with biotin as described above, and subsequently fixed with 4% (v/v) paraformaldehyde in PBS at 4° C. for 45 minutes Cells were then washed three times with PBS and permeabilized with cold methanol at −20° C. for 5 minutes Cells were then washed three times with PBS, and then incubated with primary antibody (Table 3) in PBS supplemented with 5% (w/v) BSA for 1 hour at 4° C. After washing three times with PBS, cells were then incubated with DAPI/secondary antibody, and neutravidin-Alexa Fluor647 (Table 3) in PBS supplemented with 5% (w/v) BSA for 1 hour at 4° C. Cells were then washed three times with PBS and imaged by confocal fluorescence microscopy.

Confocal imaging was performed using a Zeiss AxioObserver.Z1 microscope, outfitted with a Yokogawa spinning disk confocal head, a Cascade I1:512 camera, a Quad-band notch dichroic mirror (405/488/568/647), 405 (diode), 491 (DPSS), 561 (DPSS), and 640 (diode) nm lasers (all 50 mW). DAPI (405 laser excitation, 445/40 emission), Alexa Fluor568 (561 laser excitation, 617/73 emission), and Alexa Fluor647 (640 laser excitation, 700/75 emission), and differential interference contrast (DIC) images were acquired through a 63× oil-immersive objective; Acquisition times ranged from 50 to 100 ms. All images were collected and processed using SlideBook 6.0 software (Intelligent Imaging Innovations). The data in FIGS. 9C, 9D are representative of at least 10 fields of view.

Sample Preparation for Proteomics

HEK 293T cells were grown in T150 flasks per proteomic sample as described above. Nuclear samples were transfected with 30 µg DNA using 150 µL Lipofectamine 2000 for 4 hours. All samples were labeled as described above. Imaging of samples cultured and labeled in the same manner as the larger scale proteomic samples were prepared for quality controls (FIGS. 9C, 9D). Cell pellets were collected, 2.5% of this lysate was separated and used for quality control analysis of expression and labeling (FIGS. 9C, 9D) and estimating protein concentration in clarified lysate using Pierce BCA Protein Assay Kit (ThermoFisher). Cell pellets lysed in RIPA lysis buffer, and clarified by centrifugation at 10000 rpm for 10 minutes at 4° C.

Streptavidin Bead Enrichment of Biotinylated Material

For enrichment of biotinylated material, 350 µL streptavidin-coated magnetic beads (Pierce) were washed twice with RIPA buffer, then incubated with approximately 6 mg of each sample with rotation for 1 hour at room temperature, after which 5% of beads were removed for quality control analysis of enrichment (FIGS. 9A, 9B), and then the remaining beads were moved to 4° C. and incubated overnight. The beads were subsequently washed twice with 1 mL of RIPA lysis buffer, once with 1 mL of 1 M KCl, once with 1 mL of 0.1 M $Na_2CO_3$, once with 1 mL of 2 M urea in 10 mM Tris-HCl (pH 8.0), and twice with 1 mL RIPA lysis buffer. For quality control analysis, biotinylated proteins were eluted by boiling the beads in 75 µL of 3× protein loading buffer supplemented with 20 mM DTT and 2 mM biotin, run on SDS-PAGE gel, and stained using Pierce Silver Stain Kit.

On-Bead Trypsin Digestion of Biotinylated Peptides

To prepare proteomic samples for MS analysis, proteins bound to streptavidin beads (~300 µL of slurry) were washed twice with 200 µL of 50 mM Tris HCl buffer (pH 7.5) followed by two washes with 2 M urea/50 mM Tris (pH 7.5) buffer. The final volume of 2 M urea/50 mM Tris (pH 7.5) buffer was removed and beads were incubated with 80 µL of 2 M urea/50 mM Tris buffer containing 1 mM DTT and 0.4 µg trypsin. Beads are incubated in the urea/trypsin buffer for 1 h at 25° C. while shaking. After 1 h, the supernatant was removed and transferred to a fresh tube. The streptavidin beads were washed twice with 60 µL of 2 M urea/50 mM Tris (pH 7.5) buffer and the washes were combined with the on-bead digest supernatant. The eluate was reduced with 4 mM DTT for 30 min at 25° C. with shaking. The samples were alkylated with 10 mM iodoacetamide and incubated for 45 min in the dark at 25° C. while shaking. An additional 0.5 µg of trypsin was added to the sample and the digestion was completed overnight at 25° C. with shaking. After overnight digestion, the sample was acidified (pH<3) by adding formic acid (FA) such that the sample contained ~1% FA. Samples were desalted on C18 StageTips and evaporated to dryness in a vacuum concentrator, exactly as previously described[48].

TMT Labeling and Fractionation of Peptides

Desalted peptides were labeled with TMT (6-plex) reagents. Peptides were reconstituted in 100 µL of 50 mM HEPES. Each 0.8 mg vial of TMT reagent was reconstituted in 41 µL of anhydrous acetonitrile and added to the corresponding peptide sample for 1 h at room temperature. Labeling of samples with TMT reagents was completed with the design indicated in FIG. 2D. TMT labeling reactions were quenched with 8 µL of 5% hydroxylamine at room temperature for 15 minutes with shaking, evaporated to dryness in a vacuum concentrator, and desalted on C18 StageTips. For each TMT 6-plex cassette, 50% of the sample was fractionated by strong cation exchange (SCX) using StageTips while the other 50% of each sample was reserved for LC-MS analysis by a single-shot, long gradient. One SCX StageTip was prepared per sample using 3 plugs of SCX material (3M) topped with 2 plugs of C18 material (3M). StageTips were washed with 100 µL methanol, then with 100 µL 80% acetonitrile/0.5% acetic acid, and equilibrated with 100 µL 0.5% acetic acid. Samples were reconstituted in 0.5% acetic acid, loaded onto the StageTip and then transeluted from the C18 discs to the SCX discs using 100 µL 80% acetonitrile/0.5% acetic acid. Three step-wise elutions from the SCX disks were completed as follows: the first fraction was eluted with 50 µL of 50 mM NH4AcO; 20% MeCN (pH 5.15, adjusted with acetic acid), the second with 50 µL 50 mM NH4AcO; 20% MeCN (pH 8.25, adjusted with acetic acid), the third with 50 µL 50 mM NH4AcO; 20% MeCN (pH 10.3, adjusted with acetic acid). Each eluate was collected separately and 200 µL of 0.5% acetic acid was added to each. Each fraction was desalted on C18 StageTips and dried by vacuum centrifugation.

Liquid Chromatography and Mass Spectrometry

Desalted peptides were resuspended in 9 µL of 3% MeCN, 0.1% FA and analyzed by online nanoflow liquid chromatography tandem mass spectrometry (LC-MS/MS) using a Orbirtrap Fusion Lumos Tribrid MS (ThermoFisher Scientific) coupled on-line to a Proxeon Easy-nLC 1200 (ThermoFisher Scientific). Four microliters of each sample were loaded onto a microcapillary column (360 m outer diameter×75 m inner diameter) containing an integrated electrospray emitter tip (10 m), packed to approximately 24 cm with ReproSil-Pur C18-AQ 1.9 m beads (Dr. Maisch GmbH) and heated to 50° C. The HPLC solvent A was 3% MeCN, 0.1% FA, and the solvent B was 90% MeCN, 0.1% FA. The SCX fractions were run with 110 minute method, which used the following gradient profile: (min:% B) 0:2; 1:6; 85:30; 94:60; 95:90; 100:90; 101:50; 110:50 (the last two steps at 500 nL/min flow rate). Non-fractionated samples were analyzed using a 260 min LC-MS/MS method with the following gradient profile: (min:% B) 0:2; 1:6; 235:30; 244:60; 245:90; 250:90; 251:50; 260:50 (the last two steps at 500 nL/min flow rate).

The Orbitrap Fusion Lumos was operated in the data-dependent mode acquiring HCD MS/MS scans (r=15,000) after each MS1 scan (r=60,000) on the most abundant ions within a 2 s cycle time using an MS1 target of 3×106 and an MS2 target of 5×104. The maximum ion time utilized for MS/MS scans was 50 ms; the HCD normalized collision energy was set to 34; the dynamic exclusion time was set to 45 s, and the peptide match and isotope exclusion functions were enabled. Charge exclusion was enabled for charge states that were unassigned, 1 and >6.

Proteomic Data Analysis

Collected data were analyzed using Spectrum Mill software package v6.1pre-release (Agilent Technologies). Nearby MS scans with the similar precursor m/z were merged if they were within +60 s retention time and ±1.4 m/z tolerance. MS/MS spectra were excluded from searching if they failed the quality filter by not having a sequence tag length 0 or did not have a precursor MH+ in the range of 750-4000. All extracted spectra were searched against a UniProt database containing human reference proteome sequences. Search parameters included: parent and fragment mass tolerance of 20 ppm, 30% minimum matched peak intensity, trypsin allow P enzyme specificity with up to four missed cleavages, and calculate reversed database scores enabled. Fixed modifications were carbamidomethylation at cysteine. TMT labeling was required at lysine, but peptide N termini were allowed to be either labeled or unlabeled. Allowed variable modifications were protein N-terminal acetylation and oxidized methionine. Individual spectra were automatically assigned a confidence score using the Spectrum Mill autovalidation module. Score at the peptide mode was based on target-decoy false discovery rate (FDR) of 1%. Protein polishing autovalidation was then applied using an auto thresholding strategy. Proteins identified by 2 or more distinct peptides were considered for the dataset.

Complete MS data were obtained for both the nucleus and mitochondrial matrix. Each of the two replicates for each proteomics experiment (mitochondrial matrix and nucleus) were analyzed separately. To select cutoffs for proteins biotinylated by the indicated ligase over non-specific bead binders, we classified the detected proteins into three groups:

(1) nuclear annotated proteins (list of human proteins annotated with the following Gene Ontology[41,42] terms: GO:0016604, GO:0031965, GO:0016607, GO:0005730, GO:0001650, GO:0005654, GO:0005634).

(1) mitochondrial annotated proteins (list of human proteins present in MitoCarta2.0[43] or annotated with the following Gene Ontology[41,42] term: GO:0005739, but excluding any proteins also present in category).

(2) proteins with non-nuclear annotation (list of human proteins annotated with the following Gene Ontology[41,42] terms: GO:0015629, GO:0016235, GO:0030054, GO:0005813, GO:0045171, GO:0000932, GO:0005829, GO:0005783, GO:0005768, GO:0005929, GO:0005794, GO:0045111, GO:0005811, GO:0005764, GO:0005815, GO:0015630, GO:0030496, GO:0070938, GO:0005739, GO:0072686, GO:0005777, GO:0005886, GO:0043231; and does not contain proteins annotated with the following Gene Ontology[41,42] terms: GO:0016604, GO:0031965, GO:0016607, GO:0005730, GO:0001650, GO:0005654, GO:0005634, nucleus localization, nuclear envelope, nuclear matrix, nuclear chromatin, nuclear pore, nuclear inner membrane, nuclear chromosome, nuclear heterochromatin, nuclear euchromatin, nuclear inclusion body).

(2) proteins with non-mitochondrial annotation (previously curated list of human proteins[2,49]).

(3) all other proteins.

We then normalized the TMT ratios in order to account for differences in total protein quantity between samples within the TMT 6-plex experiments. To do this, the TMT ratios corresponding to BirA experimentals/negative control ($\text{Log}_2$(126/127), $\text{Log}_2$(128/129), $\text{Log}_2$(130/131) for replicate 1, and ($\text{Log}_2$(130/131), $\text{Log}_2$(129/126), $\text{Log}_2$(127/126) for replicate 2) were normalized to the median for class (2) proteins, which was set to 1. To calculate optimal cut-offs, we then calculated the true positive rate (TPR) and false positive rate (FPR) we would obtain if we retained only proteins above that TMT ratio. We defined TPR as the fraction of class (1) proteins above the TMT ratio in question, and FPR as the fraction of class (2) above the TMT ratio in question. We selected TMT ratios that maximize the difference between TPR and FPR as our cutoffs (FIGS. 9E-9H).

Figure 9I:
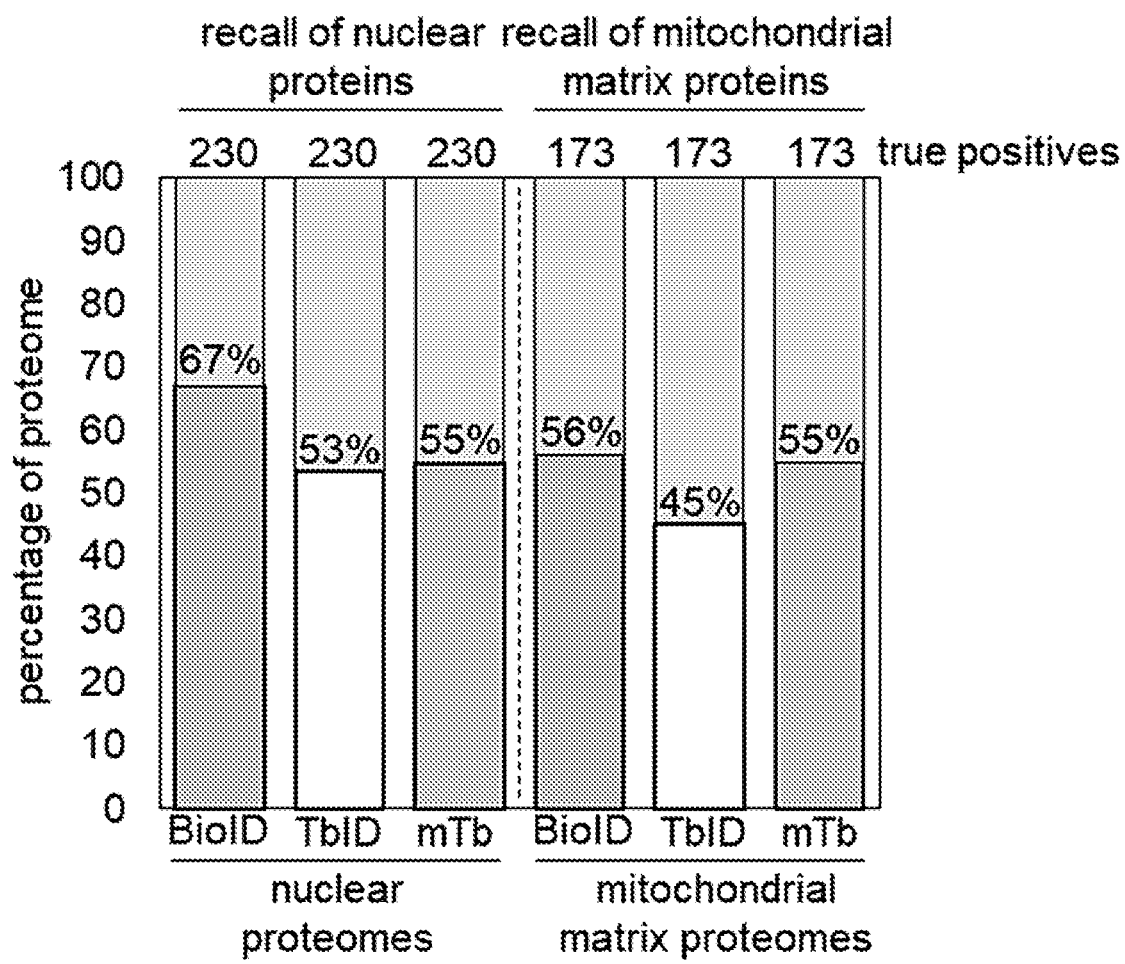
Figure 9J:
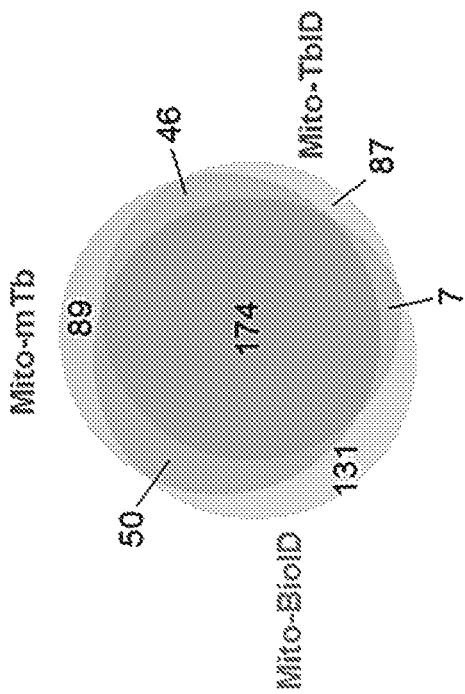
Figure 9J:
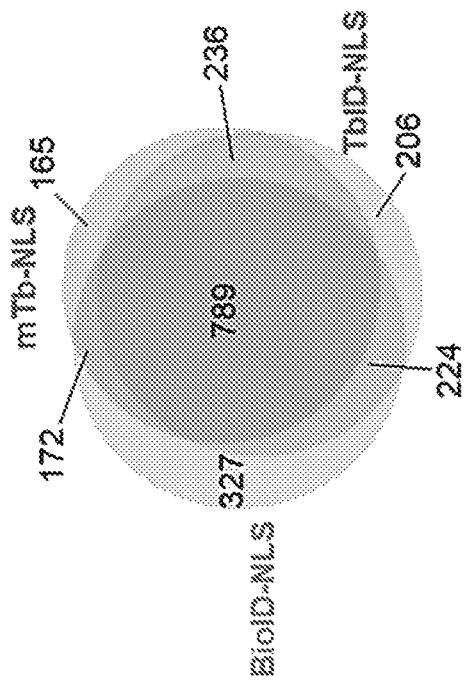

After applying cutoffs to each replicate, we then intersected both to produce the final proteomes. Overlap of proteins between proteomes obtained with BioID, TurboID, and miniTurbo for both the nucleus and mitochondrial matrix are shown in FIG. 9J. To assess the specificity of our proteomes, we determined the nuclear and mitochondrial specificity of the respective proteomes (FIG. 2E). To calculate specificity, we report the percentage of proteins present in class (I). To assess the recall of our proteomes for known proteins of the respective compartment being mapped, we determined the coverage of our proteomes for lists of known nuclear or mitochondrial proteins (FIG. 9I). To calculate coverage of our nuclear proteome, we constructed a list of proteins using Cell Atlas data and hyperLOPIT data[50] that have annotated nuclear detection by a validated antibody to nuclear bodies, nuclear membrane, nuclear speckles, nucleoli, fibrillary centers, nucleoplasm, or nucleus; and also have hyperLOPIT location annotated to nucleus, or nucleus-chromatin; and also have expression in HEK cells. To calculate coverage of our mitochondrial matrix proteome, we used a previously curated list of known mitochondrial matrix proteomes[2].

Generation of UAS-BirA Transgenic *Drosophila* Lines

V5-BioID, V5-TurboID, and V5-miniTurboID coding sequence was PCR amplified from CMV-plasmids using the same F and R primers:

V5-BirA-mut_F: ccgcggccgccccttcac-cATGGGCAAGCCCATCCCC (SEQ ID NO:5)

V5-BirA-mut_R gggtcggcgcgcccacccttCTATT-AGTCCAGGGTCAGGCG (SEQ ID NO:6)

DNA fragments were cloned into pEntr plasmids (Invitrogen) using Gibson assembly (NEB). pEntr V5-BirA-mut entry plasmids were recombined into pWalium10-roe[51] using Gateway LR Clonase II Enzyme (Invitrogen). pWalium10-roe contains 10× UAS enhancer elements for Gal4-controlled expression, attB sequence, and a white+ transgene. Transgenic flies were generated using PhiC31 integration by injecting pWalium10-V5-BirA-mut plasmids into flies carrying an attP docking site on chromosome III (attP2)[52]. Final fly strains are referred to as UAS-V5-BioID, UAS-V5-turboID, and UAS-V5-miniTurboID.

*Drosophila* Culture and Genetics

Experiments on flies were performed with wild type or transgenic strains of *Drosophila melanogaster*. The age and sex of animals involved in experiments are indicated in figure legends and methods below. The Harvard Medical School Standing Committee on Animals (through the Office of the Institutional Animal Care and Use Committee (IACUC)) deems flies as invertebrates with limited sentience and therefore not subject to formal review and approval by the committee.

Crosses were maintained on standard fly food at 25° C. Biotin food was prepared by microwaving standard fly food until liquid and adding 1 mM biotin dissolved in H20 to a final concentration of 100 µM.

Fly stocks used are the species *Drosophila melanogaster*. Additional fly stocks were obtained from the Bloomington Stock Center and are listed here with corresponding stock numbers: ptc-Gal4 (2017), Act5c-Gal4/CyO (4414), nub-Gal4 (25754), w1118 (6326), UAS-Luciferase (35788).

Western Blotting of *Drosophila* Adults

Adult flies were aged 3 days after eclosion from pupal cases (13 days old after egg deposition). For each condition, five females and five males were lysed in RIPA buffer (Thermo Fisher, 89900) on ice using a blue pestle in a microcentrifuge tube. Samples were centrifuged at 14,000 g for 20 minutes at 4° C. Supernatant was retained and transferred to a new centrifuge tube. Protein concentration was calculated using a BCA kit (Pierce 23225) and RIPA buffer was added to samples to normalize to 4 µg/µl. Normalized protein samples were mixed with an equal volume of 4×SDS sample buffer and boiled for 5 minutes at 95° C. 10 µg/sample was loaded onto a 4-20% Mini-PROTEAN TGX PAGE gel (Biorad 4561095), transferred to Immobilon-FL PVDF membrane (Millipore IPFL00010), incubated in PBS+0.1% Tween (PBST) for 15 minutes, and blocked overnight in 3% BSA in PBST (PBST-BSA) at 4° C. To detect biotinylated proteins, blots were incubated with 0.3 µg/ml streptavidin-HRP (Thermo Fisher S911) in PBST-BSA for 1 hour at room temperature. Blots were washed extensively with PBST and exposed using Pico Chemiluminescent Substrate (Thermo Fisher 34577). To detect expressed V5-tagged BirA proteins, blots were incubated with 1:10,000 mouse anti-V5 (Invitrogen R960-25) with PBST-BSA overnight at 4° C., washed with PBST, incubated with 1:5000 anti-mouse Alexa 800 (Thermo Fisher A32730), washed with PBST, and imaged on an Aerius Fluorescent imager (LI-COR 9250) (FIG. 3G).

Immunohistochemistry of *Drosophila* Wing Discs

Wandering 3$^{rd}$ instar larvae were bisected and inverted to expose the imaginal discs. These carcasses were fixed for 20 minutes in 4% paraformaldehyde in 1× PBS. Fixed carcasses with attached wing discs were permeabilized with PBS+0.1% Triton-X100 (PBST) for 20 min and blocked with PBST+5% normal goat serum (PBST-NGS) for 1 hour. Blocked carcasses were incubated overnight at 4° C. in PBST-NGS with 1:500 mouse anti-V5 (Invitrogen R960-25) and 1:500 streptavidin-555 (Invitrogen S32355). Carcasses were washed 3× with PBST and incubated for 1 hour at room temperature in PBST-NGS with 1:500 anti-mouse Alexa 647 (Thermo Fisher A-21236) and 1:1000 DAPI (stock 1 mg/ml). Samples were washed with 3× with PBST, 1× with PBS, and equilibrated in 70% Glycerol/1× PBS. Wing discs were dissected away from the carcass and mounted onto glass slides with Vectashield mounting media (Vector Labs H-1000) and glass coverslip. Mounted samples were imaged on a Zeiss 780 confocal microscope (FIG. 3D).

Quantitation of Fluorescence Signal Intensity from *Drosophila* Wing Discs

Average signal intensity of fluorescence of streptavidin-555 in wing discs was measured using raw images obtained under identical confocal settings and under non-saturating exposure settings. Using ImageJ software, the polygon tool was used to select a rectangular region of the ptc-Gal4 expressing domain in the wing pouch. This selected region was measured in ImageJ as average signal intensity. Measurements were taken from at least three wing discs for each condition. Average signal intensity measured in negative control discs was subtracted from experimental conditions. Fold change was determined by normalizing the signal intensity from TurboID and miniTurboID to the signal intensity from BioID (FIG. 3E).

Quantitation of Adult *Drosophila* Survival and Wing Size after BirA Mutant Expression During Development UAS-V5-BirA-mut transgenes were expressed during development and their effects on the adult assessed. The Act5c-Gal4 transgene was used to drive ubiquitous expression, and the nub-Gal4 transgene was used to drive expression in the larval wing imaginal disc.

Figure 10A:
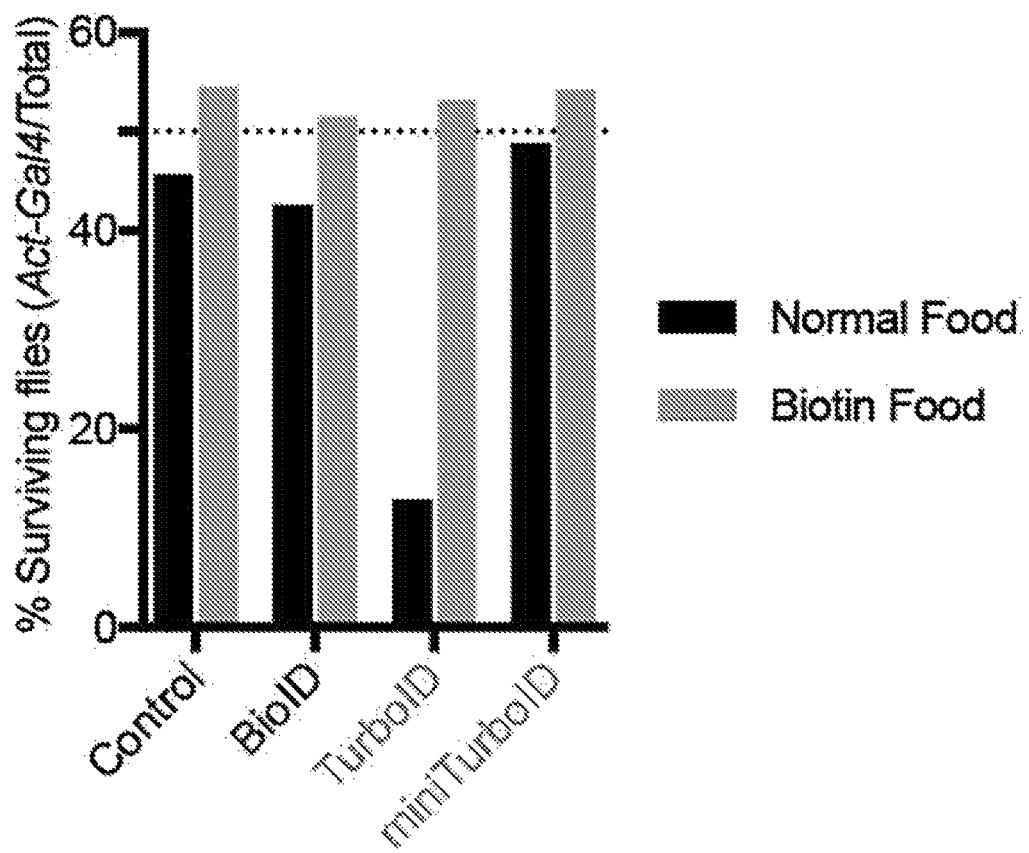
FIGS. 10A-10E show viability and morphology assays in D. melanogaster expressing promiscuous biotin ligase variants.

To determine if ubiquitous expression of BirA mutants affects viability, the number of surviving adults were counted and compared to the number of wild type siblings (FIG. 10A). The following crossing scheme was used:

P0 Act5c-Gal4/CyO x UAS-V5-BirA-mut

Segregation of the Act5c-Gal4 chromosome vs. the CyO chromosome results in two possible F1 progeny genotypes:

F1 (1) Act5c-Gal4/UAS-V5-BirA-mut
F1 (2) CyO/UAS-V5-BirA-mut

The CyO chromosome has a dominant Cy mutation that causes adult flies to have curly wings. Therefore genotype 1 have straight wings and overexpressed the BirA transgene and genotype 2 have curly wings and do not overexpress the transgene. Percent survival of flies overexpressing a transgene is calculated as:

% survival=#genotype1/(#genotype1+#genotype2)×100

For example, ~50% survival indicates no reduction in viability from an overexpressing a transgene. Whereas % survival lower than 50% indicates reduced viability.

Figure 10B:
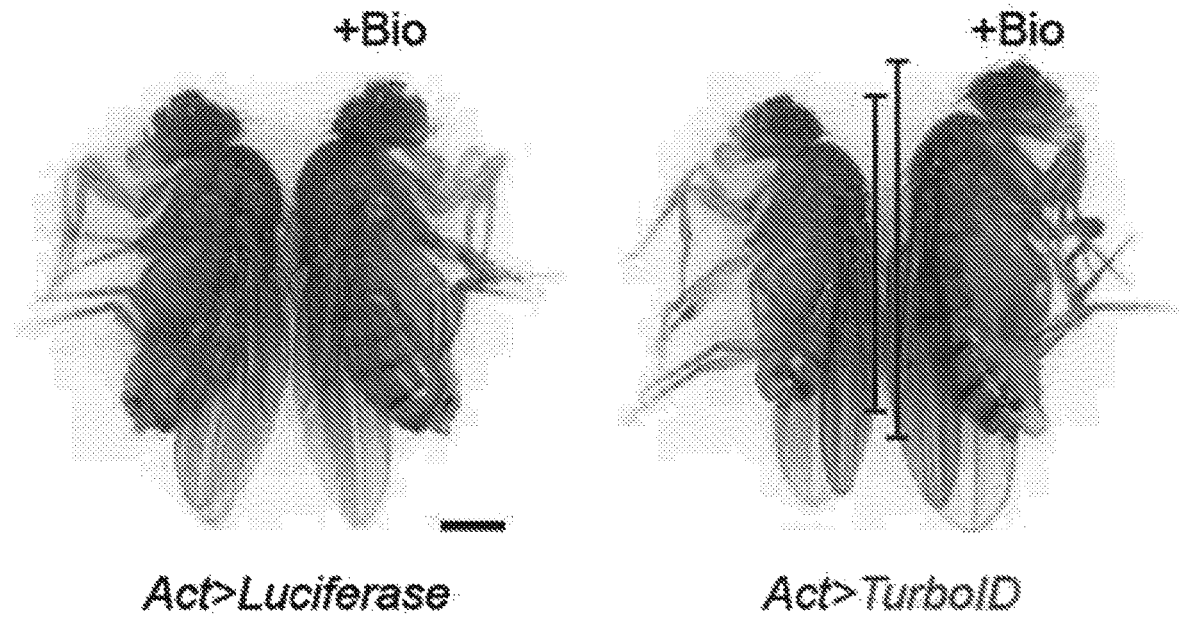
Figure 10C:
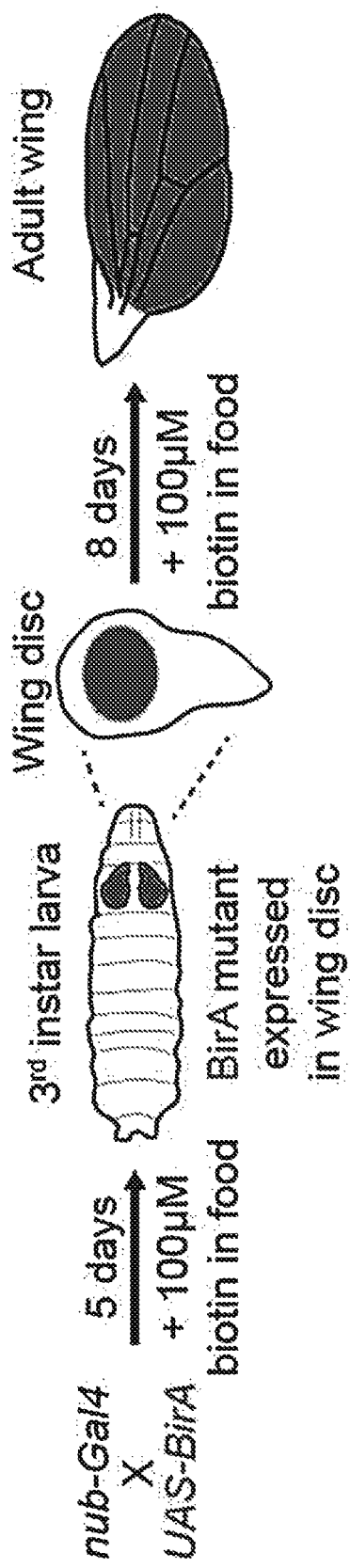
Figure 10D:
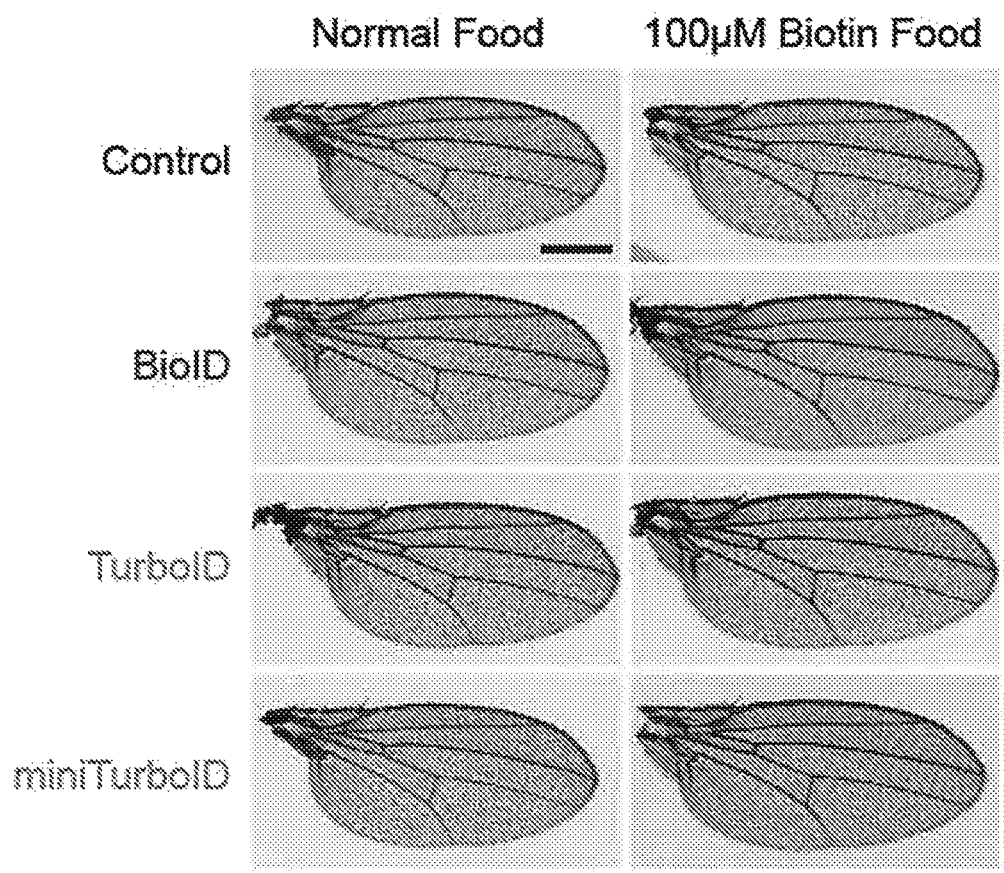
Figure 10E:
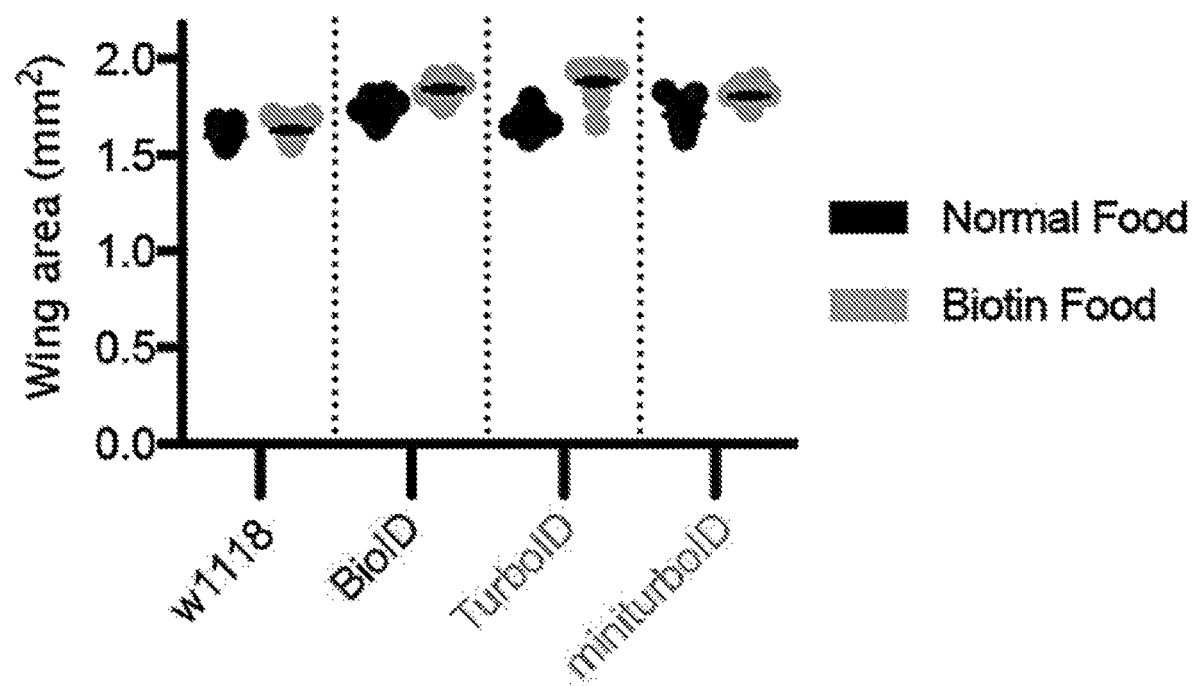
Figure 11A:
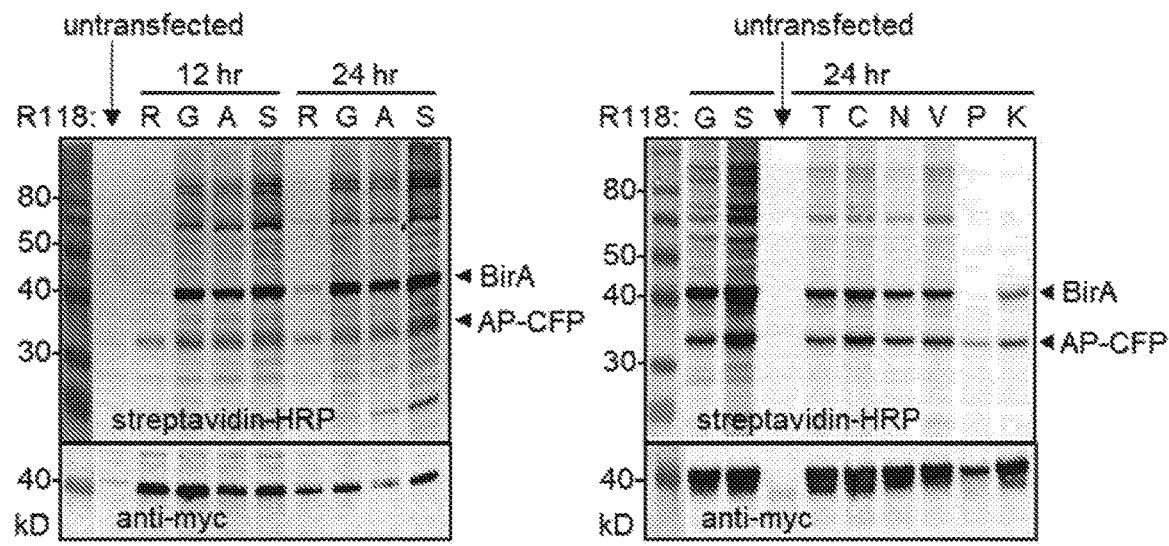
FIGS. 11A-11Y show a comparison of activities of various promiscuous BirA mutants. BirA ligases with the indicated mutations were transiently expressed as NES (nuclear export signal) fusions in the HEK cytosol. Where indicated, samples were co-transfected with AP-CFP-NES (acceptor peptide fused to cyan fluorescent protein and nuclear export signal), which is site-specifically biotinylated by BirA. After labeling with the indicated concentration of biotin for the indicated labeling time, whole cell lysates were analyzed by streptavidin-HRP blotting. Ligase expression was detected by anti-myc or anti-V5 blotting as indicated. Self-biotinylation bands are indicated with "BirA" or asterisks, as well as specific labeling of AP-CFP-NES ("AP-CFP").
Figure 11B:
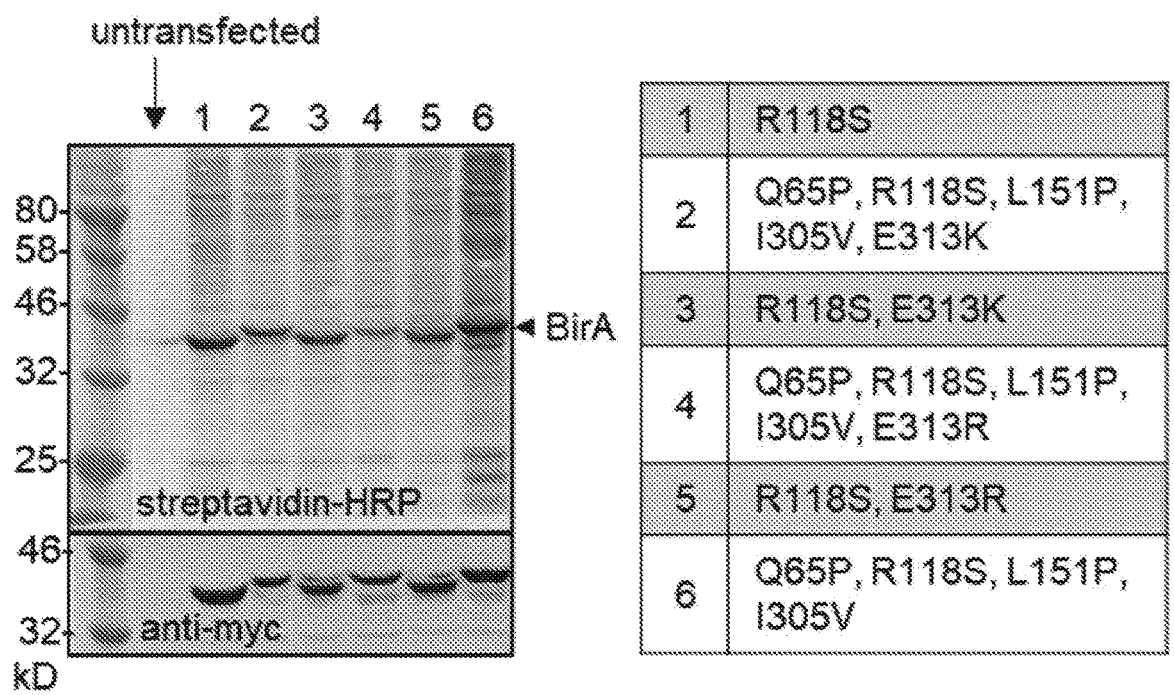
FIGS. 11B and 11C shows results with 50 µM exogenous biotin added to the cells for 24 hours.
Figure 11C:
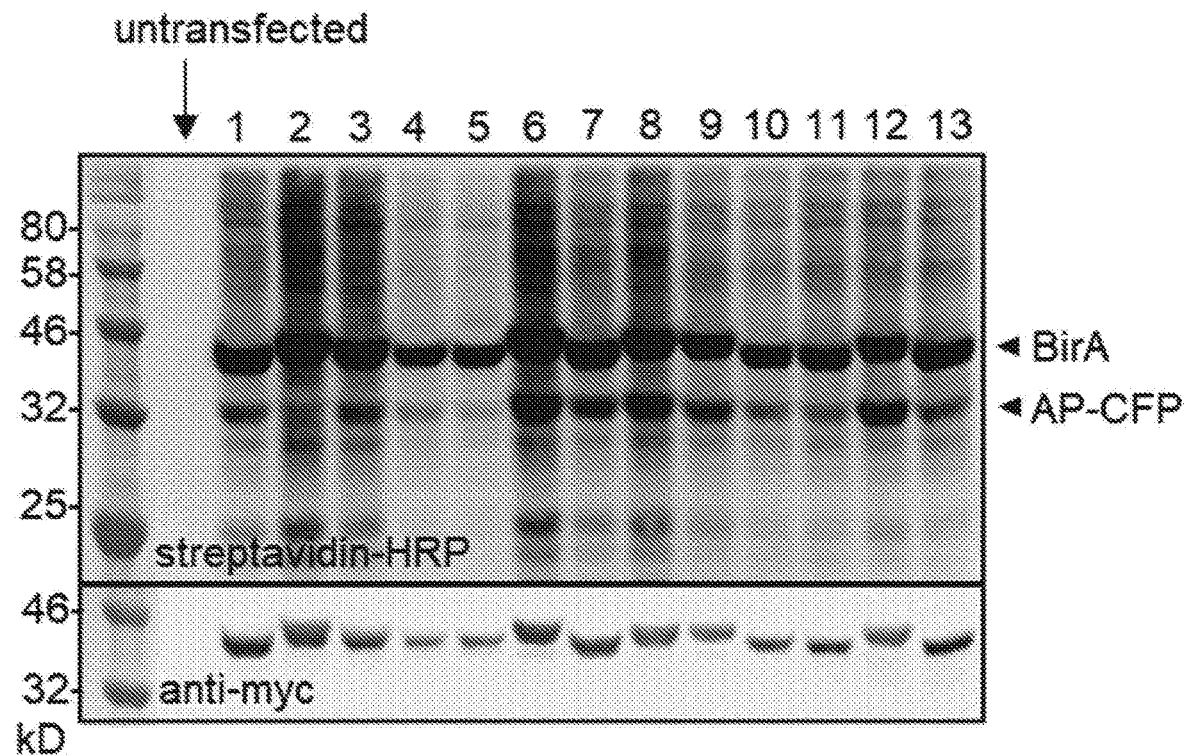
Figure 11D:
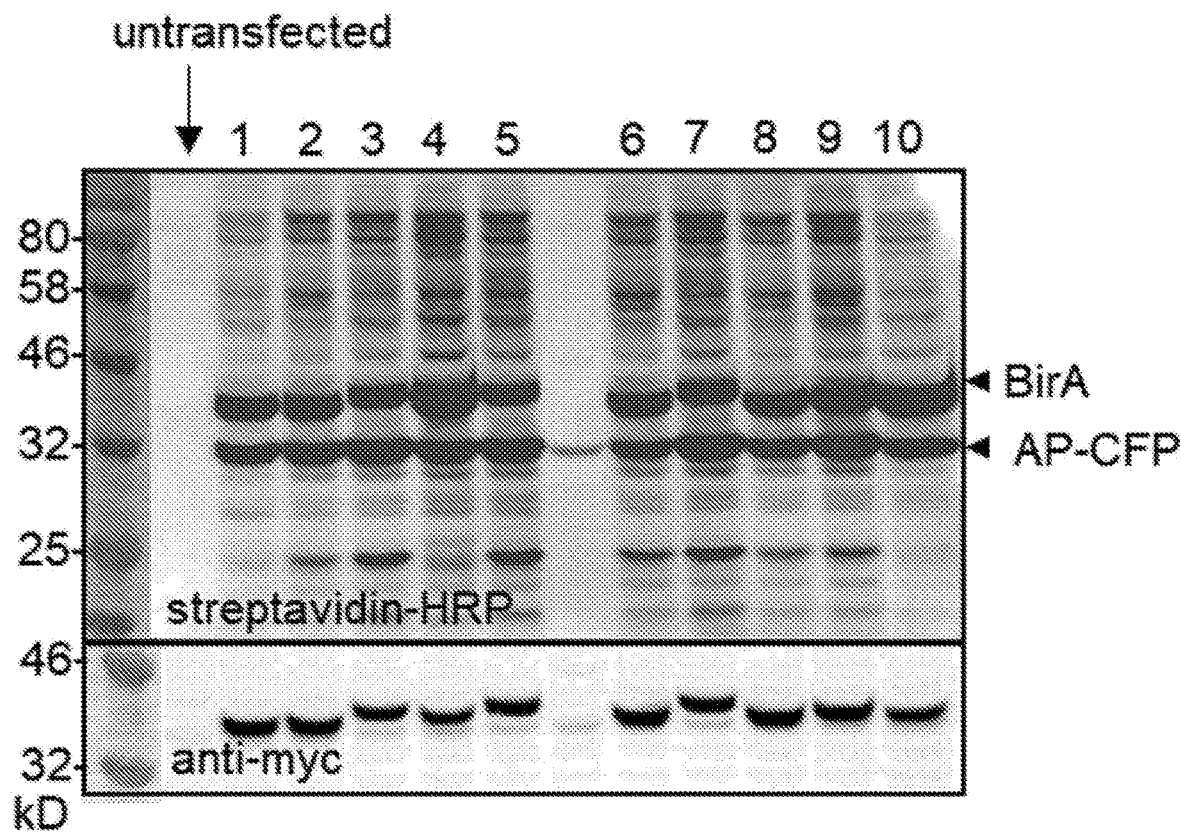
FIG. 11D shows results with 50 µM exogenous biotin added to the cells for 4 hours.
Figure 11E:
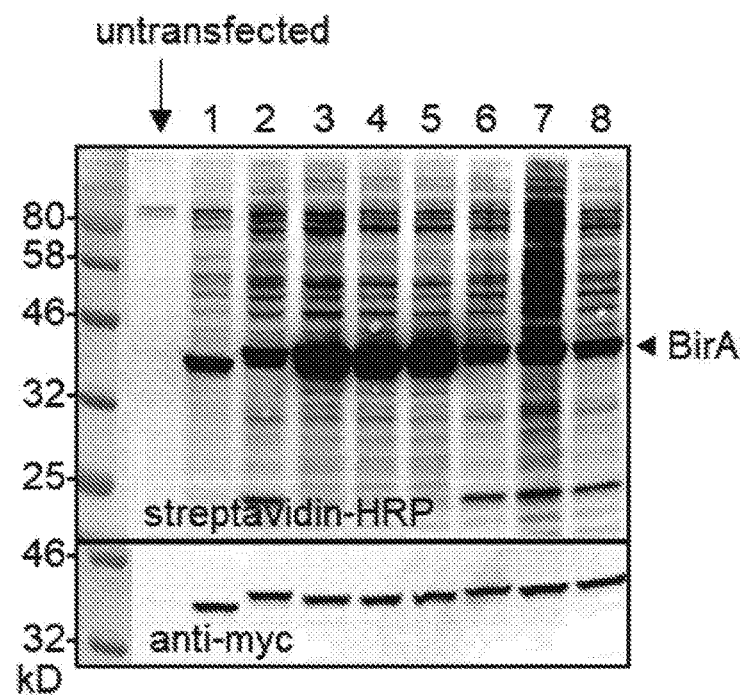
Figure 11F:
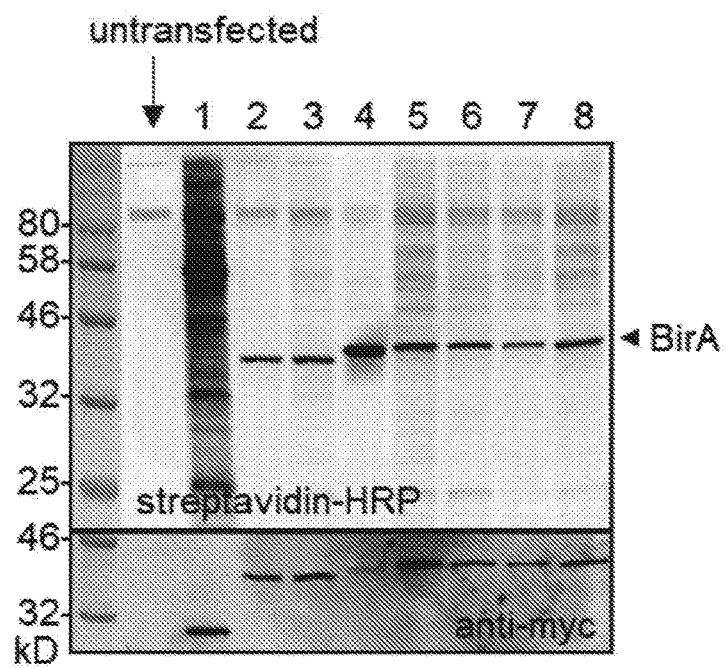
FIG. 11F shows results with 50 µM exogenous biotin added to the cells for 1 hour.
Figure 11G:
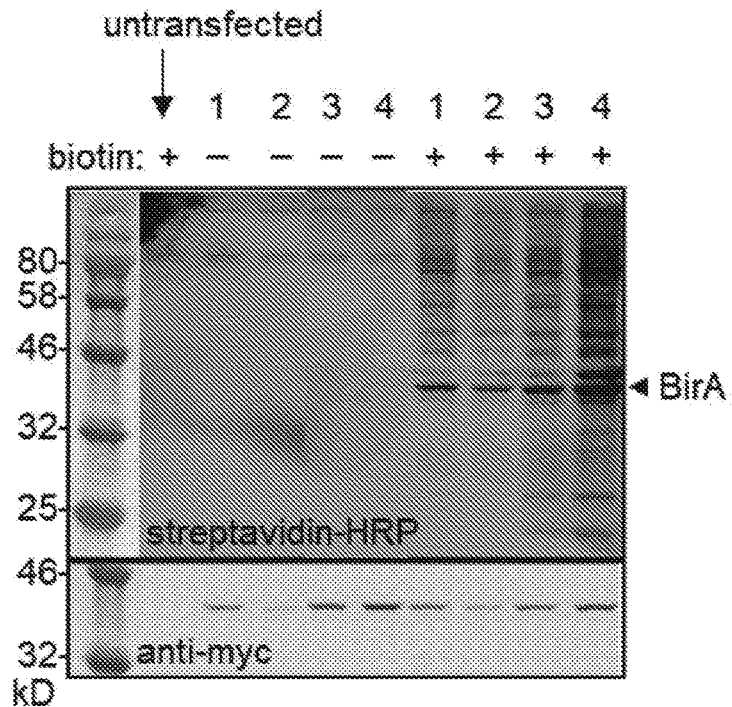
Figure 11H:
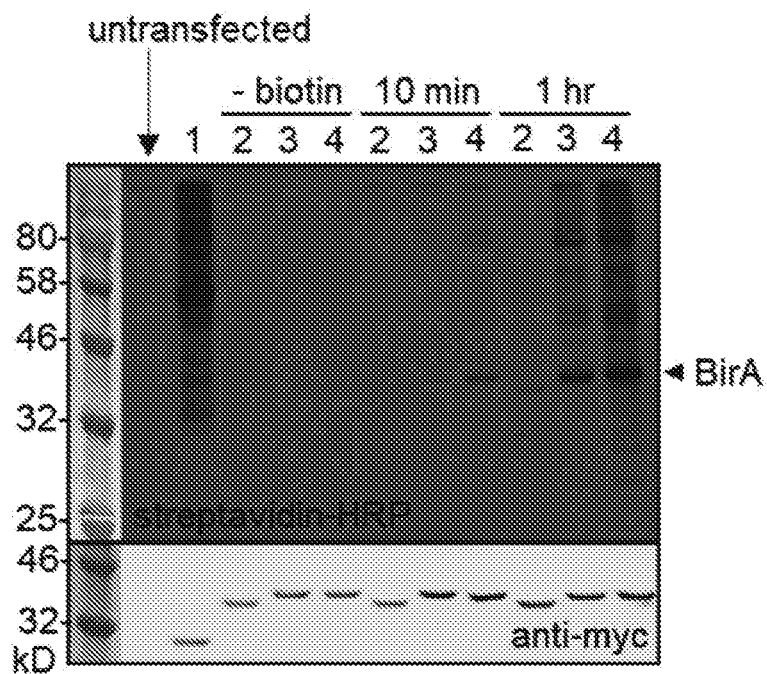
FIG. 11H shows results with 50 µM exogenous biotin added to the cells for 10 minutes or 1 hour. Sample 1 also shows APEX2-NES for comparison, labeled for 1 minute with 500 µM biotin phenol and 1 mM hydrogen peroxide at room temperature.
Figure 11I:
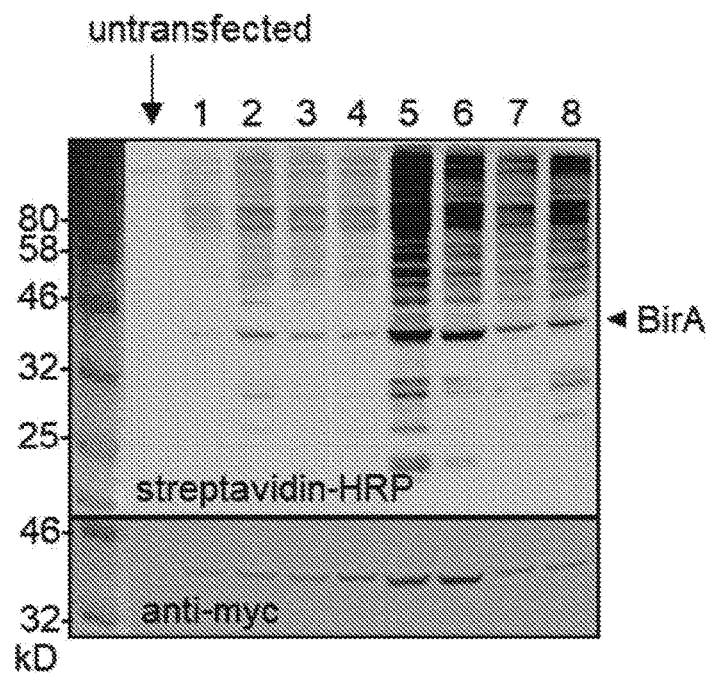
FIGS. 11I and 11J show results with 50 µM exogenous biotin added to the cells for 30 minutes.
Figure 11J:
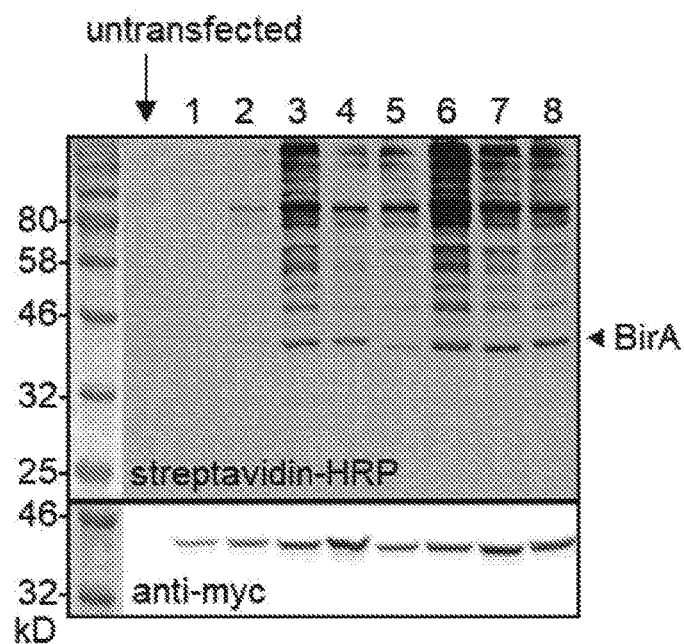
Figure 11K:
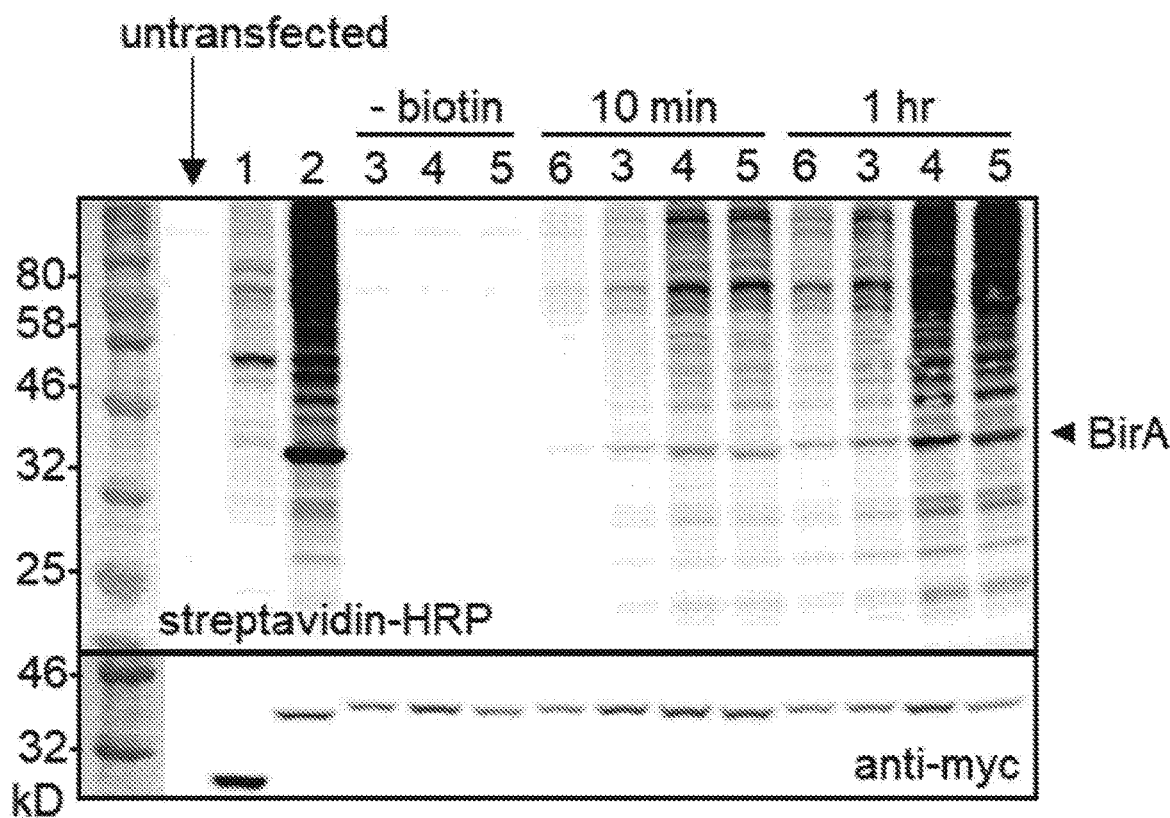
FIG. 11K shows results with 50 µM exogenous biotin added to the cells for 10 minutes or 1 hour. For comparison, sample 1 also shows APFX2-NES labeling for 1 minute with 500 µM biotin phenol and 1 mM hydrogen peroxide at room temperature; and sample 2 shows BirA (R118G) labeling for 18 hours with 50 µM exogenous biotin.
Figure 11M:
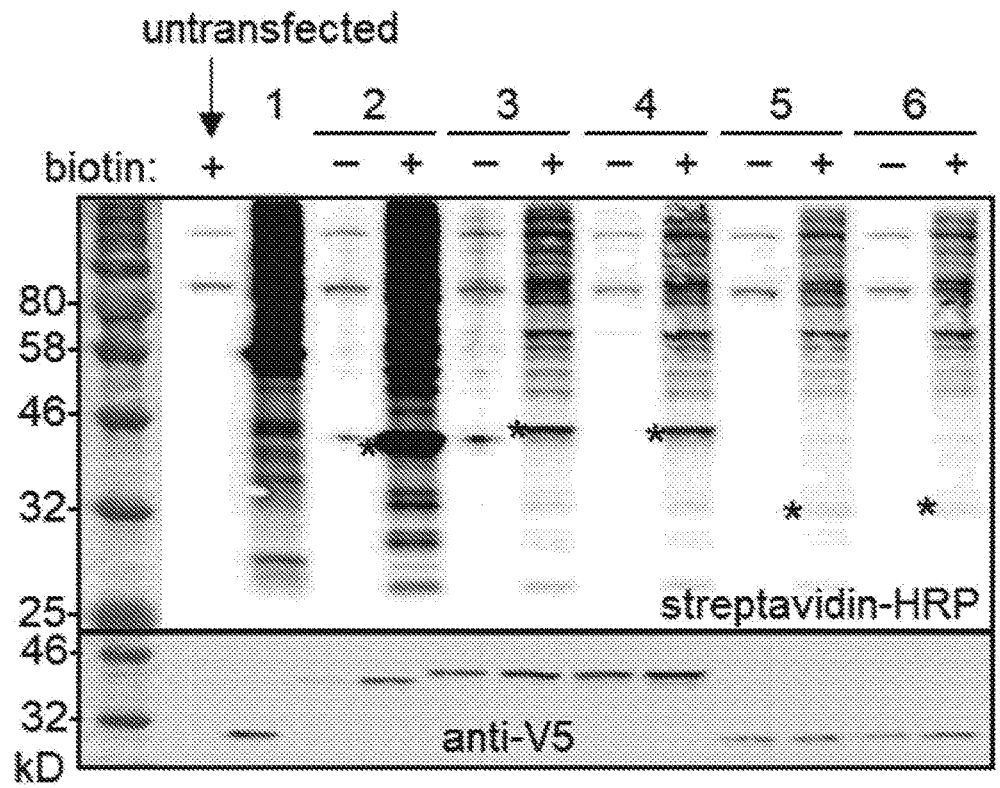
FIG. 11M shows results with 50 µM exogenous biotin added to the cells for 10 minutes. For comparison, sample 1 also shows APEX2-NES labeling for 1 minute with 500 µM biotin phenol and 1 mM hydrogen peroxide at room temperature; and sample 2 shows BirA (R118G) labeling for 18 hours with 50 µM exogenous biotin.
Figure 11N:
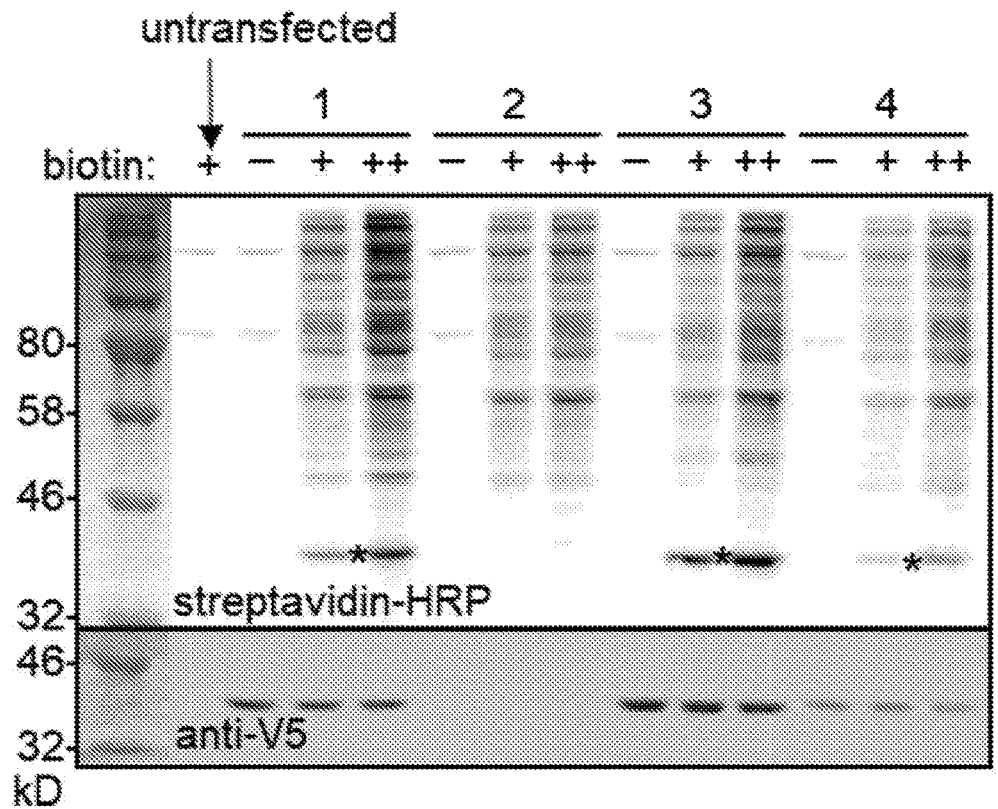
FIGS. 11N-11Q shows results with 50 µM (+) or 500 µM (++) exogenous biotin added to the cells for 10 minutes.
Figure 11O:
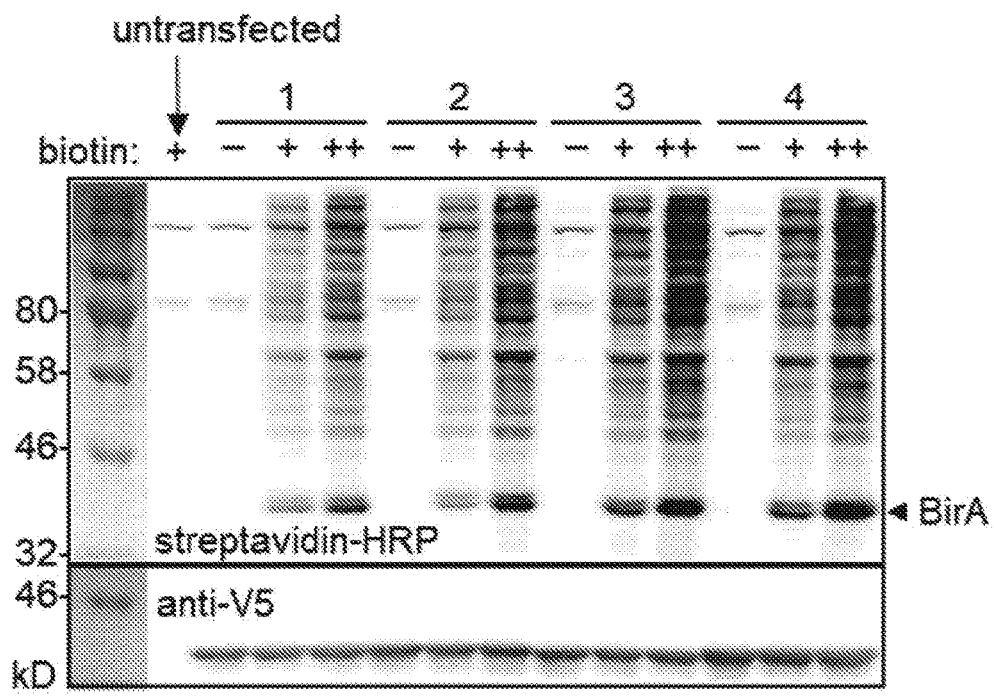
Figure 11P:
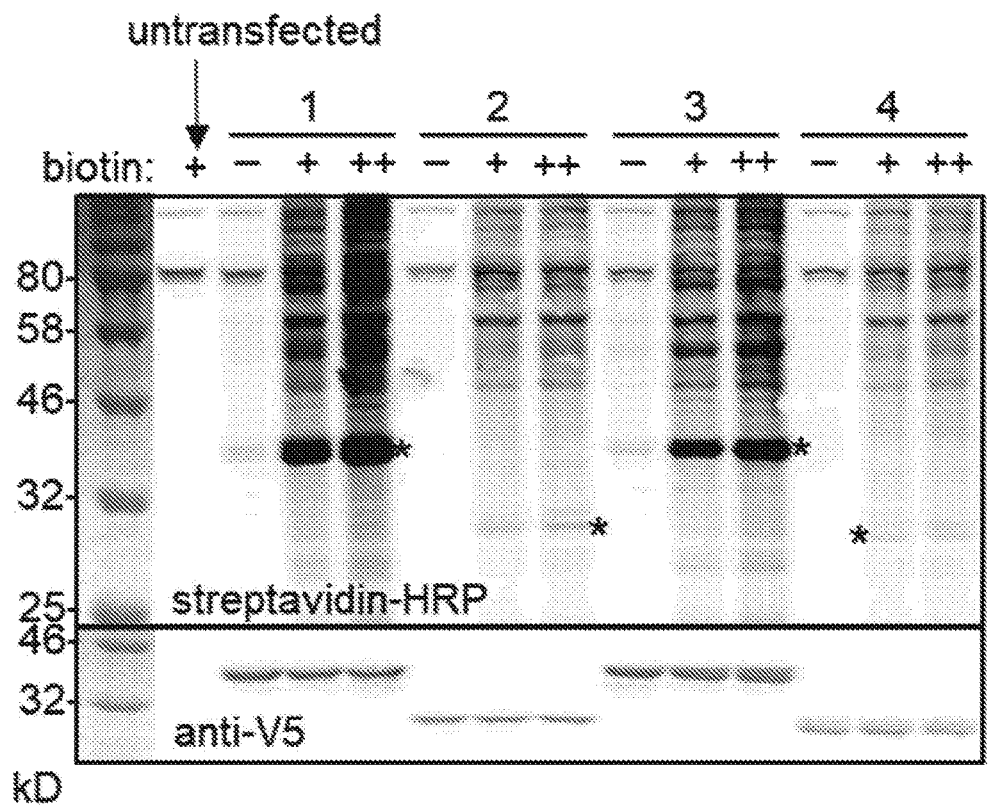
Figure 11Q:
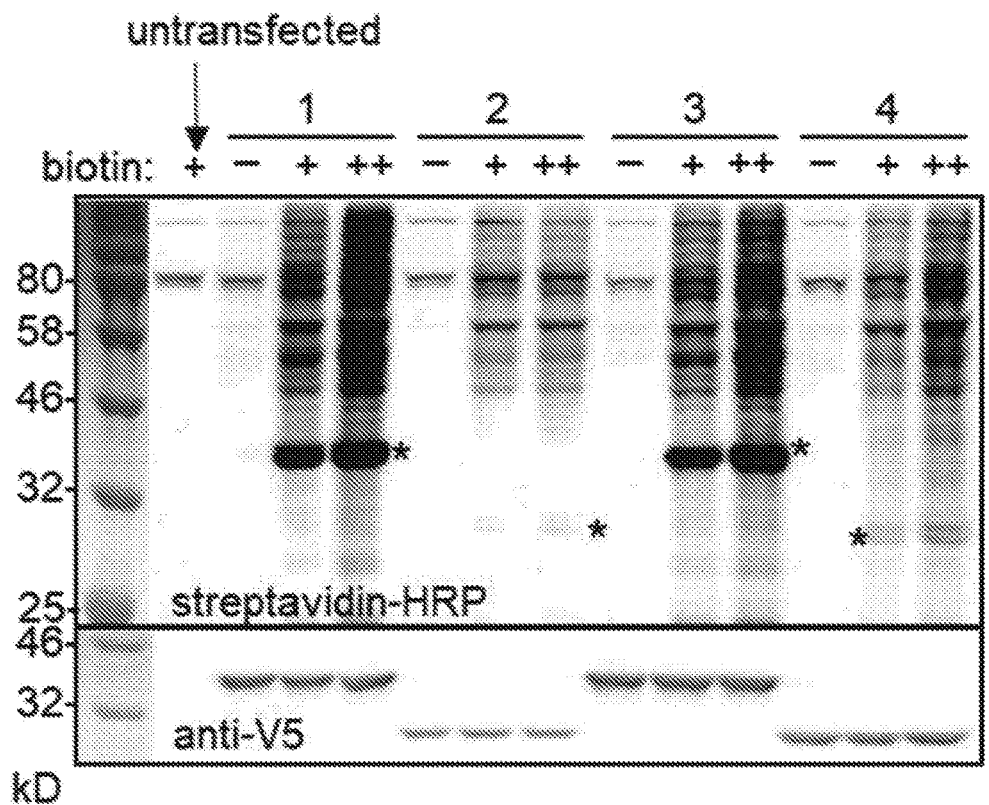
Figure 11R:
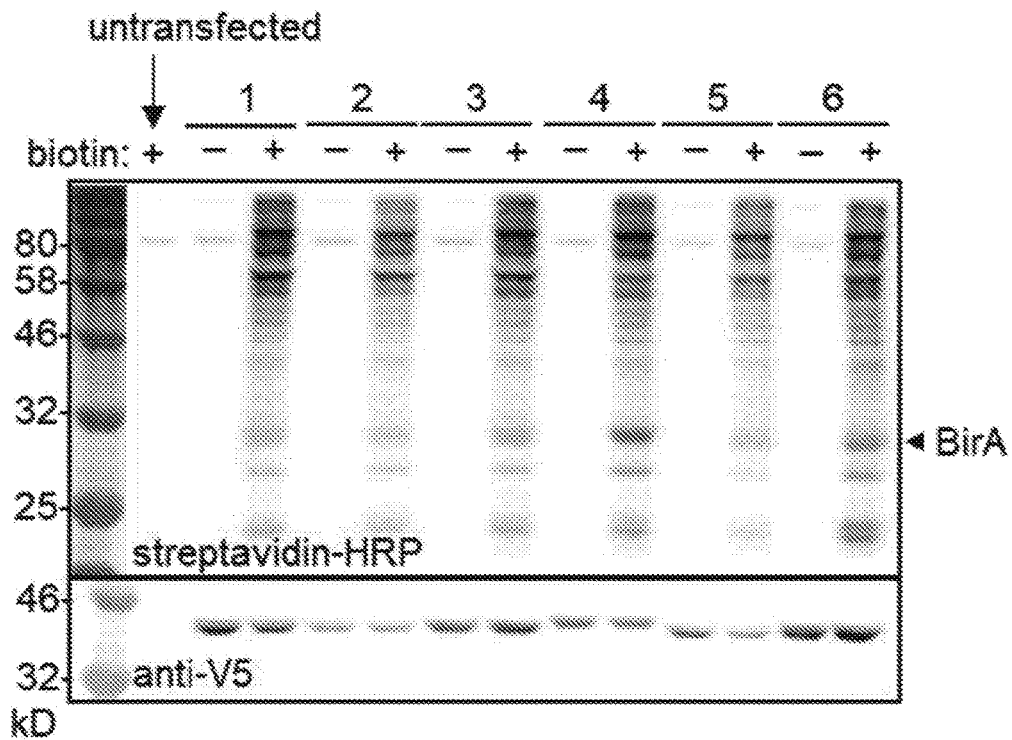
FIGS. 11R-11T show results with 500 µM exogenous biotin added to the cells for 10 minutes.
Figure 11S:
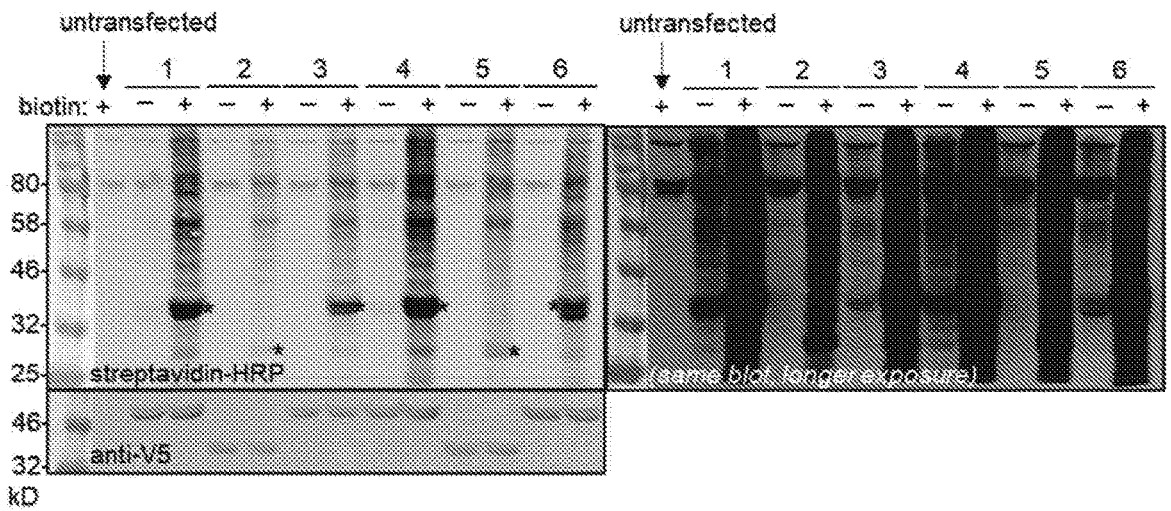
Figure 11T:
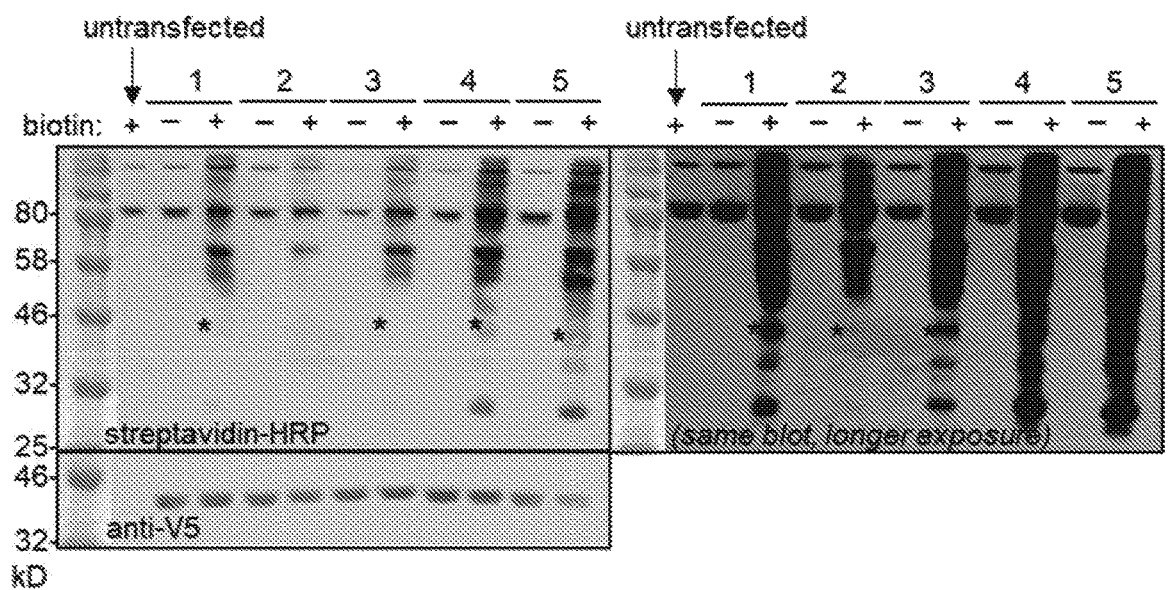
Figure 11U:
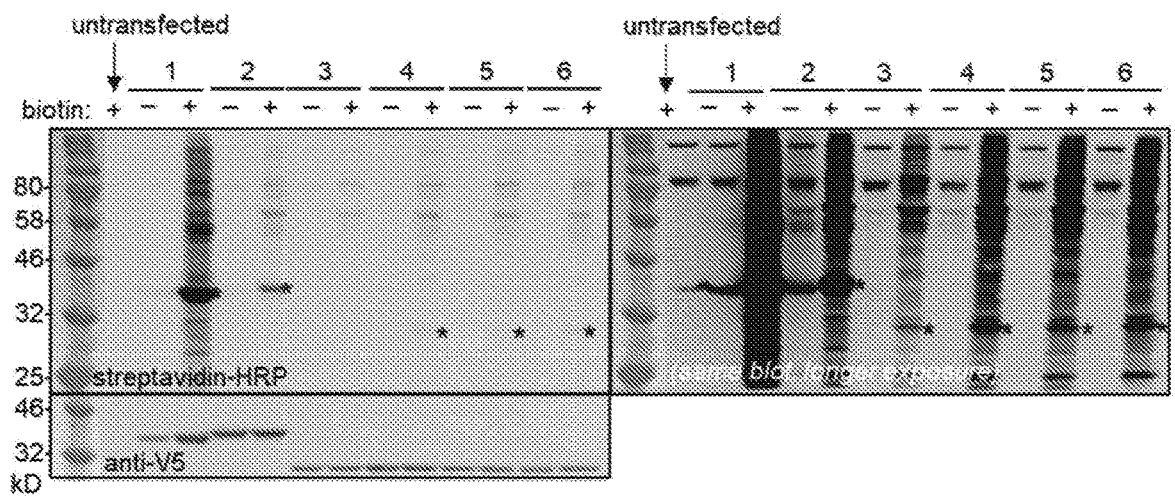
FIGS. 11U-11W show results with 500 µM exogenous biotin added to the cells for 10 minutes. For comparison, sample 1 shows BirA (R118G) labeling for 18 hours with 50 µM exogenous biotin.
Figure 11V:
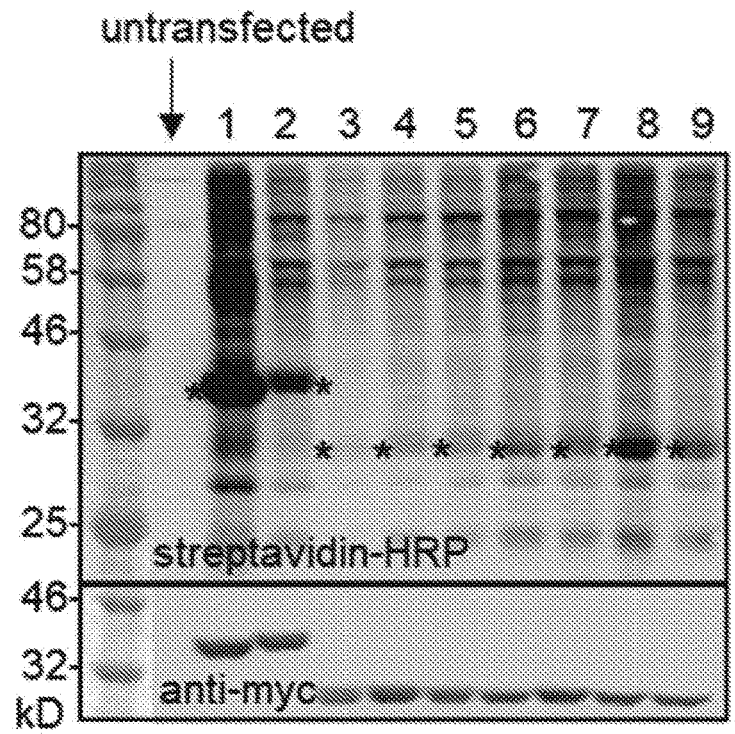
Figure 11W:
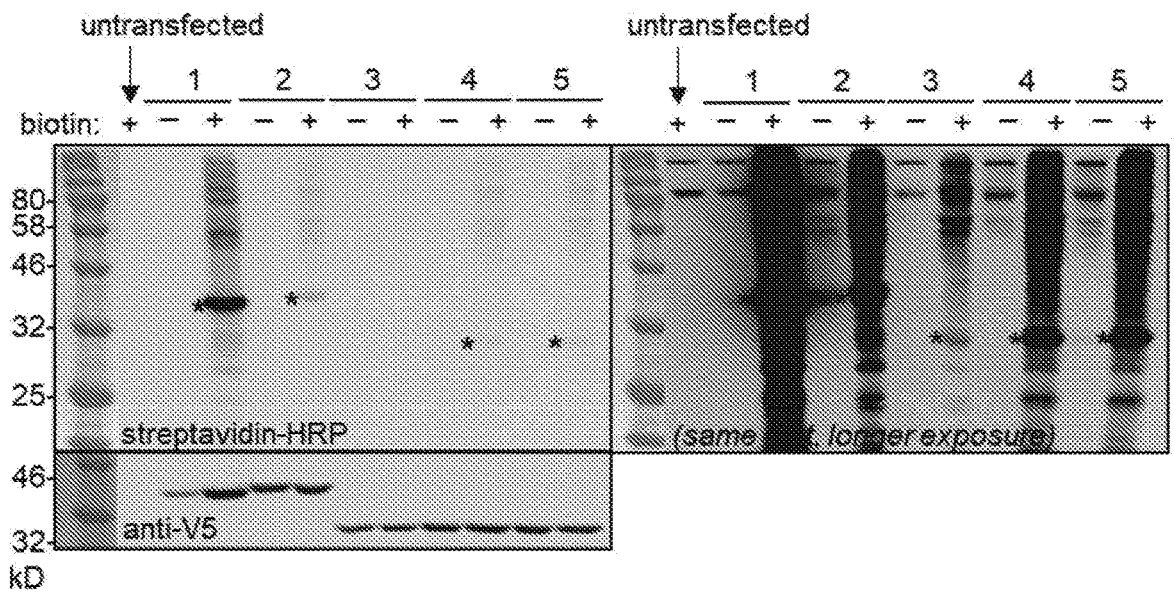
Figure 11X:
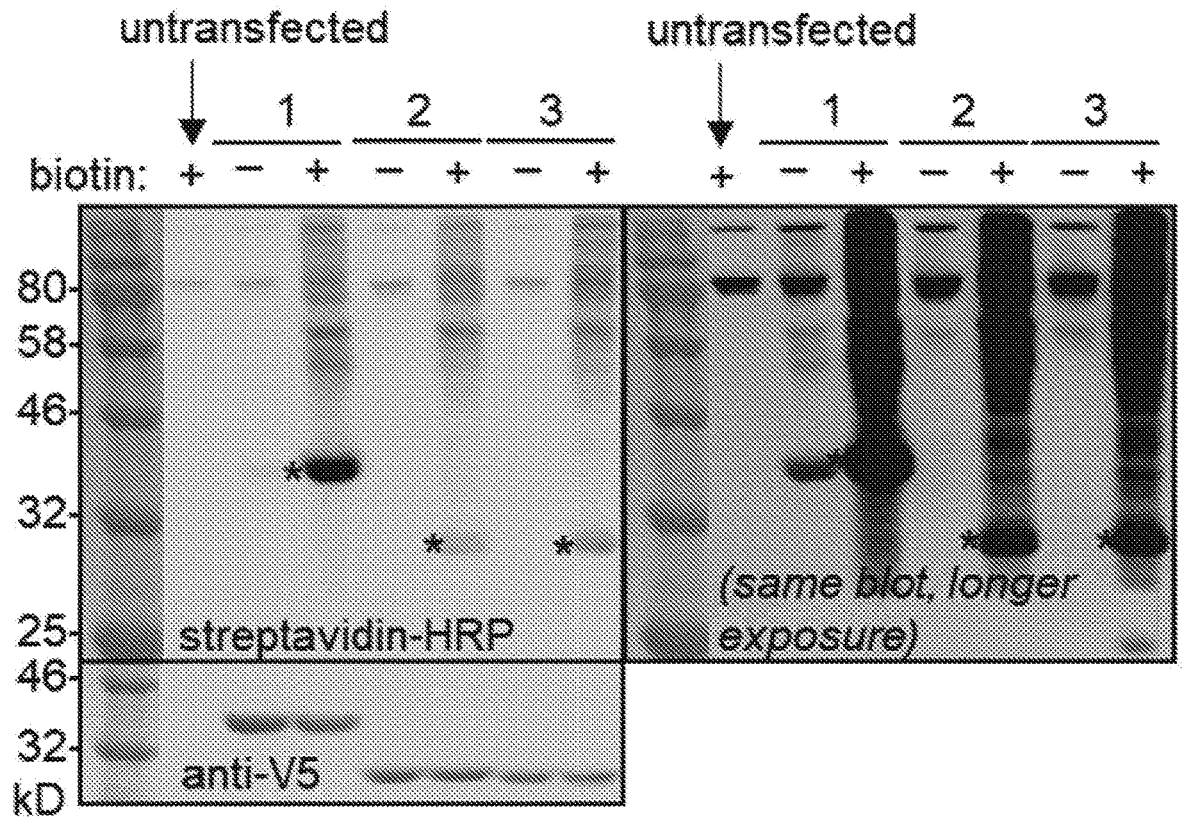
FIG. 11X shows results with 500 µM exogenous biotin added to the cells for 10 minutes.
Figure 11Y:
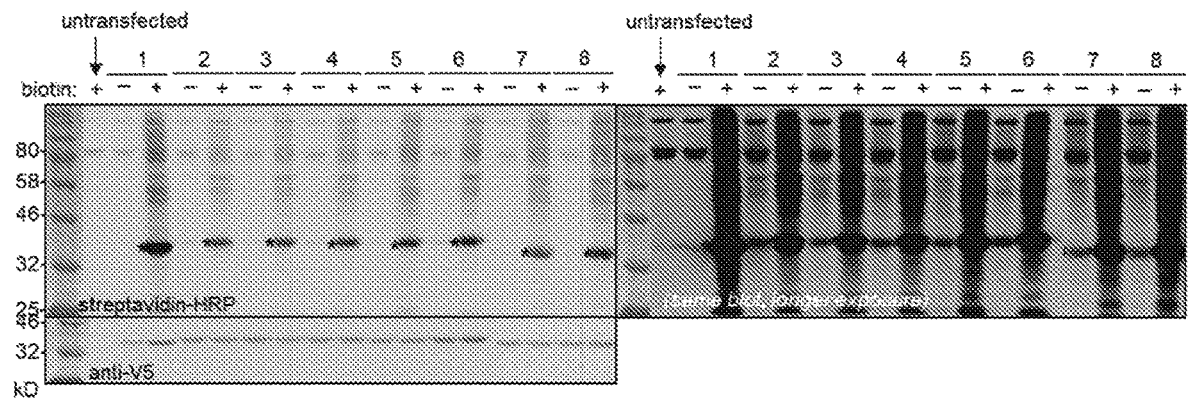
Figure 12A:
FIGS. 12A-12E show testing of TurboID and miniTurbo labeling radius.
Figure 12A:
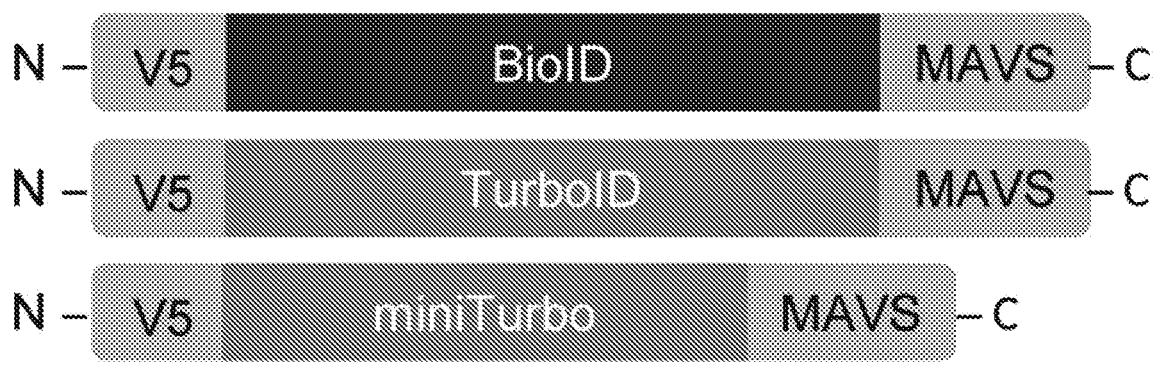
Figure 12B:
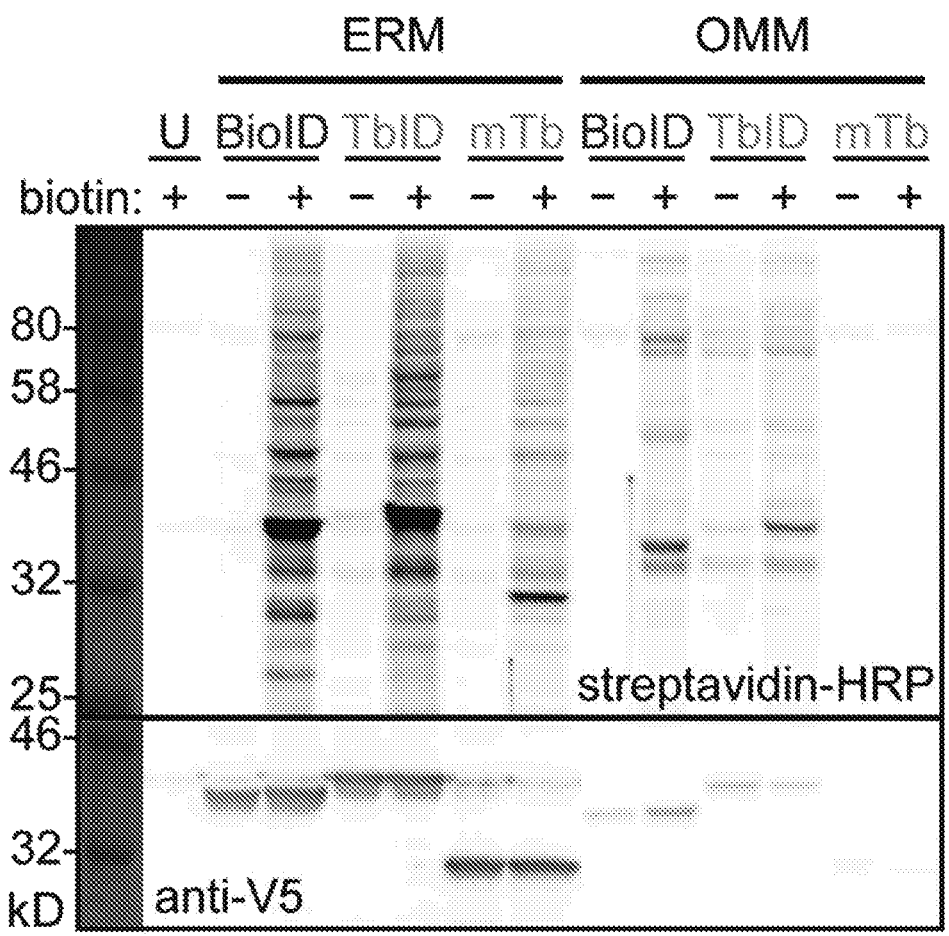
Figure 12C:
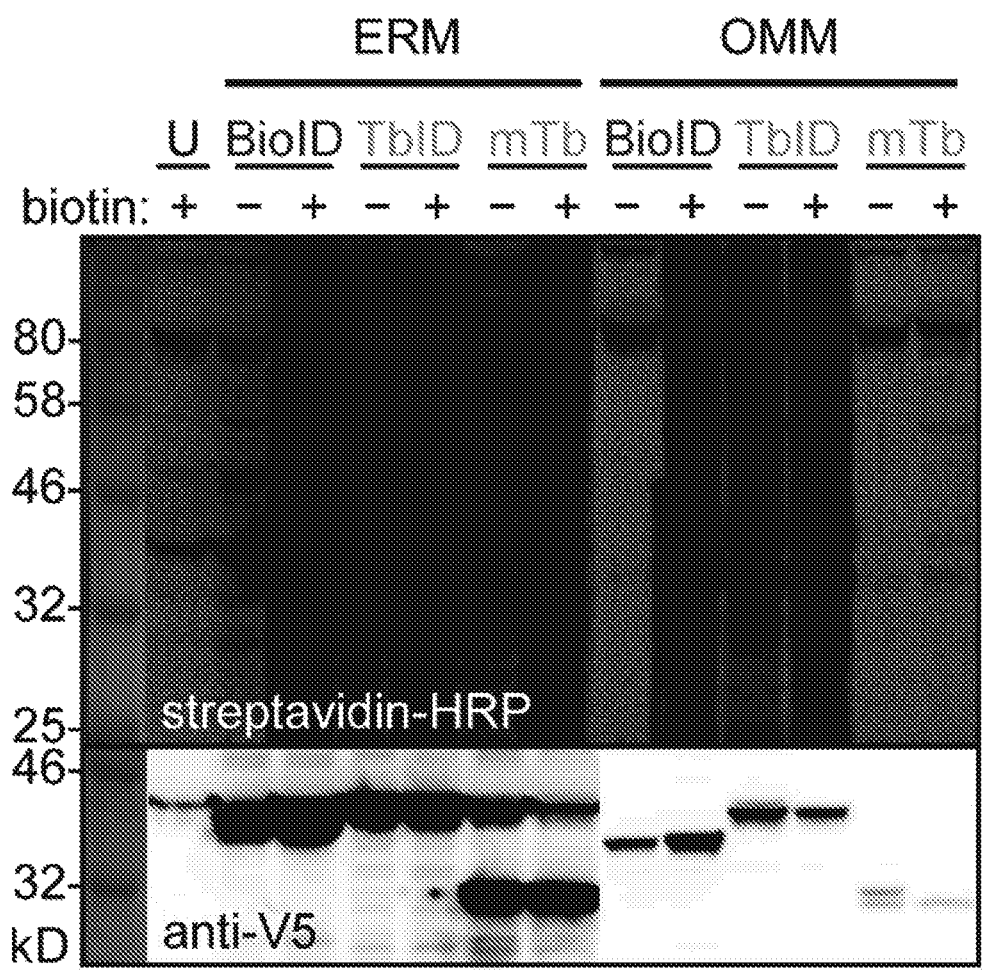
Figure 12D:
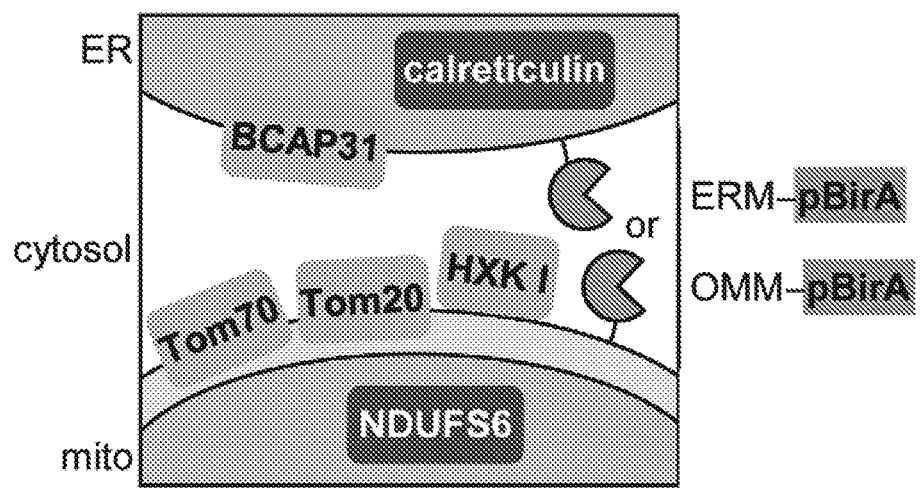
Figure 12E:
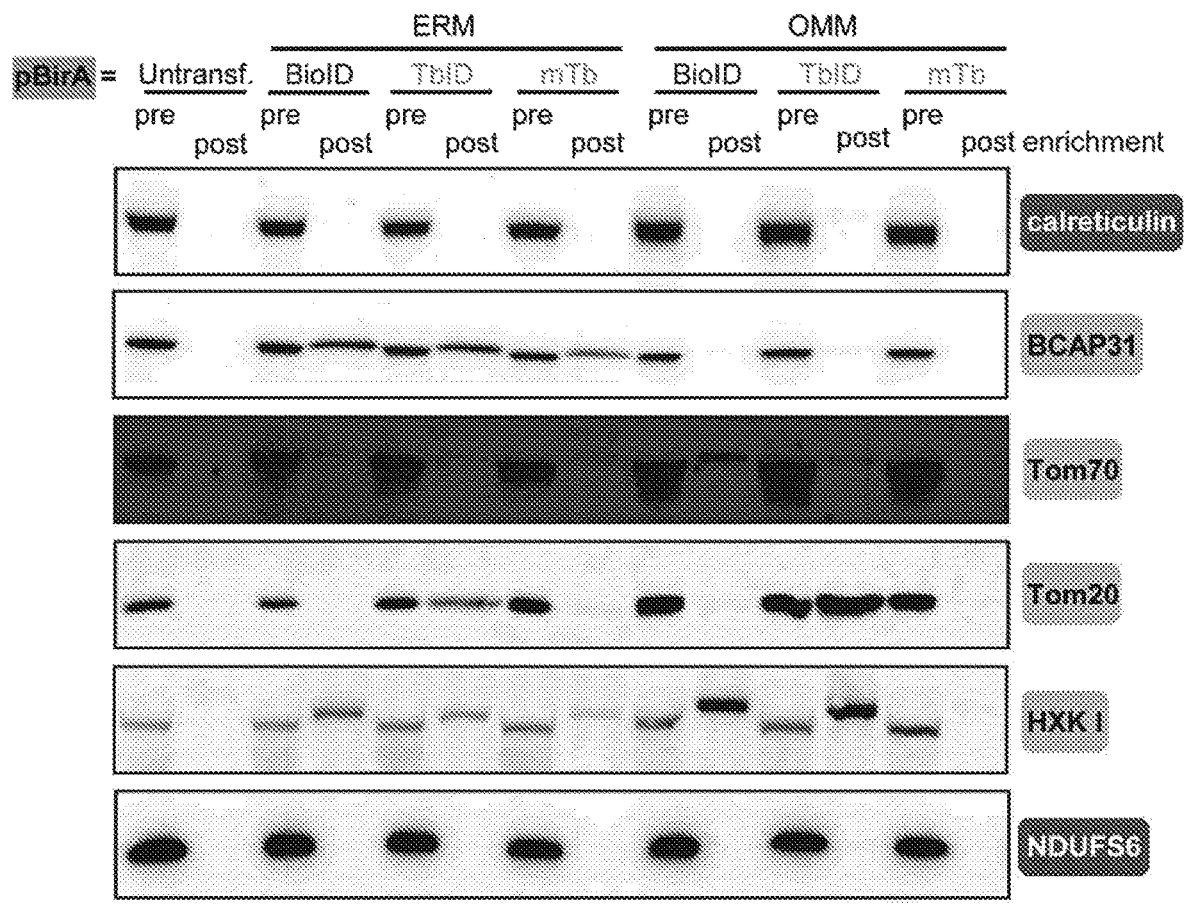

Adult flies were aged 3 days after eclosion from pupal cases before being counted. Females and males of the same genotype were counted together. Adult flies were frozen at −20° C. overnight and images of adult flies were obtained using a dissection microscope connected to a digital camera (FIG. 10B).

To determine if larval wing disc expression of BirA mutants affects adult wing morphology, nub-Gal4 was crossed with UAS-V5-BirA-mut transgenes and the F1 progeny analyzed. Adult flies were aged 3 days after eclosion from pupal cases. Wings were removed from adults, placed in a drop of 50% Permount/50% Xylenes on a glass slide, and a coverslip added. Mounted wings were imaged using a light microscope with a 10× objective. Wing area was measured using the polygon selection tool in ImageJ. Wings quantified and imaged are from female flies (FIGS. 7D, 7E).

C. elegans Strains and Culture Conditions

Experiments on *C. elegans* were performed with wild type or transgenic strains. The age and sex of animals involved in experiments are indicated in figure legends and methods below. The Stanford's Administrative Panel on Laboratory Animal Care (APLAC) deems *C. elegans* used in this study as invertebrates and not subject to formal review and approval by the committee.

*C. elegans* strains were cultured and maintained at 20° C. on OP50 bacteria as previously described[53]. To deplete the animals of excess biotin, worms were grown for 2 generations on biotin auxotrophic *E. coli* (MG1655bioB:kan)[30] washed twice with 1× M9 solution. Array positive and negative embryos dissected from one day-old adults from strain JLF269 (wowEx45[ges1p:3xHA:BirA(G3):unc-54, myo-2p:mCherry:unc-54]) were compared for this study.

Transgenic BirA Mutant Strain Construction for *C. elegans*

A *C. elegans* codon-optimized BirA-G3 ligase gene containing the 3 worm introns present in GFP was synthesized (IDT) and inserted into pJF241 to produce plasmid pAS7. Transgenic worms were generated by injecting 50 ng/μL of pAS7 and 2.5 ng/μL of the co-injection marker myo-2p: mCherry into day 1 N2 hermaphrodites.

Immunohistochemistry and Microscopy of *C. elegans*

To visualize BirA ligases and biotinylation (FIG. 3I), embryos were extracted from one day-old adults, fixed, and stained as previously described[31]. Briefly, embryos were dissected from adult hermaphrodites and attached to microscope slides with Teflon spacers coated with polylysine. Slides were frozen on dry ice and embryos were permeabilized by freeze-crack and fixed in 100% MeOH for 5 minutes. Embryos were washed in PBS and PBT, and subsequently incubated in a-HA primary antibody (Abcam, 1:200) either overnight 4° C. or 1 hour 37° C. to visualize BirA expression. Embryos were washed in PBT and then incubated in CY3-anti-mouse (Jackson Immunoresearch Laboratories, 1:200), Streptavidin Alexa Fluor 488 (Invitrogen, 1:200), and DAPI (Sigma, 1:10000). Embryos were stored in Vectashield mounting medium (Vector Laboratories) at 4° C. Images were obtained using a Nikon Ti-E inverted microscope (Nikon Instruments) and a 60× PLAN APO oil objective (NA=1.4). Images were captured using an Andor Ixon Ultra back thinned EM-CCD camera, at a rate of 0.5 μm, with 405 nm, 488 nm, and 561 nm lasers and a Yokogawa X1 confocal spinning disc head equipped with a 1.5× magnifying lens controlled by NIS Elements software (Nikon). Images were processed and assembled in NIS Elements and Adobe InDesign (FIG. 3I).

Quantitation of Fluorescence Signal Intensity in *C. elegans* Intestine

Comma stage embryos were chosen for analyses. Using a Python script, a threshold for the anti-HA:BirA signal was calculated by the Otsu method to create a mask for the intestine. These masked images were then used to calculate ratios of streptavidin-AF488 pixel intensity to anti-HA:BirA ligase pixel intensity and the mean ratios were compared between samples. A Wilcoxon rank sum test was used to compare biotin+and biotin−conditions (FIG. 3J). Samples were blinded for statistical analysis.

| Mutations in TurboID. miniTurbo. BioID and key intermediate clones relative to wild-type BirA. | | | | | | | | | |
|---|---|---|---|---|---|---|---|---|---|
| Mutant | amino acids | K2 | Q65 | I87 | R118 | E140 | Q141 | S150 | L151 | M157 |
| BioID | 1-321 | | | | R118G | | | | | |
| BirA-R118S | 1-321 | | | | R118S | | | | | |
| R6-1 | 1-321 | K2E | | | R118S | | | | | M157T |
| R6-2 | 1-321 | | Q65P | | R118S | | | | L151P | |
| G1 | 1-321 | | Q65P | | R118S | | | | L151P | |
| G2 | 1-321 | | Q65P | | R118S | | | S150G | L151P | |
| G3 | 1-321 | | Q65P | I87V | R118S | E140K | Q141R | S150G | L151P | |
| G3Δ | 64-321 | | Q65P | I87V | R118S | E140K | Q141R | S150G | L151P | |
| miniTurbo | 64-321 | | Q65P | I87V | R118S | E140K | Q141R | S150G | L151P | |
| TurboID | 1-321 | | Q65P | I87V | R118S | E140K | Q141R | S150G | L151P | |

| | V160 | T192 | K194 | M209 | M241 | S263 | L298 | I305 | E313 |
|---|---|---|---|---|---|---|---|---|---|
| BioID | | | | | | | | | |
| BirA-R118S | | | | | | | | | |
| R6-1 | | | | | | | L298P | | |
| R6-2 | | | | | | | | I305V | E313K |
| G1 | | | | | | | | I305V | |
| G2 | | T192A | | | | | | I305V | |
| G3 | V160A | T192A | | M209V | | | | I305V | |
| G3Δ | V160A | T192A | | M209V | | | | I305V | |
| miniTurbo | V160A | T192A | K194I | M209V | | | | I305V | |
| TurboID | V160A | T192A | K194I | M209V | M241T | S263P | | I305V | |

TABLE 2

| Table of plasmids used in this study. | | | | | | | | |
|---|---|---|---|---|---|---|---|---|
| Plasmid name | Plasmid vector | Promoter | Expression in | Features | Variants | Details | Used for | Used in |
| P1-P8 | pCDNA3 | CMV | mammalian | NotI-myc-NheI-BirA-NES-Stop-XhoI | BirA (R118G) (= BioID); BirA (R118S); BirA (R118T); BirA (R118C); BirA (R118N); BirA (R118V); BirA (R118P); BirA (R118K) | myc: EQKLISEEDL (SEQ ID NO:14); NES6: LQLPPLERLTLD (SEQ ID NO: 15) | transient mammalian cytosol expression | FIG. 4 |

TABLE 2-continued

Table of plasmids used in this study.

| Plasmid name | Plasmid vector | Promoter | Expression in | Features | Variants | Details | Used for | Used in |
|---|---|---|---|---|---|---|---|---|
| P9-P17 | pCTCON2 | GAL1 | yeast | EcoRI-Aga2P-HA-TEVs-15aa linker-NheI-BirA-BamHI-myc-Stop-XhoI | BirA (R118S); R6-1; R6-2; G1; G2; G3; G3A; miniTurbo; TurboID (see Table 1) | TEVs: ENLYFQG (SEQ ID NO: 16), cleavage recognition site for TEV protease, which was not employed in this study; 15aa linker: GGGGSGGGGS-GGGGS (SEQ ID NO: 17); myc: EQKLISEEDL (SEQ ID NO: 18) | inducible yeast cell surface expression for yeast display directed evolution | FIG. 1C, 1E; FIGS. 5, 6 |
| P18-P27 | pCDNA3 | CMV | mammalian | NotI-V5-NheI-BirA-NES-Stop-XhoI | BirA (R118S); G1; G2; G3; G3A; miniTurbo; TurboID; BioID (see Table 1) | V5: GKPIPNPLLGLD-ST (SEQ ID NO: 19); NES6. LQLPPLERLTLD (SEQ ID NO:20) | transient mammalian cytosol expression | FIGS. 1F, 1G; FIGS. 2A, 2B; FIG. 7; FIG. 8 |
| P28-P30 | pCDNA3 | CMV | mammalian | NotI-V5-NheI-BirA-EcoRI-3aa linker-NLS-Stop-XhoI | BioID; TurboID, miniTurbo (see Table 1) | V5: GKPIPNPLLGLD-ST (SEQ ID NO: 21); 3aa linker: SRA; NLS7: DPKKKRKVDPK-KKRKVDPKKKR-KV (SEQ ID NO: 22) | transient mammalian nucleus expression | FIGS. 2C, 2D, 2E; FIGS. 9A, 9C, 9E, 9G, 9I, 9J |
| P31-P33 | pLX304 | CMV | mammalian | attB1-BstBI-mito-BamHI-BirA-NheI-V5-Stop-attB2-NheI-AgeI | BioID; TurboID, miniTurbo (see Table 1) | mito (mitochondrial matrix targeting sequence from COX4)8: MLATRVFSLVG-KRAISTSVCVR-AH (SEQ ID NO: 23); V5: GKPIPNPLLGLD-ST (SEQ ID NO: 24) | stable mammalian mitochondrial matrix expression | FIGS. 2C, 2D, 2E; FIGS. 9B, 9D, 9F, 9H, 9I, 9J |
| P34 | pVSVG | | | | | lentiviral envelope plasmid | producing lentivirus (for P33-P35) | FIGS. 2C, 2D, 2E; FIGS. 9B, 9D, 9F, 9H, 9I, 9J |
| P35 | A8.9 | | | | | lentiviral helper plasmid | producing lentivirus (for P33-P35) | FIGS. 2C, 2D, 2E; FIG. 9B, 9D, 9F, 9H, 9I, 9J |
| P36-P38 | pCDNA3 | CMV | mammalian | HindIII-C1(1-27)-4aa linker-NotI-19aa linker-BirA-NheI-V5-Stop-BamHI | BioID; TurboID, miniTurbo (see Table 1) | C1(1-27) (endoplasmic reticulum membrane anchor derived from cytochrome P450)9: MDPVVVLGLCL-SCLLLLSLWKQ-SYGGG (SEQ ID NO: 25); 4aa linker: GSGS (SEQ ID NO: 26); 19aa linker: GSGSGSGSGS-GSGSGSGSG- (SEQ ID NO: 27); V5: GKPIPNPLLGLD- | transient mammalian ER membrane expression (cytosol facing) | FIG. 2C |

TABLE 2-continued

Table of plasmids used in this study.

| Plasmid name | Plasmid vector | Promoter | Expression in | Features | Variants | Details | Used for | Used in |
|---|---|---|---|---|---|---|---|---|
| P39-P41 | pDisplay | CMV | mammalian | EcoRI-Ig K-chain SS-HA-BglII-BirA-NheI-V5-KDEL-Stop-NotI | BioID; Turbo ID, miniTurbo (see Table 1) | ST (SEQ ID NO: 28) Ig K-chain ss: METDTLLLWVL-LLWVPGSTGD-(SEQ ID NO: 29); HA: YPYDVPDYA (SEQ ID NO: 30); V5:GKPIPNPLL-GLDST (SEQ ID NO: 31); ER localization sequence10: KDEL | transient mammalian ER lumen expression | FIG. 2C |
| P42-P44 | pRS415 | GAL1 | yeast | BamHI-BirA-NheI-V5-Stop-XhoI | BioID; TurboID, miniTurbo (see Table 1) | V5: GKPIPNPLLGLD ST (SEQ ID NO: 32) | inducible yeast cytosol expression | FIG. 3A |
| P45-P47 | pYFJ16 | T5 | bacteria | EcoRI-His6-MBP-4aa linker-AgeI-5 aa linker-BirA-Stop-AscI | BioID; TurboID, miniTurbo (see Table 1) | His6: HHHHHH (SEQ ID NO: 33); MBP: maltose binding protein; 4aa linker: GGGS (SEQ ID NO: 34); 5aa linker: GGSSG (SEQ ID NO: 35) | Inducible bacterial cytosol expression | FIG. 3B |
| P48-P50 | pEntr | | | attL1-V5-NheI-BirA-stop-attL2 | BioID; TurboID, miniTurbo (see Table 1) | V5: GKPIPNPLLGLD-ST (SEQ ID NO: 36), Thermo Fisher | Entry vector for Gateway LR recombination into destination vector | |
| P51-P53 | pWalium-roe 11 | UAS | D. melanogaster | attB1-V5-NheI-BirA-stop-attB2, white+, attB | BioID; TurboID, miniTurbo (see Table 1) | V5: GKPIPNPLLGLD-ST (SEQ ID NO: 37) | Generating trasngenic flies for Gal4-inducible expression | FIGS. 3D, 3E, 3G; FIG. 10 |
| pAS7 | pJF241 (which contains Bluescript backbone) | ges-1 | C. elegans | AscI-ges-1 p-FseI-3xHA-BirA-XmaI-unc54-XhoI | BirA-G3 | 3xHA: YPYDVPDYAYP-YDVPDYAYP-YDVPDYA (SEQ ID NO: 38) | Intestinal expression of BirA-G3 | FIGS. 3H-3J |

TABLE 3

Table of antibodies used in this study.

| antibody | source | vendor | catalog number | dilutions used |
|---|---|---|---|---|
| anti-myc | mouse | Calbiochem | OP10 | Western blotting: 1:1000 |
| anti-mouse-HRP | goat | BioRad | 170-6516 | Western blotting: match dilution of primary antibody used |
| anti-myc | chicken | Invitrogen | A-21281 | yeast surface immunostaining: 1:400 |
| anti-chicken-AlexaFluor647 | goat | Invitrogen | A-21449 | yeast surface immunostaining: 1:200 |
| streptavidin-R-phycoerythrin | — | Jackson Immunoresearch | 016-110-084 | yeast surface immunostaining: 1:100 |
| anti-biotin | rabbit | ImmuneChem | ICP0611 | yeast surface immunostaining: 1:50 |
| anti-rabbit-R- | goat | Life | P-2771MP | yeast surface immunostaining: 1:50 |

TABLE 3-continued

Table of antibodies used in this study.

| antibody | source | vendor | catalog number | dilutions used |
|---|---|---|---|---|
| phycoerythrin streptavidin-HRP | — | Technologies Invitrogen | S911 | Western blotting: 1:3000; TSA on yeast surface: 1:200 |
| anti-V5 | mouse | Invitrogen | 46-0705 | Western blotting: 1:10,000 |
| DAPI | — | | | mammalian cell immunostaining: 1:1000 |
| anti-Tom20 | rabbit | Santa Cruz Biotecnology | FL-145 | mammalian cell immunostaining: 1:500 |
| anti-rabbit-AlexaFluor568 | goat | Invitrogen | A-11011 | mammalian cell immunostaining: 1:1000 |
| neutravidin-AlexaFluor647 | — | Life Techologies (homemade) | neutravidin: A-2666; AlexaFluor647-NHS: A20006 | mammalian cell immunostaining: 1:1000 |
| anti-His6 | mouse | Calbiochem | OB05 | Western blotting: 1:200 |
| anti-mouse Alexa 647 | goat | Invitrogen | A-21236 | *Drosophila* cell immunostaining: 1:500 |
| anti-mouse Alexa 800 | goat | Invitrogen | A32730 | *Drosophila* western blotting: 1:5000 |
| DAPI | — | Sigma | | *C. elegans* immunostaining 1:10000 |
| anti-HA | mouse | Abcam | ab130275 | *C. elegans* immunostaining 1:100 |
| Streptavidin-AF488 | — | Thermo Fisher Scientific | S32354 | *C. elegans* immunostaining 1:200 |
| CY3-anti-mouse | goat | Jackson Immunoresearch Laboratories | 115-165-166 | *C. elegans* immunostaining 1:200 |

REFERENCES

1. Kim, D. I. & Roux, K. J. Filling the Void: Proximity-Based Labeling of Proteins in Living Cells. *Trends in Cell Biology* 26, 804-817 (2016).
2. Rhee, H.-W. et al. Proteomic Mapping of Mitochondria in Living Cells via Spatially Restricted Enzymatic Tagging. *Science (80-.).* 339, 1328-1331 (2013).
3. Lam, S. S. et al. Directed evolution of APEX2 for electron microscopy and proximity labeling. *Nat. Methods* 12, 51-54 (2014).
4. Choi-Rhee, E., Schulman, H. & Cronan, J. E. Promiscuous protein biotinylation by *Escherichia coli* biotin protein ligase. *Protein Sci.* 13, 3043-50 (2004).
5. Roux, K. J., Kim, D. I., Raida, M. & Burke, B. A promiscuous biotin ligase fusion protein identifies proximal and interacting proteins in mammalian cells. *J. Cell Biol.* 196, 801-810 (2012).
6. Paek, J. et al. Multidimensional Tracking of GPCR Signaling via Peroxidase-Catalyzed Proximity Labeling. *Cell* 169, 338-349.e1 1 (2017).
7. Lobingier, B. T. et al. An Approach to Spatiotemporally Resolve Protein Interaction Networks in Living Cells. *Cell* 169, 350-360.e12 (2017).
8. Gupta, G. D. et al. A Dynamic Protein Interaction Landscape of the Human Centrosome-Cilium Interface. *Cell* 163, 1483-1499 (2015).
9. Kim, D. I. et al. Probing nuclear pore complex architecture with proximity-dependent biotinylation. *Proc. Natl. Acad. Sci.* 111, E2453-E2461 (2014).
10. Lin, Q. et al. Screening of Proximal and Interacting Proteins in Rice Protoplasts by Proximity-Dependent Biotinylation. *Front. Plant Sci.* 8, (2017).
11. Morriswood, B. et al. Novel bilobe components in Trypanosoma brucei identified using proximity-dependent biotinylation. *Eukaryot. Cell* 12, 356-367 (2013).
12. Chen, A. L. et al. Novel components of the toxoplasma inner membrane complex revealed by BioID. *MBio* 6, (2015).
13. Nadipuram, S. M. et al. In Vivo biotinylation of the toxoplasma parasitophorous vacuole reveals novel dense granule proteins important for parasite growth and pathogenesis. *MBio* 7, (2016).
14. Chen, A. L. et al. Novel insights into the composition and function of the Toxoplasma IMC sutures. *Cell. Microbiol.* 19, (2017).
15. Long, S. et al. Calmodulin-like proteins localized to the conoid regulate motility and cell invasion by Toxoplasma gondii. *PLoS Pathog.* 13, (2017).
16. Zhou, Q., Hu, H. & Li, Z. An EF-hand-containing protein in Trypanosoma brucei regulates cytokinesis initiation by maintaining the stability of the cytokinesis initiation factor CIF1. *J. Biol. Chem.* 291, 14395-14409 (2016).
17. Dang, H. Q. et al. Proximity interactions among basal body components in *Trypanosoma brucei* identify novel regulators of basal body biogenesis and inheritance. *MBio* 8, (2017).
18. Kehrer, J., Frischknecht, F. & Mair, G. R. Proteomic Analysis of the *Plasmodium berghei* Gametocyte Egressome and Vesicular bioID of Osmiophilic Body Proteins Identifies Merozoite TRAP-like Protein (MTRAP) as an Essential Factor for Parasite Transmission. *Mol. Cell. Proteomics* 15, 2852-2862 (2016).
19. Gaji, R. Y. et al. Phosphorylation of a Myosin Motor by TgCDPK3 Facilitates Rapid Initiation of Motility during Toxoplasma gondii egress. *PLoS Pathog.* 11, (2015).
20. Batsios, P., Ren, X., Baumann, O., Larochelle, D. & Graf, R. Src1 is a Protein of the Inner Nuclear Membrane Interacting with the Dictyostelium Lamin NE81. *Cells* 5, 13 (2016).
21. Meyer, I. et al. CP39, CP75 and CP91 are major structural components of the Dictyostelium centrosome's core structure. *Eur. J. Cell Biol.* 96, 119-130 (2017).
22. Uezu, A. et al. Identification of an elaborate complex mediating postsynaptic inhibition. *Science (80-.).* 353, 1123-1129 (2016).

23. Martell, J. D. et al. A split horseradish peroxidase for the detection of intercellular protein-protein interactions and sensitive visualization of synapses. *Nat. Biotechnol.* 34, 774-780 (2016).
24. Bobrow, M. N., Harris, T. D., Shaughnessy, K. J. & Litt, G. J. Catalyzed reporter deposition, a novel method of signal amplification application to immunoassays. *J. Immunol. Methods* 125, 279-285 (1989).
25. Xu, Y. & Beckett, D. Evidence for interdomain interaction in the *Escherichia coli* repressor of biotin biosynthesis from studies of an N-terminal domain deletion mutant. *Biochemistry* 35, 1783-1792 (1996).
26. Wood, Z. A., Weaver, L. H., Brown, P. H., Beckett, D. & Matthews, B. W. Co-repressor induced order and biotin repressor dimerization: A case for divergent followed by convergent evolution. *J. Mol. Biol.* 357, 509-523 (2006).
27. Eginton, C., Cressman, W. J., Bachas, S., Wade, H. & Beckett, D. Allosteric coupling via distant disorder-to-order transitions. *J. Mol. Biol.* 427, 1695-1704 (2014).
28. Weaver, L. H., Kwon, K., Beckett, D. & Matthews, B. W. Corepressor-induced organization and assembly of the biotin repressor: a model for allosteric activation of a transcriptional regulator. *Proc. Natl. Acad. Sci. U.S.A* 98, 6045-50 (2001).
29. Han, S. et al. Proximity Biotinylation as a Method for Mapping Proteins Associated with mtDNA in Living Cells. *Cell Chem. Biol.* 24, 404-414 (2017).
30. Ortega-Cuellar, D. et al. Biotin starvation with adequate glucose provision causes paradoxical changes in fuel metabolism gene expression similar in rat (*Rattus norvegicus*), nematode (*Caenorhabditis elegans*) and yeast (*Saccharomyces cerevisiae*). *J. Nutrigenet. Nutrigenomics* 3, 18-30 (2010).
31. Leung, B., Hermann, G. J. & Priess, J. R. Organogenesis of the *Caenorhabditis elegans* Intestine. *Dev. Biol.* 216, 114-134 (1999).
32. Sulston, J. E., Schierenberg, E., White, J. G. & Thomson, J. N. The embryonic cell lineage of the nematode *Caenorhabditis elegans*. *Developmental Biology* 100, 64-119 (1983).
33. Dingar, D. et al. BioID identifies novel c-MYC interacting partners in cultured cells and xenograft tumors. *J. Proteomics* 118, 95-111 (2015).
34. Pinon, V. Biotin Synthesis in Plants. The First Committed Step of the Pathway Is Catalyzed by a Cytosolic 7-Keto-8-Aminopelargonic Acid Synthase. *PLANT Physiol.* 139, 1666-1676 (2005).
35. Reinke, A. W., Balla, K. M., Bennett, E. J. & Troemel, E. R. Identification of microsporidia host-exposed proteins reveals a repertoire of rapidly evolving proteins. *Nat. Commun.* 8, 14023 (2017).
36. Reinke, A. W., Mak, R., Troemel, E. R. & Bennett, E. J. In vivo mapping of tissue- and subcellular-specific proteomes in *Caenorhabditis elegans*. *Sci. Adv.* 3, e1602426 (2017).
37. Chen, C.-L. et al. Proteomic mapping in live *Drosophila* tissues using an engineered ascorbate peroxidase. *Proc. Natl. Acad. Sci. U.S.A* 112, 1-6 (2015).
38. Stack, E. C., Wang, C., Roman, K. A. & Hoyt, C. C. Multiplexed immunohistochemistry, imaging, and quantitation: A review, with an assessment of Tyramide signal amplification, multispectral imaging and multiplex analysis. *Methods* 70, 46-58 (2014).
39. Kim, D. I. et al. An improved smaller biotin ligase for BioID proximity labeling. *Mol. Biol. Cell* 27, 1188-1196 (2016).
40. Birendra, K. C. et al. VRK2A is an A-type lamin-dependent nuclear envelope kinase that phosphorylates BAF. *Mol. Biol. Cell* mbc.E17-03-0138 (2017). doi: 10.1091/mbc.E17-03-0138
41. Ashburner, M. et al. Gene Ontology: tool for the unification of biology. *Nat. Genet.* 25, 25-29 (2000).
42. Gene Ontology Consortium. Gene Ontology Consortium: going forward. *Nucleic Acids Res.* 43, D1049-56 (2015).
43. Calvo, S. E., Clauser, K. R. & Mootha, V. K. MitoCarta2.0: An updated inventory of mammalian mitochondrial proteins. *Nucleic Acids Res.* 44, D1251-D1257 (2016).
44. Chao, G. et al. Isolating and engineering human antibodies using yeast surface display. *Nat. Protoc.* 1, 755-768 (2006).
45. Jan, C. H., Williams, C. C. & Weissman, J. S. Response to Comment on 'Principles of ER cotranslational translocation revealed by proximity-specific ribosome profiling'. *Science* (80-.). 348, 1217-1217 (2015).
46. Colby, D. W. et al. Engineering antibody affinity by yeast surface display. *Methods in Enzymology* 388, 348-358 (2004).
47. Ausubel, F. M. et al. *Current Protocols in Molecular Biology. Molecular Biology* 1, (2003).
48. Hung, V. et al. Spatially resolved proteomic mapping in living cells with the engineered peroxidase APEX2. *Nat. Protoc.* 11, 456-475 (2016).
49. Pagliarini, D. J. et al. A Mitochondrial Protein Compendium Elucidates Complex I Disease Biology. *Cell* 134, 112-123 (2008).
50. Thul, P. J. et al. A subcellular map of the human proteome. *Science* (80-. ). 356, eaal3321 (2017).
51. Perkins, L. A. et al. The transgenic RNAi project at Harvard medical school: Resources and validation. *Genetics* 201, 843-852 (2015).
52. Markstein, M., Pitsouli, C., Villalta, C., Celniker, S. E. & Perrimon, N. Exploiting position effects and the gypsy retrovirus insulator to engineer precisely expressed transgenes. *Nat. Genet.* 40, 476-483 (2008).
53. Brenner, S. The genetics of *Caenorhabditis elegans*. Genetics 77, 71-94 (1974).

While the preferred embodiments of the invention have been illustrated and described, it will be appreciated that various changes can be made therein without departing from the spirit and scope of the invention.

What is claimed is:

1. A modified biotin ligase comprising at least one mutation comprising an amino acid substitution selected from the group consisting of Q65P, M209V, V160A, S150G, L151P, I305V, I87V, T192A, K194I, E140K, Q141R, M241T, and S263P, wherein positions of the amino acids are numbered relative to the reference wild-type biotin ligase sequence of SEQ ID NO:7, and wherein the biotin ligase amino acid sequence is at least 90% identical to the sequence of SEQ ID NO: 7.

2. The modified biotin ligase of claim 1, wherein the biotin ligase further comprises an N-terminal deletion of the first 63 amino acids ($\Delta$(1-63)), a deletion of A146, or a combination thereof, as numbered relative to the reference wild-type biotin ligase sequence of SEQ ID NO:7.

3. The modified biotin ligase of claim 1, wherein the modified biotin ligase comprises:
  a) Q65P, R118S, L151P, I305V, and E313K amino acid substitutions,
  b) R118S and E313K amino acid substitutions,
  c) Q65P, R118S, L151P, I305V, and E313R amino acid substitutions,
  d) R118S and E313R amino acid substitutions,
  e) R118S, L151P, and I305V amino acid substitutions,
  f) K2E, R118S, M157T, and L298P amino acid substitutions,
  g) R118S and L297P amino acid substitutions,
  h) R118S, I313N amino acid substitutions,
  i) R118S, L151P, and I305V amino acid substitutions, j) Q65P, R118S, and I305V amino acid substitutions,
k) Q65P, R118S, and L151P amino acid substitutions,
l) R118S, L151P, I305V, and K313R amino acid substitutions,
m) Q65P, R118S, I305V, and K313R amino acid substitutions,
n) Q65P, R118S, and K313R amino acid substitutions,
o) R118S, L151P, and K313R amino acid substitutions,
p) R118S, I305V, and K313R amino acid substitutions,
q) Q65P and R118S amino acid substitutions,
r) R118S and L151P amino acid substitutions,
s) R118S and I305V amino acid substitutions,
t) R118S and M157T amino acid substitutions,
u) R118S and L298P amino acid substitutions,
v) K2E, R33G, R118S, M157T, and L298P amino acid substitutions,
w) K2E, R118S, M157T, I279T, L298P, and K307N amino acid substitutions,
x) Q65P, R118S, L151P, I305V, Y111H, and R118S amino acid substitutions,
y) Q65P, R118S, S150G, L151P, T192A, I305V amino acid substitutions,
z) Q65P, R118S, L151P, I231V, and I305V amino acid substitutions,
aa) Q65P, R118S, L151P, T192A, and I305V amino acid substitutions,
bb) Q65P, R118S, S150G, L151P, and I305V amino acid substitutions,
cc) R33G, Q65P, R118S, S150G, L151P, T192A, and I305V amino acid substitutions,
dd) N37S, Q65P, R118S, S150G, L151P, T192V, E266L, and I305V amino acid substitutions,
ee) Q65P, R118S, S150G, L151P, T192A, I280V, I305V, and A318V amino acid substitutions,
ff) Q65P, R118S, Q142R, S150G, L151P, T192A, M209V, and I305V amino acid substitutions,
gg) Q65P, R118S, S150G, L151P, T192A, and I305V amino acid substitutions,
hh) Q65P, R118S, Q142R, S150G, L151P, T192A, and I305V amino acid substitutions,
ii) Q65P, R118S, S150G, L151P, T192A, M209V, and I305V amino acid substitutions,
jj) Q65P, I87V, R118S, E141K, S150G, L151P, V160A, T192A, M209V, and I305V amino acid substitutions,
kk) Q65P, I87V, R118S, E141K, S150G, L151P, T192A, and I305V amino acid substitutions,
ll) Q65P, R118S, S150G, L151P, V160A, T192A, M209V, and I305V amino acid substitutions,
mm) Q65P, R118S, Q142R, S150G, L151P, V160A, T192A, M209V, and I305V amino acid substitutions,
nn) Q65P, I87V, R118S, E141K, S150G, L151P, V160A, T192A, M209V, and I305V amino acid substitutions,
oo) Q65P, I87V, R118S, Q142R, S150G, L151P, T192A, M209V, and I305V amino acid substitutions,
pp) Q65P, R118S, E141K, Q142R, S150G, L151P, T192A, M209V, and I305V amino acid substitutions,
qq) Q65P, I87V, R118S, E141K, Q142R, S150G, L151P, V160A, T192A, M209V, and I305V amino acid substitutions,
rr) Q65P, I87V, R118S, E141K, Q142R, S150G, L151P, T192A, and I305V amino acid substitutions,
ss) Q65P, I87V, R118S, E141K, S150G, L151P, T192A, M209V, and I305V amino acid substitutions,
tt) Q65P, R118S, S150G, Q142R, L151P, T192A, M209V, and I305V amino acid substitutions,
uu) Q65P, I87V, R118S, E141K, S150G, L151P, V160A, T192A, M209V, and I305V amino acid substitutions,
vv) Q65P, I87V, R118S, E141K, Q142R, S150G, L151P, V160A, T192A, I201V, M209V, and I305V amino acid substitutions,
ww) Q65P, I87V, R118S, K140R, E141K, Q142R, S150G, L151P, V160A, T192A, M209V, K267R, I305V, and E313K amino acid substitutions,
xx) Q65P, I87V, R118S, E141K, Q142R, S150G, L151P, V160A, T192A, M209V, I305V, I306V, and E313K amino acid substitutions,
yy) Q65P, I87V, I98V, R118S, E141K, Q142R, S150G, L151P, V160A, T192A, M209V, and I305V amino acid substitutions,
zz) Q65P, I87V, R118S, E141K, Q142R, S150G, L151P, V160A, T192A, A199T, M209V, D303G, and I305V amino acid substitutions,
aaa) Q65P, I87V, R118S, G120R, E141K, Q142R, S150G, L151P, V160A, T192A, D197G, M209V, M241V, I305V, and E313K amino acid substitutions,
bbb) Q65P, I87V, R118S, E141K, Q142R, S150G, L151P, V160A, V162A, A166V, T192A, M209V, I305V, and E313K amino acid substitutions,
ccc) Q65P, I87V, R118S, E141K, Q142R, S150G, L151P, V160A, T192A, M209V, I305V, E307R, and E313K amino acid substitutions,
ddd) E27D, Q65P, I87V, R118S, E141K, Q142R, S150G, L151P, V160A, T192A, M209V, E251K, and I305V amino acid substitutions,
eee) Q65P, I87V, R118S, E141K, Q142R, S150G, L151P, V160A, T192A, M209V, M241T, and I305V amino acid substitutions,
fff) Q65P, I87V, R118S, E141K, Q142R, S150G, L151P, V160A, T192A, M209V, N270D, and I305V amino acid substitutions,
ggg) K2R, F51L, Q65P, K70T, I87V, R118S, E141K, Q142R, S150G, L151P, V160A, T192A, M209V, I305V, I306V, and E313K amino acid substitutions,
hhh) Δ(1-63), Q65P, K70T, I87V, R118S, E141K, Q142R, S150G, L151P, V160A, T192A, M209V, I305V, I306V, and E313K amino acid substitutions,
iii) Δ(1-63), Q65P, I87V, R118S, E141K, Q142R, S150G, L151P, V160A, T192A, M209V, and I305V amino acid substitutions,
jjj) Q65P, I87V, R118S, E141K, Q142R, S150G, L151P, V160A, T192A, M209V, L252R, I305V, K307R, and G311 D amino acid substitutions,
kkk) Q65P, I87V, R118S, E141K, Q142R, S150G, L151P, V160A, K168E, T192A, M209V, K267E, and I305V amino acid substitutions,
lll) Q65P, I87V, R118S, E141K, Q142R, S150G, L151P, V160A, T192A, M209V, E251K, and I305V amino acid substitutions,
mmm) Δ(1-63), Q65P, I87V, R118S, E141K, Q142R, S150G, L151P, V160A, T192A, M209V, E251K, and I305V amino acid substitutions,
nnn) Q65P, I87V, R118S, E141K, Q142R, S150G, L151P, V160A, T192A, M209V, M241T, and I305V amino acid substitutions,
ooo) Δ(1-63), Q65P, I87V, R118S, E141K, Q142R, S150G, L151P, V160A, T192A, M209V, M241T, and I305V amino acid substitutions,
ppp) Δ(1-63) Q65P, I87V, R118S, E141K, Q142R, S150G, L151P, V160A, T192A, M209V, M241T, I305V amino acid substitutions,
qqq) Δ(1-63), Q65P, I87V, R118S, E141K, Q142R, S150G, L151P, V160A, T192A, M209V, and I305V amino acid substitutions, rrr) Δ(1-63), Q65P, I87V, R118S, E141K, Q142R, S150G, L151P, V160A, L179M, T192A, M209V, N232S, I305V, and I306T amino acid substitutions, sss) Δ(1-63), Q65P, I87V, R118S, E141K, Q142R, S150G, L151P, V160A, T192A, M209V, I285V, and I305V amino acid substitutions, ttt) Δ(1-63), Q65P, I87V, R118S, E141K, Q142R, S150G, L151P, V160A, T192A, M209V, S289G, I305V, and M310V amino acid substitutions, uuu) Δ(1-63), Q65P, I87V, R118S, E141K, Q142R, S150G, L151P, V160A, D167G, T192A, M209V, N232S, and I305V amino acid substitutions, vvv) Δ(1-63), Q65P, I87V, I99V, R118S, E141K, Q142R, S150G, L151P, V160A, T192A, M209V, I305V, K307Q, and M310T amino acid substitutions, www) Q65P, I87V, R118S, E141K, Q142R, S150G, L151P, V160A, T192A, M209V, and I305V amino acid substitutions, xxx) Q65P, I87V, S89N, R118S, E141K, Q142R, S150G, L151P, V160A, T192A, M209V, and I305V amino acid substitutions, yyy) Δ(1-63) Q65P, I87V, R118S, E141K, Q142R, S150G, L151P, V160A, D167G, T192A, M209V, M241T, N232S, and I305V amino acid substitutions, zzz) Q65P, I87V, S89N, R118S, E141K, Q142R, S150G, L151P, V160A, T192A, M209V, M241T, and I305V amino acid substitutions, aaaa) Δ(1-63), Q65P, I87V, D88G, R118S, E141K, Q142R, S150G, L151P, V160A, T192A, M209V, K283E, and I305V amino acid substitutions, bbbb) Δ(1-63), Q65P, I87V, Y111H, R118S, E141K, Q142R, S150G, L151P, V160A, T192A, M209V, and I305V amino acid substitutions, cccc) Δ(1-63), Q65P, I87V, R118S, E141K, Q142R, S150G, L151P, V160A, T192A, M209V, S263P, and I305V amino acid substitutions, dddd) Δ(1-63), Q65P, I87V, R118S, E141K, Q142R, S150G, L151P, V160A, T192A, K194I, M209V, and I305V amino acid substitutions, eeee) Δ(1-63), Q65P, I87V, R118S, E141K, Q142R, S150G, L151P, V160A, T192A, M209V, and I305V amino acid substitutions, ffff) Δ(1-63), Q65P, I87V, R118S, E141K, Q142R, S150G, L151P, V160A, T192A, M209V, M241T, and I305V amino acid substitutions, gggg) Δ(1-63), Q65P, I87V, R118S, E141K, Q142R, S150G, L151P, V160A, T192A, K194I, M209V, and I305V amino acid substitutions, hhhh) Δ(1-63), Q65P, I87V, R118S, E141K, Q142R, S150G, L151P, V160A, T192A, M209V, M241T, S263P, and I305V amino acid substitutions, iiii) Δ(1-63), Q65P, I87V, R118S, E141K, Q142R, S150G, L151P, V160A, T192A, K194I, M241T, and I305V amino acid substitutions, jjjj) Δ(1-63), Q65P, I87V, R118S, E141K, Q142R, S150G, L151P, V160A, T192A, K194I, M209V, S263P, and I305V amino acid substitutions, kkkk) Δ(1-63), Q65P, I87V, R118S, E141K, Q142R, S150G, L151 P, V160A, T192A, M209V, and I305V amino acid substitutions, llll) Δ(1-63), Q65P, I87V, R118S, E141K, Q142R, S150G, L151 P, V160A, T192A, K194I, M209V, M241T, and I305V amino acid substitutions, mmmm) Δ(1-63), Q65P, I87V, R118S, E141K, Q142R, S150G, L151 P, V160A, T192A, K194I, M209V, M241T, S263P, and I305V amino acid substitutions, nnnn) Δ(1-63), Q65P, I87V, R118S, E141K, Q142R, S150G, L151P, V160A, T192A, K194I, M209V, S263P, and I305V amino acid substitutions, oooo) Q65P, I87V, R118S, E141K, Q142R, S150G, L151P, V160A, T192A, M209V, S263P, and I305V amino acid substitutions, pppp) Q65P, I87V, R118S, E141K, Q142R, S150G, L151P, V160A, T192A, K194I, M209V, and I305V amino acid substitutions, qqqq) Q65P, I87V, R118S, E141K, Q142R, S150G, L151P, V160A, T192A, M209V, M241T, S263P, and I305V amino acid substitutions, rrrr) Q65P, I87V, R118S, E141K, Q142R, S150G, L151P, V160A, T192A, K194I, M209V, M241T, and I305V amino acid substitutions, and ssss) Q65P, I87V, R118S, E141K, Q142R, S150G, L151P, V160A, T192A, K194I, M209V, M241T, S263P, and I305V amino acid substitutions.

4. The modified biotin ligase of claim 1, wherein the biotin ligase comprises:
  a) a polypeptide comprising an amino acid sequence selected from the group consisting of SEQ ID NO:11 and SEQ ID NO:13; or
  b) a polypeptide comprising an amino acid sequence having at least 90% identity to an amino acid sequence selected from the group consisting of SEQ ID NO:11 and SEQ ID NO:13, wherein the biotin ligase is capable of proximity-dependent biotinylation of proteins.

5. The modified biotin ligase of claim 1, further comprising a targeting sequence that directs the biotin ligase to a subcellular region of interest.

6. A method of using the modified biotin ligase of claim 5 for proximity labeling of proteins in a cell, the method comprising:
  a) introducing the biotin ligase of claim 5 into a cell, wherein the modified biotin ligase is targeted to a subcellular region of interest; and
  b) contacting the cell with biotin or a derivative thereof and ATP, wherein proteins in proximity to the biotin ligase are biotinylated.

7. The method of claim 6, wherein the cell is a eukaryotic cell, a prokaryotic cell, or an archaeon cell, an animal cell, a plant cell, a fungal cell, a bacterial cell, a protist cell, a mammalian cell, or a human cell.

8. The method of claim 6, wherein the cell is a live cell or a fixed cell.

9. The method of claim 6, further comprising calculating the frequencies of one or more proteins that are present within the subcellular region of interest.

10. The method of claim 6, further comprising labeling the biotinylated proteins with a biotin-binding protein conjugated to a detectable label.

11. The method of claim 6, wherein the biotin ligase is provided by a vector comprising a promoter operably linked to a polynucleotide encoding the biotin ligase.

12. The method of claim 6, wherein the cell is exposed to a test condition prior to said contacting the cell with the biotin and the ATP.

13. The method of claim 12, wherein the test condition comprises exposing the cell to a drug, a ligand for a receptor, a hormone, a second messenger, a pathogen, or a genetic modification, or a change in temperature, growth media, membrane potential, or osmotic pressure.

14. The method of claim 12, wherein the genetic modification comprises introduction of a vector, short hairpin RNA (shRNA), small interfering RNA (siRNA), microRNA (miRNA), or CRISPR-associated system into the cell.

15. The method of claim 6, further comprising analyzing the biotinylated proteins to produce a map of the subcellular localization of the proteins within an intracellular spatial location.

16. The method of claim 15, wherein a map of the subcellular localization of the proteins within the intracellular spatial location is compared to a reference map for a cell that is not exposed to the test condition or a reference map for a cell at a different developmental stage.

17. The method of claim 6, further comprising contacting the cell with a crosslinking agent before or after step (b), wherein the crosslinking agent covalently couples the biotinylated proteins to nearby nucleic acids to produce biotinylated protein-nucleic acid fusions; and isolating the biotinylated protein-nucleic acid fusions using a biotin-binding protein that binds to the biotinylated protein-nucleic acid fusions.

18. The method of claim 17, further comprising sequencing at least one RNA or DNA molecule in the biotinylated protein-nucleic acid fusions, calculating the frequencies of one or more RNA molecules that are present within the intracellular spatial location, or quantitating one or more RNA molecules that are present within the intracellular spatial location.

19. A method of proximity labeling proteins in a host subject, the method comprising:

a) introducing a recombinant polynucleotide comprising a nucleotide sequence encoding the modified biotin ligase of claim 1 into the host subject, wherein the modified biotin ligase is expressed in the host subject; and b) administering an effective amount of biotin or a derivative thereof to the host subject, wherein proteins in proximity to the biotin ligase are biotinylated in the host subject.

20. A polynucleotide sequence encoding the modified biotin ligase of claim 1.

21. The modified biotin ligase of claim 1, wherein the modified biotin ligase comprises Q65P, I87V, R118S, E140K, Q141R, S150G, L151P, V160A, T192A, K194I, M209V, M241T, S263P, and I305V amino acid substitutions and a deletion of A146, wherein the positions of the amino acids are numbered relative to the reference wild-type biotin ligase sequence of SEQ ID NO:7.

* * * * *